(12) United States Patent
Morgan et al.

(10) Patent No.: US 12,064,106 B2
(45) Date of Patent: Aug. 20, 2024

(54) DEVICES AND METHODS FOR FACILITATING EJECTION OF SURGICAL FASTENERS FROM CARTRIDGES

(71) Applicant: Cilag GmbH International, Zug (CH)

(72) Inventors: Jerome R. Morgan, Cincinnati, OH (US); Frederick E. Shelton, IV, Hillsboro, OH (US); Emily A. Schellin, Cincinnati, OH (US); Jeffrey S. Swayze, West Chester, OH (US); Gary W. Knight, West Chester, OH (US); Brian F. Dinardo, Cincinnati, OH (US); Adam Dunki-Jacobs, Cincinnati, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 142 days.

(21) Appl. No.: 17/730,723

(22) Filed: Apr. 27, 2022

(65) Prior Publication Data

US 2022/0257242 A1 Aug. 18, 2022

Related U.S. Application Data

(60) Continuation of application No. 16/592,107, filed on Oct. 3, 2019, now Pat. No. 11,317,908, which is a
(Continued)

(51) Int. Cl.
*A61B 17/064* (2006.01)
*A61B 17/072* (2006.01)
(Continued)

(52) U.S. Cl.
CPC .... *A61B 17/0644* (2013.01); *A61B 17/07207* (2013.01); *A61B 17/07292* (2013.01);
(Continued)

(58) Field of Classification Search
CPC .......... A61B 17/0644; A61B 17/07207; A61B 17/07292; A61B 2090/037;
(Continued)

(56) References Cited

U.S. PATENT DOCUMENTS

| | | |
|---|---|---|
| 3,717,294 A | 2/1973 | Green |
| 4,204,623 A | 5/1980 | Green |

(Continued)

FOREIGN PATENT DOCUMENTS

| | | |
|---|---|---|
| EP | 1 479 346 A1 | 11/2004 |
| EP | 1621140 A2 | 2/2006 |

(Continued)

OTHER PUBLICATIONS

"MicroCutter XCHANGE® 30 Videos." Cardica. Web. May 7, 2014. http://www.cardica.com/inservice-guide.php.
(Continued)

*Primary Examiner* — Julian W Woo
(74) *Attorney, Agent, or Firm* — Mintz Levin Cohn Ferris Glovsky and Popeo, P.C.

(57) ABSTRACT

Devices and methods are provided for stabilizing fasteners post-deployment. Devices and methods are also provided for facilitating ejection of surgical fasteners from a cartridge. Devices and methods are also provided for guiding surgical fasteners. Devices and methods are also provided for facilitating closing and clamping of an end effector of a surgical device. Devices and methods are also provided for securing fasteners and adjunct materials to tissue. Devices and methods are also provided for removably coupling a cartridge to an end effector of a surgical device. Devices and methods are also provided for locking a surgical device based on loading of a fastener cartridge in the surgical device. Devices and methods are provided for adjusting a tissue gap of an end effector of a surgical device. Devices and methods are also
(Continued)

provided for manually retracting a drive shaft, drive beam, and associated components.

19 Claims, 68 Drawing Sheets

Related U.S. Application Data division of application No. 15/700,278, filed on Sep. 11, 2017, now Pat. No. 10,470,761, which is a continuation of application No. 14/475,144, filed on Sep. 2, 2014, now Pat. No. 9,788,835.

(51) Int. Cl.
    *A61B 17/00*         (2006.01)
    *A61B 17/29*         (2006.01)
    *A61B 90/00*         (2016.01)

(52) U.S. Cl.
    CPC ............... *A61B 2017/00115* (2013.01); *A61B 2017/00309* (2013.01); *A61B 2017/00327* (2013.01); *A61B 2017/07228* (2013.01); *A61B 2017/0725* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/2933* (2013.01); *A61B 2017/2936* (2013.01); *A61B 2017/2937* (2013.01); *A61B 2090/037* (2016.02); *A61B 2090/0811* (2016.02)

(58) Field of Classification Search
    CPC ...... A61B 2090/081; A61B 2017/2927; A61B 2017/00115; A61B 2017/00309; A61B 2017/00327; A61B 2017/2936; A61B 2017/0725; A61B 2017/2937; A61B 2017/07257; A61B 2017/07271; A61B 2017/07278; A61B 2017/07285; A61B 2017/07228; A61B 2017/2933
    See application file for complete search history.

(56) References Cited

U.S. PATENT DOCUMENTS

| | | |
|---|---|---|
| 4,237,875 A | 12/1980 | Termanini |
| 4,321,002 A | 3/1982 | Froehlich |
| 4,608,981 A | 9/1986 | Rothfuss et al. |
| 4,633,861 A | 1/1987 | Chow et al. |
| 4,712,545 A | 12/1987 | Honkanen |
| 4,854,626 A | 8/1989 | Duke |
| 4,892,244 A | 1/1990 | Fox et al. |
| 5,129,570 A | 7/1992 | Schulze et al. |
| 5,304,185 A | 4/1994 | Taylor |
| 5,318,221 A | 6/1994 | Green et al. |
| 5,413,268 A | 5/1995 | Green et al. |
| 5,443,197 A | 8/1995 | Malis et al. |
| 5,445,304 A | 8/1995 | Plyley et al. |
| 5,465,895 A | 11/1995 | Knodel et al. |
| 5,472,132 A | 12/1995 | Savage et al. |
| 5,485,947 A | 1/1996 | Olson et al. |
| 5,503,638 A | 4/1996 | Cooper et al. |
| 5,507,773 A | 4/1996 | Huitema et al. |
| 5,569,298 A | 10/1996 | Schnell |
| 5,662,662 A | 9/1997 | Bishop et al. |
| 5,725,536 A | 3/1998 | Oberlin et al. |
| 5,785,232 A | 7/1998 | Vidal et al. |
| 5,833,695 A | 11/1998 | Yoon |
| 5,891,160 A | 4/1999 | Williamson, IV et al. |
| 6,206,903 B1 | 3/2001 | Ramans |
| 6,254,615 B1 | 7/2001 | Bolduc et al. |
| 6,554,844 B2 | 4/2003 | Lee et al. |
| 6,582,451 B1 | 6/2003 | Marucci et al. |
| 7,000,818 B2 | 2/2006 | Shelton, IV et al. |
| 7,044,353 B2 | 5/2006 | Mastri et al. |
| 7,097,650 B2 | 8/2006 | Weller et al. |
| 7,473,258 B2 | 1/2009 | Clauson et al. |
| 7,533,790 B1 | 5/2009 | Knodel et al. |
| 7,543,730 B1 * | 6/2009 | Marczyk .......... A61B 17/07207 227/176.1 |
| 7,641,671 B2 | 1/2010 | Crainich |
| 7,669,746 B2 | 3/2010 | Shelton, IV |
| 7,678,121 B1 | 3/2010 | Knodel |
| 7,721,936 B2 | 5/2010 | Shalton, IV et al. |
| 7,753,250 B2 | 7/2010 | Clauson et al. |
| 7,918,376 B1 | 4/2011 | Knodel et al. |
| 7,954,683 B1 | 6/2011 | Knodel et al. |
| 7,963,432 B2 | 6/2011 | Knodel et al. |
| 7,988,026 B2 | 8/2011 | Knodel et al. |
| 8,033,438 B2 | 10/2011 | Scirica |
| 8,056,789 B1 | 11/2011 | White et al. |
| 8,066,168 B2 | 11/2011 | Vidal et al. |
| 8,066,720 B2 | 11/2011 | Knodel et al. |
| 8,070,034 B1 | 12/2011 | Knodel |
| 8,070,036 B1 | 12/2011 | Knodel |
| 8,087,562 B1 | 1/2012 | Manoux et al. |
| 8,123,795 B1 | 2/2012 | Knodel et al. |
| 8,127,976 B2 | 3/2012 | Scirica et al. |
| 8,225,980 B1 | 7/2012 | Rivera |
| 8,261,958 B1 | 9/2012 | Knodel |
| 8,272,551 B2 | 9/2012 | Knodel et al. |
| 8,317,071 B1 | 11/2012 | Knodel |
| 8,317,072 B1 | 11/2012 | Knodel et al. |
| 8,348,127 B2 | 1/2013 | Marczyk |
| 8,356,740 B1 | 1/2013 | Knodel |
| 8,357,174 B2 | 1/2013 | Roth et al. |
| 8,365,973 B1 | 2/2013 | White et al. |
| 8,403,956 B1 | 3/2013 | Thompson et al. |
| 8,439,245 B2 | 5/2013 | Knodel et al. |
| 8,439,246 B1 | 5/2013 | Knodel |
| 8,459,522 B2 | 6/2013 | Marczyk |
| 8,496,155 B2 | 7/2013 | Knodel |
| 8,505,800 B1 | 8/2013 | Knodel et al. |
| 8,535,311 B2 | 9/2013 | Schall |
| 8,556,153 B1 | 10/2013 | Knodel |
| 8,556,935 B1 | 10/2013 | Knodel et al. |
| 8,617,203 B2 | 12/2013 | Stefanchik et al. |
| 8,631,990 B1 | 1/2014 | Park et al. |
| 8,631,992 B1 | 1/2014 | Hausen et al. |
| 8,636,189 B1 | 1/2014 | Knodel et al. |
| 8,662,369 B1 | 3/2014 | Manoux et al. |
| 8,672,209 B2 | 3/2014 | Crainich |
| 8,679,155 B2 | 3/2014 | Knodel et al. |
| 8,690,909 B2 | 4/2014 | Slater |
| 8,701,960 B1 | 4/2014 | Manoux et al. |
| 8,783,542 B2 | 7/2014 | Riestenberg et al. |
| 8,789,739 B2 | 7/2014 | Swensgard |
| 8,939,344 B2 | 1/2015 | Olson et al. |
| 9,004,339 B1 | 4/2015 | Park |
| 9,016,539 B2 | 4/2015 | Kostrzewski et al. |
| 9,084,600 B1 | 7/2015 | Knodel et al. |
| 9,168,039 B1 | 10/2015 | Knodel |
| 9,192,378 B2 | 11/2015 | Aranyi et al. |
| 9,204,877 B2 | 12/2015 | Whitman et al. |
| 9,364,217 B2 | 6/2016 | Kostrzewski et al. |
| 9,486,215 B2 | 11/2016 | Olson et al. |
| 9,554,796 B2 | 1/2017 | Kostrzewski |
| 9,757,126 B2 * | 9/2017 | Cappola .......... A61B 17/07207 |
| 9,788,835 B2 | 10/2017 | Morgan et al. |
| 9,877,722 B2 | 1/2018 | Schellin et al. |
| 10,004,496 B2 | 6/2018 | Shelton, IV et al. |
| 10,004,500 B2 | 6/2018 | Shelton, IV et al. |
| 10,206,680 B2 | 2/2019 | Schellin et al. |
| 10,470,761 B2 | 11/2019 | Morgan et al. |
| 10,729,437 B2 | 8/2020 | Shelton, IV et al. |
| 10,888,328 B2 | 1/2021 | Shelton, IV et al. |
| 11,185,326 B2 | 11/2021 | Kostrzewski et al. |
| 2005/0006431 A1 | 1/2005 | Shelton et al. |
| 2005/0023324 A1 | 2/2005 | Doll et al. |
| 2005/0033329 A1 | 2/2005 | Bombard et al. |
| 2005/0101991 A1 | 5/2005 | Ahlberg et al. |

(56) References Cited

U.S. PATENT DOCUMENTS

| | | |
|---|---|---|
| 2005/0103819 A1 | 5/2005 | Racenet et al. |
| 2005/0178813 A1 | 8/2005 | Swayze et al. |
| 2006/0053563 A1 | 3/2006 | Skinner |
| 2007/0162056 A1 | 7/2007 | Gerbi et al. |
| 2008/0083806 A1 | 4/2008 | Scirica |
| 2008/0245842 A1 | 10/2008 | Marczyk |
| 2008/0296347 A1 | 12/2008 | Shelton, IV et al. |
| 2009/0065552 A1 | 3/2009 | Knodel et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0272783 A1 | 11/2009 | Crainich et al. |
| 2009/0272786 A1 | 11/2009 | Zeiner et al. |
| 2010/0001036 A1 | 1/2010 | Marczyk et al. |
| 2010/0012702 A1 | 1/2010 | Marczyk |
| 2010/0069935 A1 | 3/2010 | Crainich |
| 2010/0155453 A1 | 6/2010 | Bombard et al. |
| 2010/0187284 A1 | 7/2010 | Crainich et al. |
| 2010/0213240 A1 | 8/2010 | Kostrzewski |
| 2010/0256675 A1 | 10/2010 | Romans |
| 2011/0036892 A1 | 2/2011 | Marczyk et al. |
| 2011/0155781 A1 | 6/2011 | Swensgard et al. |
| 2011/0204120 A1 | 8/2011 | Crainich |
| 2011/0270235 A1 | 11/2011 | Olson et al. |
| 2011/0276049 A1 | 11/2011 | Gerhardt |
| 2011/0278343 A1 | 11/2011 | Knodel et al. |
| 2011/0284615 A1 | 11/2011 | Tarinelli et al. |
| 2012/0010652 A1 | 1/2012 | Hahnen et al. |
| 2012/0074198 A1 | 3/2012 | Huitema et al. |
| 2012/0150176 A1 | 6/2012 | Weizman |
| 2012/0187179 A1 | 7/2012 | Gleiman |
| 2012/0215220 A1 | 8/2012 | Manzo et al. |
| 2012/0223121 A1 | 9/2012 | Viola et al. |
| 2012/0228358 A1 | 9/2012 | Zemlok et al. |
| 2012/0241492 A1 | 9/2012 | Shelton, IV et al. |
| 2012/0241497 A1 | 9/2012 | Mandakolathur Vasudevan et al. |
| 2012/0241503 A1 | 9/2012 | Baxter, III et al. |
| 2012/0248169 A1 | 10/2012 | Widenhouse et al. |
| 2013/0075448 A1 | 3/2013 | Schmid et al. |
| 2013/0105548 A1 | 5/2013 | Hodgkinson et al. |
| 2013/0112730 A1 | 5/2013 | Whitman et al. |
| 2013/0119109 A1 | 5/2013 | Farascioni et al. |
| 2013/0161374 A1 | 6/2013 | Swayze et al. |
| 2013/0172929 A1 | 7/2013 | Hess et al. |
| 2013/0277410 A1 | 10/2013 | Fernandez et al. |
| 2014/0025070 A1 | 1/2014 | Kerr et al. |
| 2014/0041191 A1 | 2/2014 | Knodel |
| 2014/0175146 A1 | 6/2014 | Knodel |
| 2014/0263559 A1 | 9/2014 | Williams et al. |
| 2015/0048141 A1 | 2/2015 | Felder et al. |
| 2015/0230793 A1 | 8/2015 | Kostrzewski |
| 2015/0297236 A1 | 10/2015 | Harris et al. |
| 2015/0359536 A1 | 12/2015 | Cropper et al. |
| 2016/0058439 A1 | 3/2016 | Shelton, IV et al. |
| 2016/0058440 A1 | 3/2016 | Dinardo et al. |
| 2016/0058444 A1 | 3/2016 | Shelton, IV et al. |
| 2016/0058445 A1 | 3/2016 | Morgan et al. |
| 2016/0058446 A1 | 3/2016 | Shelton, IV et al. |
| 2016/0058447 A1 | 3/2016 | Posada et al. |
| 2016/0058448 A1 | 3/2016 | Schellin et al. |
| 2016/0058449 A1 | 3/2016 | Shelton, IV et al. |
| 2016/0058450 A1 | 3/2016 | Shelton, IV et al. |
| 2016/0089149 A1 | 3/2016 | Harris et al. |
| 2016/0296226 A1 | 10/2016 | Kostrzewski |
| 2017/0020524 A1 | 1/2017 | Marczyk et al. |
| 2017/0119402 A1 | 5/2017 | Heinemann |
| 2018/0263622 A1 | 9/2018 | Shelton, IV et al. |
| 2019/0380706 A1 | 12/2019 | Morgan et al. |
| 2020/0029962 A1 | 1/2020 | Morgan et al. |

FOREIGN PATENT DOCUMENTS

| | | |
|---|---|---|
| EP | 1813201 A1 | 8/2007 |
| EP | 1943963 A2 | 7/2008 |
| EP | 2145588 A1 | 1/2010 |
| EP | 2628491 A2 | 8/2013 |
| EP | 2732772 A1 | 5/2014 |
| EP | 2764827 A2 | 8/2014 |
| EP | 2764834 A2 | 8/2014 |
| EP | 2891460 A1 | 7/2015 |
| EP | 2891789 A1 | 7/2015 |
| WO | WO-9915086 A1 | 4/1999 |
| WO | WO-2004032762 A1 | 4/2004 |
| WO | WO-2009038550 A1 | 3/2009 |
| WO | WO-2012015795 A1 | 2/2012 |
| WO | WO-2013151820 A1 | 10/2013 |

OTHER PUBLICATIONS

"MicroCutter XCHANGE® 30: The World's First and Only Articulating 5mm Stapler." Cardica. Web. May 7, 2014. http://www.cardica.com/minimally-invasive-surgery.php.

"MicroCutter XCHANGE™ M 30." Inservice Poster. (Oct. 13).

"MicroCutter XCHANGE™ 30." Instructions for Use. (2014).

European Partial Search Report for Application No. 15183388.6, dated May 3, 2016 (9 pages).

European Partial Search Report for Application No. 15183389.4, dated May 31, 2016 (5 pages).

European Search Report for Application No. 15183377.9 mailed on May 3, 2016.

European Search Report for Application No. 15183381.1 mailed May 9, 2016.

European Search Report for Application No. 15183383.7 mailed on Jun. 14, 2016.

European Search Report for Application No. 15183384.5 mailed on May 17, 2016.

European Search Report for Application No. 15183390.2 mailed on Feb. 2, 2016.

U.S. Appl. No. 14/300,954, filed Jun. 10, 2014.

U.S. Appl. No. 14/475,144, filed Sep. 2, 2014, Jerome R. Morgan et al.

U.S. Appl. No. 15/700,278, filed Sep. 11, 2017, Jerome R. Morgan et al.

U.S. Appl. No. 16/506,030, filed Jul. 9, 2019, Jerome R. Morgan et al.

U.S. Appl. No. 16/592,107, filed Oct. 3, 2019, Jerome R. Morgan et al.

\* cited by examiner

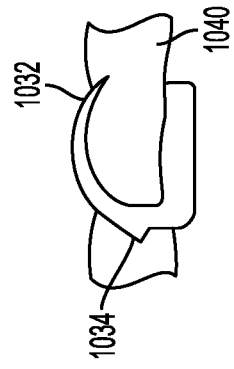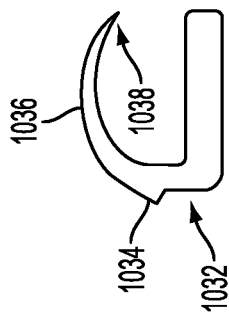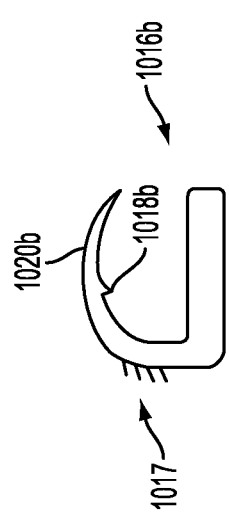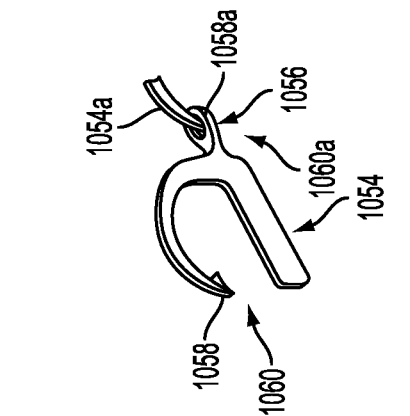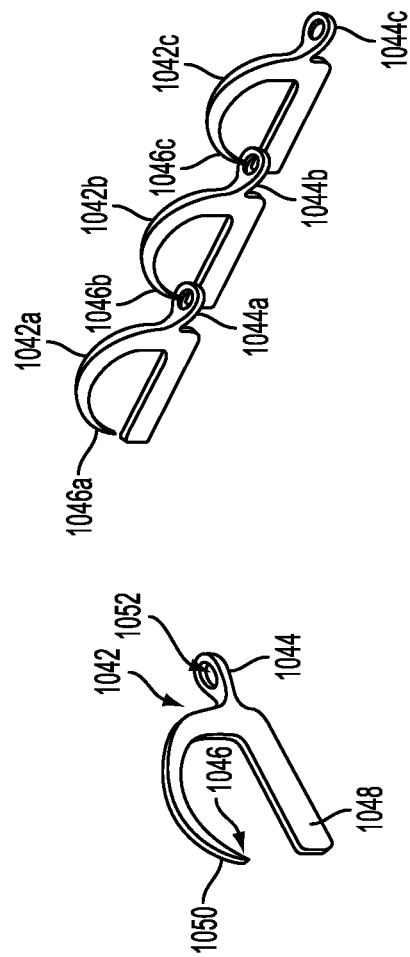

DEVICES AND METHODS FOR FACILITATING EJECTION OF SURGICAL FASTENERS FROM CARTRIDGES

The present application is a continuation of U.S. patent application Ser. No. 16/592,107, now U.S. Pat. No. 11,317,908, filed Oct. 3, 2019 and entitled "Devices And Methods For Facilitating Ejection Of Surgical Fasteners From Cartridges," which is a divisional of U.S. patent application Ser. No. 15/700,278, now U.S. Pat. No. 10,470,761 filed Sep. 11, 2017 and entitled "Devices And Methods For Facilitating Ejection Of Surgical Fasteners From Cartridges," which is a continuation of U.S. patent application Ser. No. 14/475,144, now U.S. Pat. No. 9,788,835, filed Sep. 2, 2014 and entitled "Devices And Methods For Facilitating Ejection Of Surgical Fasteners From Cartridges," which are hereby incorporated by reference in their entireties herein.

FIELD OF THE INVENTION

Background

Minimally invasive surgical instruments are often preferred over traditional open surgical devices due to the reduced post-operative recovery time and minimal scarring associated with minimally invasive procedures. Laparoscopic surgery is one type of minimally invasive surgery (MIS) procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. Endoscopic surgery is another type of MIS procedure in which elongate flexible shafts are introduced into the body through a natural orifice.

Due to the benefits associated with minimally invasive surgeries, significant efforts have gone into developing a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, stapler, clip applier, access device, drug/gene therapy delivery device, and energy device using ultrasound, radiofrequency, laser, etc.).

For example, staplers including end effectors for grasping tissue have been developed which secure tissue between two jaws. Staples contained in one of the jaws can be driven into the grasped tissue and deformed to hold the tissue by impinging on the other jaw. The staples can form a predetermined pattern (e.g., one or more lines of staples) based upon the configuration of the staples in the one of the jaws. The stapler can be a linear stapler, in which the predetermined pattern includes one or more longitudinal lines of staples. Though staplers can be effective to grasp and staple tissue, it can be difficult to grasp and/or staple the tissue based on a variety of factors, such as a size and/or shape of the staple, a thickness and/or toughness of the tissue, etc.

Some staplers can be refilled after firing staples. In some staplers, the staples can be contained in a cartridge which can be removable from the stapler's jaw to allow the stapler to be refilled with staples contained in another cartridge inserted into the jaw. However, this refilling of cartridges can be difficult since the cartridges can be relatively small and accordingly difficult to manipulate and/or properly secure within the jaw. Refilling a stapler with a new cartridge can thus be time consuming and/or can result in an improperly loaded cartridge that can misfire staples or otherwise function improperly during use on a patient.

Accordingly, there remains a need for improved methods and devices for stapling tissue.

SUMMARY

A surgical fastening device comprises an elongate shaft having an end effector coupled to a distal end thereof, wherein the end effector includes first and second opposed jaws coupled to one another and configured to engage tissue therebetween. The device also includes a staple cartridge disposed within the first jaw. The staple cartridge includes a plurality of D-shaped, plastically deformable staples, each staple being configured to rotate in a first direction into tissue engaged between the first and second jaws. Each staple has an anti-rotation mechanism configured to prevent rotation in a second direction opposite to the first direction when the staples are deployed in tissue. Each D-shaped staple of the device includes a first leg that is substantially straight, and a second leg that is curved.

The anti-rotation mechanism can take a variety of forms. In one aspect the anti-rotation mechanism comprises a barb formed on the staple and oriented in a direction to prevent counter-rotation of the staples. For example, the anti-rotation mechanism on each staple can comprise a barb is formed on an outer-facing surface of the second leg, which may be oriented towards the first leg. In another aspect the anti-rotation mechanism comprises a coupling element formed on each staple and configured to receive a tip of an adjacent staple when deployed such that counter-rotation of the staples is prevented. In yet another aspect, the anti-rotation mechanism on each staple comprises a hoop formed adjacent to an intersection between the first and second legs and configured to receive a tip of the first leg when the staples are deployed in tissue.

The plurality of staples can be attached to a carrier. The staples can be frangibly attached to the carrier and they can be arranged in longitudinal rows on the carrier.

In another embodiment, a surgical fastening device for treating tissue can comprise a handle, an elongate shaft extending distally from the handle, and an end effector coupled to a distal end of the elongate shaft, wherein the end effector has a jaw and an anvil pivotally connected to the jaw such that the jaw and the anvil being configured to engage tissue therebetween. The fastening device also includes a plurality of fasteners disposed within the jaw, wherein the fasteners are rotatable about a pivot point. Further, the device includes a sled slidable through the jaw such that distal advancement of the sled causes each of the plurality of fasteners to rotate into tissue engaged between the jaw and the anvil. Each fastener includes an anti-rotation feature configured to prevent counter-rotation of the fasteners when deployed in tissue.

In one aspect, the anti-rotation feature comprises a barb formed on the fastener and oriented in a direction to prevent counter-rotation of the fasteners. Each fastener can include a straight leg and a curved leg, and the barb can be formed on an outer surface of the curved leg so as to be oriented toward the straight leg. In another aspect, the anti-rotation feature comprises a coupling element formed on each fastener and configured to receive a tip of an adjacent fastener when deployed such that counter-rotation of the fasteners is prevented. By way of example, the coupling element can be in the form of a hoop formed on the fastener.

The fasteners can be attached to a carrier in such a way that they are frangibly attached thereto. Further, the fasteners can be arranged in longitudinal rows.

A surgical fastening device for treating tissue comprises an elongate shaft, an end effector coupled to a distal end of the elongate shaft, a plurality of fasteners disposed within the jaw and frangibly coupled to a carrier, a sled configured to advance distally through the jaw to cause each of the plurality of fasteners to rotate into tissue engaged between the jaw and the anvil, and a shearing element slidably moveable within the jaw to shear each fastener from the carrier, wherein the shearing element is separate from the sled such that the shearing element is configured to shear the fasteners from the carrier after the fasteners are driven into tissue by the sled. The end effector includes a jaw and an anvil pivotally connected to the jaw, the jaw and the anvil being configured to engage tissue therebetween. In one aspect the shearing element is positioned proximal of the sled. In another aspect the shearing element is coupled to a distal end of the sled. In one aspect the shearing element includes a plurality of upright wedges configured to shear the fasteners from the carrier.

In one aspect the fastening device further comprises an I-beam positioned proximal of the shearing element and configured to be slidably received within the anvil and the jaw. In another aspect the sled includes a plurality of wedges configured to contact and drive the fasteners into tissue, and a knife for cutting tissue engaged between the jaw and the anvil, and wherein the shearing element is positioned proximal of the wedges and the knife. The shearing element is configured such that it shears the fasteners from the carrier during proximal movement of the shearing element through the jaw. In one aspect the shearing element is pivotable between a first inactive position and a second active position, the shearing element shearing the fasteners during the second active position.

In another aspect a surgical stapling device comprises an end effector having first and second jaws pivotally coupled to one another and configured to engage tissue therebetween, a plurality of plastically deformable staples frangibly formed on a carrier and disposed within the first jaw, wherein the staples are configured to be rotatably deployed into tissue engaged between the jaws, a wedge configured to slidably advance through the first jaw to rotatably drive the staples into tissue, and a shearing element configured to shear the staples from the carrier after the staples are rotatably deployed into the tissue by the wedge. In one aspect the shearing element is positioned proximal of the wedge. In another aspect the wedge includes a plurality of upright flanges configured to rotatably drive the staples into tissue, and the shearing element includes a plurality of upright flanges configured to shear the staples from the carrier. The wedge can include a knife for cutting tissue engaged between the first and second jaws, and the shearing element can be positioned proximal of the knife.

In one aspect the shearing element is configured to shear the staples from the carrier during proximal movement of the shearing element through the first jaw. In another aspect the shearing element is pivotable between a first inactive position and a second active position, the shearing element shearing the staples during the second active position.

A surgical fastening device includes an elongate shaft and an end effector coupled to a distal end of the elongate shaft. The end effector includes first and second opposed jaws coupled to one another and configured to engage tissue therebetween. The device also includes a staple cartridge disposed within the first jaw. The staple cartridge also includes a plurality of staple-receiving recesses formed therein, a plurality of D-shaped staples configured to rotate about a pivot point into tissue engaged between the first and second jaws, wherein each staple is disposed within a staple-receiving recess, and a plurality of guide members formed on the cartridge. Each guide member extends from a surface of the cartridge at a location adjacent to a staple-receiving recess, and each guide member has an inner arcuate surface configured to guide a leg of a staple along an arcuate path and into tissue engaged between the first and second jaws. In a further aspect, each guide member includes opposed sidewalls configured to support and maintain alignment of a staple being rotatably advanced therethrough.

Each guide member is formed on and protrudes outward from a tissue-contacting surface of the cartridge. Further, each guide member can be formed on an inwardly-facing surface of the cartridge, opposite to a tissue-contacting surface. In one aspect each guide-member is substantially U-shaped such that the guide member is configured to contact three sides of a staple being advanced therethrough.

According to another aspect, a surgical stapling device comprises an elongate shaft having an end effector coupled to a distal end thereof and including a cartridge-receiving jaw and an anvil pivotally coupled to the cartridge-receiving jaw. The device also includes a staple cartridge disposed within the cartridge-receiving jaw, wherein the staple cartridge has a carrier disposed therein with a plurality of plastically deformable staples formed on the carrier. The staple cartridge also has a deck with a plurality of openings formed therein, wherein each opening is configured to receive one of the plurality of staples therethrough. Each opening further has a guide member extending outwardly from the deck that is configured to guide a staple being advanced through the opening along an arcuate path.

Each guide member can extend outwardly from the deck in a direction toward the anvil. Alternatively, each guide member can extend outwardly from the deck in a direction away from the anvil.

In one aspect, each guide member includes opposed sidewalls that engage opposed sides of a staple being advanced therethrough. Further, each guide member can include a curved inner surface that guides the staples along a curved pathway.

A surgical fastening device comprises an elongate shaft and an end effector coupled to a distal end of the elongate shaft. The end effector includes a cartridge jaw and an anvil pivotally coupled to one another at a pivot point, a cam pin disposed within a cam slot formed in each of the cartridge jaw and the anvil, and a closure mechanism proximal to the pivot point. The cam pin is slidable within the cam slots to move the anvil and cartridge jaw between a spaced-apart position and a closed position in which the cartridge jaw and the anvil are configured to engage tissue therebetween. Further, the closure mechanism is positioned adjacent to a proximal-most end of the anvil and is configured to apply a force to the proximal-most end of the anvil to compress tissue engaged between the anvil and the cartridge jaw.

The closure mechanism can be in the form of a lobe cam that rotates to apply a force to the proximal-most end of the anvil to move the proximal-most end of the anvil away from the cartridge jaw. The lobe cam can be rotatably disposed within the end effector.

In one aspect the fastening device further comprises a cable coupled to the lobe cam and configured to rotate the lobe cam to cause the lobe cam to apply a force to the proximal-most end of the anvil. The lobe cam can include a biasing element that biases the lobe cam to a position in which no force is applied to the proximal-most end of the anvil.

The closure mechanism can comprise a wedge configured to apply a force to the proximal-most end of the anvil to move the proximal-most end of the anvil away from the cartridge jaw. In one aspect the wedge is configured to advance distally to apply the force to the proximal-most end of the anvil. The wedge can be formed on a distal end of a pusher shaft slidably disposed through the elongate shaft.

According to another aspect, a surgical fastening device comprises a handle, an elongate shaft extending distally from the handle, and an end effector coupled to a distal end of the elongate shaft. The end effector can include first and second jaws pivotally coupled to one another and movable about a pivot point between an open position and a closed position for engaging tissue. The fastener also includes a lobe cam positioned proximal to the pivot point and between a proximal-most end of each of the first and second jaws. The lobe cam is rotatable to move the proximal-most ends of the first and second jaws apart to thereby move the first and second jaws to the closed position. In one aspect the lobe cam can be biased to a position in which the first and second jaws are in the open position, and rotation of the lobe cam overcomes the bias to move the first and second jaws to the closed position.

The surgical fastening device further comprises a cable coupled to the lobe cam and configured to rotate the lobe cam to cause the lobe cam to apply a force to move the first and second jaws to the closed position. The device can be constructed such that a distance between the first and second jaws at the pivot point is adjustable.

In yet another aspect, a surgical fastening device comprises a handle, an elongate shaft extending distally from the handle, and an end effector coupled to a distal end of the elongate shaft. The end effector includes first and second jaws pivotally coupled to one another and movable about a pivot point between an open position and a closed position for engaging tissue. The device further includes a two-bar linkage coupled to the first and second jaws and configured to apply a force to the proximal-most end of the first jaw to move the proximal-most end of the first jaw away from the proximal-most end of the second jaw.

The two-bar linkage can include a first bar coupled to an actuation shaft slidably disposed through the elongate shaft and a second bar coupled to the first bar and having a pin formed thereon, wherein the pin is slidably disposed within a slot formed in the second jaw. Further, the two-bar linkage is coupled to an actuation shaft that is pulled proximally to cause the two-bar linkage to apply the force to the first jaw.

A method for fastening tissue is also provided. The method comprises inserting an end effector into a body cavity of a patient's body, wherein the end effector being coupled to a distal end of an elongate shaft extending from a handle positioned outside of the patient's body, manipulating the handle of the surgical device to position tissue between a cartridge jaw and an anvil of the end effector, actuating a closure mechanism to advance a pin through cam slots formed in each of the cartridge jaw and the anvil to cause the cartridge jaw and the anvil to engage the tissue positioned therebetween, and actuating a compression mechanism to move a proximal-most end of each of the anvil and the cartridge jaw away from one another to further compress the tissue engaged therebetween.

In one aspect actuating the compression mechanism comprises rotating a lobe cam disposed between a proximal-most end of each of the anvil and the cartridge jaw. In another aspect actuating the compression mechanism comprises advancing a wedge distally along the elongate shaft and between the proximal-most end of each of the anvil and cartridge jaw. In yet another aspect actuating the compression mechanism comprises actuating a two-bar linkage mechanism coupled to the anvil and cartridge jaws.

A surgical fastening device, comprises an elongate shaft and an end effector coupled to a distal end of the elongate shaft. The end effector includes a cartridge jaw and an anvil pivotally coupled to one another and configured to engage tissue therebetween. The fastening device also includes a staple cartridge disposed within the cartridge jaw, wherein the staple cartridge includes a plurality of D-shaped staples configured to rotate about a pivot point into tissue engaged between the cartridge jaw and the anvil, and at least one adjunct material disposed on a tissue-facing surface of the cartridge jaw and configured to receive the plurality of D-shaped staples therethrough when the staples are deployed and frangibly detached from the carrier. Each staple is frangibly coupled to a carrier.

The at least one adjunct material can comprise a single foam layer disposed across the entire tissue-facing surface of the cartridge jaw and configured to receive each of the plurality of D-shaped staples therethrough. The at least one adjunct material can also comprise a plurality of adjunct materials, each of the plurality of adjunct materials being configured to receive two of the plurality of staples therethrough for interconnecting the staples. In one aspect the at least one adjunct material comprises a single adjunct material that spans an entire length and width of the tissue-facing surface of the cartridge jaw. Further, the at least one adjunct material can comprise a first adjunct material that spans across at least two staple-receiving openings formed in the tissue-facing surface of the cartridge jaw, and at least one second adjunct material that spans across at least two other staple-receiving openings formed in the tissue-facing surface of the cartridge jaw.

The at least one adjunct material can be at least partially formed from a biologically-derived material. In addition, the adjunct material can be compressible.

In another aspect, a surgical fastening device comprises an elongate shaft having an end effector at a distal end thereof, wherein the end effector including first and second jaws pivotally coupled to one another and configured to engage tissue therebetween. The fastening device also includes a plurality of D-shaped staples disposed within one of the first and second jaws, wherein each D-shaped staple being configured to rotate from a first position, in which the staple is fully contained within the jaw, and a second position in which the staple protrudes from the jaw and is configured to engage tissue positioned between the first and second jaws. Further, the fastening device comprises at least one adjunct material disposed on a tissue-facing surface of one of the first and second jaws and positioned such that at least two of the D-shaped staples will protrude therethrough when moved from the first position to the second position such that the D-shaped staples engage both the adjunct material and the tissue.

The plurality of D-shaped staples are frangibly coupled to a carrier, and they are configured to frangibly detach from the carrier during movement from the first position to the second position.

The at least one adjunct material can comprise a single foam layer disposed across an entire tissue-facing surface of the jaw and configured to receive each of the plurality of D-shaped staples therethrough. Alternatively, the at least one adjunct material comprises a plurality of adjunct materials, each of the plurality of adjunct materials is configured to receive two of the plurality of staples therethrough for interconnecting the staples. In one aspect the at least one adjunct comprises a single adjunct material that spans an entire length and width of a tissue-facing surface of the jaw. The at least one adjunct material can also comprise a first adjunct material that spans across at least two staple-receiving openings formed in the tissue-facing surface, and at least one second adjunct material that spans across at least two other staple-receiving openings formed in the tissue-facing surface.

The at least one adjunct material is at least partially formed from a biologically-derived material, and the adjunct material can be compressible.

A method for stapling tissue is also provided. The method comprises manipulating an elongate shaft of a stapling device to position tissue between opposed first and second jaws of an end effector, actuating the stapling device to cause the jaws to close and engage the tissue positioned therebetween, and actuating the stapling device to fire a plurality of D-shaped staples from one of the opposed first and second jaws, the plurality of D-shaped staples extending through at least one adjunct material positioned between the opposed first and second jaws and through the tissue engaged between the jaws such that the adjunct material is securely fastened to the tissue by the plurality of D-shaped staples. In one aspect the D-shaped staples frangibly detach from a carrier when the stapling device is actuated to fire the staples.

The plurality of D-shaped staples are configured to extend through the same adjunct material. In one aspect the adjunct material comprises at least first and second separate adjunct materials, wherein first and second of the plurality of D-shaped staples extend through the first adjunct material such that the first and second staples are interconnected, and wherein third and fourth of the plurality of D-shaped staples extend through the second adjunct material such that the third and fourth staples are interconnected.

A surgical fastening device comprises an elongate shaft and an end effector coupled to a distal end of the elongate shaft such that the end effector includes a cartridge jaw and an anvil pivotally coupled to one another and configured to engage tissue therebetween. The device also includes a staple cartridge configured to be removably disposed within a channel formed in the cartridge jaw, wherein the staple cartridge includes a plurality of staples disposed therein. The device further includes a latch formed on one of the cartridge jaw and the staple cartridge, wherein the latch is configured to extend into a corresponding engagement feature formed in the other one of the cartridge jaw and the staple cartridge when the staple cartridge is fully seated within the cartridge jaw. The latch can protrude radially outward beyond an outer diameter of the elongate shaft and end effector when the latch is not engaged with the corresponding engagement feature.

In one aspect the latch is formed on a proximal portion of the cartridge jaw and the corresponding engagement feature is formed on the staple cartridge. The corresponding engagement feature can comprise a cut-out. In one aspect the latch comprises a deflectable spring-arm configured to snap into the corresponding engagement feature when the staple cartridge is fully seated in the cartridge jaw.

The device is constructed such that the plurality of staples in the cartridge are configured to rotate about a pivot point into tissue engaged between the cartridge jaw and the anvil. Further, the plurality of staples are each frangibly coupled to a carrier.

In another aspect a surgical fastening device comprises an elongate shaft and an end effector coupled to a distal end of the elongate shaft such that the end effector includes a cartridge jaw and an anvil pivotally coupled to one another and configured to engage tissue therebetween. The device also includes a staple cartridge configured to be removably disposed within a channel formed in the cartridge jaw, wherein the staple cartridge including a plurality of staples disposed therein. The device further includes a mating element formed on one of the staple cartridge and the cartridge jaw and configured to engage a corresponding engagement feature in the other one of the staple cartridge and the cartridge jaw when the staple cartridge is fully seated within the cartridge jaw. Finally, the device includes at least one biasing element disposed within a channel formed in the cartridge jaw, wherein the at least one biasing element is configured to bias the staple cartridge out of the channel in the cartridge jaw when the mating element is not engaged with the engagement feature.

The mating element can comprise a deflectable spring arm formed on the staple cartridge, and wherein the corresponding engagement feature comprises a cut-out formed in the cartridge jaw. Alternatively, the mating element comprises first and second deflectable spring arms formed on opposed lateral sides of the staple cartridge, and wherein the corresponding engagement feature comprises first and second cut-outs formed in opposed lateral sides of the cartridge jaw. In one aspect the biasing element comprises at least one spring. The at least one spring can be compressed when the staple cartridge is fully seated in the cartridge jaw. In one aspect the biasing element is formed within a proximal portion of the channel in the cartridge jaw.

A method for attaching a staple cartridge to an end effector of a stapling device is also provided. The method comprises positioning a staple cartridge in a channel formed within a cartridge jaw of an end effector of a surgical stapling device, the cartridge jaw having an anvil pivotally coupled thereto, wherein a mating feature on one of the staple cartridge and the cartridge jaw snaps into a corresponding engagement feature on the other one of the staple cartridge and the cartridge jaw, and wherein a biasing element on the end effector and separate from the mating feature results in a positive indication to a user when the staple cartridge is not fully seated within the cartridge jaw. The method can further comprise inserting the end effector through a trocar extending through a tissue wall and into a body cavity of a patient, the deflectable spring arm preventing insertion of the end effector into the body cavity when the staple cartridge is not fully seated within the cartridge jaw.

In one aspect of the method, the biasing element comprises at least one spring that biases the staple cartridge out of the cartridge jaw when the mating element is not engaged with the corresponding engagement feature such the positive indication comprises misalignment of the staple cartridge with the cartridge jaw. In another aspect, the biasing element comprises at least one deflectable spring arm that protrudes radially outwardly from an outer diameter of the end effector to provide the positive indication when the mating element is not engaged with the corresponding engagement feature.

A surgical stapling device comprises a cartridge jaw, an anvil pivotally connected to the cartridge jaw, and a first cartridge configured to be detachably seated within a channel in the cartridge jaw. The first cartridge holds a plurality of staples of a first size and includes a first gap-setting feature defined in an exterior of the first cartridge, wherein a first clamp gap between the cartridge jaw and the anvil is set by the gap-setting feature. The stapling device also includes at least one cam plate coupled to the cartridge jaw. The cam plate has first and second positions, wherein when the cam plate is in the first position at least one of closure of the anvil and cartridge jaw and firing of the staples into tissue engaged between the anvil and the jaw is prevented, and wherein the first cartridge moves the cam plate from the first position to the second position when the first cartridge is fully seated within the anvil. In one aspect the at least one cam plate is prevented from moving from the first position to the second position when the cartridge is not fully seated within the cartridge jaw. Further, the at least one cam plate includes a central aperture having a height at a proximal end that is greater than a height at a distal end.

The stapling device further comprises a pivot pin constrained within and movable within the central aperture of the at least one cam plate, wherein the pivot pin interconnects the cartridge jaw and the anvil. The pivot pin can be movable in both lateral and longitudinal directions within the central aperture. In another aspect, a second cartridge can be configured to be detachably seated within the channel in the cartridge jaw. The second cartridge holds staples of a second size and includes a second gap-setting feature defined in an exterior of the second cartridge, wherein a second clamp gap between the cartridge jaw and the anvil is set by the second gap-setting feature, and wherein the first clamp gap is different from the second clamp gap.

In another aspect, a surgical fastening device comprises an elongate shaft and an end effector coupled to a distal end of the elongate shaft, wherein the end effector includes a cartridge jaw and an anvil pivotally coupled to one another and movable between an open position and a closed position in which tissue can be engaged therebetween. The fastening device also includes a cam pin disposed within a cam slot formed in the end effector, wherein the cam pin having first, second, and third positions within the cam slot, and wherein movement of the cam pin within the cam slot between the second and third positions is effective to change a distance between a proximal end of each of the cartridge jaw and the anvil. The fastening device further includes a staple cartridge configured to be removably disposed within a channel formed in the cartridge jaw and including a plurality of staples disposed therein. The staple cartridge is configured to cause the cam pin to move out of the first position and into one of the second and third positions when the staple cartridge is fully seated within the cartridge jaw, and the cam pin is prevented from moving out of the first position when the staple cartridge is not fully seated within the cartridge jaw. When the cam pin is in the first position, the anvil and cartridge jaw are held in the open position and prevented from moving to the closed position. Alternatively, when the cam pin is in the first position, the anvil and cartridge jaw are freely movably between the open and closed positions, and actuation of the device to fire staples from the staple cartridge is prevented.

In one aspect the cam slot has a height at a proximal end that is greater than a height at a distal end of the cam slot. The cam slot can be formed in at least one shuttle positioned adjacent to a sidewall of the cartridge jaw. In one aspect the at least one shuttle is biased distally and slidable longitudinally.

A method of attaching a staple cartridge to an end effector of a stapling device is also provided. The method comprises positioning a staple cartridge in a channel formed within a cartridge jaw of an end effector of a surgical stapling device, wherein the cartridge jaw has an anvil pivotally coupled thereto, and the end effector includes a shuttle that slides proximally from a first position to a second position in response to seating of the staple cartridge fully within the channel in the cartridge jaw. The shuttle prevents at least one of closure of the anvil and the cartridge jaw to engage tissue and firing of staples from the cartridge when the shuttle is in the first position and prior to the staple cartridge being fully seated within the channel in the cartridge jaw.

In one aspect wherein movement of the shuttle from the first position to the second position causes a pin extending through a central aperture in the shuttle to move from a first position to a second position. In another aspect positioning of the cartridge within the channel in the cartridge jaw moves the pin into one of the second position and a third position, wherein the cartridge jaw and the anvil have a first clamp gap height when the pin is in the second position, and the cartridge jaw and the anvil have a second clamp gap height when the pin is in the third position, the second clamp gap height differing from the first clamp gap height.

According to one aspect of the method, when the pin in the first position it prevents pivotal movement of the anvil and the cartridge jaw relative to one another. In another aspect, when the pin in the first position it prevents actuation of a firing mechanism to eject a plurality of staples from the staple cartridge. According to the method when the cartridge is positioned within the channel of the cartridge jaw it sets a clamp gap between the cartridge jaw and the anvil.

A surgical fastening device comprises an elongate shaft, an end effector coupled to a distal end of the elongate shaft, and a cartridge removably seated within a channel in the cartridge jaw of the end effector. The end effector includes a cartridge jaw and an anvil pivotally coupled to one another and movable between an open position and a closed position in which tissue can be engaged therebetween, wherein a distance between a proximal end of each of the cartridge jaw and the anvil is adjustable. Further, the cartridge includes an anvil coupling member slidably disposed therein and configured to couple to a drive shaft extending through the elongate shaft for advancing the anvil coupling member distally through the end effector. In one aspect a proximal end of the anvil coupling member includes a feature formed therein for receiving a corresponding feature formed in a distal end of the drive shaft. In another aspect the anvil coupling member engages and distally advances through a slot formed in the anvil, and a distal end of the anvil includes an opening formed therein for releasing the anvil coupling member to allow the anvil to be moved to an open position away from the cartridge jaw.

The anvil coupling member can include a knife formed on a distal-facing surface thereof for cutting tissue engaged between the cartridge jaw and the anvil. In addition the drive shaft can include a mating element formed on a distal end thereof that engages and slides within a slot formed in the cartridge jaw. In one aspect the anvil coupling member is configured to pivot away from the anvil when the anvil coupling member is positioned at a distal-most end of the anvil.

A staple cartridge is provided that comprises a cartridge housing, a plurality of staples disposed within the cartridge housing, wherein the plurality of staples being frangibly detached to a carrier, and an anvil coupling member slidably disposed within a track formed in the cartridge. The anvil coupling member includes a proximal portion having an engagement feature on a proximal-facing surface thereof for mating with a drive shaft, and the anvil coupling member includes a distal portion pivotally coupled to the proximal portion.

The anvil coupling member can include a knife on a distal-facing surface thereof. Further, the engagement feature can comprise a detent formed in the proximal-facing surface of the anvil coupling member. In one aspect the proximal portion includes a pin extending therethrough and protruding from lateral sides thereof. The pin is configured to engage and slide within a slot formed in an anvil of an end effector of a stapling device.

A method for stapling tissue is also provided. The method comprises positioning a cartridge having a plurality of staples and an anvil coupling member disposed therein within a first jaw of an end effector of a surgical stapler. The method also includes engaging tissue between the first jaw and a second jaw of the end effector, and advancing a drive shaft through the surgical stapler such that a distal end of the drive shaft abuts a proximal end of the anvil coupling member to distally advance the anvil coupling member through the end effector. The anvil coupling member has a first engagement feature that rides within a slot formed in a second jaw of the end effector, and the drive shaft has a second engagement feature that rides within a slot formed in the first jaw.

In one aspect of the method the anvil coupling member includes a knife on a distal facing surface thereof that cuts the tissue engaged between the first and second jaws. Another feature of the method is that the first engagement feature moves out of and releases the second jaw when the anvil coupling member reaches a distal-most end of the second jaw. Further, the anvil coupling member pivots away from the second jaw when the anvil coupling member is fully distally advanced through the second jaw, and the method further comprises opening the first and second jaws to release the tissue.

A surgical fastening device comprises a handle housing having an elongate shaft extending distally therefrom, an end effector coupled to a distal end of the elongate shaft, a drive beam disposed within the end effector and advanceable in a distal direction to drive staples into tissue engaged between the cartridge jaw and the anvil, a drive shaft extending through the elongate shaft and coupled to the drive beam for advancing the drive beam through the end effector, a first retraction mechanism coupled to the drive shaft and configured to move linearly in a proximal direction to move the drive beam proximally and thereby retract the drive beam, and a second retraction mechanism coupled to the drive shaft and configured to rotate to drive the drive shaft proximally and thereby retract the drive beam. The end effector includes a cartridge jaw and an anvil pivotally coupled to one another and movable between an open position and a closed position in which tissue can be engaged therebetween.

In one aspect the handle housing includes an actuation member having a pawl that engages a rack formed on the drive shaft for advancing the drive shaft distally. The first retraction mechanism comprises at least one retraction knob extending from the handle housing and slidable within an elongate slot formed in the handle housing and extending in a proximal-distal direction. Further, the second retraction mechanism comprises a gear having at least one tooth formed thereon that engages a rack formed on the drive shaft.

The fastening device further comprises a tool configured to removably engage the gear to cause rotation of the gear. In one aspect the tool comprises a wrench. In another aspect the handle housing includes an opening formed therein for allowing insertion of the tool therethrough for coupling with the gear. The fastening device further comprises a lever fixedly coupled to the gear and rotatable relative to the housing to rotate the gear. And in another aspect the fastening device further comprises a cartridge disposed within the cartridge jaw and containing a plurality of staples frangibly coupled to a carrier.

In another aspect a surgical fastening device comprises a handle assembly including a housing and a movable handle, an elongate shaft extending from the handle assembly, an end effector at a distal end of the elongate shaft, the end effector having an anvil and a staple cartridge containing a plurality of staples rotatably deployable into tissue, a drive assembly configured to move relative to the staple cartridge and the anvil to eject the staples from the staple cartridge, and an actuation assembly extending through the housing and the elongate shaft and having a rack formed thereon. The movable handle has a pawl configured to engage the rack on the actuation assembly to move the actuation assembly in response to movement of the movable handle, wherein movement of the actuation assembly drives the drive assembly relative to the staple cartridge and anvil to eject the staples from the staple cartridge. The fastening device also has a pair of retraction levers linearly slidable relative to the housing and coupled to the actuation assembly for retracting the actuation assembly and thus the drive assembly, and a retraction gear coupled to the rack and rotatably disposed within the housing such that rotation of the retraction gear retracts the actuation assembly and the drive assembly.

In one aspect the pair of retraction levers are each slidably disposed within an elongate slot formed in the housing. In another aspect the retraction gear has at least one tooth formed thereon that engages the rack formed on the actuation assembly. The fastening device further comprises a tool configured to removably engage the retraction gear to cause rotation of the gear. The tool can comprise a wrench.

In one aspect the housing includes an opening formed therein for allowing insertion of the tool therethrough for coupling with the gear. The fastening device further comprises a lever fixedly coupled to the retraction gear and rotatable relative to the housing to rotate the retraction gear. In another aspect the plurality of staples are frangibly coupled to a carrier. Further, each of the plurality of staples can be D-shaped.

A method for fastening tissue is provided. The method comprises engaging tissue between opposed jaws of an end effector, and advancing a sled through the end effector to rotate a plurality of fasteners into the tissue. Each fastener includes an anti-rotation mechanism that substantially prevents counter-rotation of the fastener within the tissue. In one aspect the fasteners plastically deform during rotation, and are frangibly detached from a carrier disposed within the end effector.

In another aspect a method for fastening tissue is provided, which includes engaging tissue between opposed jaws of an end effector, and advancing a sled and a shearing element through one of the jaws. According to the method the sled causes a plurality of fasteners frangibly coupled to a carrier to rotate about a pivot point and into the tissue between the jaws, wherein the fasteners at least partially shear at the pivot point, and wherein the shearing element subsequently shears the fasteners at the pivot point to separate the fasteners from the carrier. In one aspect the shearing element is coupled to a distal end of the sled such that the sled contacts the fasteners prior to the shearing element contacting the fasteners. The sled can include a knife that cuts the tissue engaged between the jaws.

Another method for fastening tissue comprises engaging tissue between opposed jaws of an end effector, and advancing a sled through at least one of the opposed jaws to rotatably deploy a plurality of fasteners from the end effector and into the tissue engaged between the jaws. Each fastener is advanced through an opening in a cartridge and through a guide member formed adjacent to the opening, wherein each guide member guides a fastener along an arcuate path and maintaining alignment of the fasteners during deployment. In one aspect each guide member contacts three sides of the fastener being advanced therethrough.

BRIEF DESCRIPTION OF THE DRAWINGS

This invention will be more fully understood from the following detailed description taken in conjunction with the accompanying drawings, in which:

FIG. 14 is a side view of an embodiment of a fastener including first and second anti-rotation mechanisms;

FIG. 15 is a side view of another embodiment of a fastener including an anti-rotation mechanism;

FIG. 16 is a side, partially transparent view of the fastener of FIG. 15 deployed in tissue;

FIG. 17 is a perspective view of another embodiment of a fastener including an anti-rotation mechanism;

FIG. 18 is a perspective view of an embodiment of a plurality of interconnected deployed fasteners;

FIG. 19 is a perspective view another embodiment of a fastener including a first anti-rotation mechanism and a second anti-rotation mechanism, with the first anti-rotation mechanism coupled to an adjacent fastener;

FIG. 119 is a perspective partially exploded view of another embodiment of a cartridge having an adjunct material disposed thereon and having a plurality of fasteners disposed therein;

FIG. 120 is a perspective partially exploded view of the adjunct material and two of the fasteners of FIG. 119;

FIG. 121 is a side partially transparent view of two of the fasteners of FIG. 120 advanced through the adjunct material;

FIG. 122 is a perspective view of two of the fasteners of FIG. 121 advanced through the adjunct material;

FIG. 123 is a perspective view of another embodiment of an adjunct material;

FIG. 124 is a perspective view of the adjunct material of FIG. 123 having a fastener disposed therethrough;

FIG. 125 is another perspective view of the adjunct material and fastener of FIG. 124;

FIG. 126 is a perspective view of the fastener of FIG. 124;

FIG. 127 is a side partially cross-sectional view of one embodiment of a distal portion of a surgical device configured to removably seat a cartridge in an end effector thereof, the cartridge being fully seated in the end effector;

FIG. 128 is a side partially transparent view of the distal portion of the surgical device of FIG. 127, the cartridge not being seated in the end effector;

FIG. 129 is a side cross-sectional view of a portion of the surgical device of FIG. 127;

FIG. 130 is a side cross-sectional view of a portion of the surgical device of FIG. 128;

Figure 128:
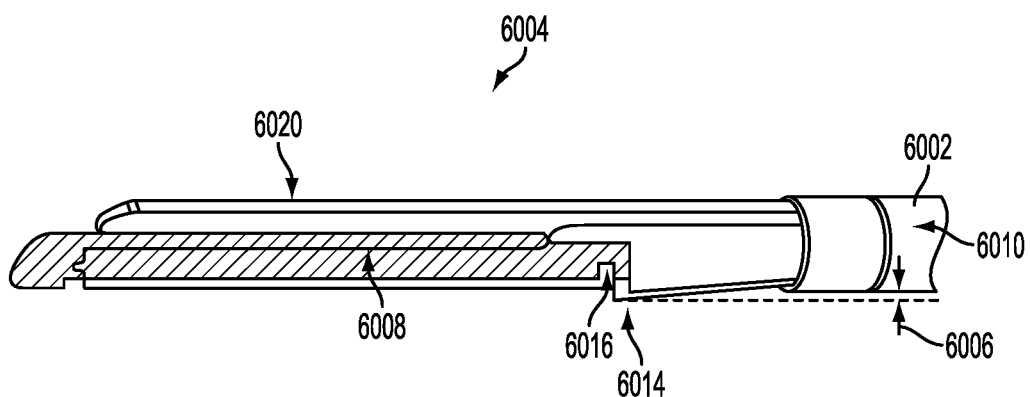
Figure 131:
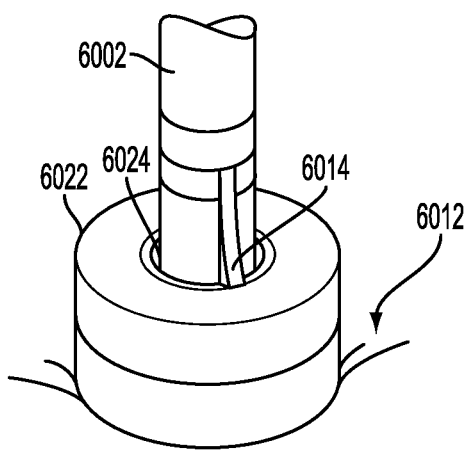
Figure 132:
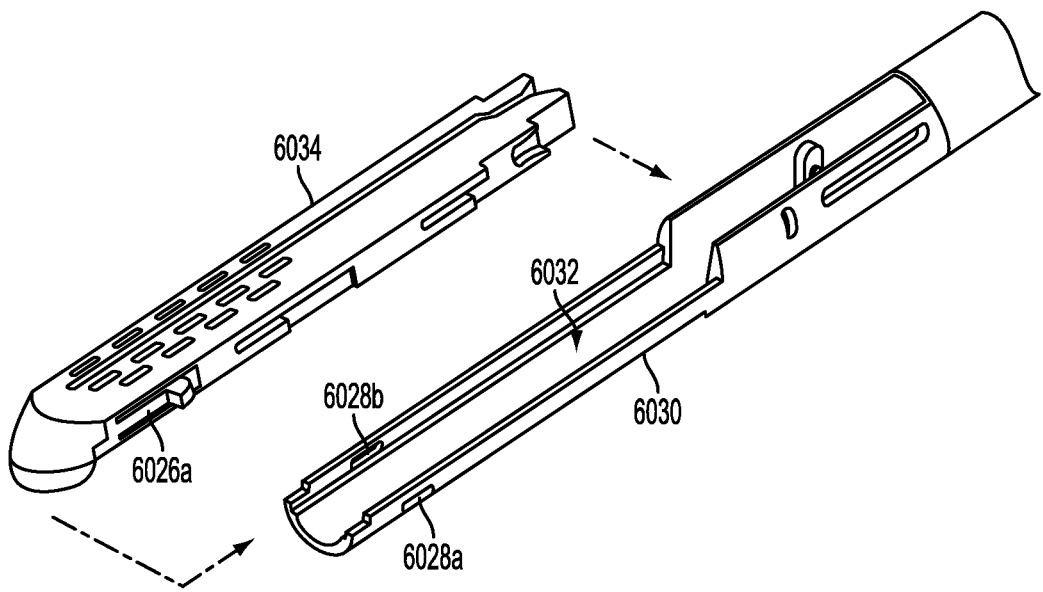
Figure 133:
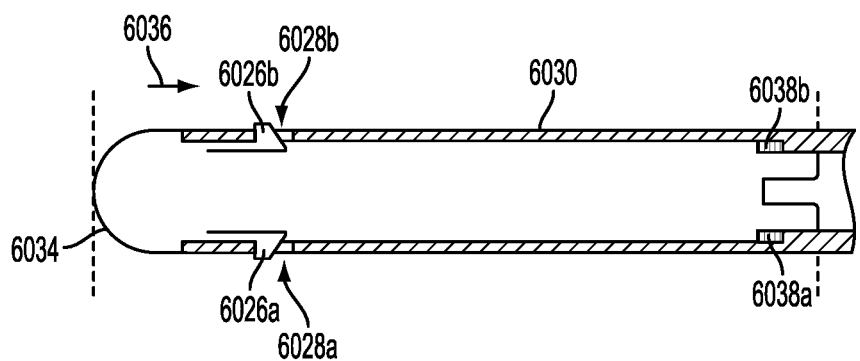
Figure 134:
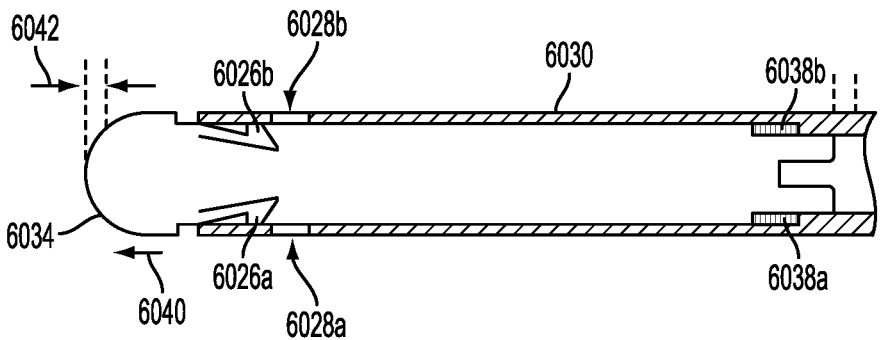
Figure 135:
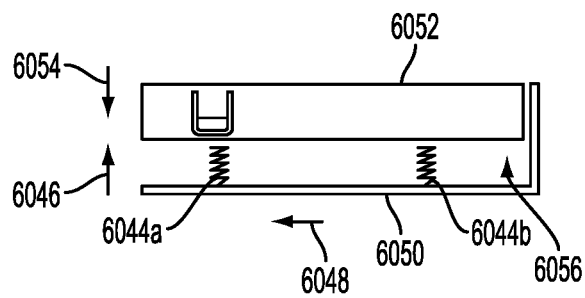
Figure 136:
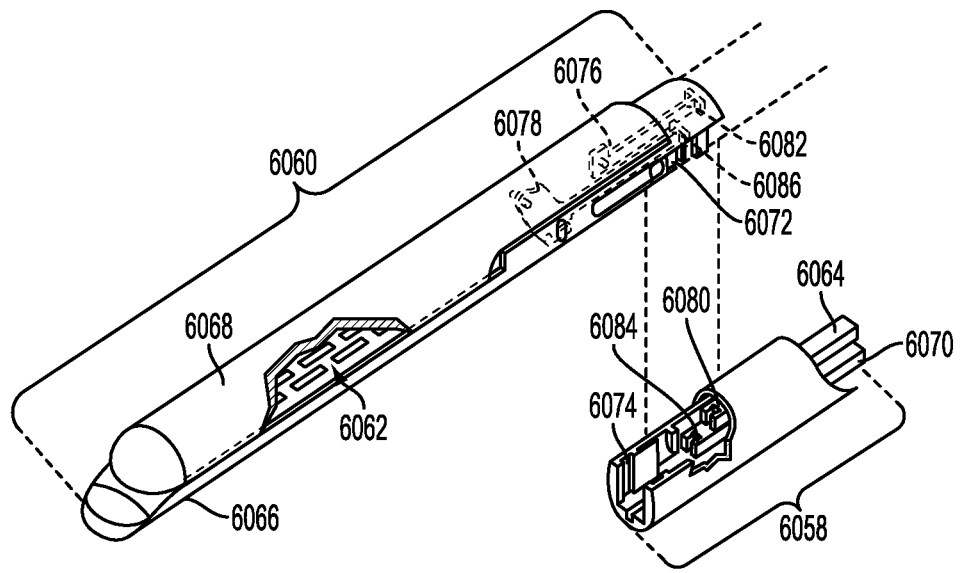
Figure 137:
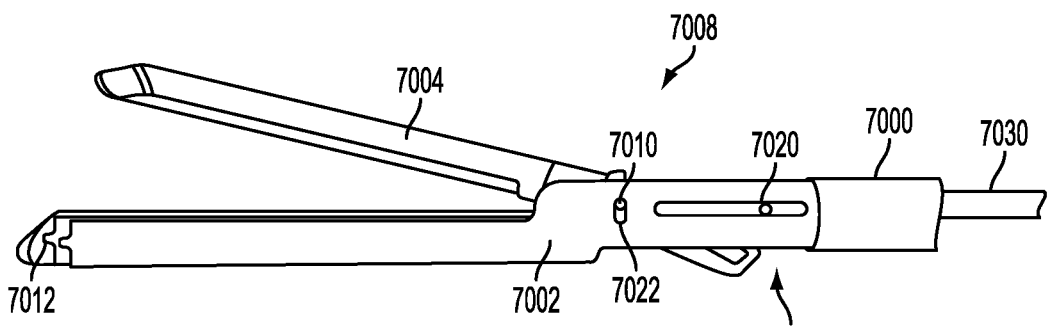
Figure 138:
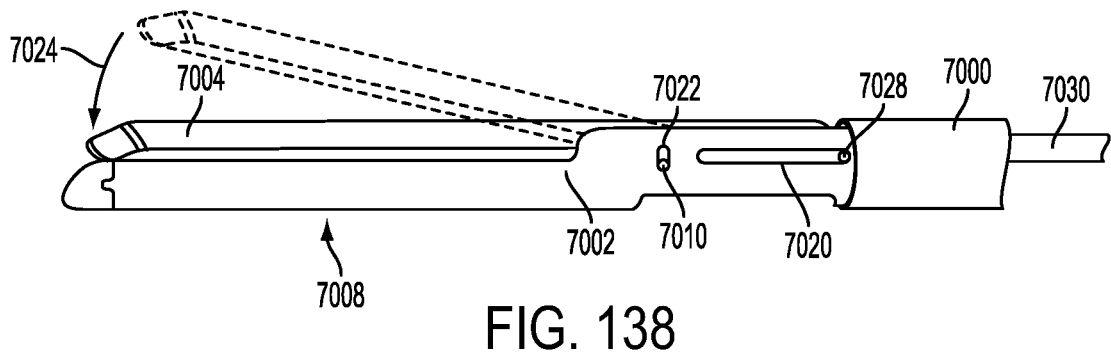
Figure 139:
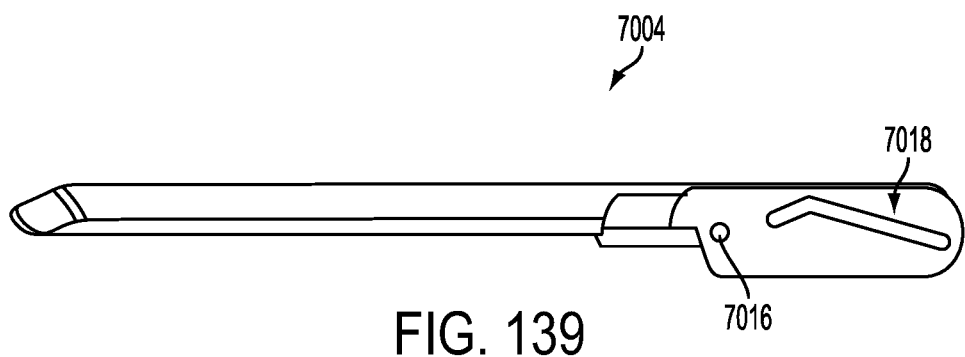
Figure 140:
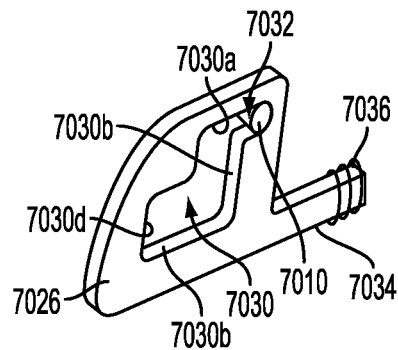
Figure 141:
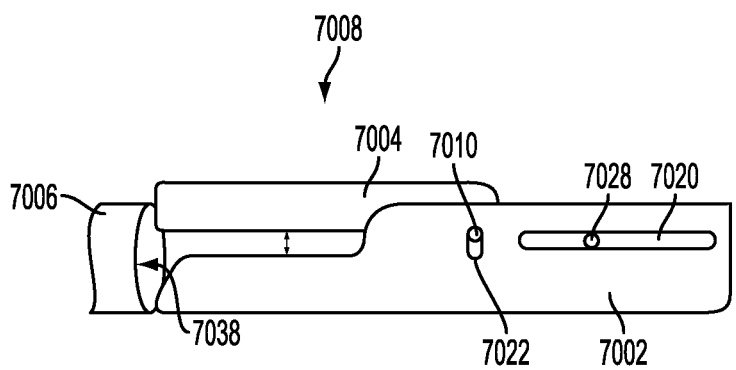
Figure 142:
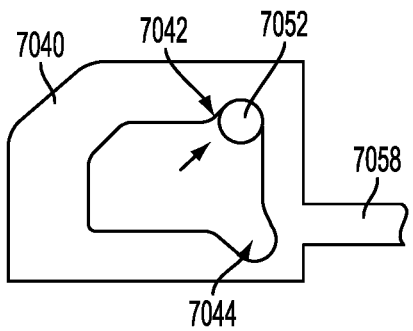
Figure 143:
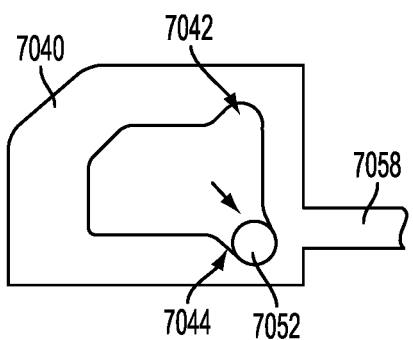
Figure 144:
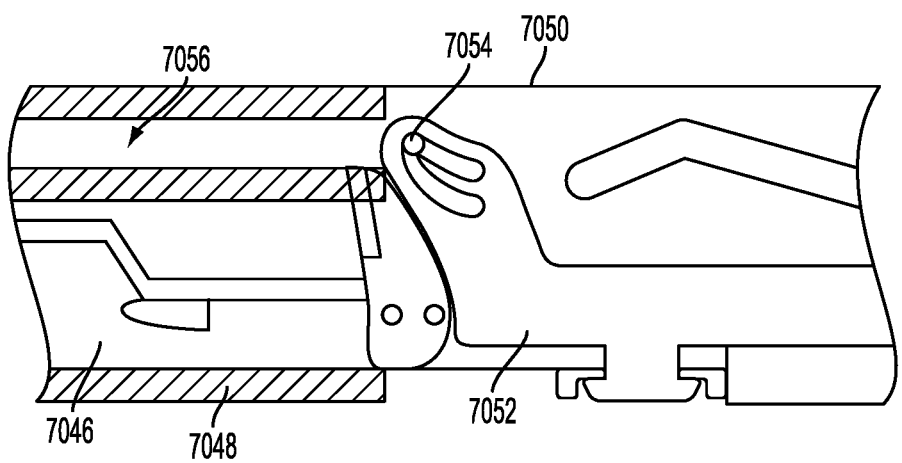
Figure 145:
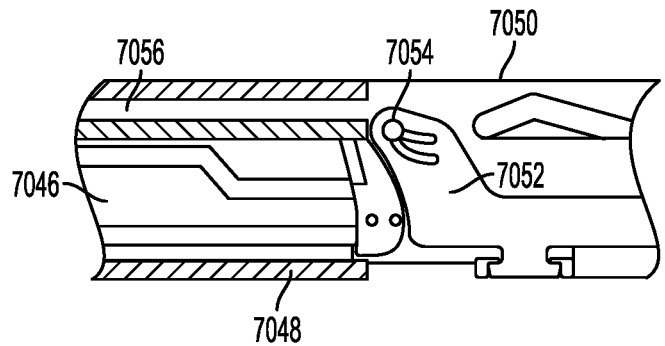
Figure 146:
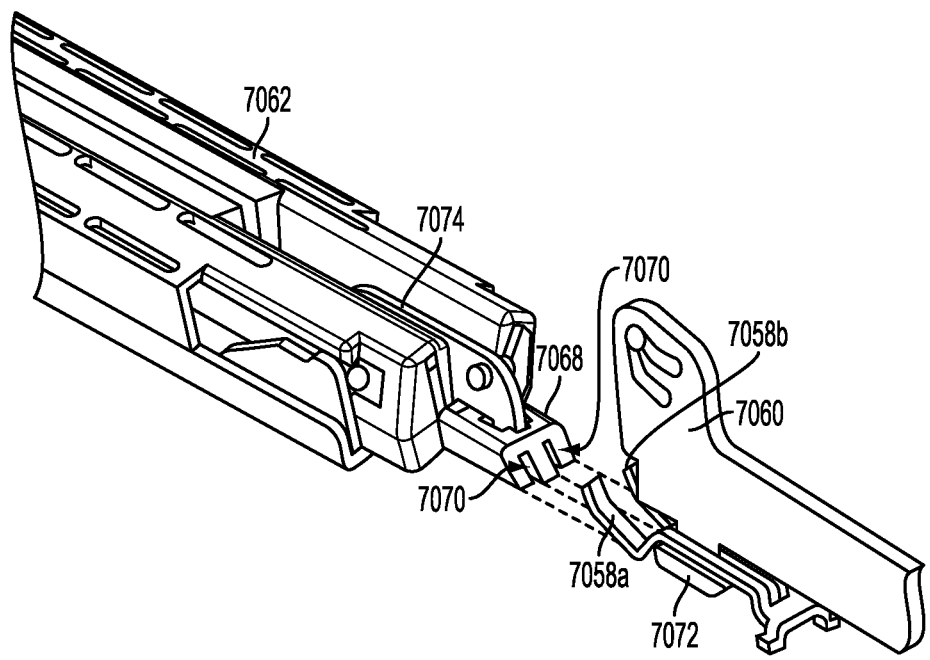
Figure 147:
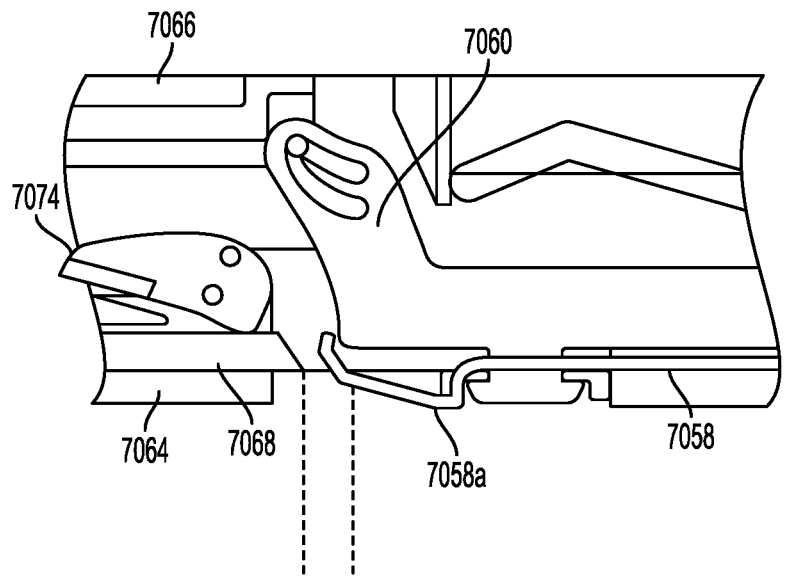
Figure 148:
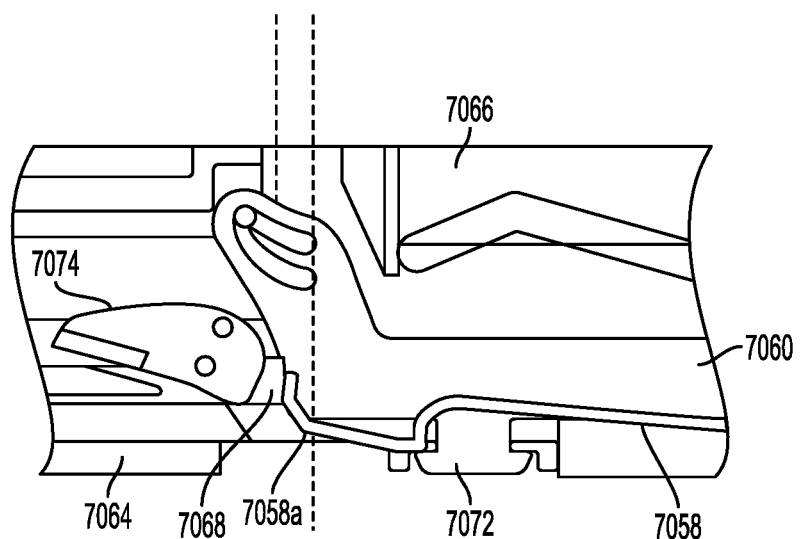
Figure 149:
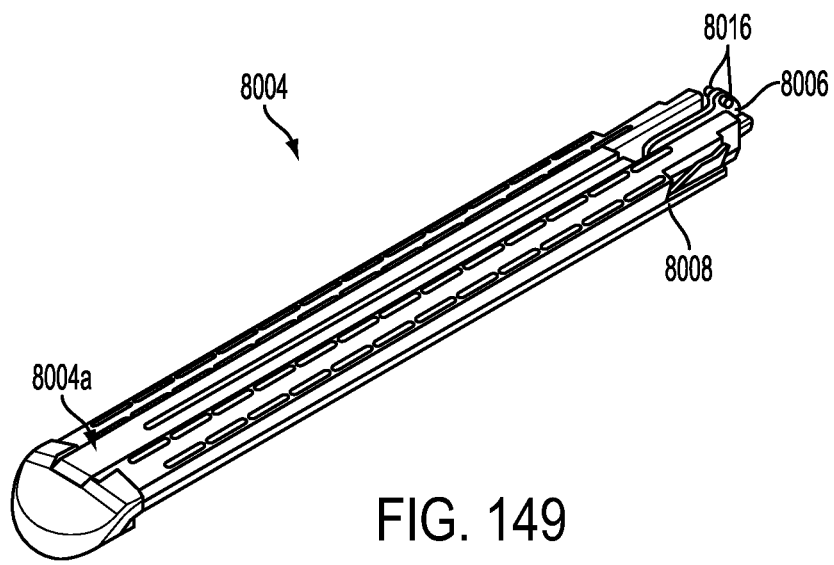
Figure 150:
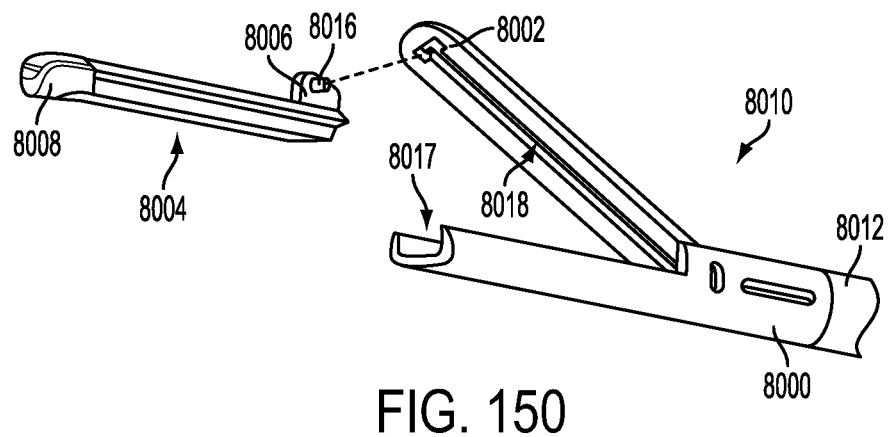
Figure 151:
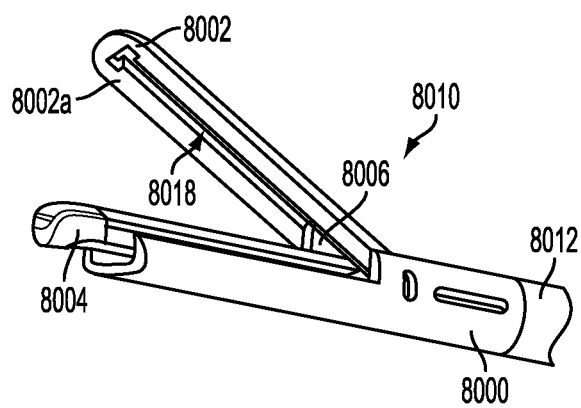
Figure 152:
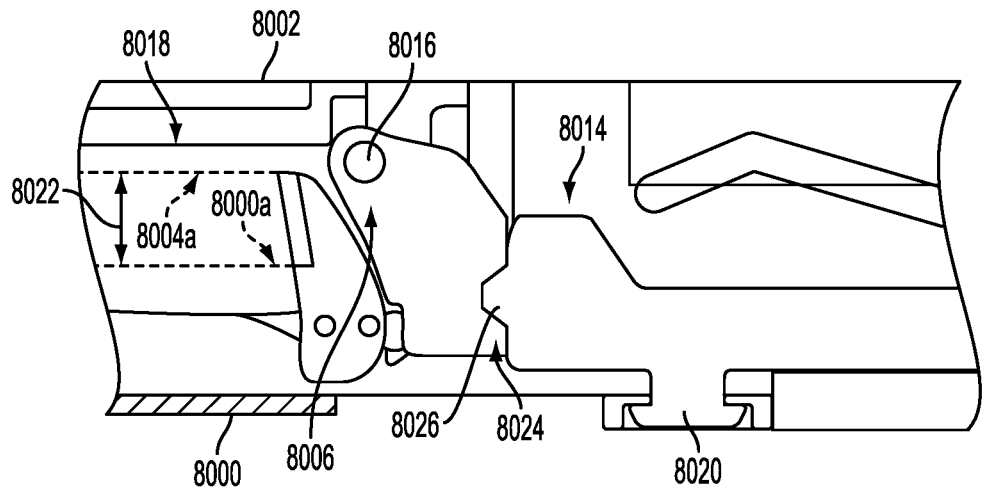
Figure 153:
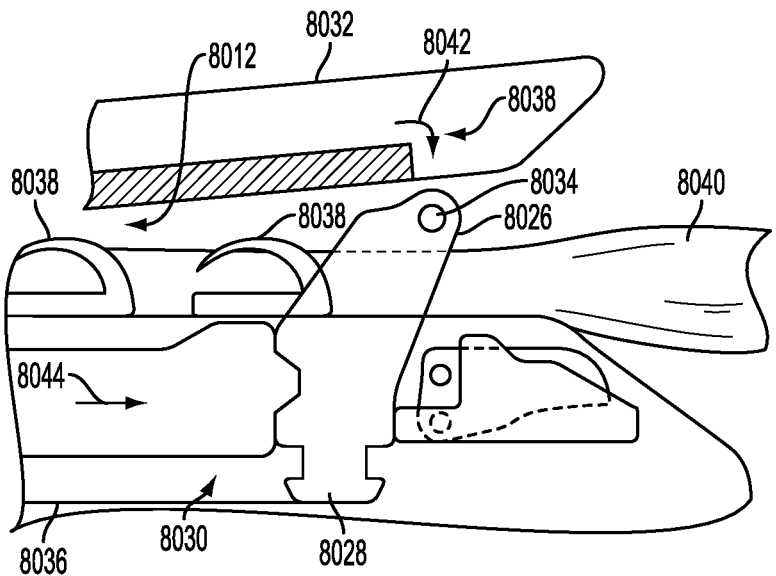
Figure 154:
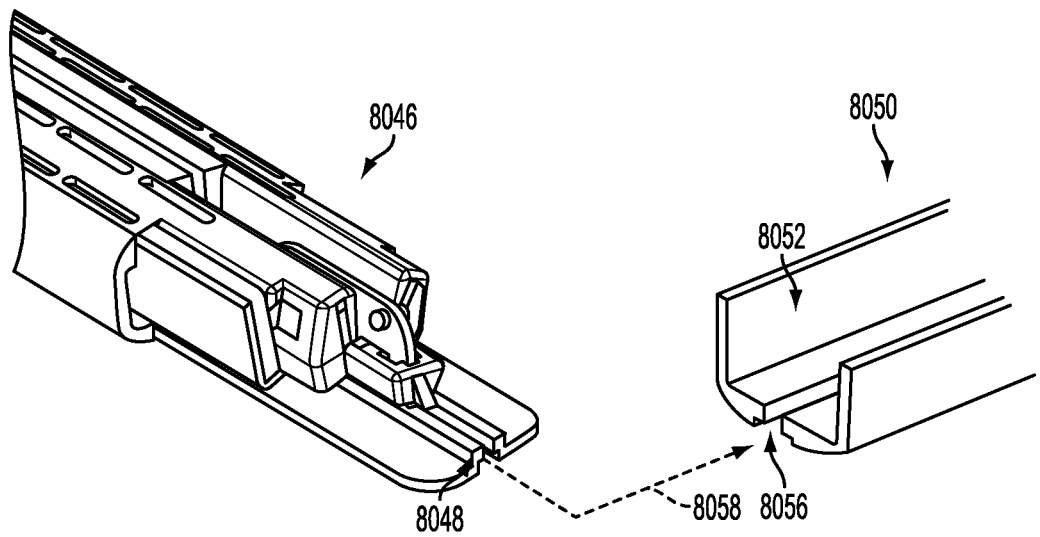
Figure 155:
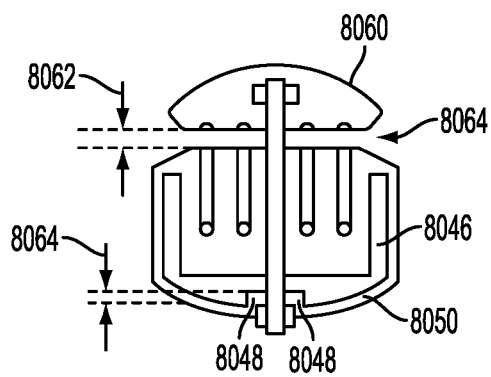
Figure 156:
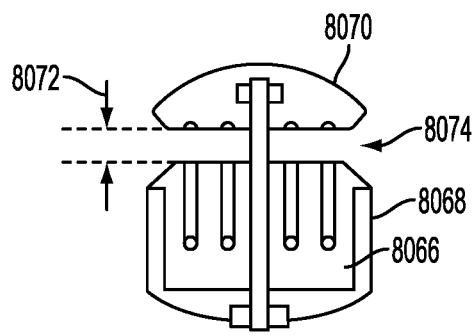
Figure 157:
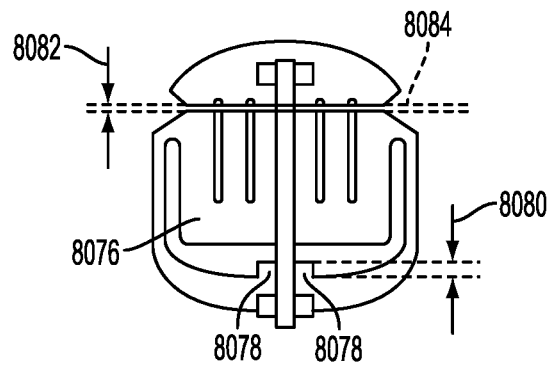
Figure 158:
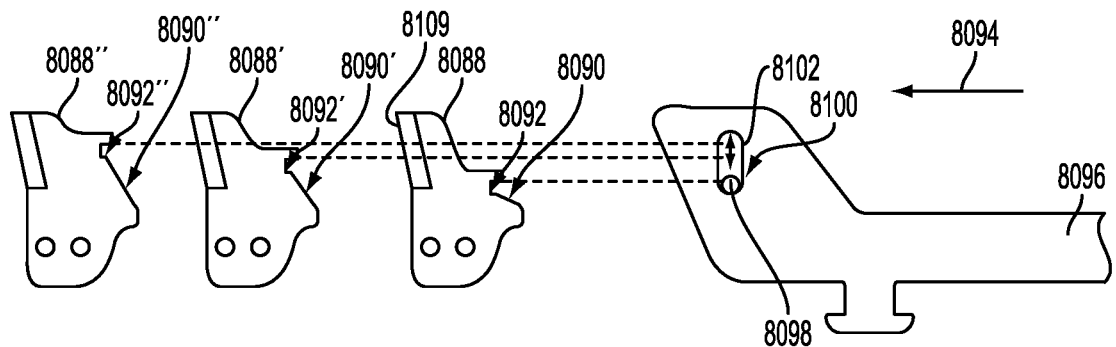
Figure 159:
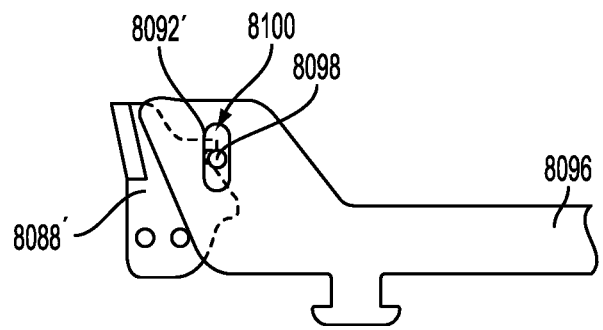
Figure 160:
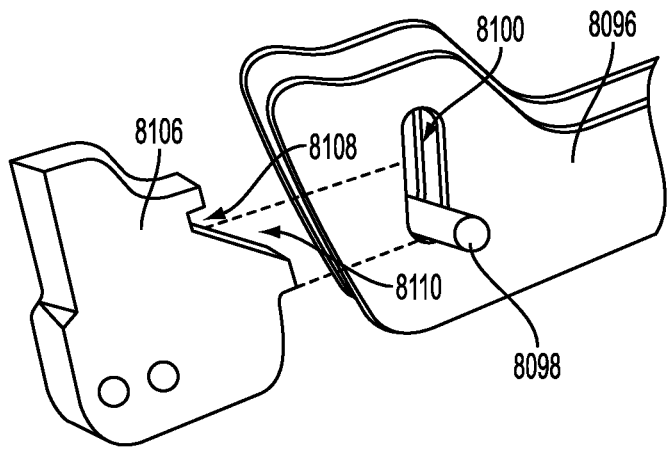
Figure 161:
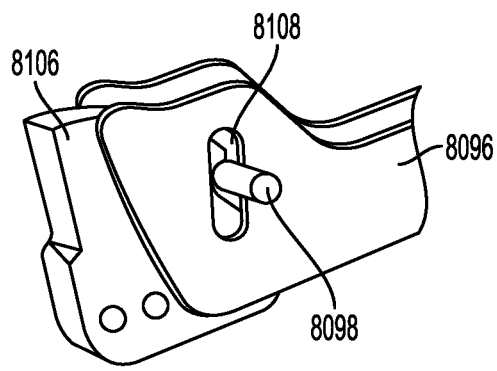
Figure 162:
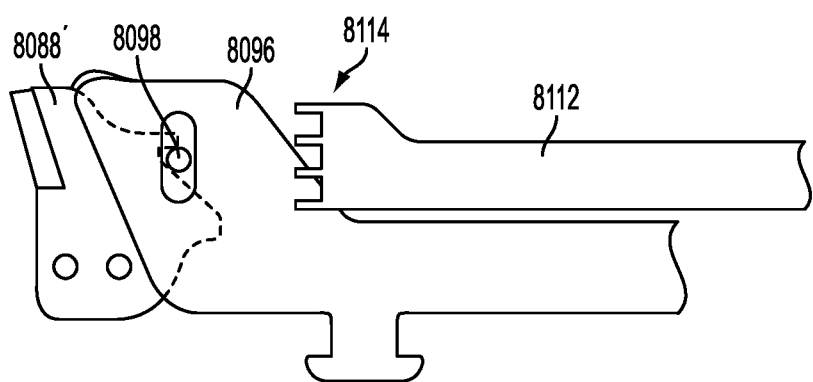
Figure 163:
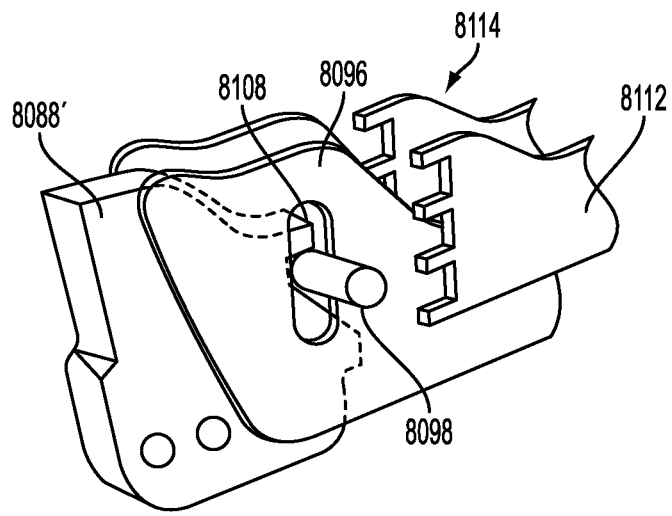
Figure 164:
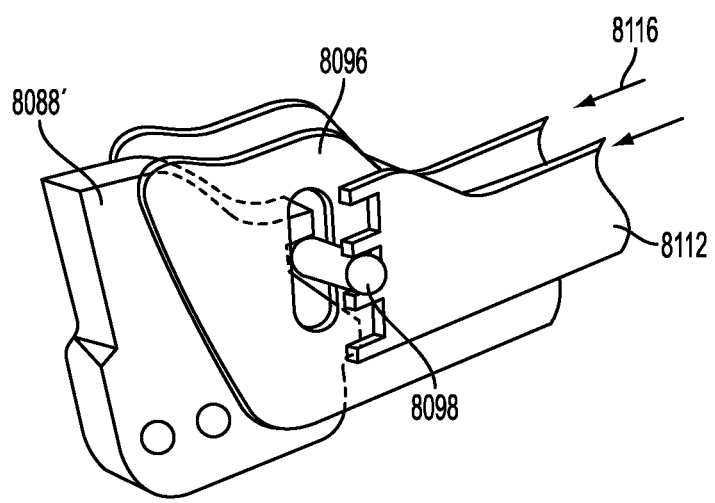
Figure 165:
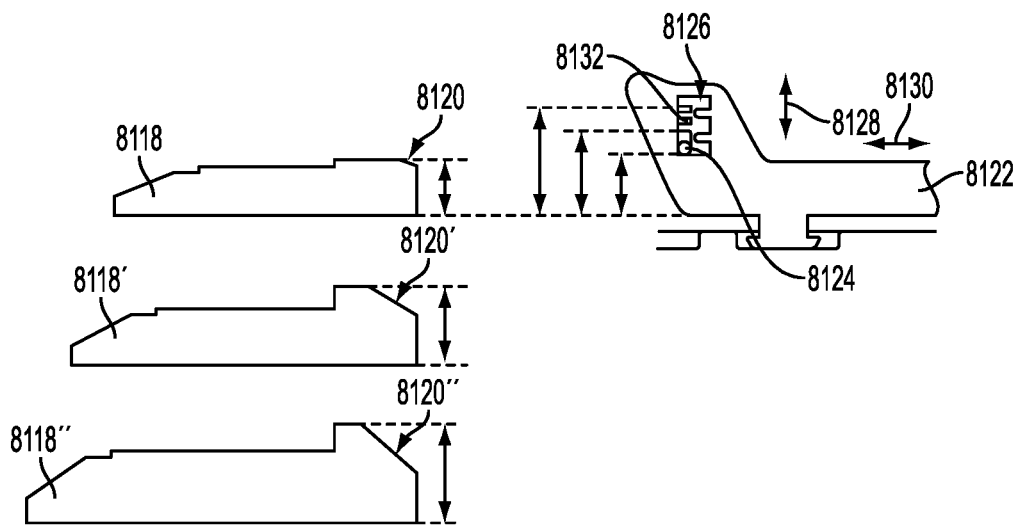
Figure 166:
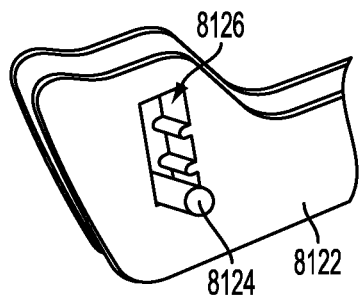
Figure 167:
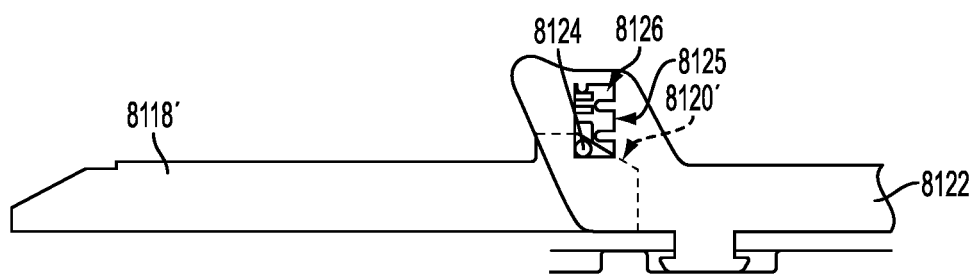
Figure 168:
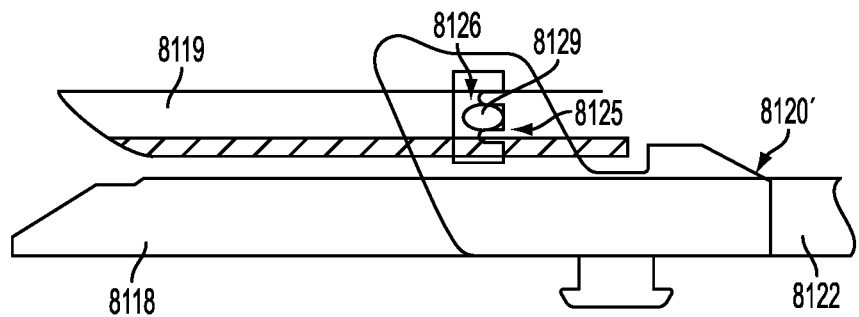
Figure 169:
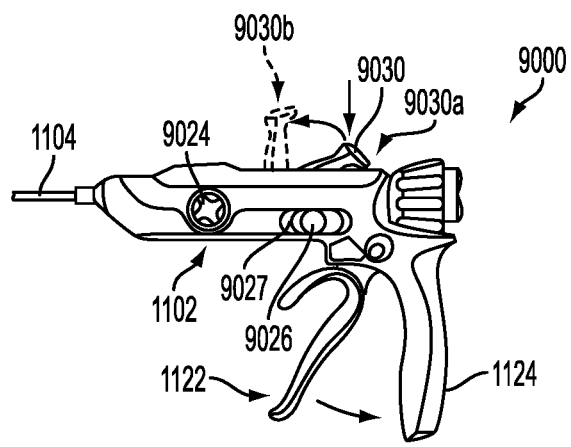
Figure 170:
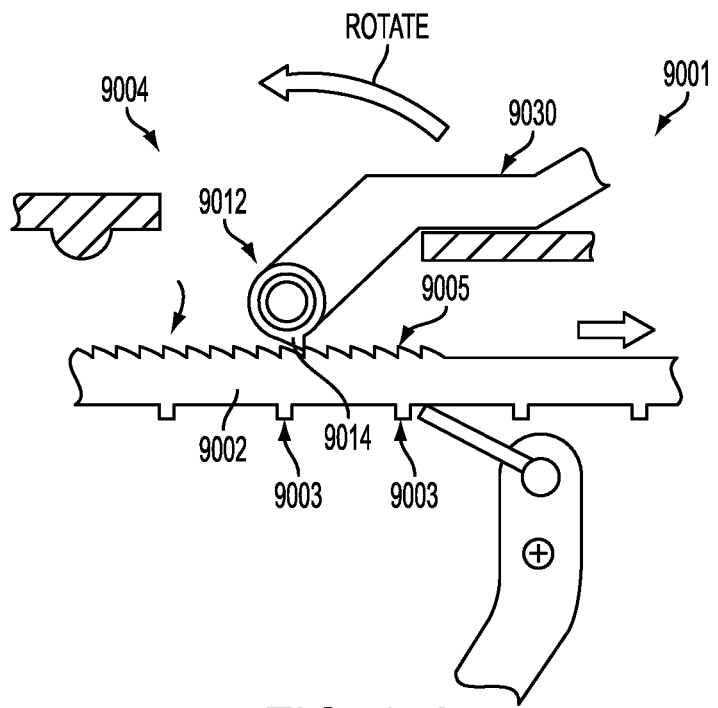
Figure 171:
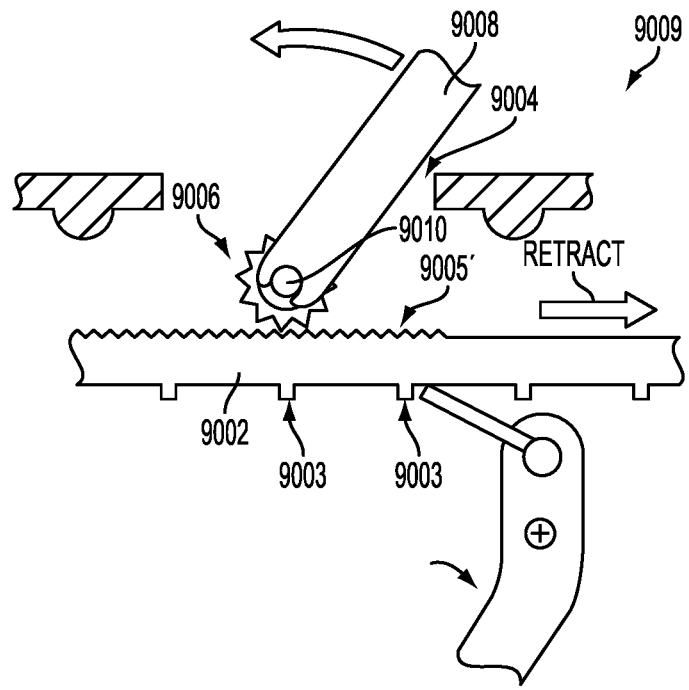
Figure 172:
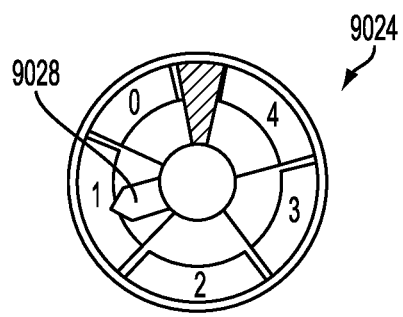
Figure 173:
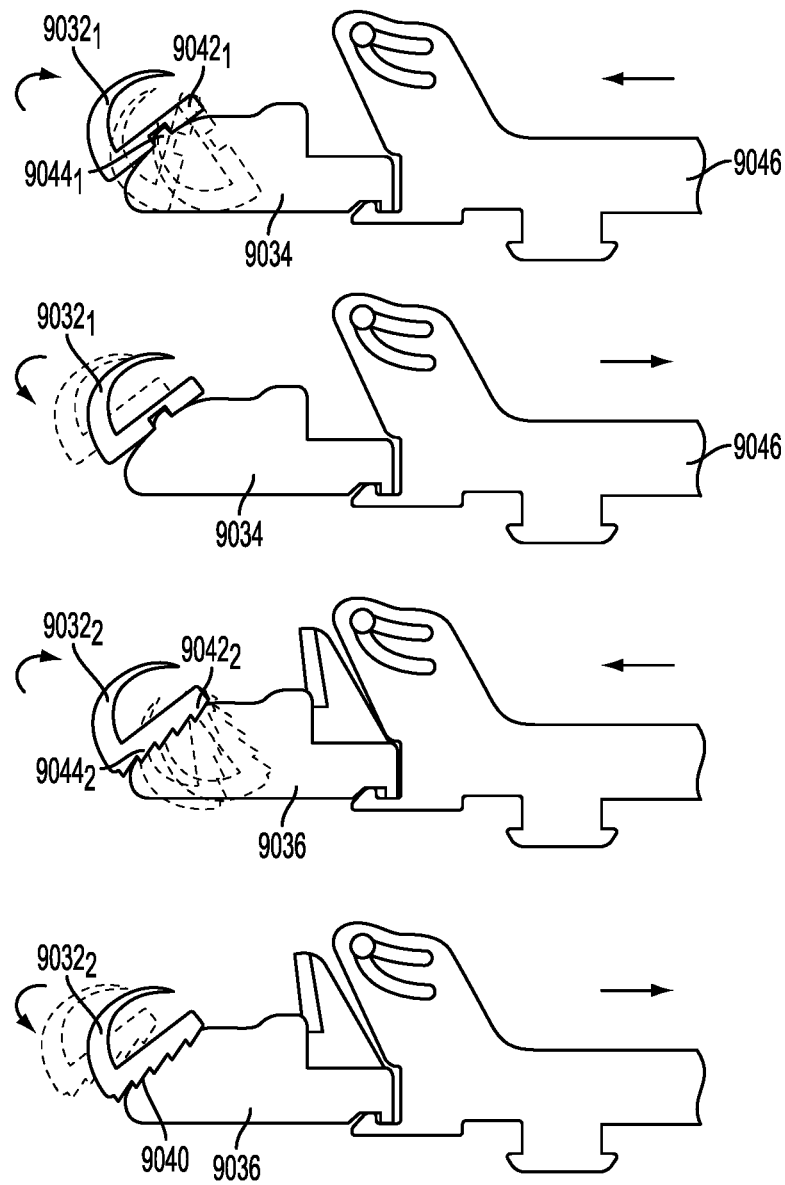
Figure 174:
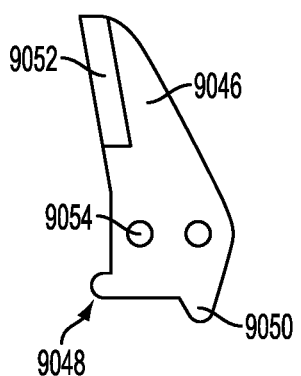
Figure 175:
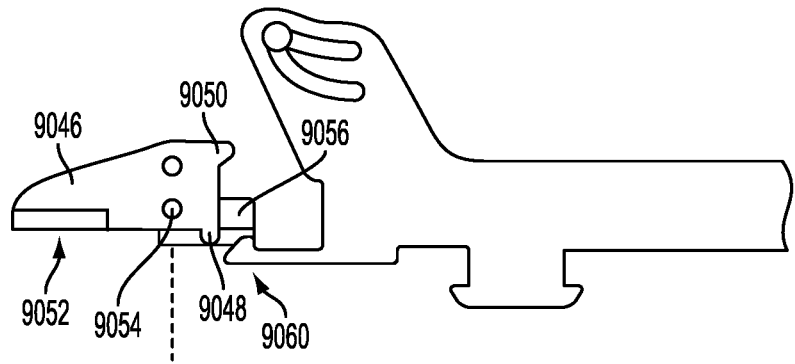
Figure 176:
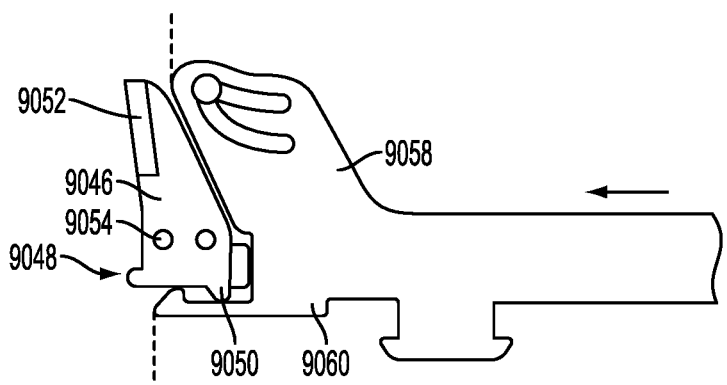
Figure 177:
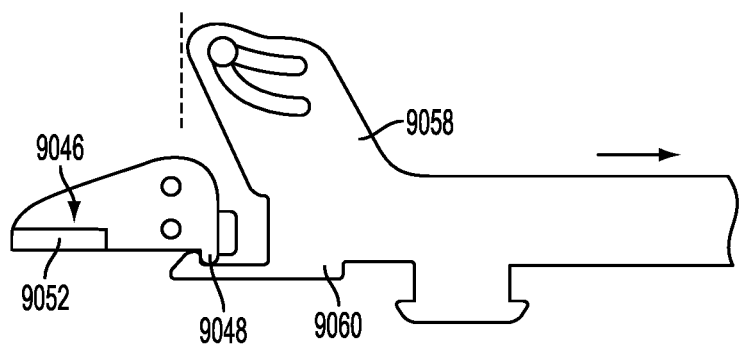
Figure 178:
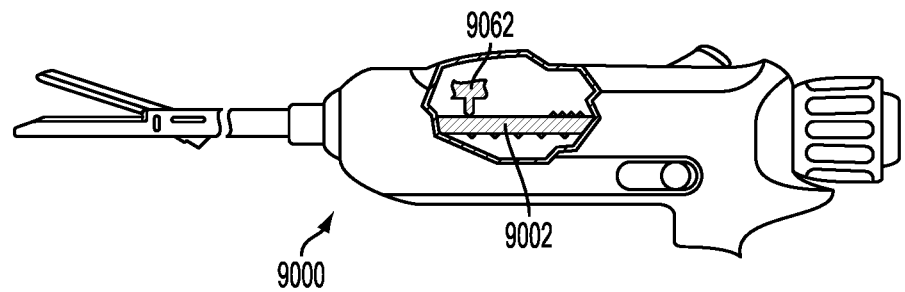
Figure 179:
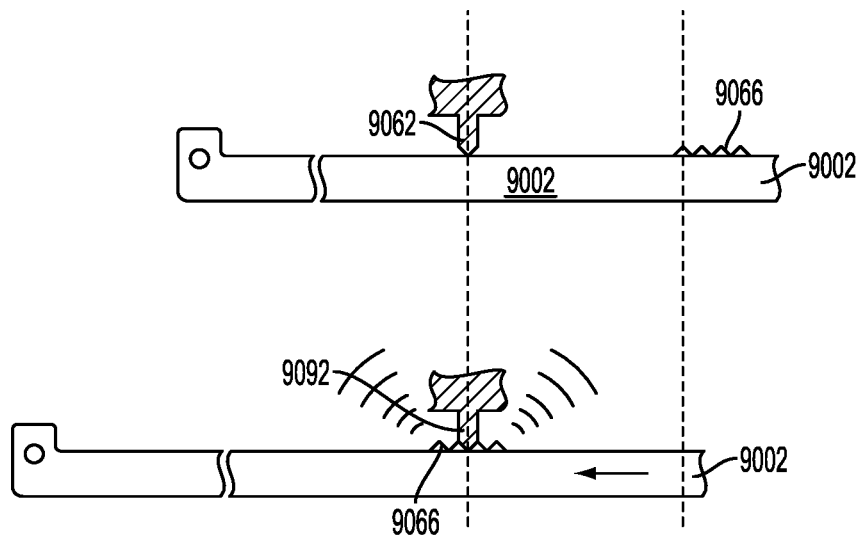
Figure 180:
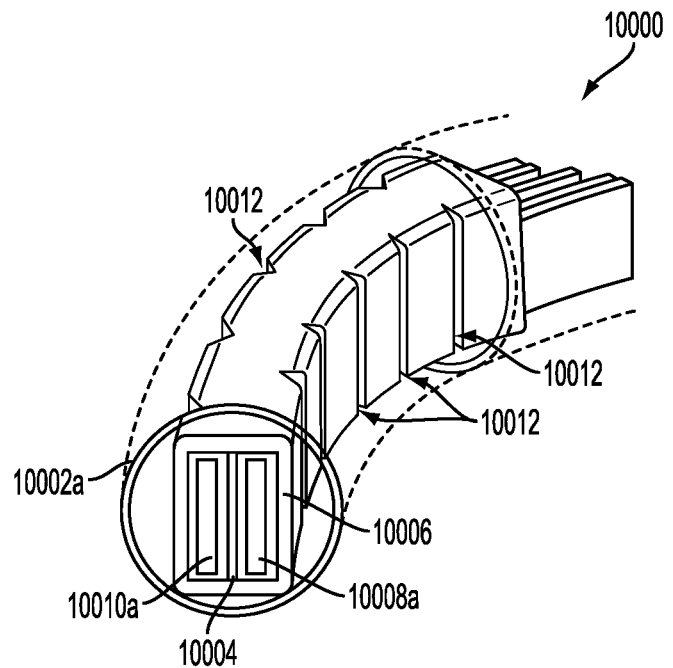
Figure 181:
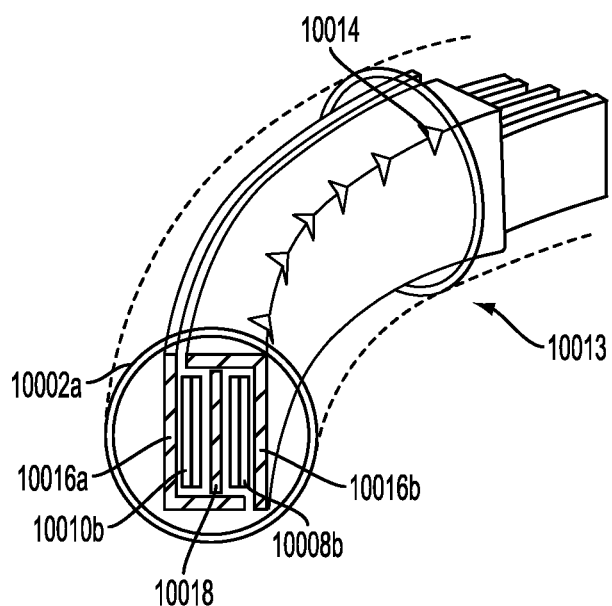
Figure 182:
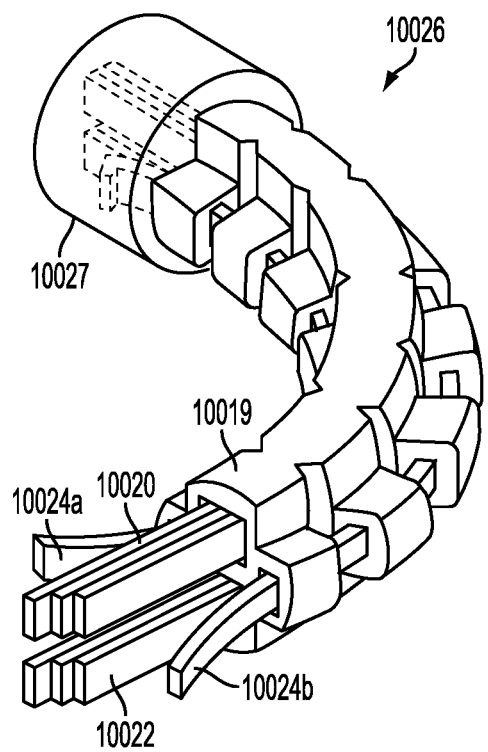
Figure 183:
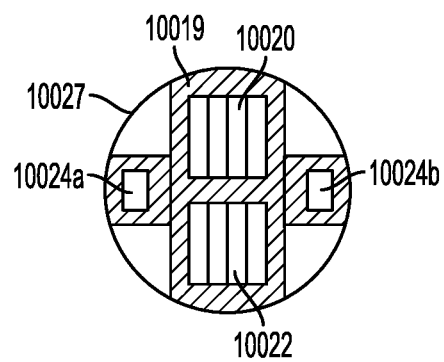
Figure 184:
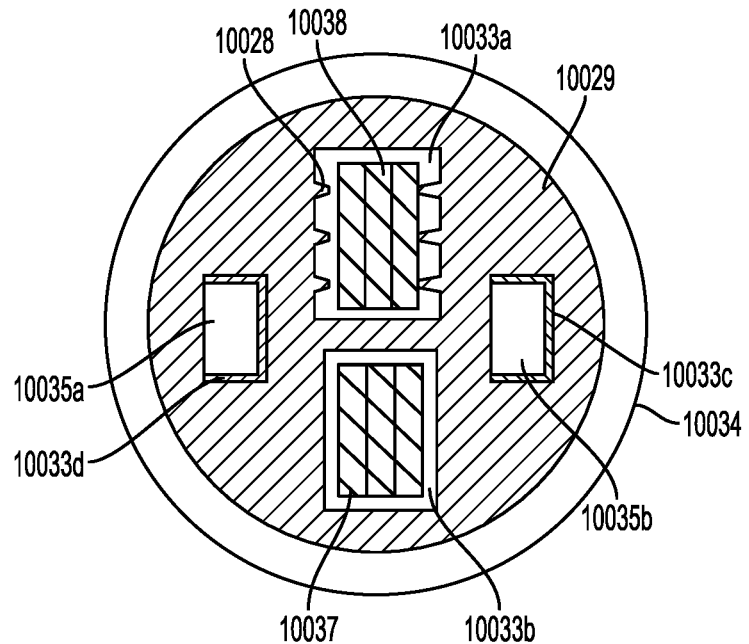
Figure 185:
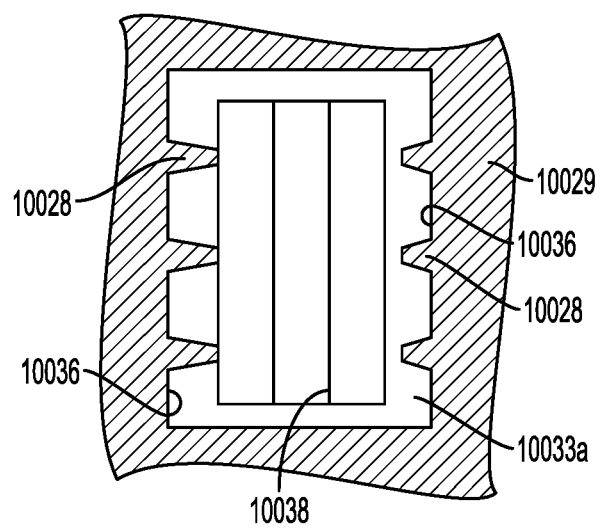
Figure 186:
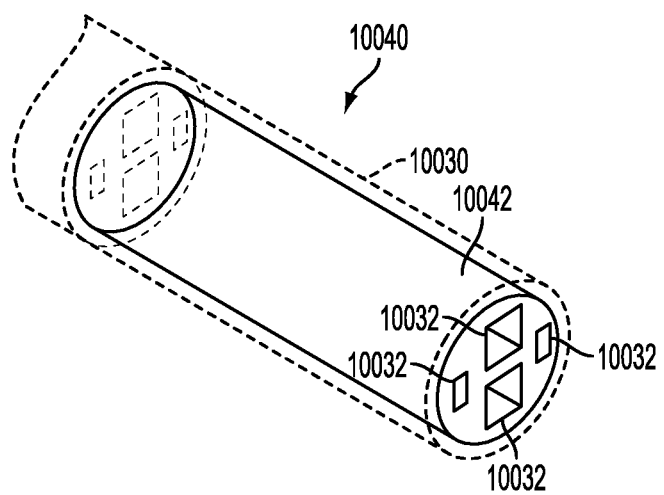
Figure 187:
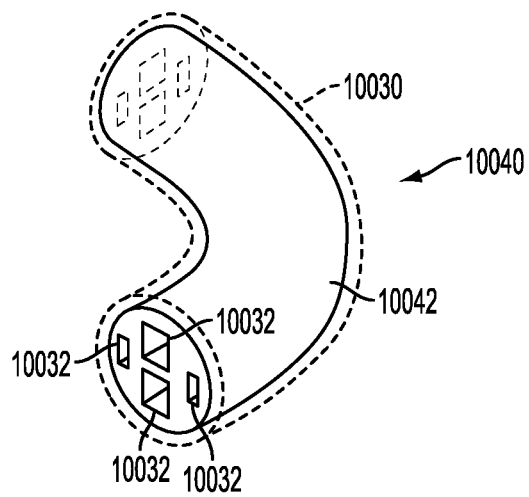
Figure 188:
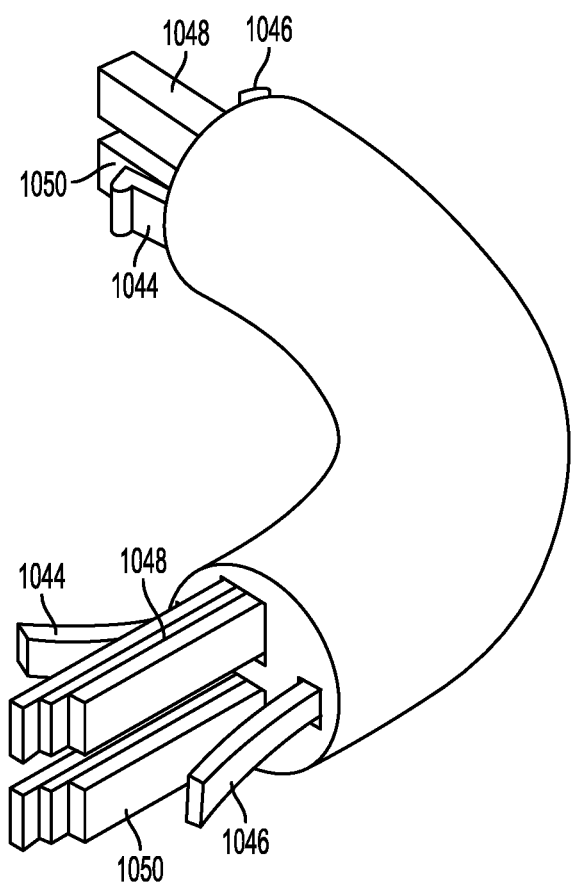

FIG. 131 is a perspective view of the distal portion of the surgical device of FIG. 128 with the end effector partially inserted into one embodiment of a trocar;

FIG. 132 is a perspective exploded view of another embodiment of a distal portion of a surgical device configured to removably seat a cartridge in an end effector thereof;

FIG. 133 is a top cross-sectional view of the cartridge of FIG. 132 fully seated in the end effector;

FIG. 134 is a top cross-sectional view of the cartridge of FIG. 132 not fully seated in the end effector;

FIG. 135 is a side cross-sectional view of another embodiment of a distal portion of a surgical device configured to removably seat a cartridge in an end effector thereof, the cartridge being fully seated in the end effector;

FIG. 136 is a perspective exploded, partially cross-sectional view of one embodiment of a distal portion of a surgical device including an elongate shaft and an end effector configured to removably couple to the elongate shaft;

FIG. 137 is a side view of one embodiment of a distal portion of a surgical device that includes an end effector and a lockout element, the end effector being in an open position;

FIG. 138 is a side view of the distal portion of the surgical device of FIG. 137, the end effector being in a closed position;

FIG. 139 is a side view of an anvil of the end effector of FIG. 137;

FIG. 140 is a perspective view of the lockout element of FIG. 137;

FIG. 141 is a side view of the end effector of FIG. 137 adjacent a trocar;

FIG. 142 is a side view of another embodiment of a lockout element, the lockout element having a pivot pin in an upper proximal portion thereof;

FIG. 143 is another side view of the lockout element and pivot pin of FIG. 142, the pivot pin being in a lower proximal portion thereof;

FIG. 144 is a side cross-sectional view of another embodiment of a distal portion of a surgical device that includes an end effector and a lockout element, a cartridge being fully seated in the end effector;

FIG. 145 is another side cross-sectional view of the end effector, the cartridge not being fully seated in the end effector;

FIG. 146 is a perspective exploded view of another embodiment of a distal portion of a surgical device that includes an end effector and a lockout element;

FIG. 147 is a side cross-sectional view of the end effector and lockout element of FIG. 146, a cartridge not being fully seated in the end effector;

FIG. 148 is another side cross-sectional view of the end effector and lockout element of FIG. 146, the cartridge being fully seated in the end effector;

FIG. 149 is a perspective view of one embodiment of a cartridge including an anvil coupling member;

FIG. 150 is a perspective exploded view of the cartridge of FIG. 149 and a distal portion of a surgical device configured to releasably and replaceable seat the cartridge;

FIG. 151 is a perspective view of the cartridge and the distal portion of the surgical device of FIG. 150, the cartridge partially seated within the distal portion;

FIG. 152 is a side cross-sectional view of the distal portion of the device of FIG. 151, the cartridge being fully seated therein;

FIG. 153 is a side cross-sectional view of another embodiment of a cartridge including an anvil coupling member;

FIG. 154 is a perspective exploded view of one embodiment of a cartridge including a shim and a cartridge jaw configured to releasably and replaceably seat the cartridge therein;

FIG. 155 is a side cross-sectional view of the cartridge of FIG. 154 seated in the cartridge jaw, the cartridge jaw being coupled to an anvil;

FIG. 156 is a side cross-sectional view of another embodiment of a cartridge seated in a cartridge jaw, the cartridge jaw being coupled to an anvil;

FIG. 157 is a side cross-sectional view of another embodiment of a cartridge including a shim seated in a cartridge jaw, the cartridge jaw being coupled to an anvil;

FIG. 158 is a side view of first, second, and third embodiments of a cutting element each configured to removably couple to an I-beam;

FIG. 159 is a side partially transparent view of the second cutting element of FIG. 158 coupled to the I-beam;

FIG. 160 is a perspective exploded view of another embodiments of a cutting element configured to removably couple to the I-beam of FIG. 158;

FIG. 161 is a perspective view of the cutting element of FIG. 160 removably coupled to the I-beam;

FIG. 162 is a side partially transparent view of the second cutting element and I-beam of FIG. 159 and one embodiment of a push rod;

FIG. 163 is a perspective view of the second cutting element, I-beam, and push rod of FIG. 162;

FIG. 164 is a perspective view of the second cutting element and the I-beam removably coupled to the push rod of FIG. 163;

FIG. 165 is a side view of first, second, and third embodiments of a cartridge configured to removably couple to an I-beam;

FIG. 166 is a perspective view of a distal portion of the I-beam of FIG. 165;

FIG. 167 is a perspective view of the second cartridge of FIG. 165 removably coupled to the I-beam, the second cartridge being partially seated in an end effector;

FIG. 168 is a side cross-sectional view of the second cartridge of FIG. 167 removably coupled to the I-beam and fully seated in the end effector;

FIG. 169 is a perspective view of one embodiment of a surgical device having a mechanism configured to retract a drive shaft;

FIG. 170 is a schematic view of components within a handle portion of the device shown in FIG. 169, illustrating one embodiment of a retraction mechanism;

FIG. 171 is a schematic view of components within a handle portion of the device shown in FIG. 169, illustrating another embodiment of a retraction mechanism;

FIG. 172 is a detailed view of an indicator shown on the device of FIG. 169;

FIG. 173 is a schematic view of a sled mechanism, in various positions, for counter rotating partially fired fasteners;

FIG. 174 is a perspective view of a cutting element configured to be rotated between operative and non-operative conditions;

FIG. 175 is a perspective view of the cutting element of FIG. 174 engaged by a drive beam in a non-operative condition prior to firing;

FIG. 176 is a perspective view of the cutting element of FIG. 174 engaged by a drive beam in an operative condition;

FIG. 177 is a perspective view of the cutting element of FIG. 174 engaged by a drive beam in a non-operative condition following positioning in an operative condition;

FIG. 178 is a perspective view of a surgical device including a mechanism that audibly indicates the end of a closing stroke;

FIG. 179 is a perspective view of a portion of the audible indicator mechanism of FIG. 178 before and after reaching the end of a closing stroke, with an indication of an audible signal upon reaching the end of the stroke;

FIG. 180 is a perspective cross-sectional partially transparent view of one embodiment of an articulation joint, the articulation joint being in an articulated position;

FIG. 181 is a perspective cross-sectional partially transparent view of another embodiment of an articulation joint, the articulation joint being in an articulated position;

FIG. 182 is a perspective cross-sectional partially transparent view of another embodiment of an articulation joint, the articulation joint being in an articulated position;

FIG. 183 is a cross-sectional view of the articulation joint of FIG. 182;

FIG. 184 is an end cross-sectional partially transparent view of another embodiment of an articulation joint;

FIG. 185 is an end cross-sectional view of a portion of the articulation joint of FIG. 184;

FIG. 186 is a perspective cross-sectional partially transparent view of another embodiment of an articulation joint, the articulation joint being in an unarticulated position;

FIG. 187 is another perspective cross-sectional partially transparent view of the articulation joint of FIG. 186, the articulation joint being in an articulated position; and FIG. 188 is a perspective cross-sectional partially transparent view of the articulation joint of FIG. 187 without a casing thereof and with a plurality of bands disposed therethrough.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Figure 1:
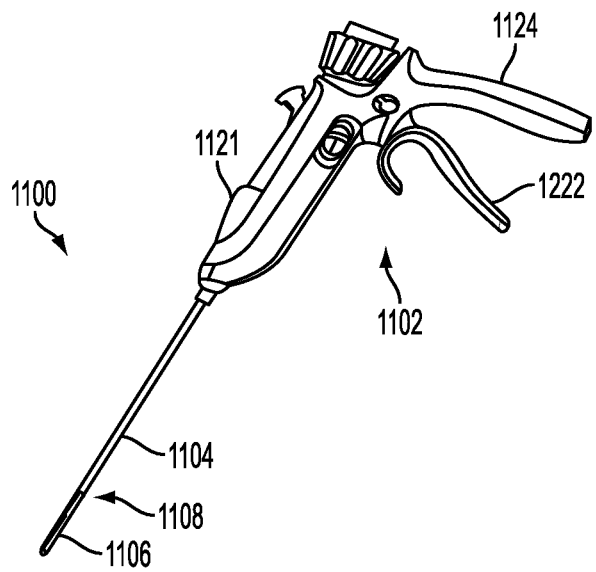
FIG. 1 is a perspective view of one embodiment of a surgical device configured to apply fasteners to tissue and including an end effector, the end effector being in a closed position.

FIG. 1 illustrates one embodiment of a surgical device 1100 that can be configured to apply staples to tissue. The device 1100 in this illustrated embodiment includes a linear stapler configured to apply linear rows of staples. Other embodiments of surgical devices that can be configured to apply staples to tissue are described in U.S. Pat. No. 5,465,895 entitled "Surgical Stapler Instrument" filed Feb. 3, 1994, U.S. Pat. No. 7,000,818 entitled "Surgical Stapling Instrument Having Separate Distinct Closing And Firing Systems" filed May 20, 2003, U.S. Pat. No. 7,669,746 entitled "Staple Cartridges For Forming Staples Having Differing Formed Staple Heights" filed on Aug. 31, 2005, and U.S. Pat. Pub. No. 2014/0175146 entitled "Microcutter Stapling Apparatus Clamp And Deploy Mechanisms Systems And Methods" filed Dec. 19, 2013, which are hereby incorporated by reference in their entireties.

Figure 2:
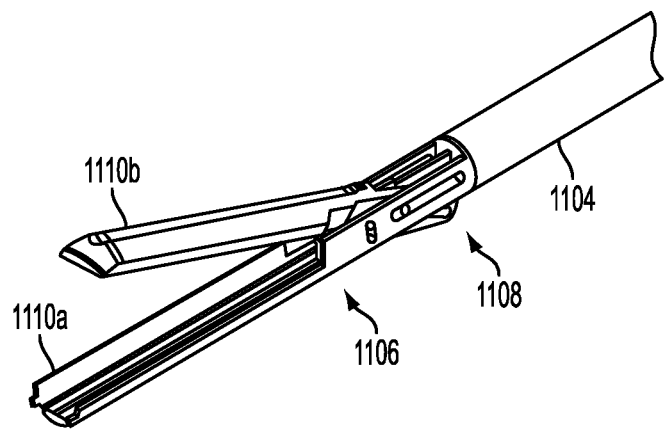
FIG. 2 is a perspective view of the end effector of FIG. 1 in an open position.
Figure 3:
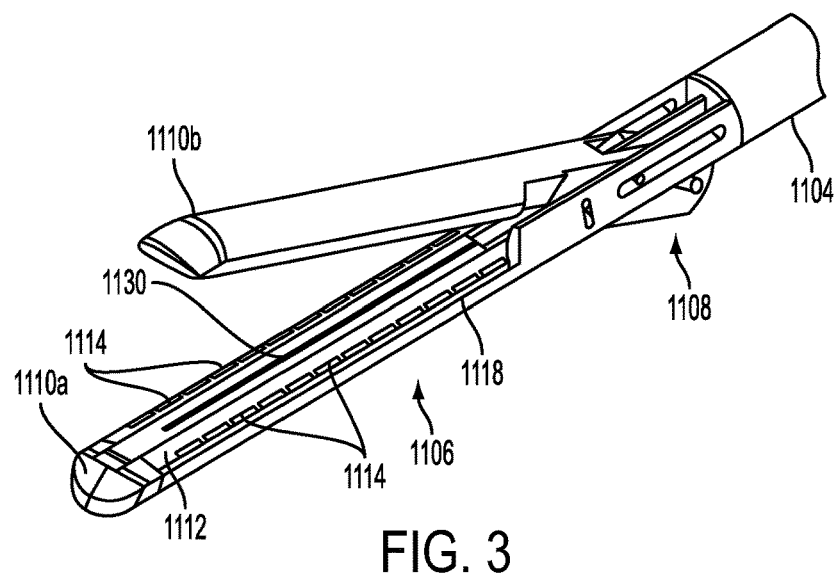
FIG. 3 is a perspective view of the end effector of FIG. 2 with one embodiment of a cartridge removably coupled thereto.

Referring again to FIG. 1, the device 1100 can include a proximal handle portion 1102 having an elongate shaft 1104 extending distally therefrom. As also shown in FIG. 2 and FIG. 3, the shaft 1104 can have an end effector 1106 coupled to a distal end thereof. The end effector 1106 can be coupled to the shaft 1104 at a pivot joint 1108. A proximal end of the end effector 1106 can be pivotally coupled to the joint 1108 at a distal end of the shaft 1104. The end effector 1106 in this illustrated embodiment includes a tissue grasper having a pair of opposed first and second jaws 1110a, 1110b configured to move between open and closed positions. The first jaw is also referred to herein as a "bottom jaw" and a "cartridge jaw," and the second jaw is also referred to herein as an "upper jaw" and an "anvil." As discussed further below, the handle portion 1102 can be configured to be manipulated to effect the opening and closing of the opposed jaws 1110a, 1110b, e.g., movement of one or both the jaws 1110a, 1110b about the pivot joint 1108, and the handle portion 1102 can be configured to be manipulated to effect the firing of staples (not shown) from a one of the jaws 1110a, 1110b, e.g., a bottom or cartridge one of the jaws 1110a. The staple firing can be independent of the opening and closing of the jaws 1110a, 1110b.

The handle portion 1102 can have a variety of sizes, shapes, and configurations. The handle portion 1102 can include a main housing 1121, which can house a variety of elements therein and can have some elements accessible outside thereof, such as a movable trigger 1122 and a stationary handle 1124. The movable trigger 1122 can be configured to be manually manipulated to move the movable trigger 1122 relative to the stationary handle 1124 so as to, e.g., effect closing of the jaws 1110a, 1110b.

The shaft 1104 can have a variety of sizes, shapes, and configurations. In an exemplary embodiment, the shaft 1104 can be rigid, e.g., made from a generally non-bendable material such as a metal (e.g., stainless steel, titanium, etc.) or a hard polymer. In other embodiments, the shaft 1104 can be configured to bend, such as being made from a generally flexible material, by including one or more articulation regions, etc. The shaft 1104 can have any longitudinal length, although in an exemplary embodiment it can be long enough to allow the handle portion 1102 to be manipulated outside a patient's body while the shaft 1104 extends through an opening in the body with the end effector 1106 disposed within a body cavity. In this way, the end effector 1106 can be easily manipulated when the device 1100 is in use during a surgical procedure. The shaft 1104 can have any diameter. For example, the shaft's diameter can be less than or equal to about 10 mm, e.g., less than or equal to about 7 mm, less than or equal to about 5 mm, etc., which can allow for insertion of the shaft 1104 through an minimally invasive access device, e.g., a trocar, a cannula, a multiport access device, etc., such as during a laparoscopic surgical procedure. The end effector 1106 coupled to the shaft's distal end can have a diameter equal to or less than the shaft's diameter, at least when the jaws 1110a, 1110b are in the closed position, which can facilitate insertion of the device's distal portion into a patient's body.

The end effector 1106 can have a variety of sizes, shapes, and configurations. In an exemplary embodiment, the end effector 1106 can be rigid. As shown in FIG. 2 and FIG. 3, the end effector 1106 including the first and second jaws 1110a, 1110b can be disposed at a distal end of the surgical device 1100. As in this illustrated embodiment, when the jaws 1110a, 1110b move between the open and closed positions, the second jaw 1110b can be configured to remain stationary relative to the shaft 1104, and the first jaw 1110a can be configured to move relative to the shaft 1104 and the second jaw 1110b by pivoting at the pivot joint 1108.

Figure 4:
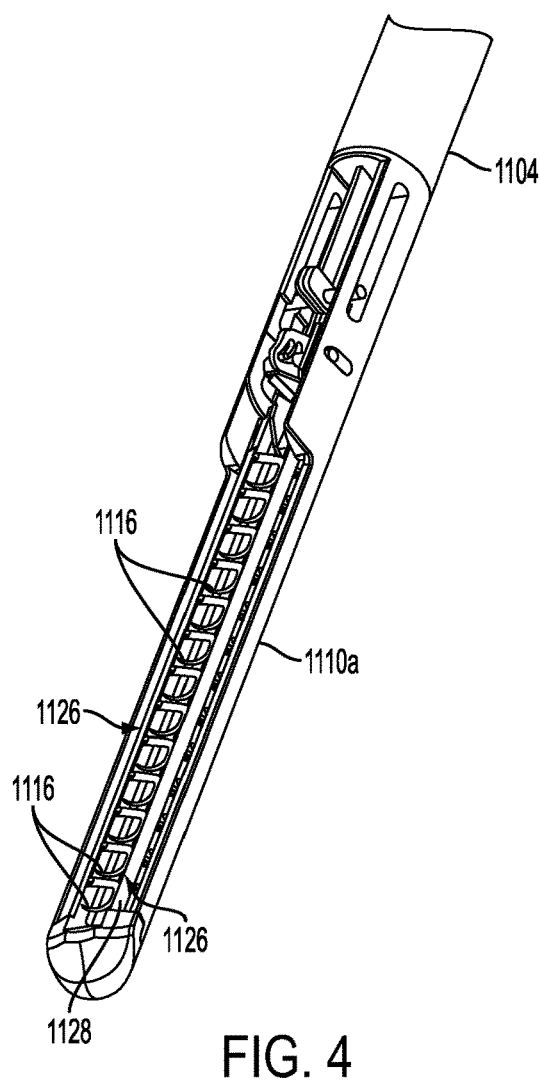
FIG. 4 is a perspective, partially cross-sectional view of the end effector and the cartridge of FIG. 3.

The end effector 1106 can be configured to releasably and replaceably seat a cartridge 1112 therein, as shown in FIG. 3 and FIG. 4. In this way, when the staples have been fired from the cartridge 1112, the cartridge 1112 can be removed from the second jaw 1110b and, optionally, replaced with another cartridge having another plurality of staples disposed therein. FIG. 2 shows the end effector 1106 without the cartridge 1112 seated therein. The end effector 1106 can be configured to receive the cartridge 1112 in the first jaw 1110a thereof, e.g., in a channel formed in the first jaw 1110a. The first jaw 1110a can be configured to seat cartridges of different sizes, thereby facilitating versatility of the device 1100.

Figure 5:
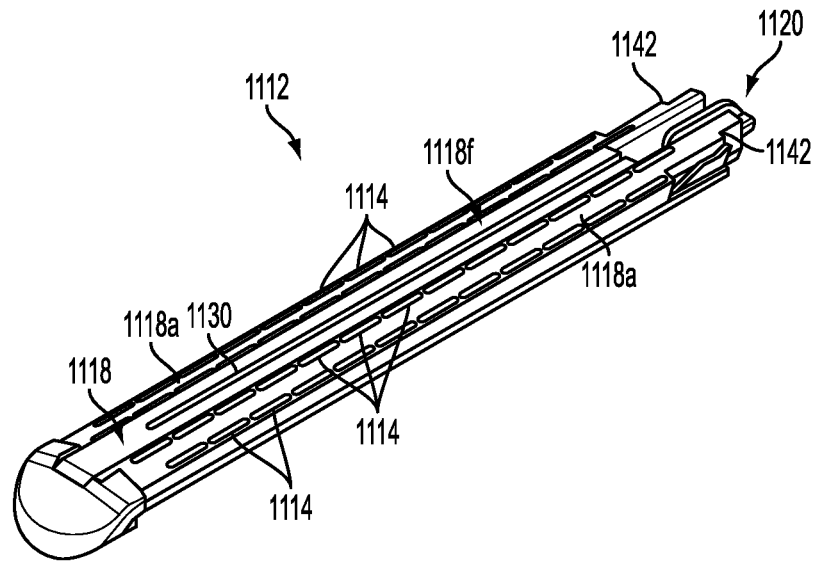
FIG. 5 is a perspective view of the cartridge of FIG. 3.
Figure 6:
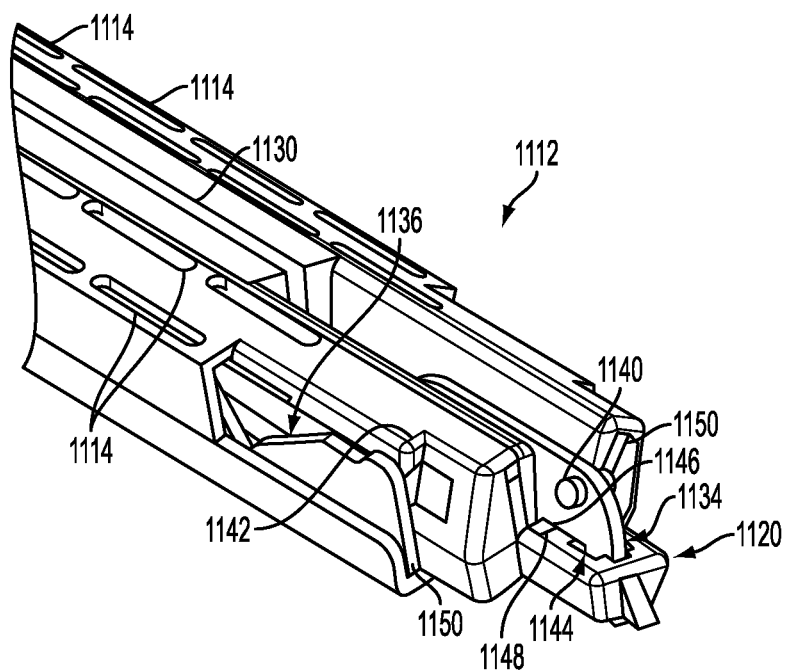
FIG. 6 is another perspective view of the cartridge of FIG. 3.
Figure 7:
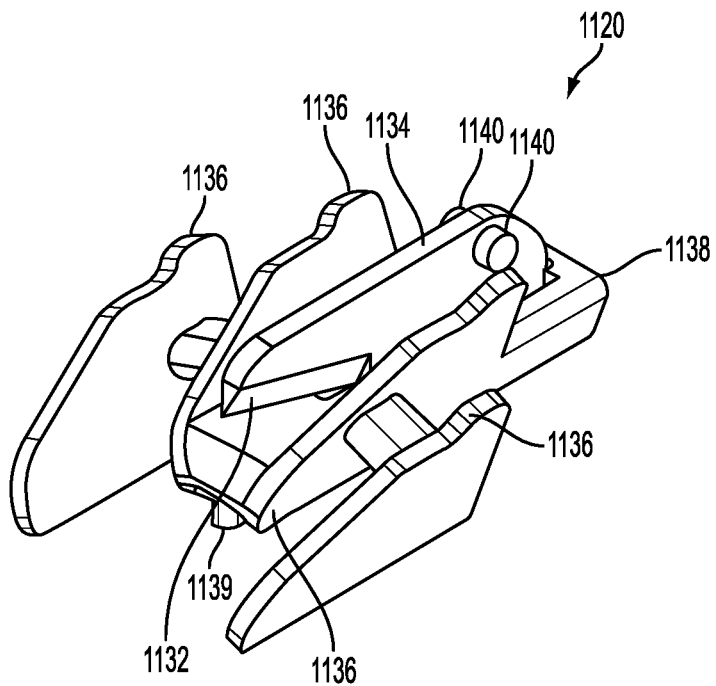
FIG. 7 is a perspective view of a sled of the cartridge of FIG. 3, the sled including a cutting element, and the cutting element being in a first position.
Figure 8:
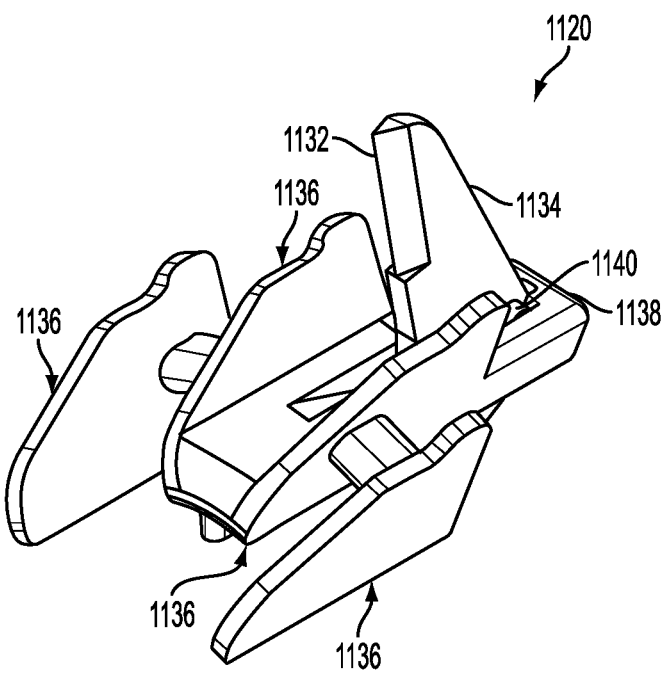
FIG. 8 is a perspective view of the sled of FIG. 7 with the cutting element in a second position that is different from the first position.

The cartridge 1112 can have a variety of sizes, shapes, and configurations, as will be appreciated by a person skilled in the art. As shown in FIG. 4, FIG. 5, and FIG. 6, the cartridge 1112 can include a sled 1120 and can have a plurality of staples 1116 disposed therein. The sled 1120 is also illustrated in FIG. 7 and FIG. 8. The cartridge 1112 can include a plurality openings 1114 formed in a tissue engaging surface 1118 thereof, as shown in FIG. 3, FIG. 5, and FIG. 6. The staples 1116 disposed in the cartridge 1112 can be configured to be ejected from the cartridge 1112 through the openings 1114, e.g., one staple 1116 out of each opening 1114 (as in this illustrated embodiment), two staples out of each opening 1114, etc. The openings 1114 can define staple-receiving recesses of the cartridge 1112 in which the staples 1116 are seated prior to being ejected from the cartridge 1112.

The staples 1116 can have a variety of sizes, shapes, and configurations. In this illustrated embodiment, the staples 1116 each have a D-shape and include a first leg that is substantially straight and a second leg that is curved. A person skilled in the art will appreciate that the first leg may not be precisely straight, e.g., due to manufacturing tolerances, but nevertheless be considered to be substantially straight. Each of the staples 1116 can be configured to be plastically deformable such that the staples 1116 can each be configured to change shape, such as when the staple 1116 is pressed against a tissue engaging surface (not shown) of the first jaw 1110a that faces the tissue engaging surface 1118 of the second jaw 1110b, while remaining a single unit, e.g., without either of the first and second legs breaking. A gap of space can exist between a terminal end of the first leg and a terminal end of the second leg. In other words, the "D" shape can have a gap therein. The gap of space can facilitate plastic deformation of the staple 1116.

The staples 1116 can each be frangibly attached to a carrier 1126, also referred to herein as a "carrier strip," disposed within the cartridge 1112. The staples 1116 can be frangibly attached to the carrier 1126 by, e.g., being stamped together with the carrier 1126 such that the staples 1116 and the carrier 1126 forms a single piece. The staples 1116 can each be configured to detach from the carrier 1126 when fired from the cartridge 1112. In some embodiments, some or all of the staples 1116 can be frangibly attached to another element, such as another element disposed within the cartridge 1112, an inner surface of the cartridge 1112, the tissue-engaging surface 1118 of the cartridge 1112, etc. The carrier 1126 can be fixedly attached to an upper surface of one or more rails 1128 defined by the cartridge 1112. The carrier 1126 can be configured to remain stationary relative to the cartridge 1112.

As shown in FIG. 3, FIG. 5, and FIG. 6, the cartridge 1112 can have a longitudinal slot 1130 formed therein. The longitudinal slot 1130 can extend along a substantially flat central portion 1118f of the tissue-engaging surface 1118. The slot 1130 can be configured to have a cutting element such as a knife (not shown) extend therethrough so as to be configured to cut tissue engaged by the tissue-engaging surface 1118, as discussed further below. The openings 1114 can be formed in angled portions 1118a of the tissue-engaging surface 1118 on both sides of the slot 1130, as shown in FIG. 3, FIG. 5, and FIG. 6. In some embodiments, the tissue-engaging surface 1118 can be substantially flat, e.g., not have angled portions, while in other embodiments, the tissue-engaging surface 1118 can be angled, e.g., not have any substantially flat portions.

As shown in FIG. 5 and FIG. 6, the cartridge 1112 can include a gap-setting feature 1142 configured to set of gap of space between the first and second jaws 1110a, 1110b when the jaws 1110a, 1110b are closed and the cartridge 1112 is seated in the second jaw 1110b. In this way, the gap-setting feature 1142 can be configured to define a minimum distance between the facing tissue-engaging surfaces of the first and second jaws 1110a, 1110b. The gap-setting feature 1142 can have a variety of sizes, shapes, and configurations. As in this illustrated embodiment, the gap-setting feature 1142 can include an indentation inward toward a lateral center of the cartridge 1112, where a portion of a lateral edge of the cartridge 1112 immediately proximal to the gap-setting feature 1142 is located laterally inward relative to a portion of a lateral edge of the cartridge 1112 located immediately distal to the gap-setting feature 1142.

The sled 1120 of the cartridge 1112 can have a variety of sizes, shapes, and configurations. The sled 1120 can be configured to translate longitudinally along the cartridge 1112 to cause deployment of the staples 1116 therefrom and to cause tissue engaged by the end effector 1106 to be cut with the cutting element extending through the slot 1130. The staples 1116 can be arranged longitudinally in the cartridge 1112, as shown in FIG. 4, and the sled 1120 can be configured to sequentially engage the longitudinally arranged staples 1116 as the sled 1120 translates longitudinally. As illustrated in FIG. 7 and FIG. 8, the sled 1120 can include a plurality of wedges 1136 and can include a cutting element 1134, which in this illustrated embodiment includes a knife with a blade 1132. The sled 1120 in this illustrated embodiment includes four wedges 1136 but the sled 1120 can include another number of wedges 1136 as appropriate for the arrangement of the staples 1116 in the cartridge 1112. Each of the wedges 1136 can have a shape configured to cause the staples 1116 contacted by that wedge 1136 to move upward toward the second jaw 1110b through the openings 1114 and deform against the second jaw 1110b. As shown in FIG. 6, the cartridge 1112 can include a plurality of longitudinal slots 1150 formed therein, each of the slots 1150 being configured to slidably receive one of the wedges 1136 therein. The slots 1150 can facilitate consistent, straight movement of the wedges 1136 through the cartridge 1112 to help ensure proper engagement of the wedges 1136 with the staples 1116.

Each of the wedges 1136 can be attached to a base 1138 of the sled 1120 and can be in a fixed position relative thereto. The base 1138 can have a guide element 1139 extending generally downward therefrom. The guide element 1139 can be configured to slide within a channel formed in the cartridge 1112 that includes the sled 1120. The cutting element 1134 can also be attached to the base 1138, but the cutting element 1134 can be configured to move relative to the base 1138. The cutting element 1134 can be substantially laterally centered in the base 1138, which can facilitate substantially central positioning of the cutting element 1134 relative to tissue engaged by the end effector 1106.

The cutting element 1134 can be configured to be movable relative to a remainder of the sled 1120 between a first position, shown in FIG. 7, and a second position, shown in FIG. 6 and FIG. 8. The first position can be an initial position of the cutting element 1134. In the first position, also referred to herein as a "stowed position," the blade 1132 can be generally obscured, e.g., oriented generally downward as shown in the embodiment of FIG. 4, FIG. 5, FIG. 6, and FIG. 7, which can help prevent the blade 1132 from inadvertent cutting, such as accidentally cutting a user of the device 1100 during seating of the cartridge 1120 within the end effector 1104 and/or premature cutting of tissue engaged by the end effector 1104. The base 1138 can have a cavity 1144 formed therein, as shown in FIG. 6, which can be configured to seat the cutting element 1134 at least partially therein when the cutting element 1134 is in the first position. In the second position, also referred to herein as an "upright position," the blade 1132 can be generally unobscured and facing a distal direction as shown in the embodiment of FIG. 6 and FIG. 8, which can allow the blade 1132 to extend through the slot 1130 and cut tissue engaged by the end effector 1106.

The sled 1120 can include a pivot member 1140 configured to facilitate movement of the cutting element 1134 relative to the remainder of the sled 1120. The pivot member 1140 can have a variety of sizes, shapes, and configurations. The pivot member 1140 can be attached to the cutting element 1134 such that engagement of the pivot member 1140 can cause the cutting element 1134 to pivot about a pivot point so as to move relative to the remainder of the sled. As in this illustrated embodiment the pivot member 1140 can include two separate pins extending laterally from opposite sides of the cutting element 1134. In other embodiments, the pivot member 1140 can include a single pin extending through the cutting element 1134 to extend laterally from opposite sides therefrom, a single pin extending laterally from one side of the cutting element 1134, etc. At the pivot point, the sled 1120 can include a pivot axle 1146 extending laterally from the cutting element 1134, and can include an axle cavity 1148 formed in the base 1138 and configured to receive the pivot axle 1146 therein.

The surgical devices described herein can be used in a variety of surgical procedures. In an exemplary embodiment, the procedure can be a minimally invasive procedure in which the surgical device can be advanced into a body of a patient through a relatively small opening in the patient. In a minimally invasive surgical procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. As will be appreciated by a person skilled in the art, the surgical device can be advanced into the patient's body in a variety of ways, such as by being inserted transorally therein, inserted through an introducer device, inserted through a scoping device, inserted directly through an incision, etc. Although the following embodiment of use of a surgical device in a surgical procedure is described with respect to the device 1100 of FIG. 1, any of the surgical devices described herein can be similarly used.

The surgical devices described herein can have any one or more variations to facilitate effective use of the device. Examples of such variations are described further below.

In some embodiments, a surgical device such as the above-mentioned surgical device 1100 can be configured to stabilize fasteners post-deployment. In general, the fasteners can be configured to resist counter rotation after being deployed. Fasteners can have a tendency to shift position relative to tissue that the fasteners are securing. The position shifting can be caused by any one or more factors, such as a type of the tissue, a thickness of the tissue, a shape of the fasteners (e.g., a curved shape thereof), and a strength of a bias urging a fastener into a certain position or configuration. The position shifting can take the form of counter rotation, in which the fastener rotates in a direction opposite to a direction in which the fastener was deployed into the tissue. This counter rotation can reduce the fastener's effectiveness in fastening the tissue because the fastener is "slipping" out of the tissue and/or reducing its hold on the tissue as a result of the counter rotation. The adverse effects of counter rotations can be exacerbated when, as in typical surgical procedures that use fasteners, a plurality of fasteners, all of which may all counter rotate to varying degrees, are deployed in tissue. The adverse effects of counter rotations can be exacerbated when tissue is relatively thick such that staples may not close to a great extent when deployed in the tissue. Fasteners being configured to resist counter rotation can help keep the staples secured in tissue into which the staples have been deployed, thereby helping to keep the tissue securely fastened and/or facilitating effective treatment of the tissue.

A fastener can be configured to resist counter rotation in a variety of ways. In the embodiments described below, staples are used as examples of fasteners, but as will be appreciated by a person skilled in the art, other types of fasteners can be similarly configured and used.

Figure 9:
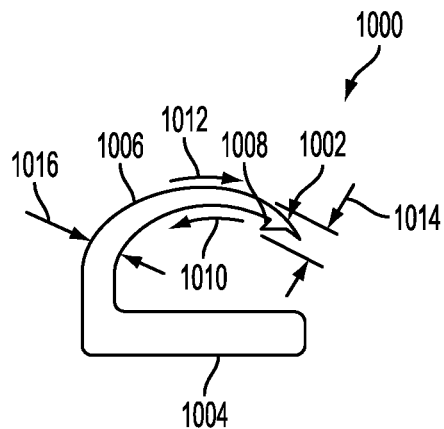
FIG. 9 is a side view of one embodiment of a fastener including an anti-rotation mechanism.

In some embodiments, a staple can include one or more anti-rotation mechanisms configured to resist counter rotation of the staple when the staple is deployed in tissue. FIG. 9 illustrates one embodiment of a staple 1000 that includes one or more anti-rotation mechanisms 1008 configured to resist counter rotation. The staple 1000 in this illustrated embodiment is generally configured like the previously described staples 1116 and has a D-shape with a pointed tip 1002, a first leg 1004 that is substantially straight and a second leg 1006 that is curved. The pointed tip 1002 can be a terminal end of the second leg 1006, as in this illustrated embodiment.

The staple 1000 can include one or more anti-rotation mechanisms 1008, which in this illustrated embodiment includes a barb 1008. This illustrated embodiment includes only one barb 1008, but the staple 1000 can include one or more barbs 1008 that are substantially identical to one another. The barb 1008 can be located in a variety of locations on the staple 1000. As in this illustrated embodiment, the one or more barbs 1008 can be formed on an inner-facing surface of the second leg 1006 at the pointed tip 1002. The barb 1008 can be oriented in a first direction 1010 that is opposite to a second direction 1012 in which the pointed tip 1002 points. The second direction 1012 can be the direction in which the staple 1000 is deployed into tissue, with the pointed tip 1002 leading the staple 1000 into the tissue. When the staple 1000 is deployed in the tissue, the barb 1008 can thus be configured to prevent counter rotation of the staple 1000 therein, thereby helping to retain the staple securely within the tissue.

The barb 1008 can have a variety of sizes. In an exemplary embodiment, the barb 1008 can have a maximum diameter 1014 is less than or substantially equal to a maximum diameter 1016 of the second leg 1006. In this way, a hole created by the barb 1008 when the barb 1008 penetrates into tissue can be less than or substantially equal to a hole created by the second leg 1006 when the second leg 1006 passes through the tissue, thereby helping to reducing any potential hemostasis issues that may arise from the barb 1008. The second leg 1006 can be tapered toward the pointed tip 1002 such that the maximum diameter 1016 of the second leg 1006 is adjacent a terminal end thereof that is opposite the pointed tip 1002.

Figure 10:
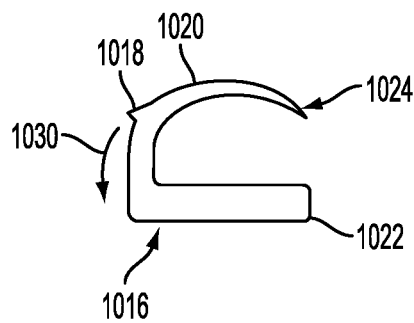
FIG. 10 is a side view of another embodiment of a fastener including an anti-rotation mechanism.
Figure 11:
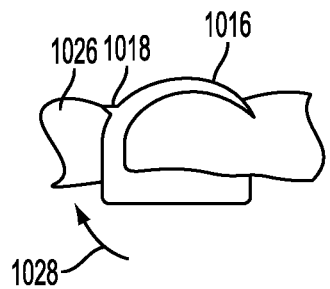
FIG. 11 is a side, partially transparent view of the fastener of FIG. 10 deployed in tissue.

FIG. 10 and FIG. 11 illustrate another embodiment of a staple 1016 that includes one or more anti-rotation mechanisms 1018 configured to resist counter rotation. The staple 1016 and the one or more anti-rotation mechanisms 1018, e.g., one or more barbs 1018, can be generally configured and used similar to the staple 1000 and the one or more barbs 1008, respectively, of FIG. 9. The one or more barbs 1018 in this illustrated embodiment, however, are formed in an intermediate portion of the staple's second leg 1020 between proximal and distal ends thereof, and the one or more barbs 1018 are formed on an outer-facing surface of a second leg 1020 of the staple 1016 that includes a pointed tip 1024 of the staple 1016 and that is connected to a first leg 1022 of the staple 1016.

FIG. 11 illustrates an embodiment of the staple 1016 as deployed in a tissue 1026. The staple 1016 can be deployed into the tissue 1026, e.g., fired from a cartridge such as the above-mentioned cartridge 1112, in a first direction 1028. The one or more barbs 1018 can be oriented in a second direction 1030 that is opposite to the first direction 1028, thereby helping to secure the staple 1016 to the tissue 1026 and helping to prevent counter rotation of the staple 1016 within the tissue 1026. The one or more barbs 1018 can be formed in the second leg's intermediate portion at a location substantially where the staple 1016 exits the tissue 1026, as in this illustrated embodiment. An exterior surface of the tissue 1026 can cooperate with the one or more barbs 1018 at such a location to help prevent counter rotation of the staple 1018, e.g., help prevent the staple 1016 from rotating in the second direction 1030 after being deployed in the tissue 1026.

Figure 12:
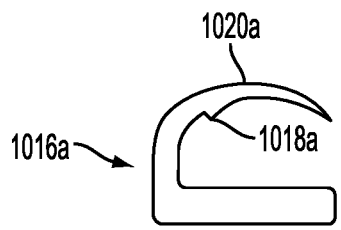
FIG. 12 is a side view of yet another embodiment of a fastener including an anti-rotation mechanism.
Figure 13:
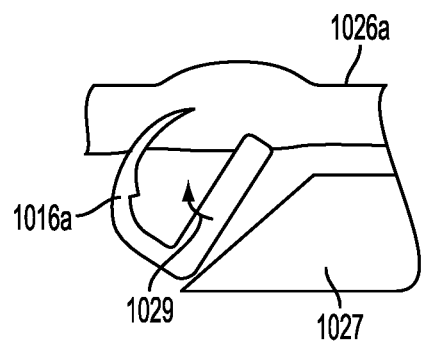
FIG. 13 is a side, partially transparent view of the fastener of FIG. 12 being deployed in tissue.

In another embodiment, the one or more barbs can be formed on an inner-facing surface of the second leg in addition to or in alternative to the one or more barbs formed on the outer-facing surface of the second leg. FIG. 12 illustrates such an embodiment of a staple 1016*a* with one or more barbs 1018*a* formed on an inner-facing surface of a second leg 1020*a* of the staple 1016*a*. The staple 1016*a* and the one or more anti-rotation mechanisms 1018*a* can be generally configured and used similar to the staple 1000 and the one or more barbs 1008, respectively, of FIG. 9. FIG. 13 illustrates an embodiment of the staple 1016*a* being deployed in a tissue 1026*a* by being pushed by a wedge 1027 of a sled so as to rotate the staple 1016*a* in a direction of an arrow 1029. FIG. 14 illustrates another embodiment of a staple 1016*b* with one or more barbs 1018*b* formed on an inner-facing surface of a second leg 1020*b* of the staple 1016*b*. The staple 1016*b* is like the staple 1016*a* of FIG. 12 except the staple 1016*b* of FIG. 14 includes at least one second anti-rotation mechanism 1017 on an outer-facing surface of the second leg 1020*b*. The at least one second anti-rotation mechanism 1017 in this illustrated embodiment include a plurality of spikes extending outward from the outer-facing surface of the second leg 1020*b*.

FIG. 15 and FIG. 16 illustrate another embodiment of a staple 1032 that includes one or more anti-rotation mechanisms 1034 configured to resist counter rotation. The staple 1032 and the one or more anti-rotation mechanisms 1034, e.g., one or more barbs 1034, can be generally configured and used similar to the staple 1000 and the one or more barbs 1008, respectively, of FIG. 9. The one or more barbs 1034 in this illustrated embodiment, however, are formed on an outer-facing surface of a second leg 1036 of the staple 1032 closer to a first leg 1037 of the staple 1032 than in the FIG. 9 embodiment, and are formed adjacent a terminal end of the second leg 1036 that is opposite to a terminal end thereof that includes a pointed tip 1038. In another embodiment, the one or more barbs can be formed on an inner-facing surface of the second leg 1036 in addition to or in alternative to the one or more barbs 1034 formed on the outer-facing surface of the second leg 1036.

FIG. 16 illustrates an embodiment of the staple 1032 deployed in a tissue 1040. The one or more barbs 1034 of the staple 1032 can be oriented similar to the one or more barbs 1026 of FIG. 10 and FIG. 12 so as to be oriented in a direction that is opposite to a direction in which the staple 1032 was deployed into the tissue 1040. The one or more barbs 1034 can be formed on the second leg 1036 at a location disposed within the tissue 1040 when the staple 1032 is within the tissue 1040, as in this illustrated embodiment. The tissue 1040 can thus completely surround the one or more barbs 1034 so as to help the one or more barbs 1034 prevent counter rotation.

In some embodiments, an anti-rotation mechanism of a first staple can be configured to engage a second staple deployed adjacently thereto in tissue. The anti-rotation mechanism can be configured to help prevent counter rotation of the first and second staples. In an exemplary embodiment, an anti-rotation mechanism of a staple configured to engage an adjacent staple can be in the form of a coupling element configured to receive a pointed tip of the adjacent staple when both of the staples are deployed in tissue.

FIG. 17 illustrates one embodiment of a staple 1042 that includes an anti-rotation mechanism 1044 in the form of a coupling element configured to engage an adjacently deployed staple. The staple 1042 in this illustrated embodiment is generally configured and used like the previously described staples 1116 and has a D-shape with a pointed tip 1046, a first leg 1048 that is substantially straight and a second leg 1050 that is curved. The pointed tip 1046 can be a first terminal end of the second leg 1050, as in this illustrated embodiment. The anti-rotation mechanism 1044 can be formed on an outer-facing surface of the staple 1042 and can be located at a junction of the first and second legs 1048, 1050. The anti-rotation mechanism 1044 can include a ring or hoop configured to receive a pointed tip of an adjacent staple therein. The pointed tip can extend partially or all the way through a hole 1052 defined by the anti-rotation mechanism 1044. The anti-rotation mechanism 1044 having the adjacent staple's tip at least partially captured by the anti-rotation mechanism 1044 can help prevent counter rotation of the staple 1042 as well as the adjacent staple engaged by the staple 1042. Because the staple 1042 can be rotated to be deployed in tissue and can be one of a plurality of staples deployed in a longitudinal row, as discussed herein, the staple's tip 1046 can rotate into a previously deployed staple's anti-rotation mechanism. In this way, staples deployed in the longitudinal row can all be interconnected with one another via the anti-rotation mechanisms, thereby helping to stabilize the entire row of staples in tissue.

FIG. 18 illustrates a plurality of staples 1042a, 1042b, 1042c, each similar to the staple 1042 of FIG. 17, having been deployed such that a pointed tip of a staple is captured as it rotates by an anti-rotation mechanism of the one of the staples having been deployed immediately prior thereto. In other words, a pointed tip 1046b of the staple 1042b deployed second has been captured by an anti-rotation mechanism 1044a of the staple 1042a deployed first, and a pointed tip 1046c of the staple 1042c deployed third has been captured by an anti-rotation mechanism 1044b of the staple 1042b deployed second. As shown in this illustrated embodiment, a pointed tip 1046a of the first staple 1042a can not be coupled to an anti-rotation mechanism, and an anti-rotation mechanism of a last one of the deployed staples 1042c can not be coupled to another staple. Only three staples 1042a, 1042b, 1042c are shown in this illustrated embodiment, but nay number of staples can be so interconnected using anti-rotation mechanisms.

FIG. 19 illustrates another embodiment of a staple 1054 that includes an anti-rotation mechanism 1056 in the form of a coupling element configured to engage an adjacently deployed staple. The staple 1054 in this illustrated embodiment is generally configured and used like the staple 1042 of FIG. 17 except that the staple 1054 includes a second anti-rotation mechanism 1058. The second anti-rotation mechanism 1058 in this illustrated embodiment a pointed tip 1060 of the staple 1056 having a barb similar to the barb 1008 of FIG. 9. The second anti-rotation mechanism 1058 in the form of a barb can be configured to help hold the staple 1054 in tissue and can be configured to help prevent the pointed tip 1060 from de-coupling from an adjacent staple's anti-rotation mechanism, e.g., from moving out of a hole of a ring or loop once advanced therein. FIG. 19 also shows an adjacent staple 1054a (partially illustrated), which is generally configured and used similar to the staple 1054, with its pointed tip 1060a and second anti-rotation mechanism 1058a engaged by the anti-rotation mechanism 1056 of the staple 1054.

In some embodiments, an orientation of a fastener relative to an orientation of one or more fasteners deployed adjacent thereto can be configured to help prevent counter rotation. In an exemplary embodiment, fasteners in one longitudinal row can all face in a first direction, e.g., proximally, and fasteners in a longitudinal row adjacent thereto can all face in an opposite direction, e.g., distally. In this way, forces exerted on tissue in which the fasteners facing opposite directions are deployed can help hold the fasteners in the tissue.

Figure 20:
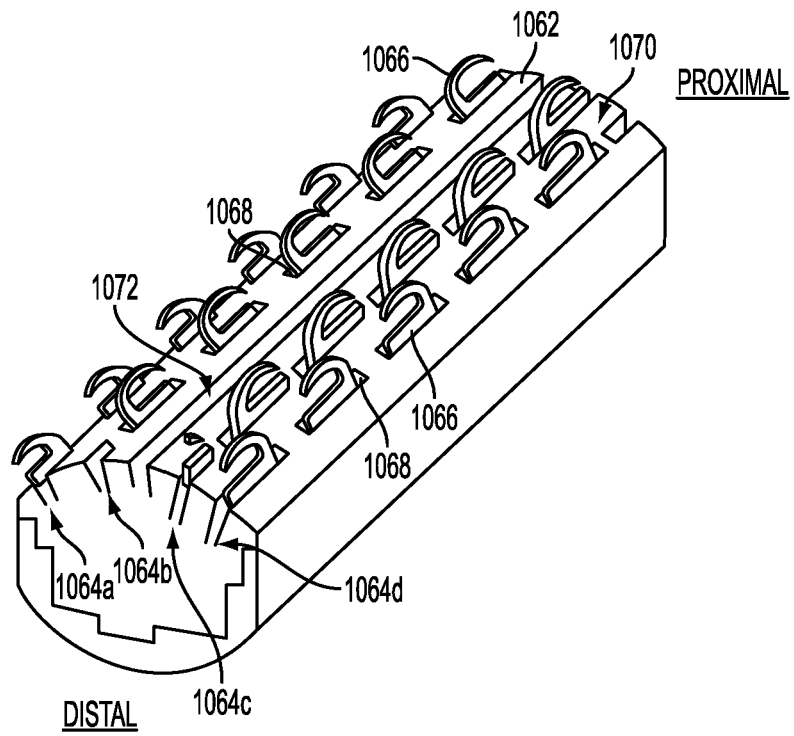
FIG. 20 is a perspective view of an embodiment of a cartridge and staples that can be deployed therefrom in opposite-facing longitudinal rows.

FIG. 20 illustrates one embodiment in which a cartridge 1062 has staples 1066 in adjacent longitudinal rows facing in opposite directions. The staples 1066 are shown deployed out of the cartridge 1062 for ease of explanation. The cartridge 1062 in this illustrated embodiment has first, second, third, and fourth longitudinal rows 1064a, 1064b, 1064c, 1064d rows of staples 1066. The staples 1066 in the first and fourth rows 1064a, 1064d can face a first direction, e.g., a distal direction, when deployed, and the staples 1066 in the second and third rows 1064b, 1064c can face a second, opposite direction, e.g., a proximal direction, when deployed. In this way, when the staples 1062 are in tissue, the adjacent first and second rows 1064a, 1064b of staples 1066 can face opposite directions, and the adjacent third and fourth rows 1064c, 1064d of staples 1066 can face opposite directions. A cutting element (not shown) can extend through a longitudinal slot 1072 in the cartridge 1062 and cut tissue between the second and third rows 1064b, 1064c as discussed herein such that the second and third rows 1064b, 1064c having staples 1066 facing the same direction generally will not affect counter rotation.

As discussed herein, the staples 1066 can be deployed from the cartridge 1062 by rotating out of openings 1068 formed in the cartridge's tissue-engaging surface 1070. Typically, all staples in a cartridge are deployed as a sled moves longitudinally through the cartridge, e.g., as the sled translates distally. However, the staples 1066 facing in opposite directions can be deployed in two passes of a sled through the cartridge 1062, one pass in which the sled translates distally to deploy the staples 1066 facing in one direction and another pass in which the sled translates proximally to deploy the staples facing the opposite direction.

Figure 21:
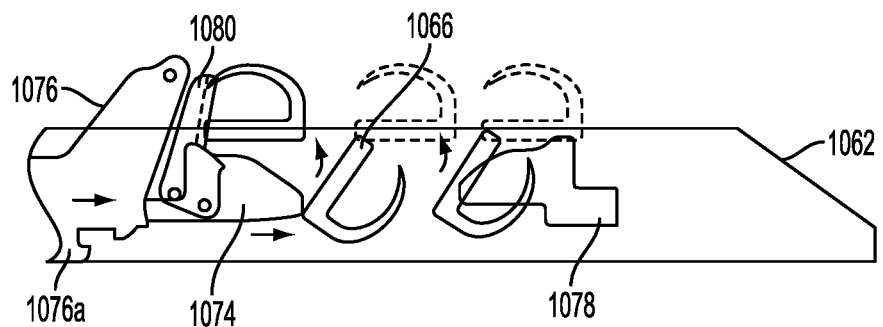
FIG. 21 is a side, partially transparent view of the staples of FIG. 20 that face in one direction being deployed from the cartridge with a drive beam engaged with a first sled translating distally through the cartridge.
Figure 23:
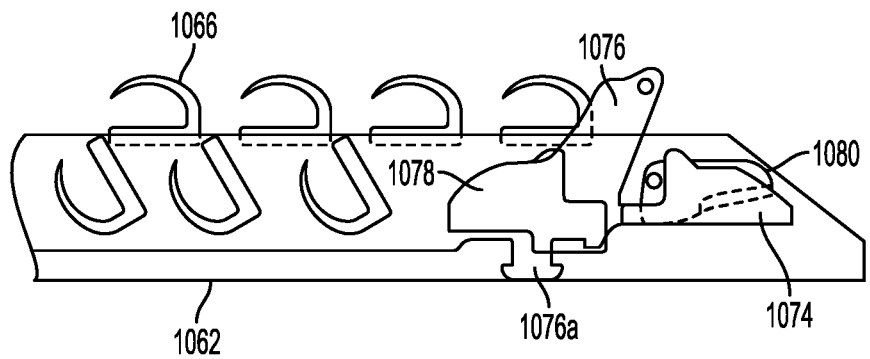
FIG. 23 is a side, partially transparent view of the drive beam engaged with the second sled of FIG. 22 and disengaged from the first sled.
Figure 24:
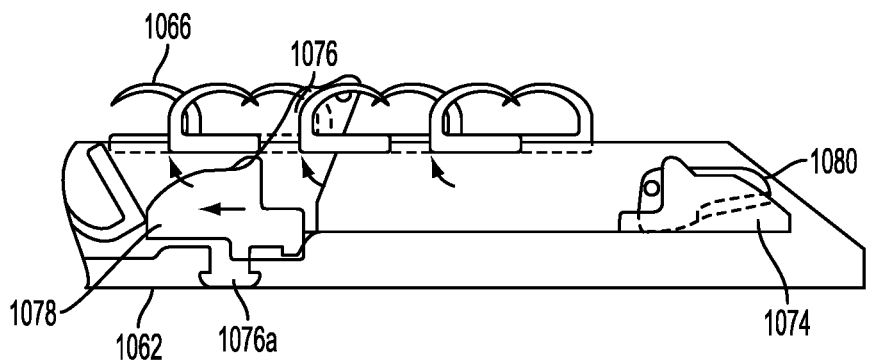
FIG. 24 is a side, partially transparent view of the staples of FIG. 23 facing in an opposite direction being deployed from the cartridge with the drive beam engaged with a second sled translating proximally through the cartridge.
Figure 25:
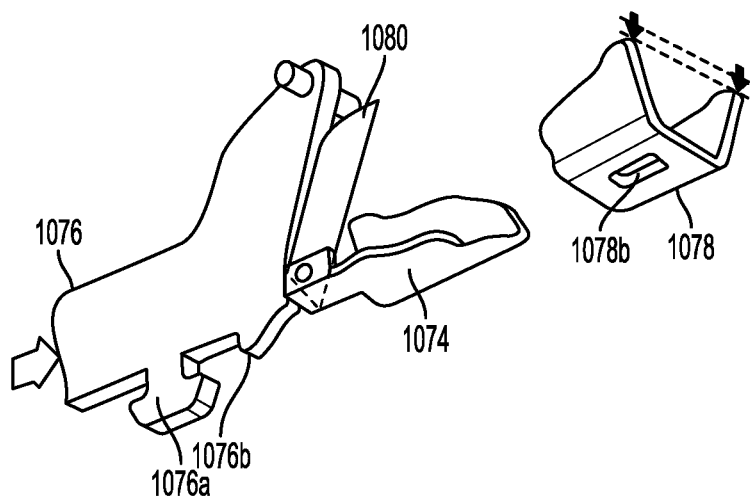
FIG. 25 is a perspective view of the drive beam and the first sled of FIG. 24 coupled together and moving distally, and a perspective view of second sled not coupled to and positioned distal to the drive beam and the first sled.

FIG. 21, FIG. 22, FIG. 23, and FIG. 24 illustrate one embodiment of deploying the staples 1066 that face in opposite directions using a first sled 1074, a drive beam 1076 (also referred to herein as a "drive rod" and an "I-beam"), and a second sled 1078, which are also shown in FIG. 25, FIG. 26, FIG. 27, and FIG. 28. Although this illustrated embodiment shows deployment of the staples 1066 disposed in the cartridge 1062, other staples disposed in other cartridges in facing opposite direction can be similarly deployed. The relative positions of the first sled, drive beam 1076, and second sled 1078 in FIG. 25, FIG. 26, FIG. 27, and FIG. 28 correspond respectively to their positions in FIG. 21, FIG. 22, FIG. 23, and FIG. 24. The first sled 1074 can be generally configured and used similar to the previously described sled 1120. The first sled 1074 can include a cutting element 1080, which includes a knife in this illustrated embodiment. The cutting element 1080 can be configured to pivot between a stowed position in which the cutting element's blade 1082 is generally obscured, as shown in FIG. 22, FIG. 23, FIG. 24, FIG. 26, FIG. 27, and FIG. 28, and an upright position in which the cutting element 1080 extends through the slot 1072 such that the blade 1082 can cut tissue, as shown in FIG. 21 and FIG. 25.

As shown in FIG. 21 and FIG. 25, the second sled 1078 can be parked in an initial position near a distal end of the cartridge 1062. The drive beam 1076 can be advanced distally, e.g., by manipulating a handle of a surgical device including the cartridge 1062 seated in an end effector thereof, so as to cause the cutting element 1080 to move from the stowed position to the upright position and so as to push the first sled 1074 distally. The drive bean 1076 can include a guide member 1076a configured to slide within a corresponding guide track (not shown) formed in the cartridge 1062, which can help the drive beam 1076 translate straight and smoothly within the cartridge 1062. The distal movement of the first sled 1074 can cause the second and third rows 1064b, 1064c of staples 1066 to be deployed.

Figure 22:
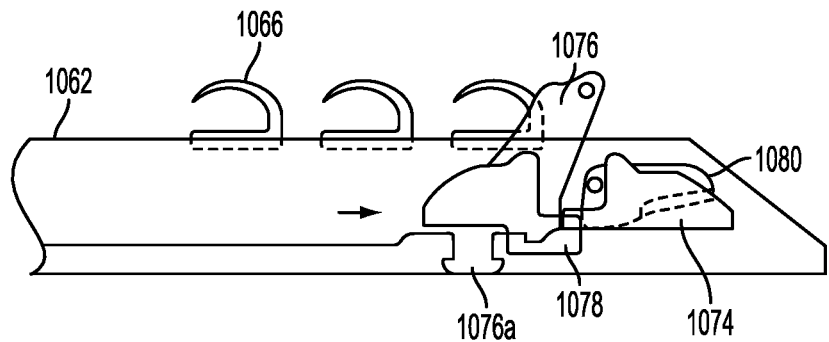
FIG. 22 is a side, partially transparent view of the first wedge sled of FIG. 21 at a distal end of the cartridge and passing over a second sled.
Figure 26:
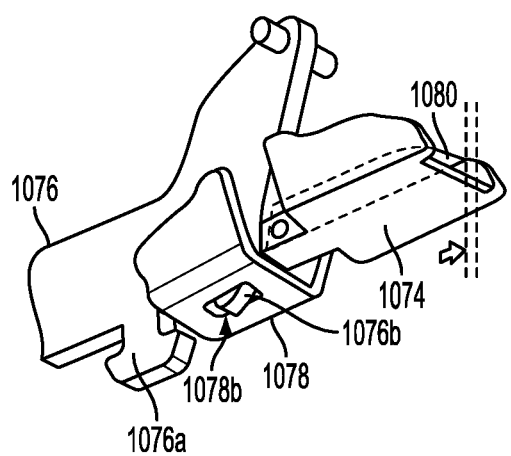
FIG. 26 is a perspective view of the drive beam and the first sled of FIG. 22 coupled together and the first sled passing by the second sled.
Figure 27:
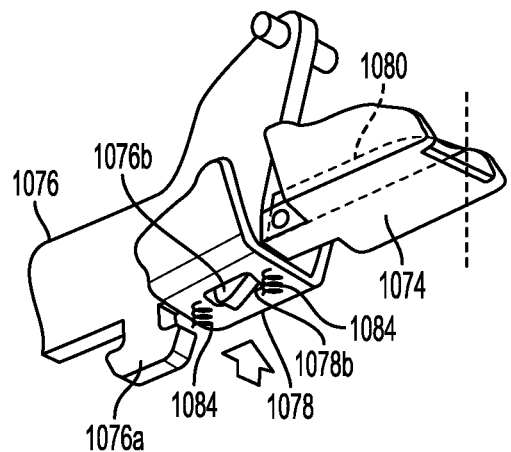
FIG. 27 is a perspective view of the drive beam and the second sled of FIG. 23 coupled together and a perspective view of first sled not coupled to and positioned distal to the drive beam and the second sled.
Figure 28:
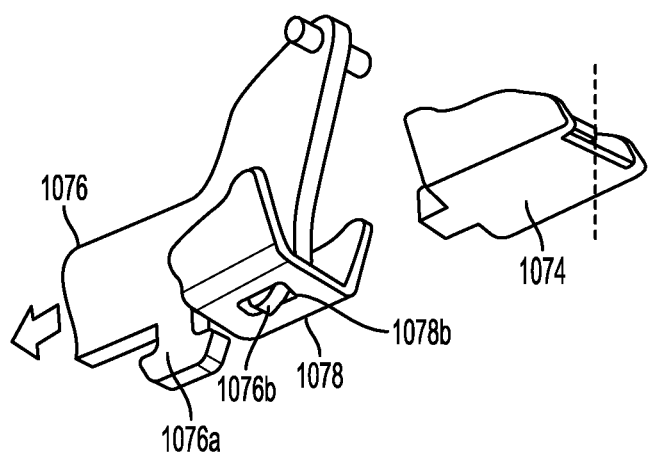
FIG. 28 is a perspective view of the drive beam and the second sled of FIG. 24 coupled together and moving proximally, and a perspective view of first sled not coupled to and positioned distal to the drive beam and the second sled.

After deploying the staples 1066 in the second and third rows 1064b, 1064c, the distally advancing first sled 1074 can advance distally beyond the parked second sled 1078, as shown in FIG. 22 and FIG. 26, and the drive rod 1076 can engage the parked second sled 1078, as shown in FIG. 23 and FIG. 27. The drive rod 1076 can engage the second sled 1078 in a variety of ways. As in this illustrated embodiment, the drive rod 1076 can include a protrusion 1076b extending therefrom and configured to engage a corresponding opening 1078b formed in the second sled 1078. The first sled 1076 being advanced to its distal-most position relative to the cartridge 1062 can cause a spring 1084, shown in FIG. 27, to be released. The spring 1084 can be coupled to the second sled 1078 and can be biased upward such that release of the spring 1084 can cause the second sled 1078 to move upward, thereby allowing the protrusion 1076b to engage the opening 1078 as shown in FIG. 23 and FIG. 27. The drive rod 1076 can be advanced proximally, e.g., by manipulating the handle of the surgical device, so as to cause the second sled 1078 engaged with the drive rod 1076 to move from the parked position and be advanced proximally with the drive rod 1076 due to the engagement of the protrusion 1076b and the opening 1078b. As shown in FIG. 25 and FIG. 28, the proximal movement of the second sled 1078 can cause the first and fourth rows 1064a, 1064d of staples 1066 to be deployed. The first sled 1074 can be parked near the distal end of the cartridge 1062 during the drive beam's and second sled's proximal movement, as also shown in FIG. 24 and FIG. 28. In this illustrated embodiment, the tissue is thus cut before all of the staples 1066 have been deployed since the tissue is cut by the cutting element 1080 during firing of the staples 1066 in the second and third rows 1064b, 1064c and prior to firing of any of the staples in the first and fourth rows 1064a, 1064d.

Two-pass deployment of the staples 1066 in which a first portion of the staples 1066 are deployed in one pass, e.g., a distal pass of the drive beam 1076, and a second, remaining portion of the staples 1066 are deployed in a second pass, e.g., a proximal pass of the drive beam 1076, can reduce a force needed to fire the staples 1066. A first force can be required to deploy the staples 1066 in the first pass, and a second force can be required to deploy the staples 1066 in the second pass. In this way, instead of requiring a sum of the first and second forces to deploy all of the staples 1066, two smaller forces can be applied to deploy all of the staples. These reduced forces for firing can make firing of staples much easier in devices having relative small diameters, such as those used in minimally invasive surgical procedures. For example, it can be difficult to generate a force required to deploy staples from an end effector of a 5 mm device, so effectively dividing the force required in half by having two passes can make the device easier to use and/or more effective in deploying staples properly.

In another embodiment of deploying staples from a cartridge in which some of the staples are disposed therein facing one direction and a remainder of the staples are disposed therein facing another, opposite direction, a sled can be configured to advance distally through the cartridge so as to cause deployment of all of the staples. In other words, the sled's distal movement can be configured to cause deployment of staples facing in opposed directions. Such a sled can include sides that extend upward and downward on left and right sides thereof so as to allow movement of the sled in one direction to cause deployment of staples facing in opposite directions.

In some embodiments, a surgical device such as the above-mentioned surgical device 1100 can be configured to facilitate ejection of fasteners from a cartridge that has the fasteners disposed therein. In general, the device can include at least one separation feature configured to facilitate complete removal of one or more fasteners from within the cartridge. The fasteners can thus each be more likely to be deployed into and remain within the tissue after a firing operation ejecting the fasteners into the tissue, thereby facilitating complete sealing of the tissue with the fasteners and/or facilitating healing of the tissue. The at least one separation feature can be configured to facilitate complete ejection of the one or more fasteners after the one or more fasteners have been deformed by an anvil, which can significantly reduce a force required to fire the one or more fasteners from the cartridge. In other words, a force to fire can be reduced as fastener forming and fastener disconnection can be timed separately with the fastener being deformed prior to the fastener being fully disconnected from the cartridge. In an exemplary embodiment, the device can be configured to facilitate disconnection of fasteners from a carrier to which the fasteners are frangibly attached. In general, the device can include a separation feature in the form of a shearing element configured to facilitate separation of the fasteners from the carrier when the fasteners are deployed from a cartridge that has the fasteners and the carrier disposed therein. The shearing element can be disposed between a sled of the device and a drive beam of the device, which can facilitate complete ejection of the one or more fasteners after the one or more fasteners have been urged toward the anvil by the sled.

The surgical device can be configured to facilitate ejection of fasteners from a cartridge in a variety of ways. In the embodiments described below, staples are used as examples of fasteners, but as will be appreciated by a person skilled in the art, other types of fasteners can be similarly configured and used. In exemplary embodiments, the fasteners can be D-shaped fasteners such as the above-mentioned staples 1116.

Figure 29:
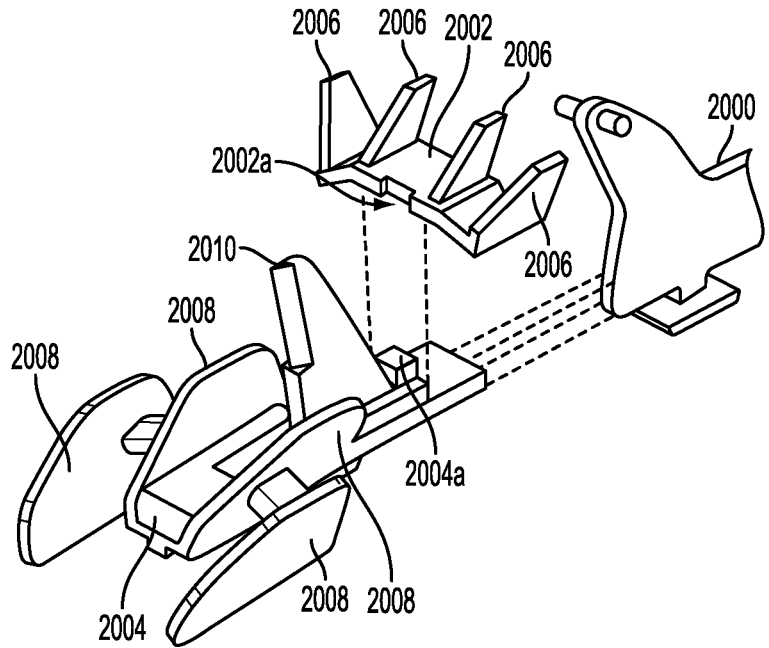
FIG. 29 is a perspective view of one embodiment of a shearing element configured to couple to a sled and an I-beam and be positioned therebetween.
Figure 30:
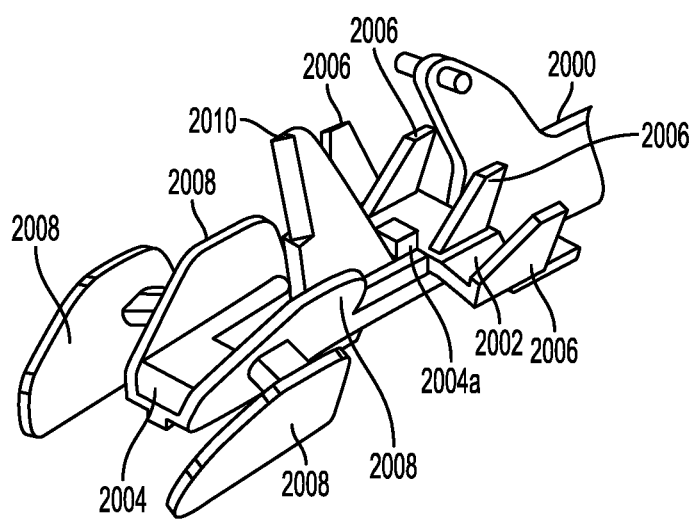
FIG. 30 is a perspective view of the shearing element of FIG. 29 positioned between and coupled to the sled and the I-beam.

FIG. 29 and FIG. 30 illustrate one embodiment of a separation feature 2002 configured to facilitate ejection of fasteners (not shown) from a cartridge (not shown) that has the fasteners disposed therein and connected to a carrier (not shown). As in this illustrated embodiment, the separation feature 2002 can include a shearing element configured to shear one or more of the fasteners from a carrier (not shown) to which the one or more fasteners are frangibly attached. The shearing element 2002 can be coupled to a sled 2004 configured to urge the fasteners out of the cartridge, as discussed herein. The shearing element 2002 can be a discrete element from the sled 2004, as shown in FIG. 29, or the shearing element and the sled can be integrally formed. When the shearing element 2002 is independent from the sled 2004 as in this illustrated embodiment, the sled 2004 and the shearing element 2002 can include corresponding mating features 2002a, 2004a configured to securely couple the sled 2004 and the shearing element 2002 together.

The shearing element 2002 can have a variety of sizes, shapes, and configurations. As in this illustrated embodiment, the shearing element 2002 can include a plurality of shearing wedges 2006 each configured to shear at least one fastener from the carrier. In an exemplary embodiment, a number of the shearing wedges 2006 can equal a number of the sled's wedges 2008 such that each of the fasteners deployed by a one of the wedges 2008 can be sheared by an associated one of the shearing wedges 2006. The shearing wedges 2006 can generally extend upright and be oriented at angles corresponding to the sled's wedges 2006. In an exemplary embodiment, the shearing wedges 2006 can be taller than the sled's wedges 2008, e.g., extend thereabove when the shearing element 2002 and the sled 2004 are coupled together as shown in FIG. 30. This greater upward reach of the shearing wedges 2006 can help ensure that the shearing wedges 2006 contact the fasteners so as to shear the fasteners. The shearing wedges 2006 may in some embodiments have enough upward reach that they can slide against and/or otherwise contact the cartridge when translating therethrough, which may damage the cartridge. However, releasable and replaceable cartridges are typically used only once, e.g., to once eject fasteners disposed therein, such that damaging the cartridge does not affect effective use of the cartridge.

The shearing wedges 2006 can be sharp, e.g., have sharpened edges, which can help break deployed fasteners off the carrier. The shearing wedges 2006 can be sharp and/or can extend upward of the sled's wedges 2008.

As shown in FIG. 29 and FIG. 30, the shearing element 2002 can be positioned on a proximal side of the sled 2004. The shearing element 2002 can thus be positioned proximal to the wedges 2008 of the sled 2004. The sled 2004 includes four wedges 2008 in this illustrated embodiment, but as mentioned above, a sled can include any number of wedges. In an exemplary embodiment, at least the wedges 2006 of the shearing element 2002 can be positioned entirely proximal to the wedges 2008 of the sled 2004, as in this illustrated embodiment, which can help ensure that the fasteners have been pushed upward as fully as possible by the wedges 2008 prior to the shearing element 2002 shearing the fasteners from the carrier. The shearing element 2002 can be positioned proximal to a cutting element 2010 of the sled 2004, which in this illustrated embodiment includes a knife similar to the above-mentioned cutting element 1134. In an exemplary embodiment, at least the wedges 2006 of the shearing element 2002 can be positioned entirely proximal to the cutting element 2010, as in this illustrated embodiment, which can allow tissue to be cut and fasteners to be deployed into the tissue before the shearing element 2003 facilitates complete detachment of the fasteners from the carrier.

The shearing element 2002 can be disposed within a cartridge. In this way, when the cartridge is configured to be releasably and replaceably coupled to an end effector, the shearing element 2002 can also be so coupled.

A drive beam 2000 can be configured to advance the sled 2004 distally through the cartridge, as discussed herein. Thus, the drive beam 2000 can also be configured to advance the shearing element 2002 distally through the cartridge when the drive beam 2000 advances the sled 2004 therethrough.

Figure 31:
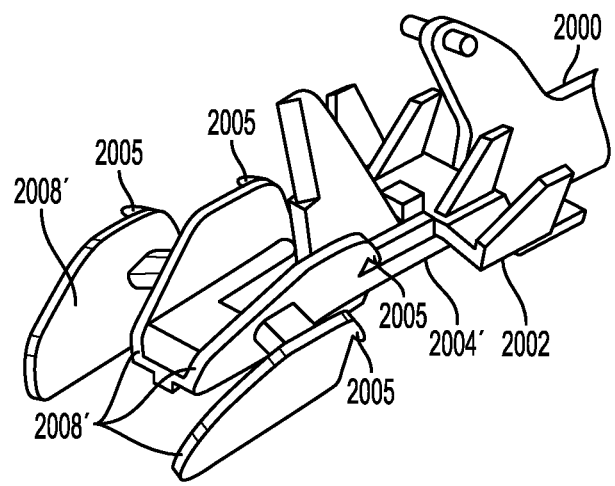
FIG. 31 is a perspective view of the shearing element of FIG. 29 coupled to another embodiment of a sled and to the I-beam of FIG. 29.

FIG. 31 illustrates an alternate embodiment of a sled 2004' that can be configured and used similar to the sled 2004 of FIG. 29 and FIG. 30. Each wedge 2008' of the sled 2004' of FIG. 3 includes a protrusion 2005 extending laterally therefrom. A wedge's protrusion 2005 can be configured to crimp a fastener (not shown) pushed by that wedge 2008', which can help ensure that the fastener is fully crimped, e.g., fully closed, before the shearing element 2002 shears the fastener from the carrier.

As in the embodiments of FIG. 29, FIG. 30, and FIG. 31, the sled 2004 and the shearing element 2002 can be configured to remain in a distal portion of the cartridge after the I-beam 2000 has advanced the sled 2004 and the shearing element 2002 distally through the cartridge. In other words, proximal retraction of the I-beam 2000 through the cartridge after firing of the fasteners does not proximally retract the sled 2004 or the shearing element 2002. The shearing element 2002 thus performs all shearing during distal movement of the shearing element 2002 through the cartridge. In some other embodiments, a sled and a shearing element can be configured to be proximally retracted after an I-beam has advanced the sled and the shearing element distally through a cartridge. The shearing elements in these embodiments can perform all shearing during proximal movement of the shearing element through the cartridge. The fasteners can all be ejected from the cartridge during the distal movement of the sled and the cartridge such that all shearing by the shearing element can be performed after all of the fasteners have been deployed from the cartridge.

Figure 32:
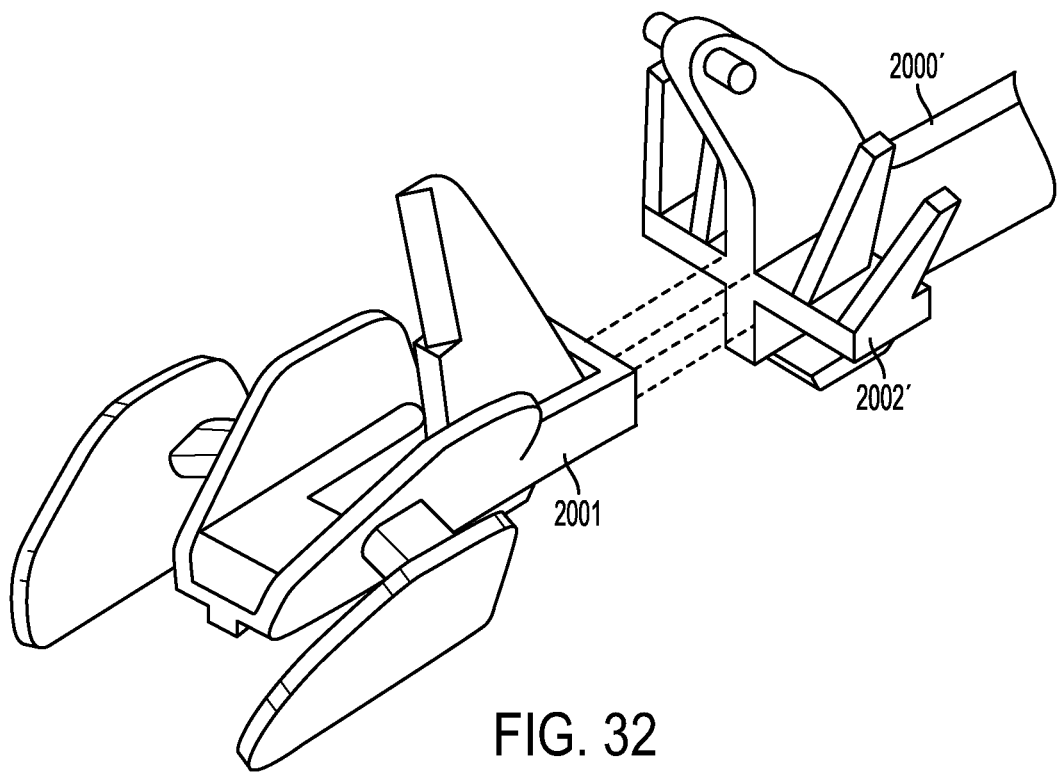
FIG. 32 is a perspective view of another embodiment of a shearing element configured to couple to a sled and an I-beam and be positioned therebetween.
Figure 33:
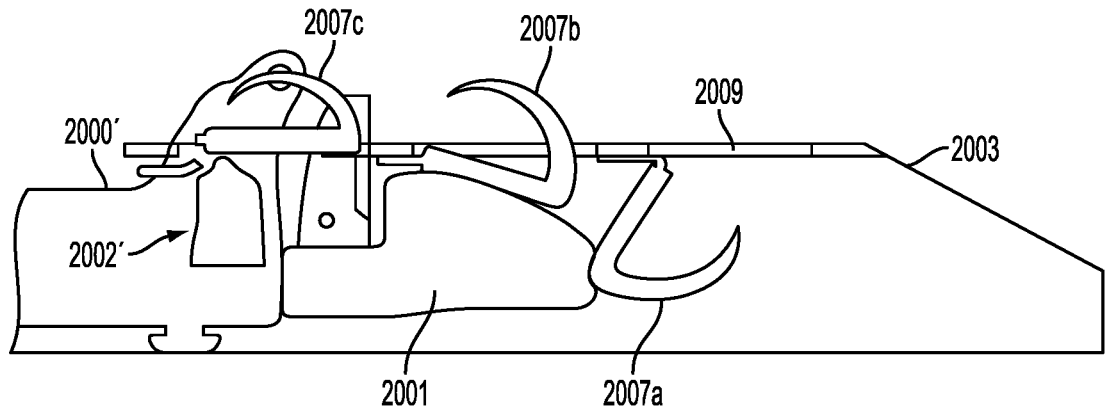
FIG. 33 is a side cross-sectional view of the shearing element, sled, and I-beam of FIG. 32 firing fasteners from a bottom jaw of an end effector.

FIG. 32 illustrates an alternate embodiment of a shearing element 2002' that can be configured and used similar to the shearing element 2002 of FIG. 29 and FIG. 30 except that in this illustrated embodiment, the shearing element 2002' is coupled to an I-beam 2000' instead of to a sled 2001. The shearing element 2002' can thus be included as an integral part of a surgical device, as opposed to being part of a cartridge removably and replaceably attachable to a surgical device. FIG. 33 illustrates the shearing element 2002' disposed within a cartridge (not shown) seated in a bottom jaw 2003 and including a plurality of fasteners 2007a, 2007b, 2007c frangibly attached to a carrier 2009. Two of the fasteners 2007a, 2007b are shown frangibly attached to the carrier 2009. A third one of the fasteners 2007c is shown detached from the carrier 2009, e.g., having been sheared thereof by the shearing element 2002'.

Figure 34:
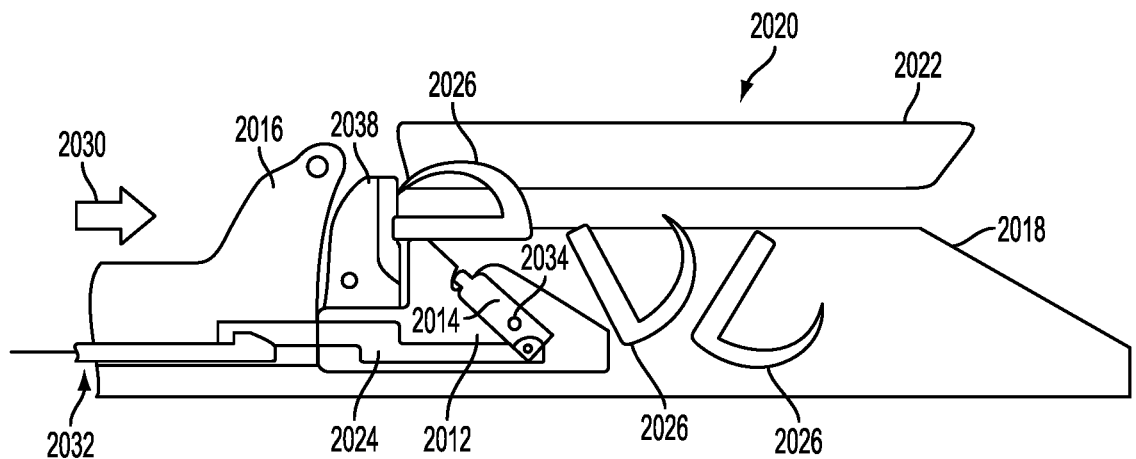
FIG. 34 is a side cross-sectional view of another embodiment of a shearing element, the shearing element being coupled to a sled and an I-beam translating distally through a bottom jaw of an end effector, the shearing element being in a first position.
Figure 35:
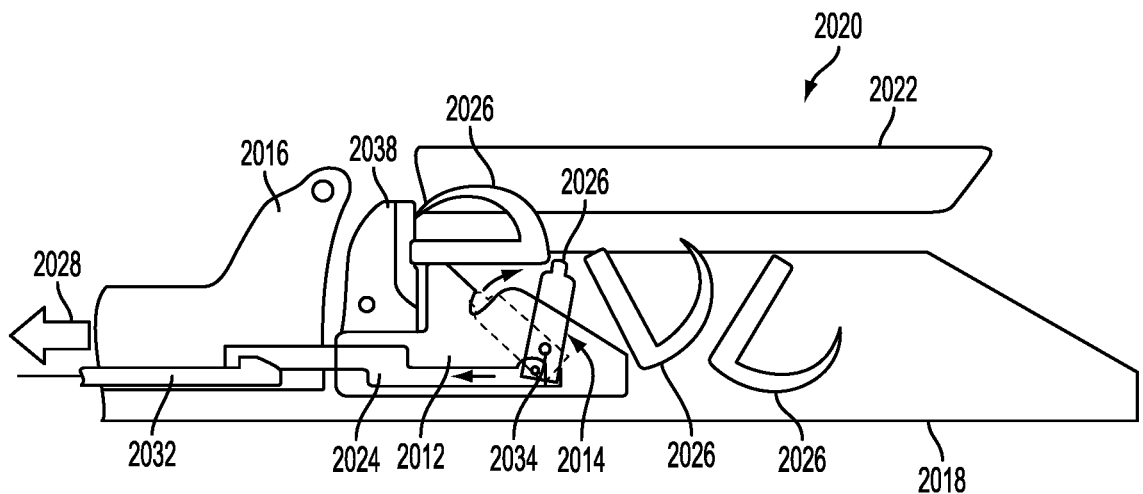
FIG. 35 is a side cross-sectional view of the shearing element, sled, and I-beam of FIG. 34 translating proximally through the bottom jaw, the shearing element being in a second position that is rotated from the first position.

FIG. 34 and FIG. 35 illustrate one embodiment of a sled 2012 and a shearing element 2014 coupled to the sled 2012 that are configured to be proximally retracted in a proximal direction 2028 after an I-beam 2016 has advanced the sled 2012 and the shearing element 2014 distally through a bottom jaw 2018 in a distal direction 2030. The jaw 2018 in this illustrated embodiment is part of an end effector 2020 that also includes an anvil 2022, and has a cartridge (not shown) releasably and replaceably seated in the bottom jaw 2018.

The shearing element 2014 can have a variety of sizes, shapes, and configurations. As in this illustrated embodiment, the shearing element 2014 can include a movable bar. The shearing element 2014 can be movable between a first position, shown in FIG. 34, in which the sled 2012 nests the shearing element 2014, and a second position, shown in FIG. 35, in which the shearing element 2014 extends upwardly above the sled 2012. The shearing element 2014 in the first position can be configured to not shear any fasteners 2026, and the shearing element 2014 in the second position can be configured to shear fasteners 2026. The shearing element 2014 can be configured to move from the first position to the second position, e.g., pivot about a pivot joint 2034, in response to a drive bar 2032 coupled to the drive beam 2016 being moved proximally so as to proximally retract the drive beam 2016. The shearing element 2014 can thus be configured to automatically move from the first position to the second position.

The cartridge can include an attachment bar 2024 configured to removably couple to the drive bar 2032. In response to the cartridge being seated in the bottom jaw 2018, the attachment bar 2024 can clip onto the drive bar 2032, e.g., by a protrusion at a proximal end of the attachment bar 2024 engaging a corresponding protrusion at a distal end of the drive bar 2032. Thus, when the drive bar 2032 moves distally or proximally, the attachment bar 2024 can also move distally or proximally. The attachment bar 2024 can be attached to the sled 2012 such that the movement of the attachment bar 2024 can also cause movement of the sled 2012 and the shearing element 2014 attached thereto. FIG. 34 shows the drive bar 2032 coupled to the attachment bar 2024 and advancing distally in the distal direction 2030 so as to advance the sled 2012 distally with a cutting element 2036 of the sled 2012 pivoted to an upright position and with the shearing element 2014 in the first position. FIG. 35 shows the drive bar 2032 coupled to the attachment bar 2024 and advancing proximally in the proximal direction 2028 so as to advance the sled 2012 proximally with a cutting element 2036 of the sled 2012 in the upright position and with the shearing element 2014 in the second position. Moving the drive bar 2032 proximally can cause the shearing element 2014 to pivot from the first position to the second position since the pivot joint 2034 about which the shearing element 2014 can be configured to pivot can be an attachment point between the shearing element 2014 and the attachment bar 2024.

Figure 36:
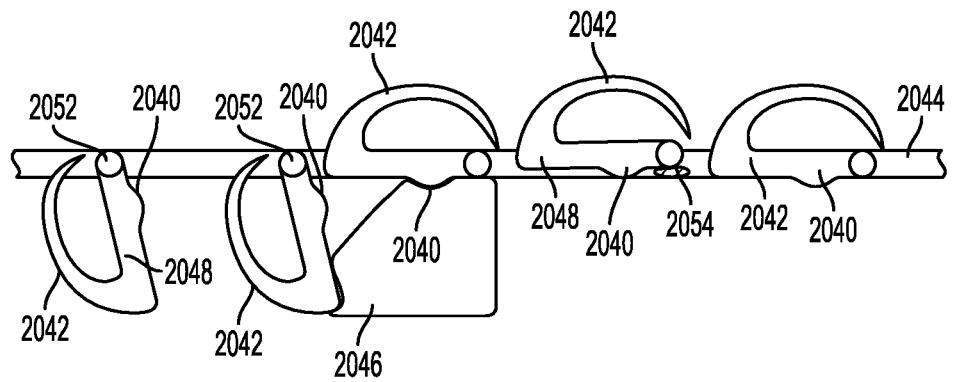
FIG. 36 is a side view of one embodiment of a plurality of fasteners each including a separation feature and each being frangibly attached to a carrier strip, a sled translating relative to the fasteners and the carrier and engaging one of the separation features.
Figure 37:
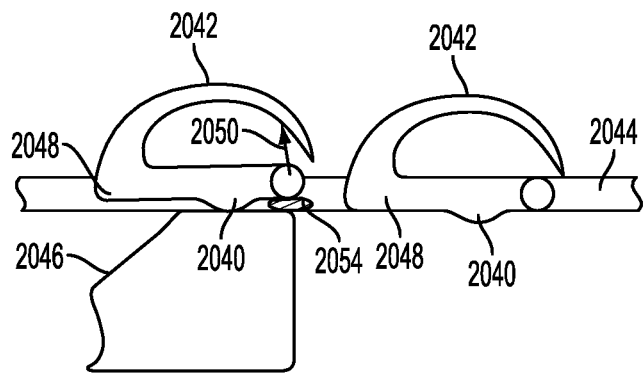
FIG. 37 is a side view of the sled and one of the fasteners of FIG. 36.

In some embodiments, a separation feature can be formed on a fastener. FIG. 36 and FIG. 37 illustrate another embodiment of a separation feature 2040 formed on a fastener 2042 and configured to facilitate ejection of the fastener 2042 from a cartridge (not shown) that has the fastener 2042 disposed therein and connected to a carrier strip 2044. As in this illustrated embodiment, the separation feature 2040 can include a bump formed on the fastener 2042 and configured to engage a sled 2046.

The bump 2040 can have a variety of sizes, shapes, and configurations. The bump 2040 can be formed on a substantially straight leg 2048 of the fastener 2042 and can be formed on an outward-facing surface thereof, thereby allowing the sled 2046 to engage the bump 2040 when contacting and deploying the fastener 2040. The bump 2040 can be configured to bias the fastener 2042 in an upward direction 2050, e.g., toward an anvil coupled to a jaw having the cartridge seated therein. This bias can increase stress on the fastener 2042 at a joint 2052 where the fastener 2042 is frangibly connected to the carrier 2044, thereby allowing the fastener 2042 to more reliably disconnect from the carrier strip 2044. A size of the bump 2040 can be tuned to the stress needed to disconnect the fastener 2042 from the carrier 2044. FIG. 36 and FIG. 37 show one of the fasteners 2042 disconnected from the carrier 2044 such that the joint where the fastener 2042 was frangibly connected to the carrier 2044 is now a broken joint 2054.

In some embodiments, a sled can include a separation feature in the form of a bump similar to the above-mentioned bump 2040. The sled can include the bump in alternative to or in addition to a fastener including a bump such as the above-mentioned bump 2040. The sled and the fastener each including a bump can exert more stress on a joint where the fastener frangibly connects to a carrier than when only one of the sled and the fastener includes a bump, which can allow the fastener to more reliably disconnect from the carrier.

Figure 38:
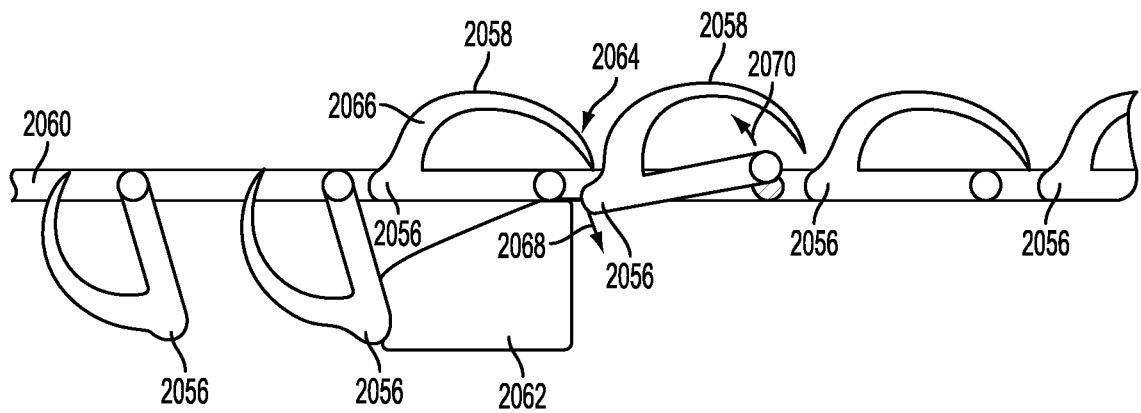
FIG. 38 is a side view of another embodiment of a plurality of fasteners each including a separation feature and each being frangibly attached to a carrier strip, a sled translating relative to the fasteners and the carrier.

FIG. 38 illustrates another embodiment of a separation feature 2056 formed on a fastener and configured to facilitate ejection of the fastener 2058 from a cartridge (not shown) that has the fastener 2058 disposed therein and connected to a carrier strip 2060. Similar to the above-mentioned separation feature 2040, the separation feature 2056 can include a bump formed on the fastener 2056. However, in this illustrated embodiment, the separation feature 2056 is formed at a distal end of the fastener 2058, with the fastener's distal end being with reference to the fastener's position as deployed from a sled 2062 translating distally through the cartridge. The bump 2056 being formed at the fastener's distal end can allow the bump 2056 to engage the fastener 2058 being deployed immediately after the fastener 2056 having its bump 2056 positioned distally with reference to the fastener's position as deployed from the sled 2062. More particularly, a pointed tip 2064 of the fastener's curved leg 2066 can be configured to push against the bump 2056 of the fastener 2056 longitudinally aligned therewith and deployed immediately prior to the fastener 2056 whose tip 2064 pushes the bump 2056, as shown by an arrow 2068. This force applied to the bump 2056 can facilitate detachment from the carrier 2060 of the fastener 2956 whose bump 2056 is being pushed, as shown by an arrow 2070.

In some embodiments, a separation feature can be formed on a cartridge, e.g., the above-mentioned cartridge 1112. In general, the separation feature being formed on the cartridge can be configured to provide counter resistance to a fastener, e.g., the above-mentioned fastener 1116, after the fastener has been pushed upward by a sled, e.g., the sled, and formed. The separation feature can thus help ensure that the fastener disconnects from a carrier to which the fastener is frangibly attached within the cartridge pre-deployment.

Figure 39:
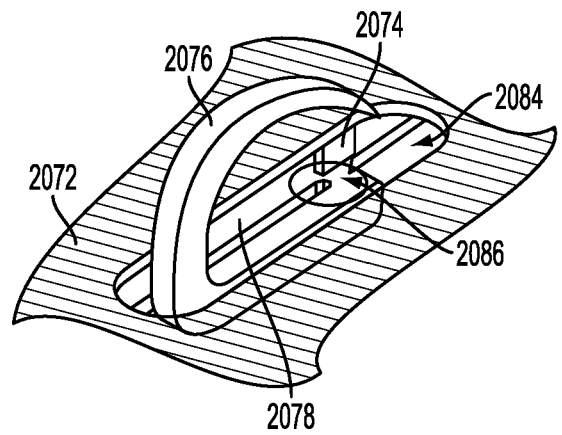
FIG. 39 is a perspective view of one embodiment of a cartridge including a separation feature formed thereon adjacent to a fastener ejectable from the cartridge and frangibly attached to a carrier.
Figure 40:
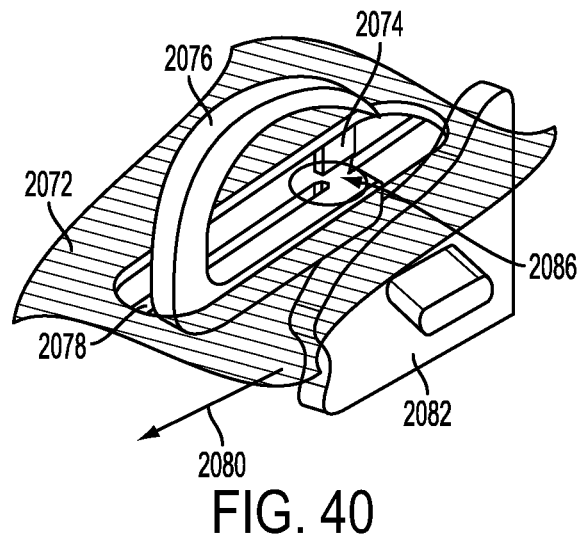
FIG. 40 is a perspective view of the fastener of FIG. 39 translating distally and engaging the fastener.
Figure 41:
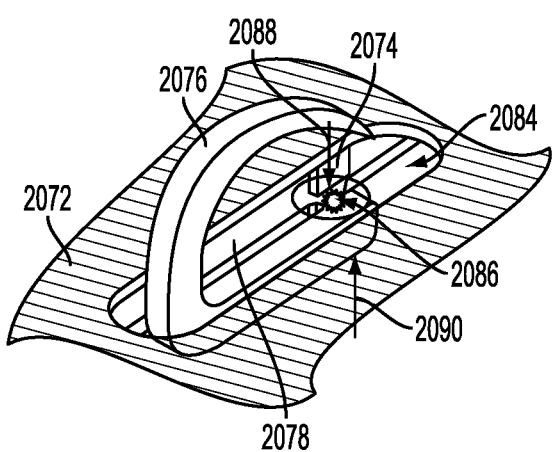
FIG. 41 is a perspective view of the separation feature of FIG. 39 facilitating separation of the fastener of FIG. 40 from the carrier.

FIG. 39, FIG. 40, and FIG. 41 illustrate an embodiment of a cartridge 2072 that includes a plurality of separation features 2074 that can each be configured to facilitate separation of one of a plurality of fasteners 2076 disposed within the cartridge 2072 and frangibly attached to a carrier 2078 disposed within the cartridge 2072. The separation feature 2074 can have a variety of sizes, shapes, and configurations. As in this illustrated embodiment, the separation feature 2074 can include a wall extending upward-downward, e.g., in a direction substantially perpendicular to a direction 2080 in which a sled 2082 can be configured to translate to eject the fasteners 2074 from the cartridge 2072 through openings 2084 formed in the cartridge 2072. For ease of illustration, the sled 2082 is only partially shown in FIG. 40. The wall is rectangular shaped in this illustrated embodiment, but the wall can have other shapes, e.g., square, semi-circular, triangular, etc. In other embodiments, instead of a wall, the separation feature 2074 can include a protrusion, such as a bump, extending from a surface of the cartridge 2072.

Each of the separation features 2074 can be positioned adjacent to a connection point 2086 where its associated fastener 2076 is frangibly attached to the carrier 2078. As in this illustrated embodiment, the separation feature 2074 can be adjacent to and positioned above the connection point 2086. When the sled 2082 translates in the direction 2080, e.g., distally, as shown in FIG. 40, the sled 2082 can cause the fastener 2076 to rotate out of the opening 2084 to be deployed, as discussed herein. As shown in FIG. 41, the separation feature 2074 can be configured to exert a force 2088, e.g., a downward directed force, that opposes a force 2090, e.g., an upward directed force, exerted by the sled 2082. The separation feature's force 2088 can resist the sled's force 2090, thereby facilitating breakage of the fastener 2074 from the carrier 2078 at the connection point 2086.

FIG. 42, FIG. 43, FIG. 44, FIG. 45, and FIG. 46 illustrate another embodiment of a cartridge 2092 that includes a separation feature 2094 that can be configured to facilitate separation of one of a plurality of fasteners 2096 disposed within the cartridge 2092. In this illustrated embodiment, the fasteners 2096 can be disposed within the cartridge 2092 as discrete elements not attached to a carrier, e.g., each of the fasteners 2096 can be disposed in its own pocket formed in the cartridge 2092 below a tissue-engaging surface 2100 of the cartridge 2092. Fasteners being discrete element unattached to a carrier can better guide fasteners during fastener forming and/or can help prevent the fastener from having any jagged edges where the fastener detaches from a carrier. Such jagged edges can be sharp and/or otherwise irritating to tissue in which the fastener is secured. The pocket can have a shape corresponding to a shape of the fastener, which can facilitate rotational forming of the fastener and/or facilitate easy separation of the fastener from the cartridge.

The separation feature 2094 in this illustrated embodiment includes a retainer plate. The retainer plate 2094 can have a variety of sizes, shapes, and configurations. The retainer plate 2098 can define the tissue-engaging surface 2100 and can have a plurality of openings 2102 formed therein through which the fasteners 2096 can be ejected from the cartridge 2092. Each of the openings 2102 can include a first slot extending in a proximal-distal direction and a second slot extending laterally and substantially perpendicular to the first slot such that the opening 2102 can have a "T" shape or a cross shape. The openings 2102 each have a cross shape in this illustrated embodiment. The fasteners 2096 can each include a retention pin 2104 configured to move through the opening 2102, e.g., the second slot thereof, when aligned therewith. The retention pin 2104 can be formed adjacent a proximal end of the fastener 2096, as in this illustrated embodiment, with the fastener's proximal end being with reference to the fastener's position as deployed from a sled 2106 translating in a distal direction 2110 through a bottom jaw 2108 having the cartridge 2092 seated therein. The openings 2102 can thus be configured as key holes through which the fasteners 2096 can be configured to pass so as to be fired out of the cartridge 2092.

Figure 42:
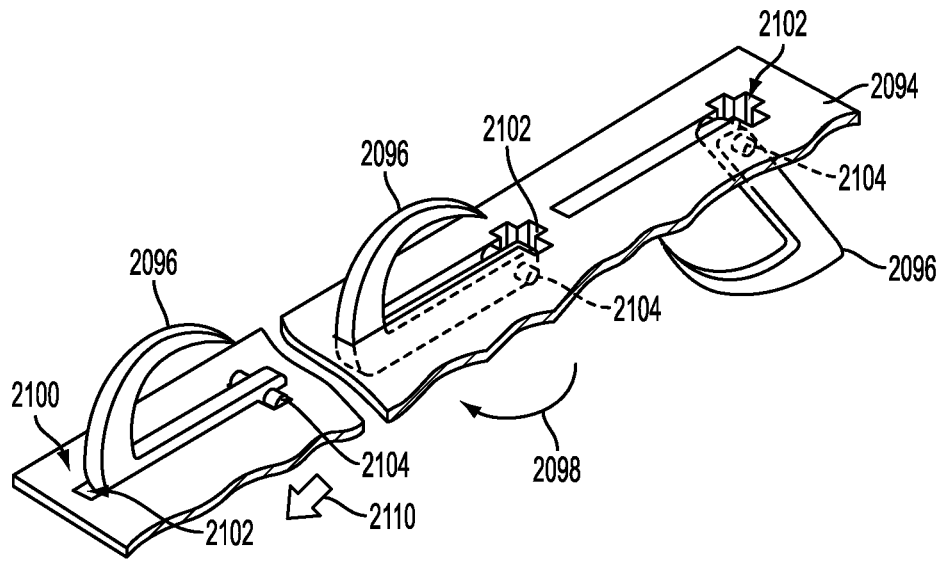
FIG. 42 is a perspective view of another embodiment of a cartridge including a separation feature adjacent to fasteners ejectable from the cartridge and each disposed within a pocket formed in the cartridge.
Figure 43:
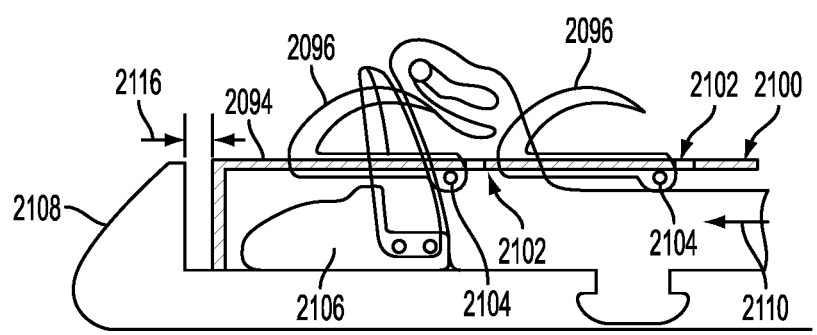
FIG. 43 is a side cross-sectional view of the separation feature of FIG. 42 within a bottom jaw of an end effector, the end effector being in a closed position.

The retainer plate 2094 can be configured to move relative to the fasteners 2096 and to the bottom jaw 2108 to facilitate ejection of the fasteners 2096 from the cartridge 2092. This movement can allow the fasteners 2096 to pass through the openings 2102 by aligning the retention pins 2104 with the opening's second slot. By way of example, a right-most one of the fasteners 2096 in FIG. 42 is shown in a stowed position within the cartridge 2092 below the tissue-engaging surface 2100 prior to the sled's engagement therewith. The middle fastener 2096 in FIG. 42 shows the fastener 2096 moved from the right-most fastener's position, the fastener 2096 having been engaged by the sled 2106 as shown in FIG. 43 to move the fastener 2096 through the opening 2102, e.g., through the first slot thereof, by rotation 2098 thereof. The retention pin 2104 is not aligned with the opening's second slot and is located under the tissue-engaging surface 2100. The left-most fastener 2096 in FIG. 42 shows the fastener 2096 released from the cartridge 2092 after the retention plate 2094 has moved relative to the fasteners 2096 and the bottom jaw 2092.

Figure 44:
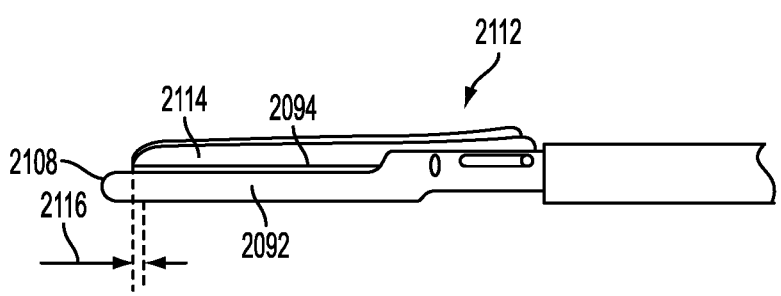
FIG. 44 is a side view of the end effector of FIG. 43.
Figure 45:
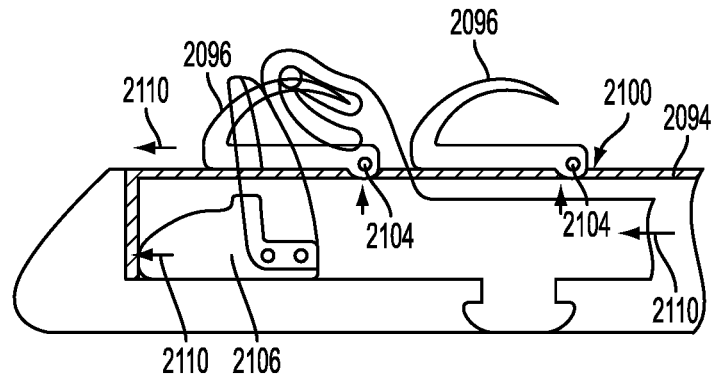
FIG. 45 is a side cross-sectional view of the separation feature of FIG. 43 within the bottom jaw of the end effector, the end effector being in an open position.
Figure 46:
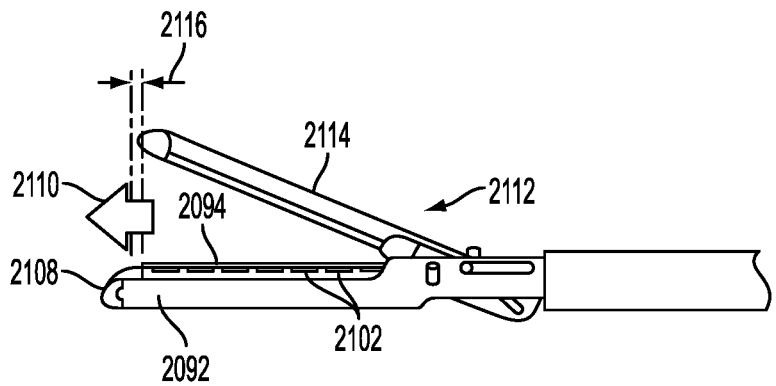
FIG. 46 is a side view of the end effector of FIG. 45.

The retention plate 2094 can be configured to move relative to the fasteners 2096 and the bottom jaw 2092 in response to an end effector 2112 that includes the bottom jaw 2092 and an upper jaw 2114 moving from a closed position, shown in FIG. 43 and FIG. 44, to an open position, shown in FIG. 45 and FIG. 46. As shown in FIG. 43, FIG. 44, FIG. 45, and FIG. 46, the retention plate 2094 can be configured to move distally in response to the opening of the end effector 2112, thereby causing the openings 2102 to align with the fastener 2096 such that the retention pins 2104 can pass therethrough, e.g., pass through the opening's second slots. The fasteners 2096 can thus be configured to all be released from the cartridge 2092 substantially simultaneously in response to the movement of the retention plate 2094. As shown in FIG. 43, FIG. 44, FIG. 45, and FIG. 46 illustrate that the retention plate 2094 can move a distance 2116 in the distal direction 2110 in response to the end effector 2112 opening.

FIG. 47, FIG. 48, FIG. 49, FIG. 50, FIG. 51, and FIG. 52 illustrate another embodiment of a cartridge 2118 that includes a separation feature 2120 that can be configured to facilitate separation of one of a plurality of fasteners 2122 disposed within the cartridge 2118. In this illustrated embodiment, the fasteners 2122 can be disposed within the cartridge 2118 as discrete elements not attached to a carrier.

The separation feature 2120 in this illustrated embodiment includes at least one tab. In general, each of the at least one tabs 2120 can be configured to retain one of the fasteners 2122 within the cartridge 2118 until a sled 2124 engages the fastener 2122 and urges the fastener 2122 upward, e.g., toward an anvil (not shown). The at least one tab 2120 can have a variety of sizes, shapes, and configurations. As in this illustrated embodiment, the at least one tab 2120 can include opposed tabs, one proximal tab and one distal tab. The cartridge 2118 can include a plurality of openings 2126 formed in a tissue-engaging surface 2128 thereof, with one of the separation features 2120 being adjacent to each one of the openings 2126, e.g., with each of the openings 2126 having associated therewith one proximal tab and one distal tab. Similar to the openings 2102 of FIG. 42, each of the openings 2126 can include a first slot extending in a proximal-distal direction and a second slot extending laterally and substantially perpendicular to the first slot such that the opening 2126 can have a "T" shape or a cross shape. The separation feature 2120 can be located at the second slot, as in this illustrated embodiment.

Figure 47:
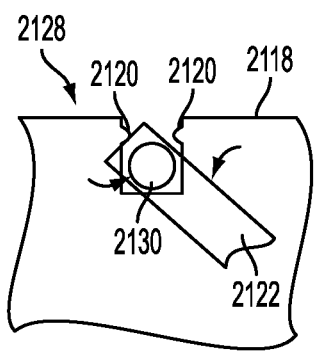
FIG. 47 is a side view of another embodiment of a cartridge including a separation feature adjacent to a fastener ejectable from the cartridge and disposed in a first position within a pocket formed in the cartridge.
Figure 48:
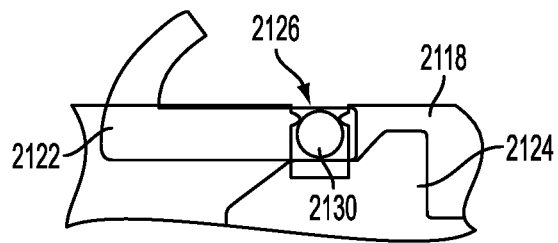
FIG. 48 is a side view of the separation feature and fastener of FIG. 47 with a sled engaging the fastener and with the fastener moved to a second position from the first position.
Figure 49:
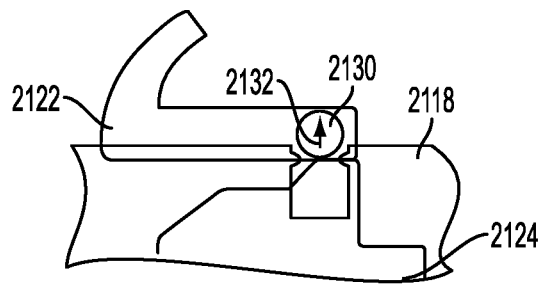
FIG. 49 is a side view of the separation feature and fastener of FIG. 48 with the sled engaging the fastener and with the fastener moved to a third position from the second position.
Figure 50:
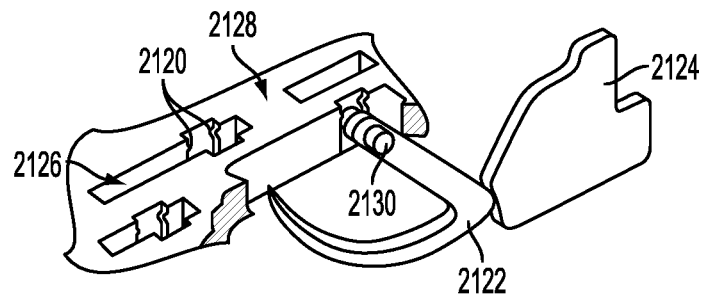
FIG. 50 is a perspective view of the fastener of FIG. 47 engaged with the sled of FIG. 48.
Figure 51:
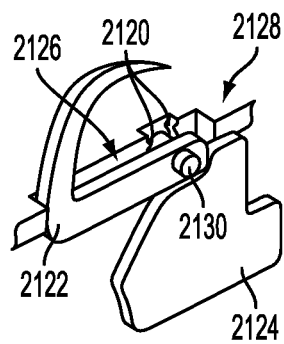
FIG. 51 is a perspective view of the fastener and sled of FIG. 48.
Figure 52:
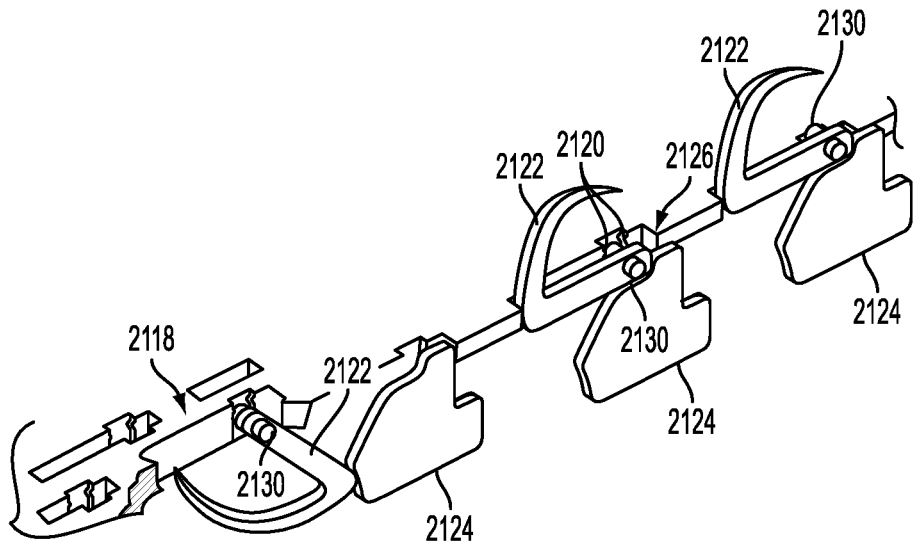
FIG. 52 is a perspective view from left to right of the fastener and sled of FIG. 50, the fastener and sled of FIG. 51, and the fastener and sled of FIG. 49.

Each of the fasteners 2122 can include a retention pin 2130. The retention pin 2130 and the at least one tab 2120 can be configured to cooperate to retain the fastener 2122 within the cartridge 2118 pre-deployment, as shown in FIG. 47, FIG. 50, and FIG. 52 (the left-most fastener 2122). In response to the sled 2124 engaging the fastener 2122, e.g., by translating distally through the cartridge 2118, the sled 2124 can cause the fastener 2122 to rotate, as shown in FIG. 48, FIG. 51, and FIG. 52 (the middle fastener 2122). The sled's continued distal advancement can, as shown in FIG. 49 and FIG. 52 (the right-most fastener 2122), cause the fastener 2122 to be pushed over the at least one tab 2120 and thereby be released from the cartridge 2118. The sled 2124 can thus be configured to provide enough of an upward force 2132, shown in FIG. 49, to push the fastener's retention pin 2130 past the at least one tab 2120. The fasteners 2122 can thus be released sequentially from the cartridge 2118 as the sled 2124 engages and pushes each of the fasteners 2122.

Figure 53:
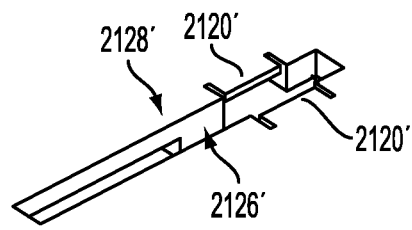
FIG. 53 is a perspective view of another embodiment of a cartridge including a separation feature.

FIG. 53 illustrates an alternate embodiment of a separation feature 2120' in the form of at least one tab that can be configured and used similar to the at least one tab 2120 of FIG. 47. In this illustrated embodiment, the at least one tab 2120' includes first and second tabs positioned on lateral sides of an opening 2126' formed in a tissue-engaging surface 2128' of a cartridge. Similar to the openings 2126 of FIG. 47, each of the openings 2126' can include a first slot extending in a proximal-distal direction and a second slot extending laterally and substantially perpendicular to the first slot such that the opening 2126' can have a "T" shape or a cross shape, and the separation feature 2120' can be extend into the second slot.

Figure 54:
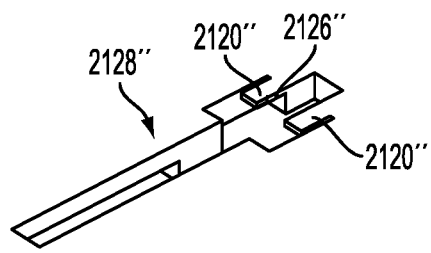
FIG. 54 is a perspective view of yet another embodiment of a cartridge including a separation feature.
Figure 55:
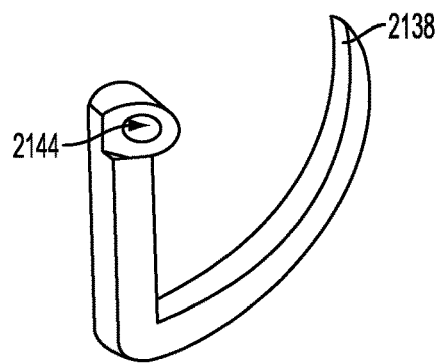
FIG. 55 is a perspective view of one embodiment of a fastener that includes a camming surface.
Figure 56:
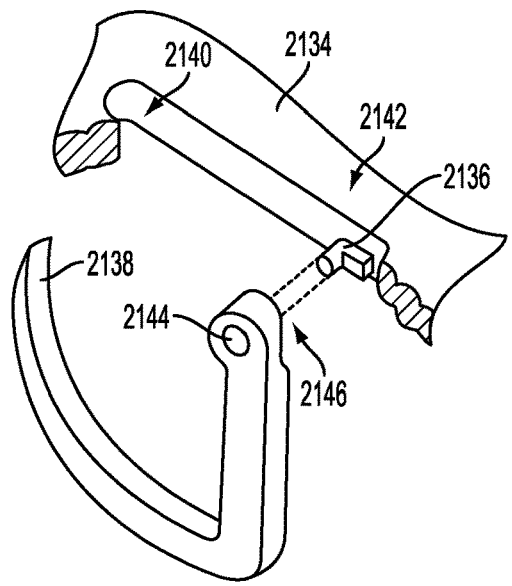
FIG. 56 is a perspective view of the fastener of FIG. 55 and another embodiment of a cartridge including a separation feature.

FIG. 54 illustrates another alternate embodiment of a separation feature 2120" in the form of at least one tab that can be configured and used similar to the at least one tab 2120 of FIG. 47. In this illustrated embodiment, the at least one tab 2120" includes first and second tabs positioned on a proximal side of an opening 2126" formed in a tissue-engaging surface 2128" of a cartridge. Similar to the openings 2126 of FIG. 47, each of the openings 2126" can include a first slot extending in a proximal-distal direction and a second slot extending laterally and substantially perpendicular to the first slot such that the opening 2126"

can have a "T" shape or a cross shape, and the separation feature 2120" can extend into the second slot.

FIG. 55, FIG. 56, FIG. 57, FIG. 58, and FIG. 59 illustrate another embodiment of a cartridge 2134 that includes a separation feature 2136 that can be configured to facilitate separation of one of a plurality of fasteners 2138 disposed within the cartridge 2134. In general, each one of the separation features 2136 can be configured to cooperate with one of the fasteners 2138 to cause the fastener 2138 to move laterally relative to the separation feature 2136, e.g., relative to the cartridge 2134, to facilitate firing of the fastener 2138 through one of a plurality of openings 2140 formed in the cartridge 2134. In this illustrated embodiment, the fasteners 2138 can be disposed within the cartridge 2134 as discrete elements not attached to a carrier.

Figure 57:
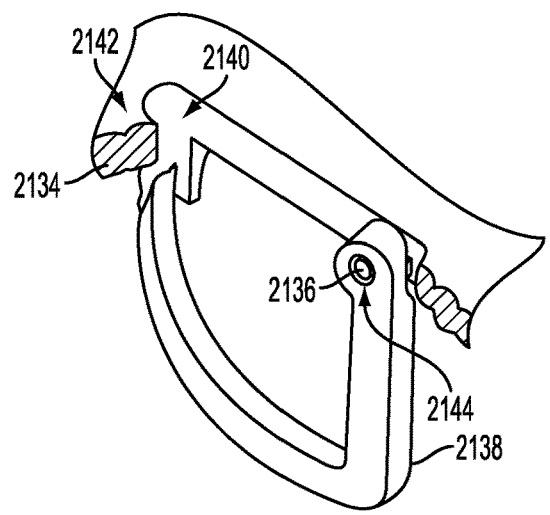
FIG. 57 is a perspective view of the fastener and cartridge of FIG. 56 with the fastener removably coupled to the separation feature and in a first position.
Figure 58:
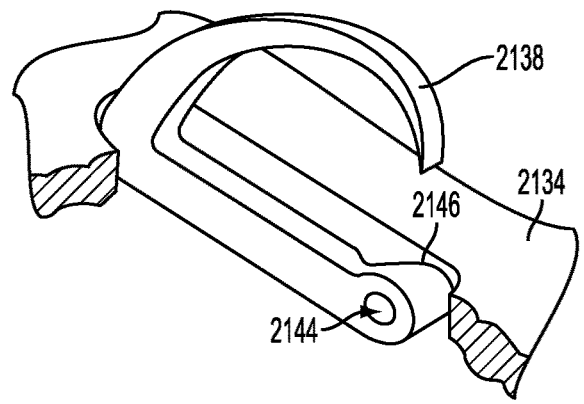
FIG. 58 is a perspective view of the fastener and cartridge of FIG. 57 with the fastener moved to a second position from the first position.
Figure 59:
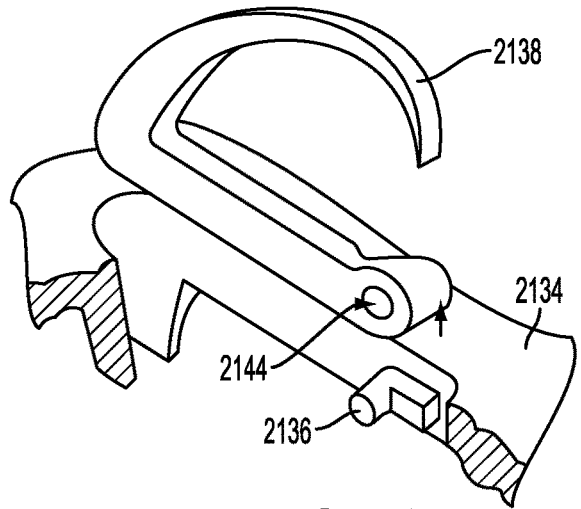
FIG. 59 is a perspective view of the fastener and cartridge of FIG. 58 with the fastener moved to a third position from the second position.
Figure 60:
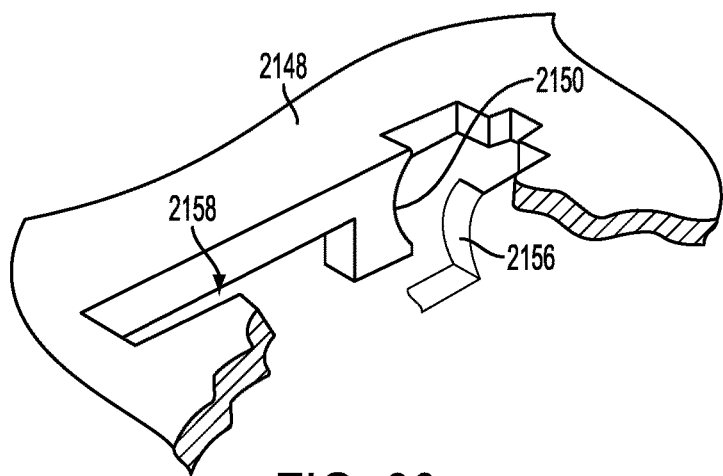
FIG. 60 is a perspective view of another embodiment of a fastener that includes a camming surface and another embodiment of a cartridge including a separation feature.
Figure 61:
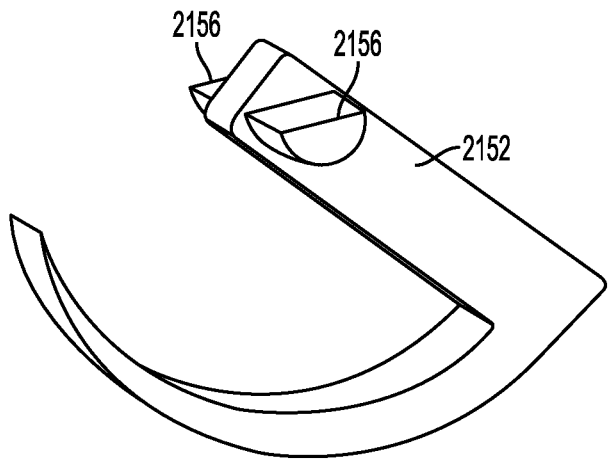
FIG. 61 is a perspective view of the fastener of FIG. 60.

The separation feature 2136 in this illustrated embodiment includes a post configured to releasably engage the fastener 2138. The post 2136 can have a variety of sizes, shapes, and configurations. As in this illustrated embodiment, the post 2136 can be located adjacent the opening 2140 and can extend laterally from an internal surface of the cartridge 2134 below a tissue-engaging surface 2142 of the cartridge 2134. The post 2136 can be configured to be seated in a hole 2144 formed in its associated fastener 2136 when the fastener 2136 is disposed within the cartridge 2134, as shown in FIG. 57. The fastener 2136 can include a cam surface 2146 adjacent the hole 2144 that can be configured to slidably engage the post 2136 when the fastener 2138 is being rotated out of the opening 2140 in response to an urging force from a sled (not shown) translating through the cartridge 2134, as shown in FIG. 58. A longitudinal axis of the post 2136 can define an axis of the fastener's rotation. The cam surface's engagement with the post 2136 can cause the fastener 2138 to move laterally relative to the post 2136 and a remainder of the cartridge 2134. In other words, the cam surface 2146 can cause the fastener 2138 to be cammed laterally. The lateral movement of the fastener 2136 can cause the post 2136 to move out of the hole 2144, thereby allowing the fastener 2136 to exit the opening 2140, as shown in FIG. 59. The fasteners 2138 can thus be released sequentially from the cartridge 2134 as the sled engages and pushes each of the fasteners 2138.

FIG. 60, FIG. 61, FIG. 62, FIG. 63, FIG. 64, and FIG. 65 illustrate another embodiment of a cartridge 2148 that includes a separation feature 2150 that can be configured to facilitate separation of one of a plurality of fasteners 2152 disposed within the cartridge 2148. In this illustrated embodiment, the fasteners 2152 can be disposed within the cartridge 2148 as discrete elements not attached to a carrier. In general, each one of the separation features 2150 can be configured to cooperate with a retention feature 2156 of one of the fasteners 2152 to cause the fastener 2152 to exit the cartridge 2148 through one of a plurality of openings 2158 formed in the cartridge 2148.

Figure 62:
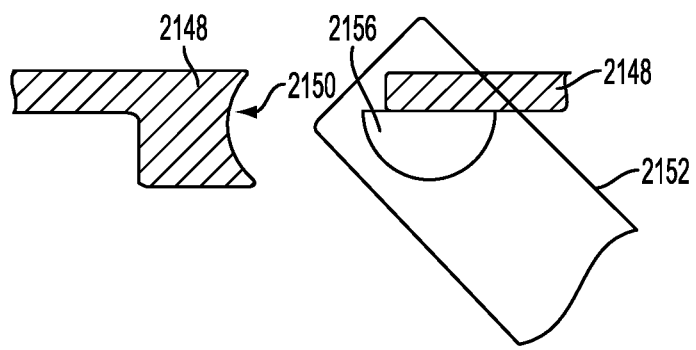
FIG. 62 is a side, partially cross-sectional view of the fastener and cartridge of FIG. 60, the fastener being in a first position.
Figure 63:
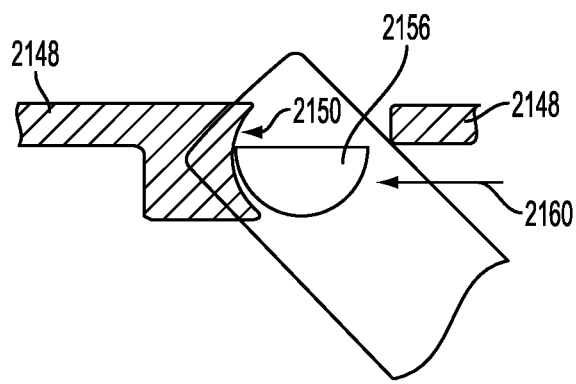
FIG. 63 is a perspective view of the fastener and cartridge of FIG. 62 with the fastener moved to a second position from the first position.
Figure 64:
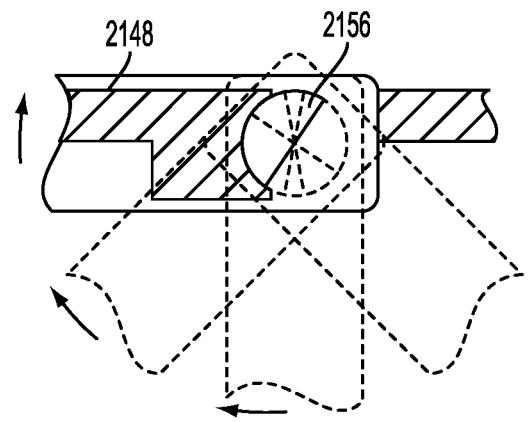
FIG. 64 is a perspective view of the fastener and cartridge of FIG. 63 with the fastener moved to a third position from the second position.

The separation feature 2150 in this illustrated embodiment includes a cam surface 2154 configured to engage the corresponding retention feature 2156, e.g., a cam, of the fastener 2152. The cam surface 2154 and the cam 2156 can have a variety of sizes, shapes, and configurations. As in this illustrated embodiment, the cam surface 2154 can have a curved shape, and the cam 2156 can have a corresponding curved shape configured to slidably engage the cam surface 2154, as shown in FIG. 63 and FIG. 64. In addition to its curved surface, the cam 2156 can have a substantially flat surface. The cam's substantially flat surface can be configured to engage an inner surface of the cartridge 2148 when the fastener 2152 is disposed within its pocket formed in the cartridge 2148, as shown in FIG. 62. The engagement of the cam's substantially flat surface and the cartridge's inner surface can facilitate retention of the fastener 2152 within the cartridge 2148 until a sled (not shown) translates through the cartridge 2148 to rotate the fastener 2152 and thereby urge the fastener 2152 out of the opening 2158. In this illustrated embodiment, the cam 2156 includes two pins each having a half moon shape and each extending laterally from the fastener 2152 adjacent a proximal end of the fastener 2152, but the cam 2156 can, as mentioned above, have other shapes and configurations. For example, a fastener can include only one pin extending laterally from one side of the fastener, can include only one pin extending through the fastener to extend laterally from opposed sides thereof, etc.

Figure 65:
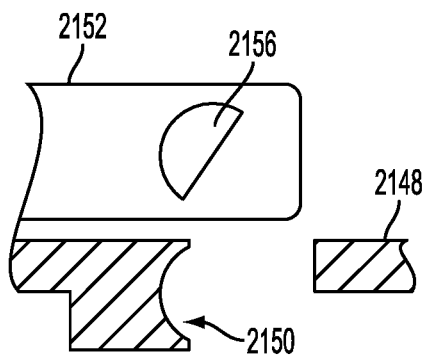
FIG. 65 is a perspective view of the fastener and cartridge of FIG. 63 with the fastener moved to a fourth position from the third position.

As shown in FIG. 62, the fastener 2152 can be disposed within the cartridge 2148 in a first position with the cam 2156, e.g., the substantially flat surface thereof, engaging the inner surface of the cartridge 2148. When the sled translates in a distal direction 2160 through the cartridge 2148 and engages the fastener 2152, the fastener 2152 can be pushed in the distal direction 2160 such that the cam 2156 disengages from the inner surface of the cartridge 2156 and contacts the cam surface 2150, as shown in FIG. 63. As shown in FIG. 64, continued distal movement of the sled can cause the cam 2156, e.g., the curved surface thereof, to slidably engage the cartridge's cam surface 2150, thereby causing the fastener 2152 to rotate. The fastener 2152 can then rotate out of the opening 2158, as shown in FIG. 65.

In some embodiments, a surgical device such as the above-mentioned surgical device 1100 can be configured to facilitate guidance of fasteners during deployment of the fasteners into tissue. In general, the surgical device can include one or more guidance features configured to facilitate guidance of the fasteners during ejection of the fasteners from the cartridge. The one or more guidance features can be configured to reduce lateral movement of the fasteners during deployment thereof, thereby allowing the fasteners to be more accurately positioned within the tissue relative to one another and relative to the tissue. By helping to guide the fastener into the tissue, the fastener can be less likely to skew laterally during deployment into the tissue due to resistance of the tissue and/or tissue flow can be reduced during fastener deployment. The fasteners can thus be effectively positioned relative to one another and to the tissue to facilitate proper healing and/or sealing of the tissue. This can be particularly beneficial in relatively thick tissue because the tissue can provide relatively high resistance to the fastener being deployed therein. In an exemplary embodiment, each of the one or more guidance features can be configured to support a fastener on three sides thereof during deployment of the fastener, thereby helping to minimize lateral movement of the fastener during the deployment. The one or more guidance features can be formed on the cartridge, e.g., formed on a surface thereof or formed on a sled disposed in the cartridge, and/or can be formed on a jaw that seats the cartridge.

A surgical device can be configured to guide fasteners during deployment thereof in a variety of ways. In the embodiments described below, staples are used as examples of fasteners, but as will be appreciated by a person skilled in the art, other types of fasteners can be similarly configured and used.

Figure 66:
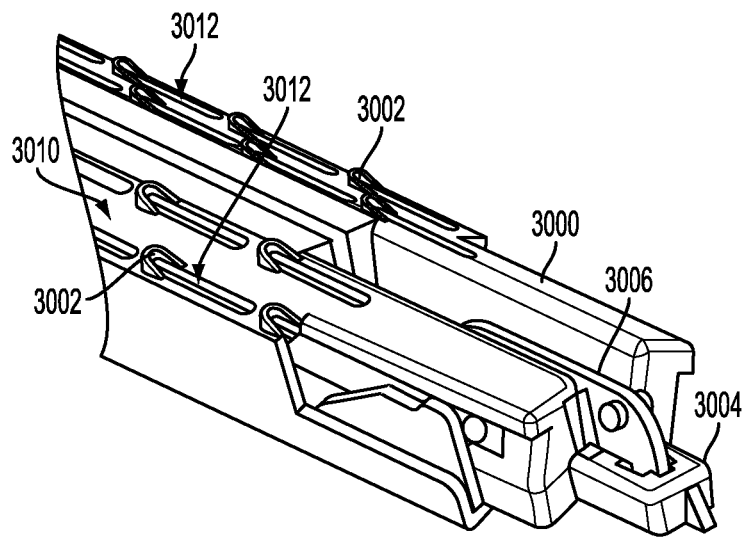
FIG. 66 is a perspective view of one embodiment of a cartridge including a plurality of guidance features and having a plurality of fasteners disposed therein.
Figure 67:
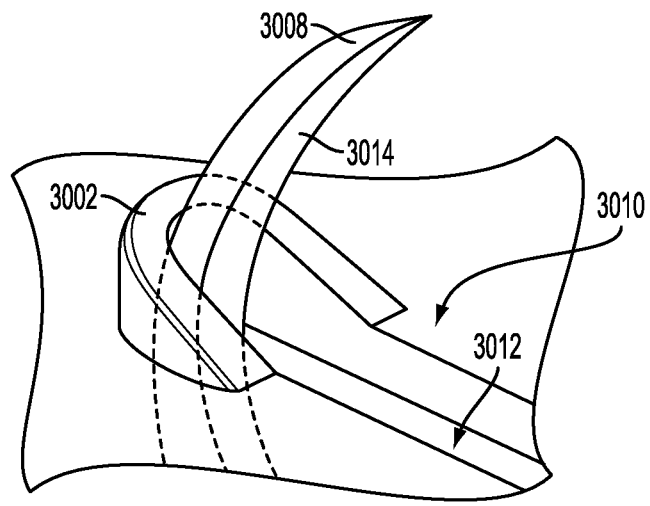
FIG. 67 is a perspective view of one of the fasteners of FIG. 66 being deployed and guided by one of the guidance features.

In some embodiments, a cartridge having a plurality of fasteners disposed therein can include one or more guidance features, also referred to herein as "guide members," configured to guide the fasteners during firing of the fasteners from the cartridge. As discussed herein, the cartridge can be configured to be removably and replaceably seated in an end effector of a surgical device. FIG. 66 and FIG. 67 illustrate one embodiment of a cartridge 3000 that includes a plurality of fasteners 3008 disposed therein, a sled 3004 including a movable cutting element 3006, and one or more guide members 3002 configured to guide the fasteners 3008 during firing of the fasteners 3008 from the cartridge 3000. In this illustrated embodiment, the fasteners 3008 include staples similar to the above-mentioned staples 1116, but as also mentioned above, other types of staples or fasteners can be used. As in this illustrated embodiment, the one or more guide members 3002 can each be formed on and protrude upward from a tissue-engaging surface 3010 of the cartridge 3000, e.g., in a direction toward an anvil (not shown) of the surgical device. The guidance provided by the guide members 3002 can thus be provided after the fasteners 3008 have at least partially exited their respective fastener-receiving recesses 3012 so as to pass above the tissue-engaging surface 3010. The guide members 3002 protrude upward from the tissue-engaging surface 3010 can allow the guide members 3002 to be located in a gap of space between the tissue-engaging surface 3010 and a tissue-engaging surface (not shown) of the anvil, which can help grip tissue positioned within the gap of space. Movement or flow of the tissue within the gap of space can thus be reduced, which can allow the tissue to be more effectively fastened.

The guide members 3002 can have a variety of sizes, shapes, and configurations. Each of the guide members 3002 can have an inner arcuate surface, as in this illustrated embodiment. The inner arcuate surface can be configured to guide a second leg 3014 of the staple 3008 along an arcuate path as the staple 3008 is being deployed into a tissue (not shown). As discussed herein, the staple 3008 can also include a substantially straight first leg (not shown) connected to the curved second leg 3014. The inner arcuate surface of each of the guide members 3002 can be shaped to mimic a curvature of the fastener's second leg 3014, thereby helping to maximize an amount of movement support for the fastener 3008 during deployment thereof. As in this illustrated embodiment, the guide members 3002 can each be U-shaped with opposed sidewalls and a curved intermediate portion connecting the sidewalls. As shown in FIG. 67, the sidewalls can be configured to support and maintain alignment of the fastener during deployment. Being opposed, the sidewalls can help prevent lateral movement of the fastener 3008 during deployment. As shown in FIG. 67, the opposed sidewalls and the curved intermediate portion can be configured to contact three sides of the fastener 3008 as the fastener is guided by the guide member 3002 during deployment, thereby helping to prevent lateral movement of the fastener 3008 due to the sidewalls and helping to prevent distal movement of the fastener 3008 due to the intermediate portion.

Each of the guide members 3002 can be formed adjacent to and on a distal side of their respective fastener-receiving recesses 3012, as shown in this illustrated embodiment. In this way, when the fasteners 3008 are driven out of the cartridge 3000 in response to distal translation of the sled 3004 through the cartridge, the guide members 3002 can be configured to guide their respective fasteners' second legs 3014 as the second legs 3014 rotate out of the cartridge 3002 to lead the fasteners 3008 out of the cartridge 3002.

In the embodiment of FIG. 66, the one or more guide members 3002 are located above the tissue-engaging surface 3010. In other embodiments, a cartridge can include one or more guide members located below a tissue-engaging surface of the cartridge. Being located below the tissue-engaging surface can help prevent the guide members from snagging on and/or otherwise interfering with tissue engaged by the cartridge and/or from affecting an amount of space between facing tissue engagement surfaces of an end effector within which tissue can be positioned and clamped. In some embodiments, a cartridge can include one or more guide members that are located both above and below a tissue-engaging surface thereof.

Figure 68:
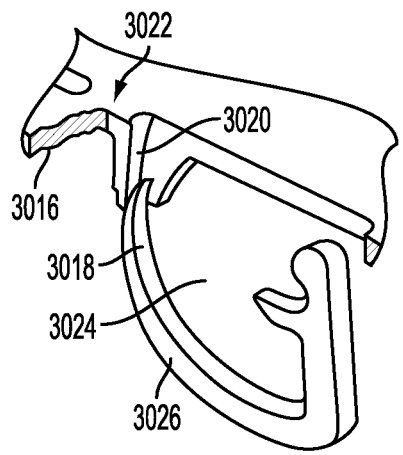
FIG. 68 is a perspective, partially cross-sectional view of another embodiment of a cartridge including a plurality of guidance features and having a plurality of fasteners disposed therein.
Figure 69:
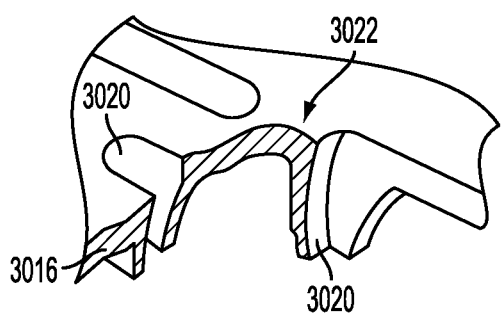
FIG. 69 is another perspective, partially cross-sectional view of the cartridge of FIG. 68 without the fasteners disposed therein.
Figure 70:
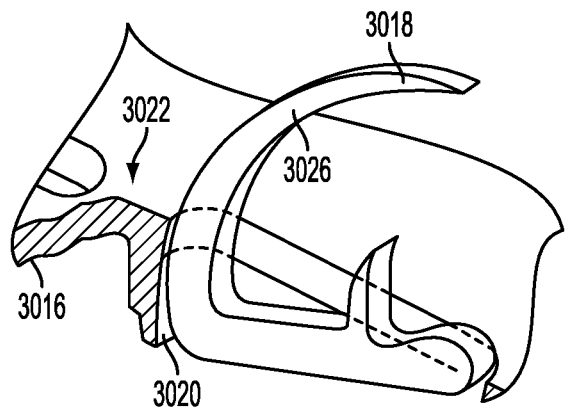
FIG. 70 is another perspective, partially cross-sectional view of the cartridge of FIG. 68 with one of the fasteners being deployed and guided by one of the guidance features.

FIG. 68, FIG. 69, and FIG. 70 illustrate another embodiment of a cartridge 3016 that includes a plurality of fasteners 3018 disposed therein, a sled (not shown), and one or more guide members 3020 configured to guide the fasteners 3018 during firing of the fasteners 3018 from the cartridge 3016. The fasteners 3018, the cartridge 3016, and the guide members 3020 can be generally configured and used similar to the fasteners 3008, the cartridge 3000, and the guide members 3002, respectively, of FIG. 66 and FIG. 67. In this illustrated embodiment, however, the one or more guide members 3020 are each located below a tissue-engaging surface 3022 of the cartridge 3016 and are each formed adjacent to and on a distal side of a staple-receiving recess 3024. Similar to the guide members 3002 of FIG. 66, the guide members 3020 can each include opposed sidewalls (best shown in FIG. 69) and an inner arcuate surface shaped to mimic a curvature of the fastener's second leg 3026, thereby allowing the guide members 3020 to support their associated fasteners 3008 on three sides thereof during fastener deployment.

As discussed above, one or more guide members can be formed on a surface of a cartridge. In other embodiments, as mentioned above, a cartridge can include one or more guide members formed on a sled disposed within the cartridge and configured to translate therethrough to drive fasteners out of the cartridge. The sled can thus be configured to support and maintain alignment of fasteners being deployed in response to the sled's translation relative thereto. The sled including guidance features can help allow existing cartridges to be only slightly modified, or not modified at all, in order to include guidance features because the sleds including guidance features can be incorporated into the existing cartridges.

Figure 71:
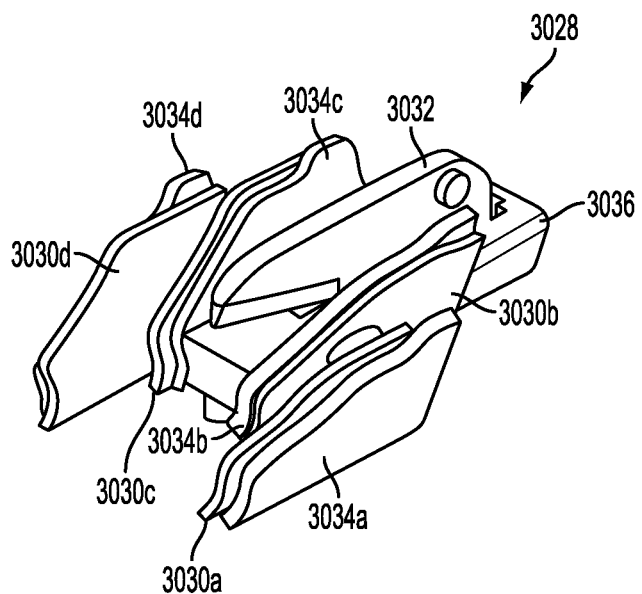
FIG. 71 is a perspective view of one embodiment of a sled that includes a plurality of guidance features.
Figure 72:
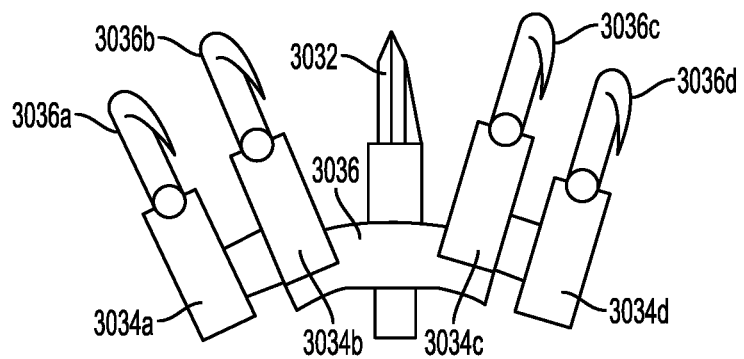
FIG. 72 is an end view of the sled of FIG. 71 with a plurality of fasteners engaged with the plurality of guidance features.
Figure 73:
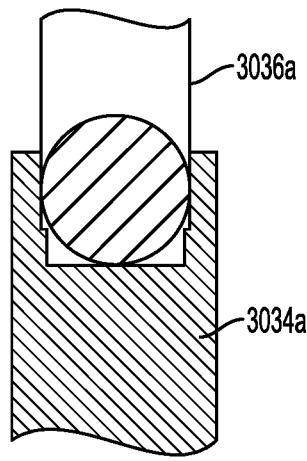
FIG. 73 is a cross-sectional view of one of the fasteners and one of the guidance features of FIG. 72.

FIG. 71 illustrates one embodiment of a sled 3028 that includes one or more guide members 3030a, 3030b, 3030c, 3030d, a cutting element 3032 configured to move between first and second positions, one or more wedges 3034a, 3034b, 3034c, 3034d configured to drive fasteners from the cartridge, and a base 3036. The sled 3028 can be used with any of the cartridges discussed herein. Each of the wedges 3034a, 3034b, 3034c, 3034d can have one of the guide members 3030a, 3030b, 3030c, 3030d associated therewith. Thus, a number of the wedges 3034a, 3034b, 3034c, 3034d can equal a number of the guide members 3030a, 3030b, 3030c, 3030d. As in this illustrated embodiment, as also shown in FIG. 72 and FIG. 73, the guide members 3030a, 3030b, 3030c, 3030d can include lateral guide walls of the wedges 3034a, 3034b, 3034c, 3034d. The guide walls can be configured to provide lateral support to fasteners being deployed by the sled 3028 via engagement with the wedges 3034a, 3034b, 3034c, 3034d. Without the guide walls, the fastener may only receive guidance from a pivot point about which the fastener rotates during deployment thereof. This pivot point, however, is weak when the fastener is configured to break off from the pivot point during fastening, such as with the fasteners 1116 in the above-mentioned device 1100.

As shown in FIG. 72 and FIG. 73, when the sled 3028 engages fasteners 3036a, 3036b, 3036c, 3036d so as to push and deploy the fasteners 3036a, 3036b, 3036c, 3036d, the guide walls defined by the guide members 3030a, 3030b, 3030c, 3030d can engage the fasteners 3036a, 3036b, 3036c, 3036d and provide directional movement guidance such that lateral movement of the fasteners 3036a, 3036b, 3036c, 3036d can be minimized. In this illustrated embodiment, the fasteners 3036a, 3036b, 3036c, 3036d include staples similar to the above-mentioned staples 1116, but as also mentioned above, other types of staples or fasteners can be used.

As discussed above, one or more guide members can be formed on a surface of a cartridge and/or can be formed on a sled. In other embodiments, as mentioned above, a jaw that seats a cartridge, e.g., a jaw configured to releasably and replaceably receive a cartridge, can include one or more guide members. The jaw, and hence an end effector that includes the jaw, can thus be configured to support and maintain alignment of fasteners being deployed therefrom. The jaw including guidance features can help allow existing cartridges to be used with a device including guidance features without the cartridges having to be modified.

Figure 74:
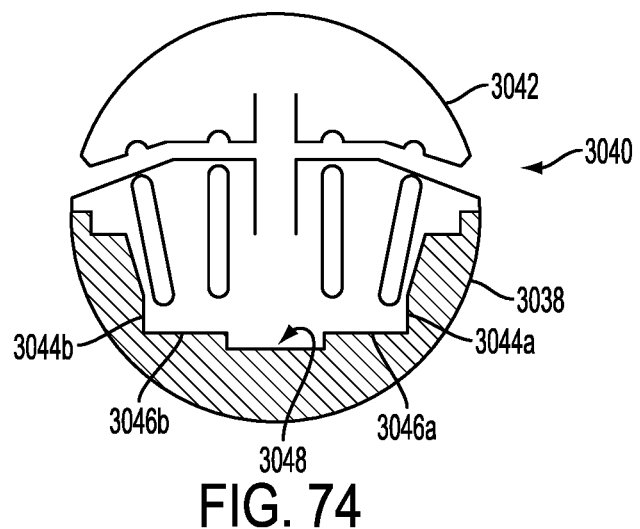
FIG. 74 is a cross-sectional view of one embodiment of a bottom jaw that includes a plurality of guidance features, the bottom jaw being part of an end effector that also includes an upper jaw.
Figure 75:
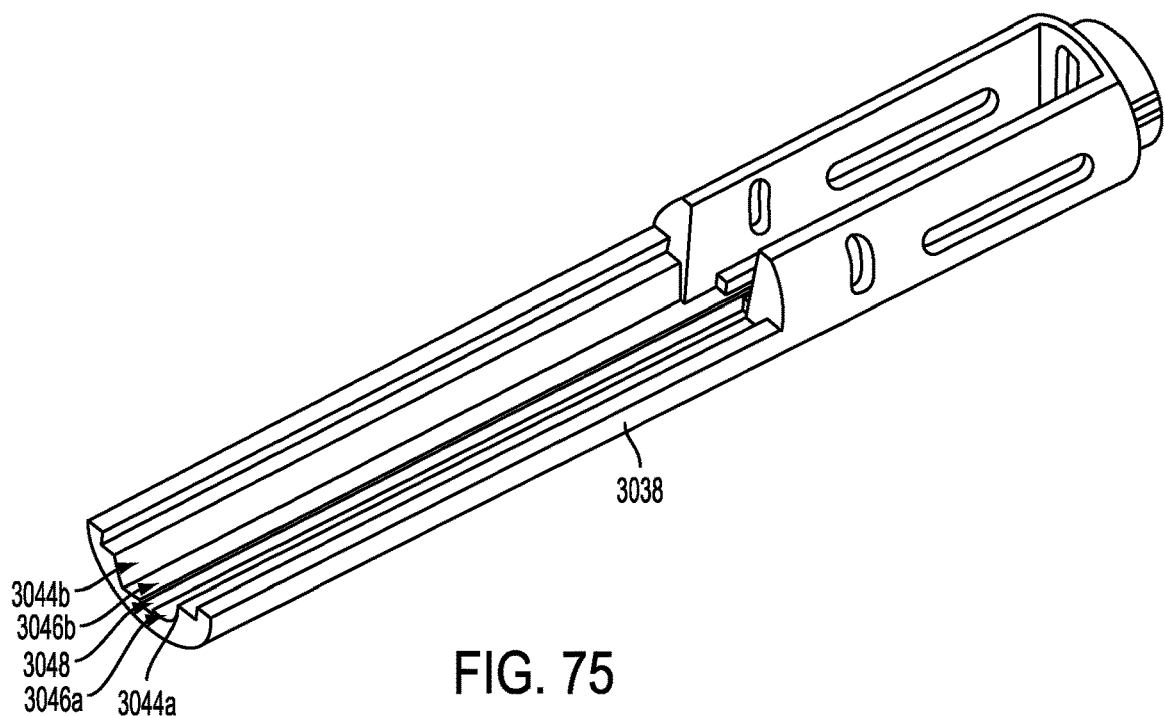
FIG. 75 is a perspective view of the bottom jaw of FIG. 74.

FIG. 74 and FIG. 75 illustrate an embodiment of a jaw 3038 that includes one or more guide members. The jaw 3038 is shown in FIG. 74 as part of an end effector 3040 that includes the jaw 3038 and a second jaw 3042, e.g., an anvil. The one or more guide members can be in the form of opposed substantially vertical sidewalls 3044a, 3044b configured to engage side of a cartridge received within the jaw 3038, and substantially flat bottom surfaces 3046a, 3046b on either side of a central longitudinal channel 3048 configured to slidably receive a drive beam, also referred to herein as an "I-beam," through the jaw 3038. A person skilled in the art will appreciate that the vertical sidewalls 3044a, 3044b may not be precisely vertical, e.g., due to manufacturing tolerances, but nevertheless be considered to be substantially vertical. Similarly, a person skilled in the art will appreciate that the flat bottom surfaces 3046a, 3046b may not be precisely flat, e.g., due to manufacturing tolerances, but nevertheless be considered to be substantially flat. The substantially flat bottom surfaces 3046a, 3046b can help provide a better seat for the cartridge within the jaw 3038 for vertically created tissue loads. The substantially vertical sidewalls 3044a, 3044b can be configured to help minimize cartridge spread, e.g., movement of the cartridge within the jaw 3038 in which it is seated, during fastener deployment, e.g., due to the I-beam slot, which can help provide more robust fastener formation. Cartridge spread can become more pronounced the thicker the tissue being grasped and fastened by the end effector 3040. The substantially vertical sidewalls 3044a, 3044b can help resist the vertical forces created during movement of the I-beam for fastener deployment and can provide about three times more resistance than sidewalls that are not substantially vertical.

Figure 76:
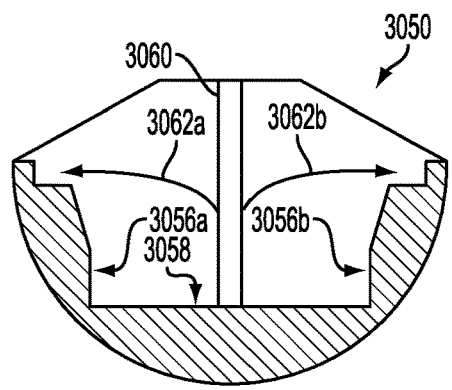
FIG. 76 is a cross-sectional view of another embodiment of a bottom jaw that includes a plurality of guidance features.
Figure 77:
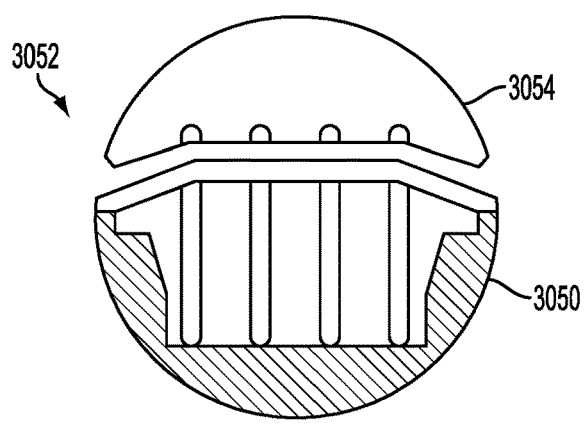
FIG. 77 is another cross-sectional view of the bottom jaw of FIG. 76, the bottom jaw being part of an end effector that also includes an upper jaw.

FIG. 76 and FIG. 77 illustrate another embodiment of a jaw 3050 that includes one or more guide members. The jaw 3050 is shown in FIG. 77 as part of an end effector 3052 that includes the jaw 3052 and a second jaw 3054, e.g., an anvil. The jaw 3050 can be generally configured and used similar to the jaw 3038 of FIG. 74 and FIG. 75. The jaw 3050 in this illustrated embodiment includes one or more guide members in the form of opposed substantially vertical sidewalls 3056a, 3056b configured to engage side of a cartridge received within the jaw 3050, and a substantially flat bottom surface 3058 along which an drive beam 3060 can be configured to translate through the jaw 3050. FIG. 74 illustrates an embodiment of spreading forces 3062a, 3062b that the substantially vertical sidewalls 3056a, 3056b can be configured to counter during fastener deployment.

In some embodiments, a surgical device such as the above-mentioned surgical device 1100 can be configured to facilitate closing of an end effector and clamping of tissue by the end effector. In general, the surgical device can be configured to increase a moment arm of the end effector, thereby increasing a closure force of the end effector. The end effector can thus be more securely closed and can more securely grasp tissue. The tissue can therefore be less likely to shift position once grasped by the end effector, which can facilitate grasping of target tissue by the end effector and/or can allow fasteners to be fired more accurately into the tissue from the end effector. The increased moment arm can provide significantly higher end effector closure efficacy in response to an actuation force, e.g., manipulation of the device's handle to effect end effector closure, than in response to the same actuation force applied. The smaller a diameter of an elongate shaft of the device, the lower the load that an end effector at a distal end of the shaft can tolerate without breaking and/or other reduced effectiveness. By increasing a moment arm at the end effector's proximal end, the shaft can have a relatively small diameter, e.g., diameters appropriate for use of the device in a minimally invasive surgical procedure, while having an end effector that is relatively easy to close and while providing relatively strong clamping of tissue engaged by the end effector. In an exemplary embodiment, a surgical device can include a closure mechanism configured to provide an increased moment arm at the device's end effector, such as at a proximal end thereof.

Figure 78:
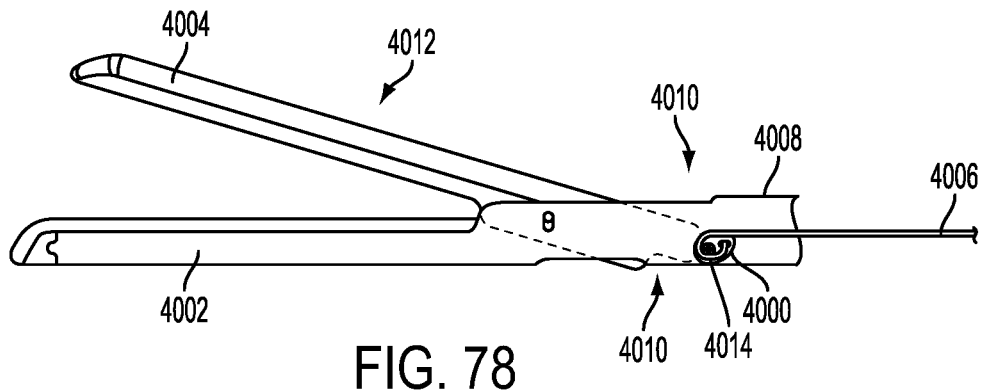
FIG. 78 is a side, partially transparent view of one embodiment of a surgical device including an end effector and a closure mechanism in the form of a lobe cam, the end effector being in an open position.

In some embodiments, a surgical device can include a closure mechanism in the form of a lobe cam. FIG. 78 illustrates one embodiment of a surgical device that includes a closure mechanism 4000 in the form of a lobe cam. In general, the lobe cam 4000 can be configured to improve closing of the device's end effector 4012 and clamping of tissue by the end effector 4012. The end effector 4012 can be coupled to a distal end of the device's elongate shaft 4008, and can include an upper jaw 4004 and a bottom jaw 4002. The lobe cam 4000 can be configured to be pulled in a proximal direction 4016 to improve the moment arm.

The lobe cam 4000 can have a variety of sizes, shapes, and configurations. As in this illustrated embodiment, the closure mechanism 4000 can be positioned adjacent a proximal end 4010 of the upper jaw 4004, as in this illustrated embodiment. The lobe cam 4000 can be pivotally coupled to the bottom jaw 4002 at a pivot point 4014 about which the lobe cam 4000 can be configured to move. The device can include an actuator 4006 configured to be actuated via manipulation of the device's handle (not shown) so as to move the closure mechanism 4000, as discussed further below. The actuator 4006 can extend along the shaft 4008, e.g., through an inner lumen thereof, and can be coupled to the closure mechanism 4000. The actuator 4006 includes a cable in this illustrated embodiment, but the actuator 4006 can have other sizes, shapes, and configurations.

Figure 79:
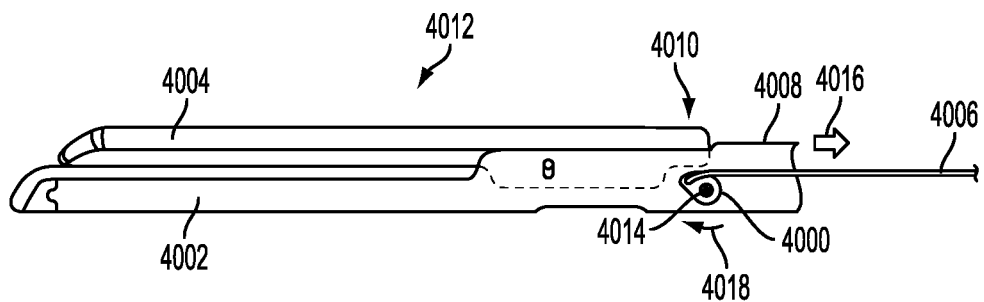
FIG. 79 is a side, partially transparent view of the device of FIG. 78, the end effector in an intermediate position between open position and a closed position.
Figure 80:
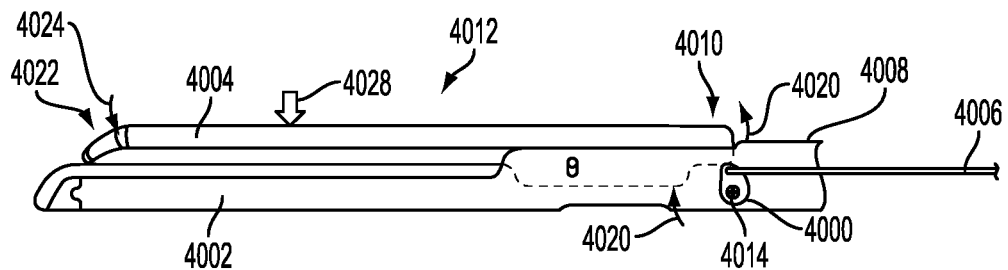
FIG. 80 is a side, partially transparent view of the device of FIG. 79, the end effector being in the closed position.

The lobe cam 4000 can be configured to move between first and second positions. The lobe cam 4000 can be in a first position when the end effector 4012 is in the open position, as shown in FIG. 78, and can be in the second position when the end effector 4012 is in the closed position, as shown in FIG. 80. FIG. 79 shows the lobe cam 4000 in an intermediate position between the first and second positions when the end effector 4012 is moving from the open position to the closed position. The lobe cam 4000 can be biased to the first position, e.g., by the actuator 4006 applying a biasing force thereto. In other embodiments, the lobe cam 4000 can be biased to the second position, e.g., by the actuator 4006 applying a biasing force thereto.

When the end effector 4012 begins to move from the open position of FIG. 78, the actuator 4006 can be pulled in the proximal direction 4016, as shown in FIG. 79. The pulling of the actuator 4006 can cause the lobe cam 4000 to rotate, as shown by an arrow 4018 in FIG. 79, thereby causing the lobe cam 4000 to push against the upper jaw 4004 so as to apply a force to the proximal end 4010 thereof. This force can increase closure of the end effector 4012. As the end effector 4012 continues closing, the lobe cam 4000 can continue applying the force to the upper jaw's proximal end 4010. When the end effector 4012 is in the closed position, as shown in FIG. 80, the lobe cam 4000 can continue applying the force to the upper jaw 4004, which can increase a clamping force of the end effector 4012 by forcing the upper jaw's proximal end in an upward direction 4020, thereby forcing the upper jaw's distal end 4022 in a downward direction 4024 toward the bottom jaw 4002. An end reaction force when the end effector 4012 is in the closed position can be in a direction 4028 that is substantially perpendicular to a longitudinal axis of the shaft 4008 along which the actuator 4006 extends and along which the actuator 4006 applies force to the lobe cam 4000. The end effector 4012 can thus be effectively closed and effectively clamp tissue engaged since substantially all of the pulling force in the proximal direction 4016 is applied to the end reaction force in the substantially perpendicular direction 4028. When the end effector 4012 moves from the closed position to the open position, the lobe cam 4000 can move from the second position back to the first position.

Figure 81:
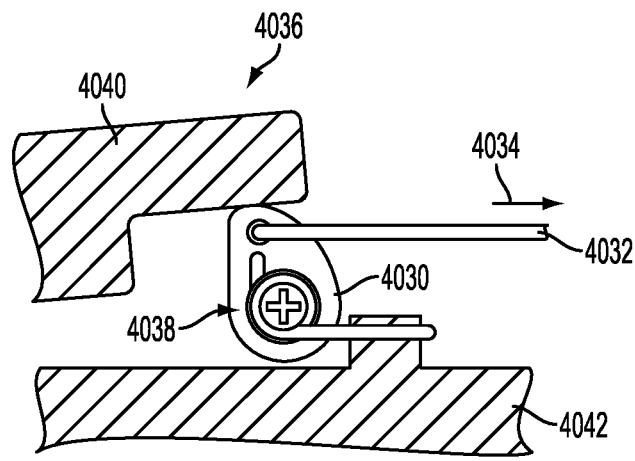
FIG. 81 is a side, partially cross-sectional view of another embodiment of a surgical device including an end effector and a closure mechanism in the form of a lobe cam, the end effector being in a closed position.
Figure 82:
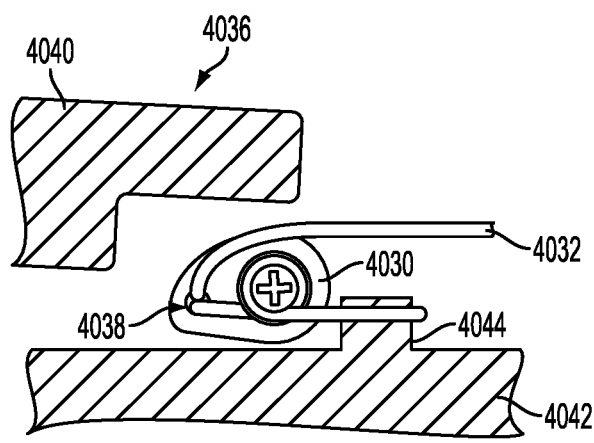
FIG. 82 is a side, partially cross-sectional view of a portion of the device of FIG. 81, the end effector being in an open position.

FIG. 81 and FIG. 82 illustrate an alternate embodiment of a closure mechanism 4030 in the form of a lobe cam that can be configured and used similar to the closure mechanism 4000 of FIG. 78. In this illustrated embodiment, the lobe cam 4030 can be biased to a second position, shown in FIG. 82, corresponding to an end effector 4036 being in an open position, e.g., first and second jaws 4042, 4040 jaws thereof being open. A spring 4038 coupled to the lobe cam 4030 can provide a biasing force that biases the lobe cam 4030 to the second position. The surgical device can include a support member 4044 configured to couple to the spring 4038. An actuator 4032, e.g., a cable, can be configured to be pulled in a proximal direction 4034 to counteract the bias and move the lobe cam 4030 from the second position to a first position, shown in FIG. 81, corresponding to the end effector 4036 being in a closed position.

Figure 83:
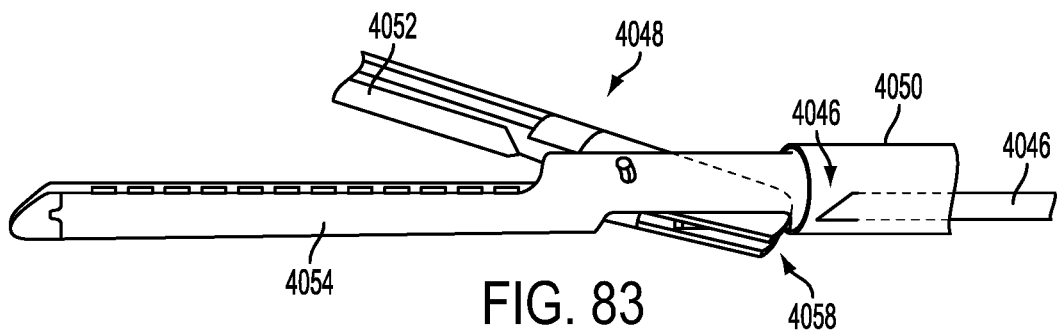
FIG. 83 is a side, partially transparent view of one embodiment of a surgical device including an end effector and a closure mechanism in the form of a wedge, the end effector being in an open position.
Figure 84:
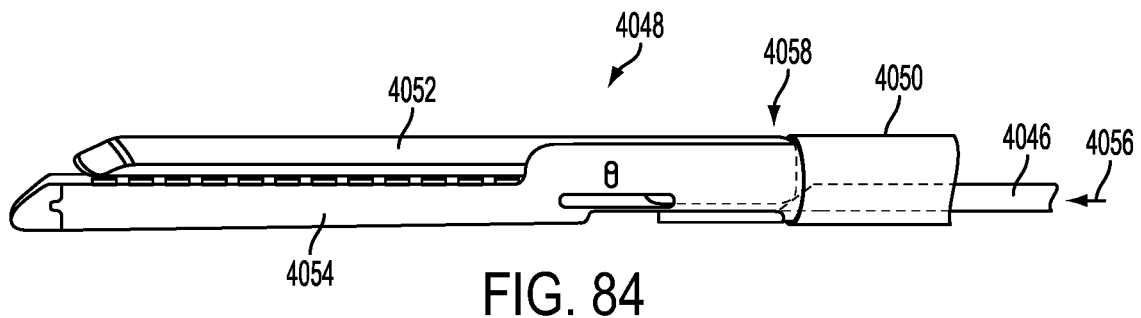
FIG. 84 is a side, partially transparent view of the device of FIG. 83, the end effector in an intermediate position between open position and a closed position.
Figure 85:
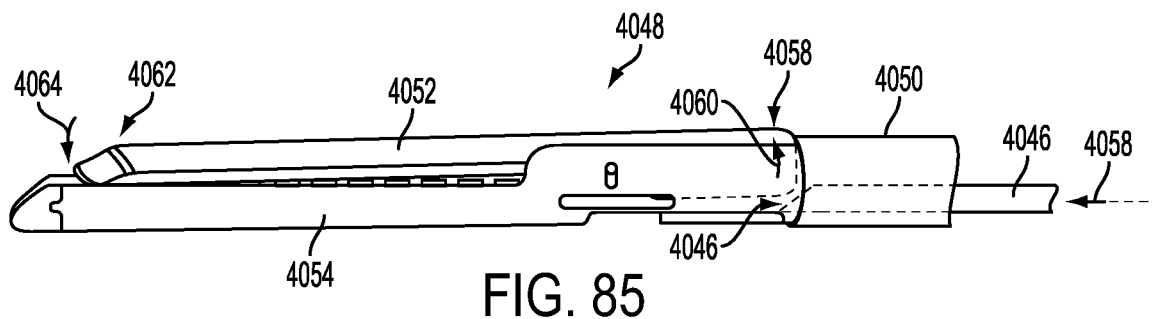
FIG. 85 is a side, partially transparent view of the device of FIG. 84, the end effector being in the closed position.

In some embodiments, a surgical device can include a closure mechanism in the form of a wedge. FIG. 83, FIG. 84, and FIG. 85 illustrate one embodiment of a surgical device that includes a closure mechanism 4046 in the form of a wedge. In general, the wedge 4046 can be configured to improve closing of the device's end effector 4048 and clamping of tissue by the end effector 4048. The end effector 4048 can be coupled to a distal end of the device's elongate shaft 4050, and can include an upper jaw 4052 and a bottom jaw 4054. The wedge 4046 can be configured to be pushed in a distal direction 4056 to improve the moment arm.

The wedge 4046 can have a variety of sizes, shapes, and configurations. As in this illustrated embodiment, the wedge 4046 can be configured to be slidably movable within an inner lumen of the shaft 4050 and can be configured to engage a proximal end 5058 of the upper jaw 4052, as shown in FIG. 84 and FIG. 85. The wedge 4046 can be configured to be so slidably movable by, e.g., manipulating a handle (not shown) of the device. When the end effector 4048 is in an open position, as shown in FIG. 83, the wedge 4046 can be configured to not apply a force to the upper jaw 4052, such as by not being engaged therewith. When the end effector 4048 is moving from the open portion to a closed position, the wedge 4046 can be advanced in the distal direction 4056 such that a cam surface 4046a of the wedge 4046, e.g., a sloped distal end of the wedge 4046, engages the upper jaw 4052 and applies a force to the proximal end 4058 thereof. By being sloped at the distal end thereof, the wedge 4046 can have a relatively low profile at the distal end, which can help the wedge 4046 fit into the relatively small space available at the end effector 4048 while providing the mechanical advantage of an increased moment arm. As in the illustrated embodiment, the wedge 4046 can be advanced under the upper jaw's proximal end 4058 so as to push upward thereon. As the end effector 4048 continues closing, the wedge 4046 can continue applying the force to the upper jaw's proximal end 4058. When the end effector 4048 is in the closed position, as shown in FIG. 85, and similar to the embodiment of FIG. 80, the wedge 4046 can continue applying the force to the upper jaw 4052, which can increase a clamping force of the end effector 4048 by forcing the upper jaw's proximal end in an upward direction 4060, thereby forcing the upper jaw's distal end 4062 in a downward direction 4064 toward the bottom jaw 4054. The upper and bottom jaws 4052, 4054 can be more rigid mechanically in the closed position due to the presence of the wedge 4046. An end reaction force when the end effector 4048 is in the closed position can be in a direction 4064 that is substantially perpendicular to a longitudinal axis of the shaft 4050 along which the wedge 4046 extends. When the end effector 4048 moves from the closed position to the open position, the wedge 4046 can move from the second position back to the first position.

In some embodiments, a surgical device can include a closure mechanism in the form of a two-bar linkage. FIG. 86, FIG. 87, FIG. 88, and FIG. 89 illustrate one embodiment of a surgical device that includes a closure mechanism 4066 in the form of a two-bar linkage. In general, the two-bar linkage 4066 can be configured to improve closing of the device's end effector 4068 and clamping of tissue by the end effector 4068. The end effector 4068 can be coupled to a distal end of the device's elongate shaft 4070, and can include an upper jaw 4072 and a bottom jaw 4074. The two-bar linkage 4066 can be configured to be pulled in a proximal direction 4076 to improve the moment arm.

The two-bar linkage 4066 can have a variety of sizes, shapes, and configurations. As in this illustrated embodiment, the two-bar linkage 4066 can include a first or proximal bar 4078 and a second or distal bar 4080. The first bar 4078 can be coupled to an actuation shaft 4086 slidably disposed along the shaft 4070, e.g., slidably disposed within an inner lumen of the shaft 4070, and actuatable via manipulation of the device's handle (not shown). In some embodiments, the first bar 4078 can be directed manipulated via the handle. The second bar 4080 can be coupled to the first bar 4078, such as at a pivot point 4084, and can be configured to be movable relative thereto, e.g., by pivoting at the pivot point 4084. The second bar 4080 can also be operatively connected to the upper jaw 4072. The second bar 4080 can have a pin 4076 formed thereon. The pin 4076 can be slidably disposed within a slot 4082 formed in the bottom jaw 4074. The pin 4076 can define a pivot point about which the end effector 4068 opens and closes.

Figure 86:
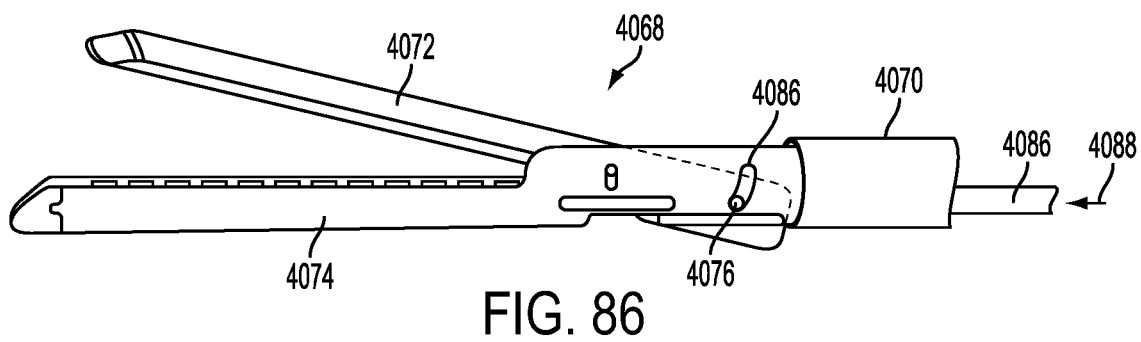
FIG. 86 is a side view of one embodiment of a surgical device including an end effector and a closure mechanism in the form of a two-bar linkage, the end effector being in an open position.
Figure 87:
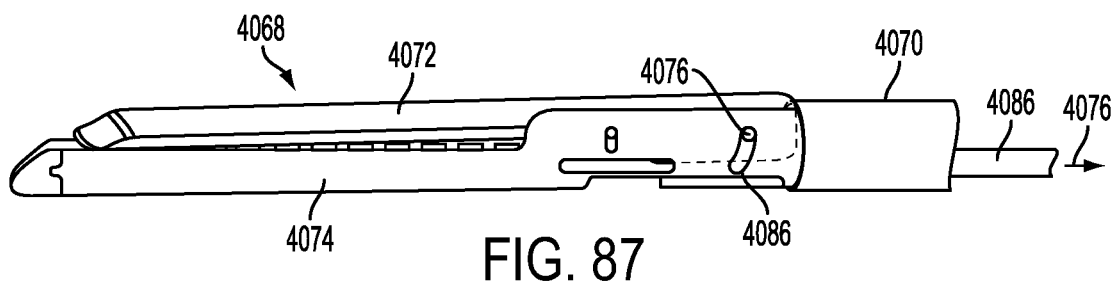
FIG. 87 is a side view of the device of FIG. 86, the end effector being in a closed position.
Figure 88:
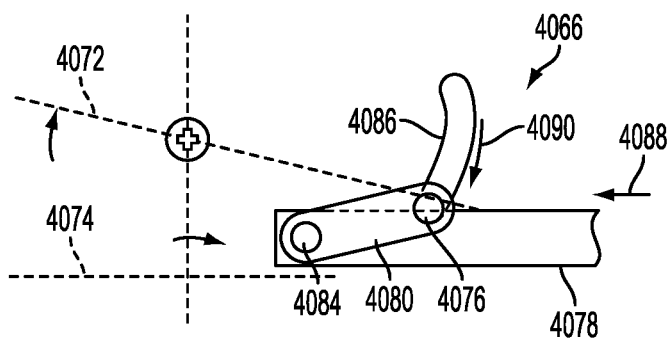
FIG. 88 is a side, partially schematic view of a portion of the device of FIG. 86.
Figure 89:
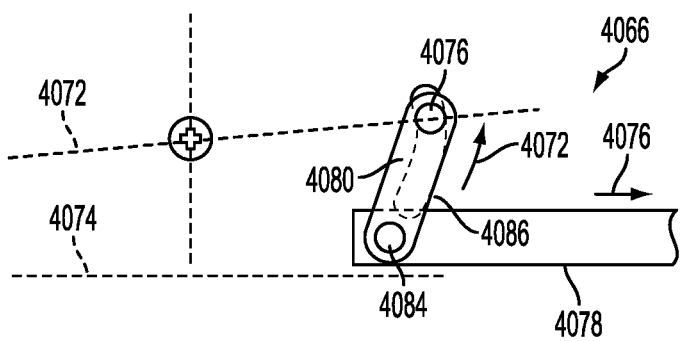
FIG. 89 is a side, partially schematic view of a portion of the device of FIG. 87.

The actuation shaft 4086 and the first bar 4078 coupled thereto can be slidably movable in a distal direction 4088, as shown in FIG. 86 and FIG. 88, and in the proximal direction 4076, as shown in FIG. 87 and FIG. 89. In response to the actuation shaft 4086 and the first bar 4078 moving in the distal direction 4088, the second bar 4080 can move in a downward direction 4090 such that the pin 4076 slides in the downward direction 4090 within the slot 4086, thereby urging the end effector 4068 toward the open position. In response to the actuation shaft 4086 and the first bar 4078 moving in the proximal direction 4076, the second bar 4080 can move in an upward direction 4092 such that the pin 4076 slides in the upward direction 4092 within the slot 4086, thereby urging the end effector 4068 toward the closed position. The upper and bottom jaws 4072, 4074 can be more rigid mechanically in the closed position due to the presence of the two-bar linkage 4066. An end reaction force when the end effector 4068 is in the closed position can be in the downward direction 4090 that is substantially perpendicular to a longitudinal axis of the shaft 4070 along which the actuation shaft 4086 and the first bar 4078 extend.

Figure 90:
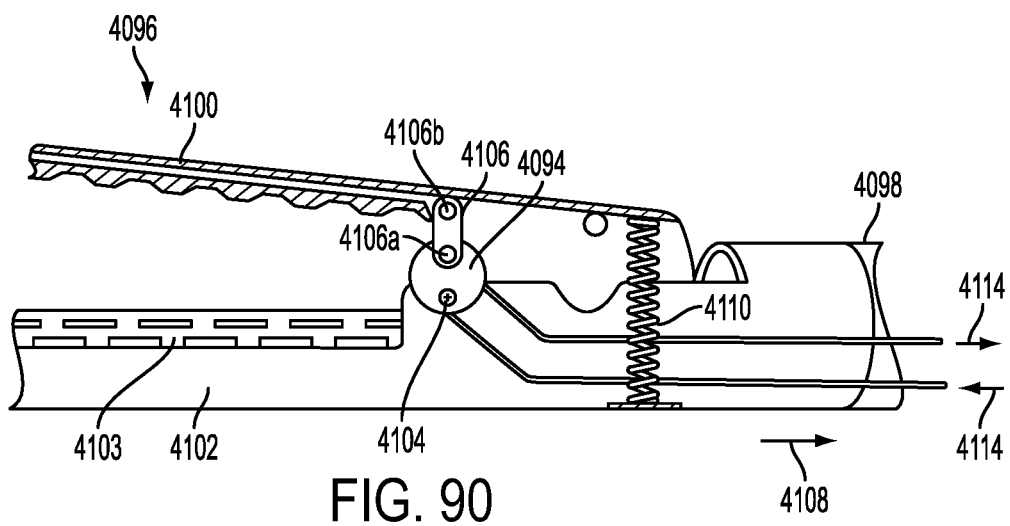
FIG. 90 is a side, partially transparent view of one embodiment of a surgical device including an end effector and a closure mechanism in the form of a rotating element, the end effector being in an open position.
Figure 91:
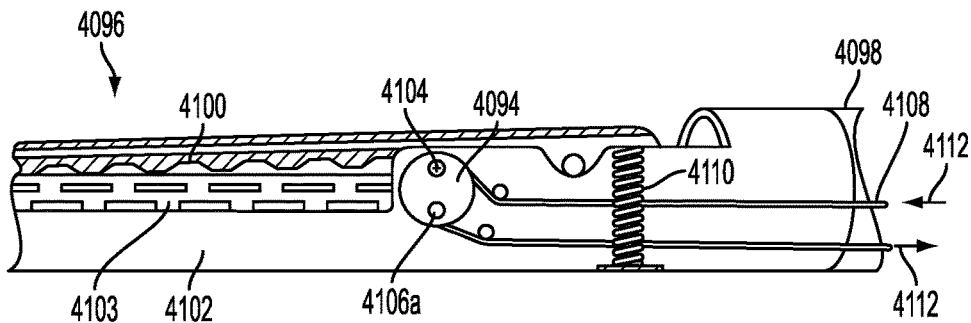
FIG. 91 is a side, partially transparent view of the device of FIG. 90, the end effector being in a closed position.

In some embodiments, a surgical device can include a closure mechanism in the form of a rotating element. FIG. 90 and FIG. 91 illustrate one embodiment of a surgical device that includes a closure mechanism 4094 in the form of a rotating element. In general, the rotating element 4094 can be configured to improve closing of the device's end effector 4096 and clamping of tissue by the end effector 4096. The end effector 4096 can be coupled to a distal end of the device's elongate shaft 4098, and can include an upper jaw 4100 and a bottom jaw 4102. A cartridge 4103 can be seated in the bottom jaw 4102, as shown in this illustrated embodiment. The rotating element 4094 can be configured to rotate to improve the moment arm.

The rotating element 4094 can have a variety of sizes, shapes, and configurations. As in this illustrated embodiment, the rotating element 4094 can include a wheel attached to the bottom jaw 4102 at a fixed point 4104 and attached to the upper jaw 4100 via a link bar 4106. The link bar 4106 can have one end 4106a attached to the wheel 4094 and an opposite end 4106b attached to the upper jaw 4100. The wheel 4094 can be coupled to an actuator 4108 configured to cause rotation of the wheel 4094 at the fixed point 4014. The actuator 4108 can be configured to be actuated via the device's handle (not shown) and can extend along the shaft 4098, as in tis illustrated embodiment. The actuator 4108 can have a variety of sizes, shapes, and configurations. As in this illustrated embodiment, the actuator 4108 can include a cable.

The device can include a bias element 4110, e.g., a spring, configured to bias the end effector 4096 to an open position, shown in FIG. 90. As shown in FIG. 91, in response to the actuator 4108 being moved in a first direction 4112, e.g., counterclockwise, the wheel 4094 can be configured to rotate in the first direction 4112 about the fixed point 4104, thereby causing the ends 4106a, 4106b of the link 4106 to move and the upper jaw 4100 to move toward the bottom jaw 4102. The rotation of the wheel 4094 in the first direction 4112 can thus move the end effector 4096 to the closed position. The movement of the actuator 4108 in the first direction 4112 can overcome the bias force provided by the spring 4110 to allow the end effector 4096 to close. Similarly, as shown in FIG. 90, in response to the actuator 4108 being moved in a second direction 4114, e.g., clockwise, that is opposite to the first direction 4112, the wheel 4094 can be configured to rotate in the second direction 4114 about the fixed point 4104, thereby causing the ends 4106a, 4106b of the link 4106 to move and the upper jaw 4100 to move away from bottom jaw 4102. The rotation of the wheel 4094 in the second direction 4114 can thus move the end effector 4096 to the open position. The bias force provided by the spring 4110 can facilitate the opening of the end effector 4096.

FIG. 92, FIG. 93, FIG. 94, and FIG. 95 illustrate another embodiment of a surgical device that includes a closure mechanism in the form of a rotating element. In this illustrated embodiment, the rotating element includes a plurality of rotating elements 4116a, 4116b, e.g., rotating wheels. The rotating wheels 4116a, 4116b can generally be configured and used similar to the above-mentioned wheel 4094 and can be coupled to and actuated by first and second actuators 4130a, 4130b, respectively. By including a second wheel 4116b, motions of the wheels 4116a, 4116b can be timed to effect various types of end effector closures. Closure of the device's end effector 4122 can thus be selectively controlled at a user's discretion. In general, the wheels 4116a, 4116b can allow the end effector 4122 to be selectively closed in parallel fashion, closed distal end first, and closed proximal end first.

Figure 92:
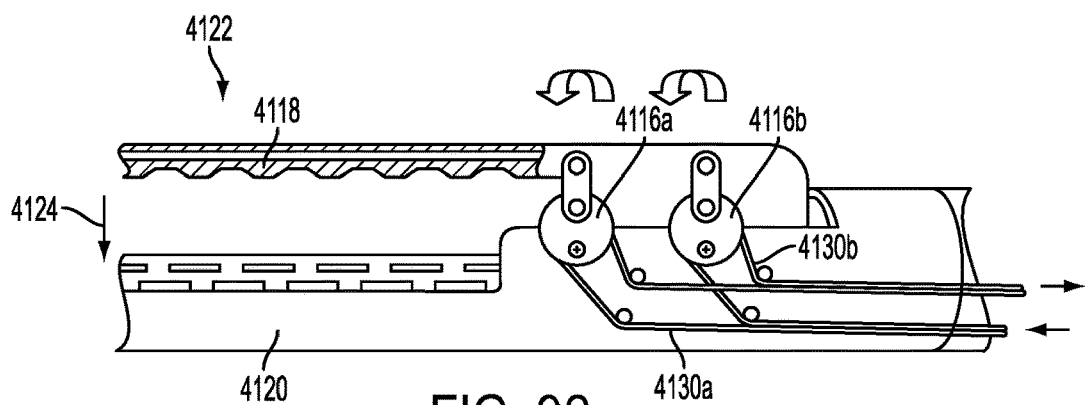
FIG. 92 is a side, partially transparent view of another embodiment of a surgical device including an end effector and a closure mechanism in the form of a rotating element, the end effector being in an open position.
Figure 93:
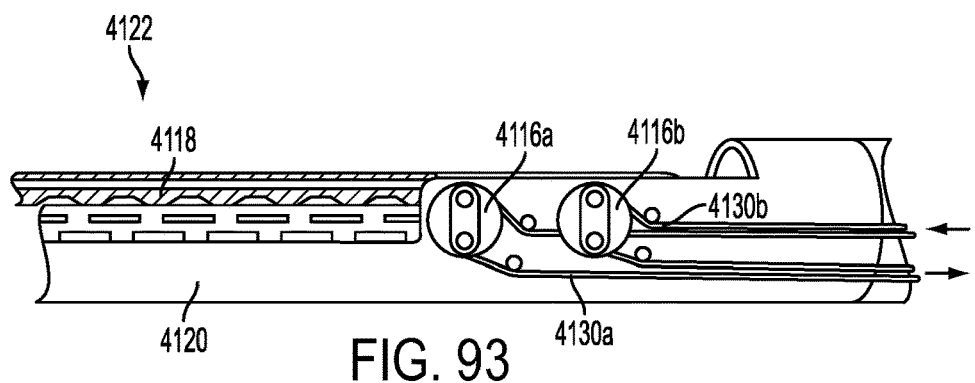
FIG. 93 is a side, partially transparent view of the device of FIG. 92, the end effector being in a closed position.

By including a second wheel 4116b, motions of the wheels 4116a, 4116b can be timed so that they can cause the end effector 4122 to which the wheels 4116a, 4116b are attached to close in a parallel fashion, as shown in FIG. 92 and FIG. 93. In other words, an upper jaw 4118 of the end effector 4112 can move in a downward direction 4124 toward a bottom jaw 4120 of the end effector 4122, as opposed to the rotational "alligator" type closing of the end effector 4096 coupled to a single wheel 4094.

Figure 94:
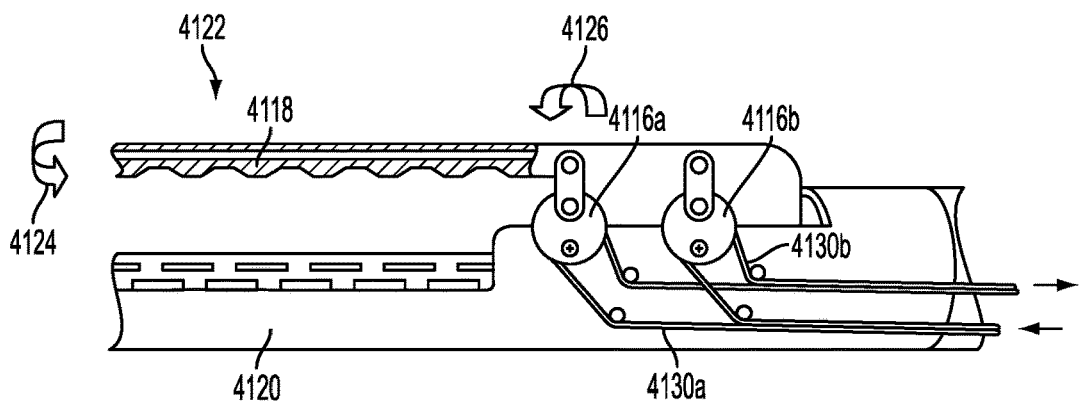
FIG. 94 is a side, partially transparent view of the device of FIG. 92, the rotating element being actuated to cause closing of a distal end of the end effector.

Including a second wheel 4116b can allow the motions of the wheels 4116a, 4116b to be timed so that a distal end (not shown) of the end effector 4122 begins closing first, as indicated by an arrow 4124 in FIG. 94, e.g., before movement of the end effector's proximal end. Closing the distal end first can aid with tissue capture between the jaws 4118, 4120. The motions of the wheels 4116a, 4116b can be controlled to first allow distal closure of the end effector 4122 by starting motion of the distal one of the wheels 4116a, as shown by an arrow 4126, before starting motion of the proximal one of the wheels 4116b.

Figure 95:
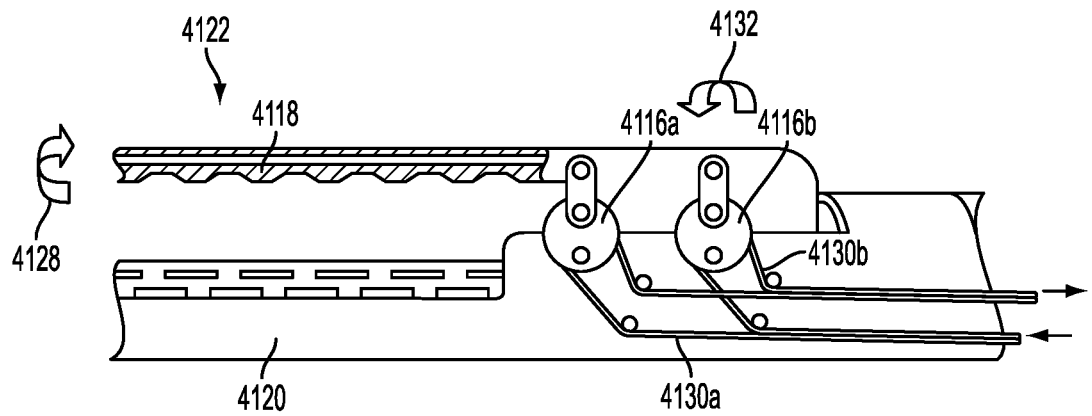
FIG. 95 is a side, partially transparent view of the device of FIG. 92, the rotating element being actuated to cause closing of a proximal end of the end effector.

Including a second wheel 4116b can allow the motions of the wheels 4116a, 4116b to be timed so that the end effector 4112 closes in an "alligator" type fashion by beginning to close the proximal end of the end effector 4122 before beginning to close the distal end of the end effector 4122, as shown in FIG. 95. The motions of the wheels 4116a, 4116b can be controlled to first allow proximal closure of the end effector 4122 by starting motion of the proximal one of the wheels 4116b, as shown by an arrow 4132, before starting motion of the distal one of the wheels 4116a.

Figure 96:
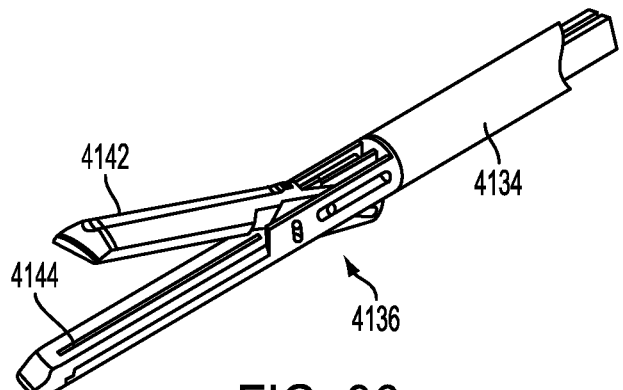
FIG. 96 is a perspective view of one embodiment of a surgical device including an end effector and a closure mechanism in the form of a closure tube, the end effector being in an open position.
Figure 97:
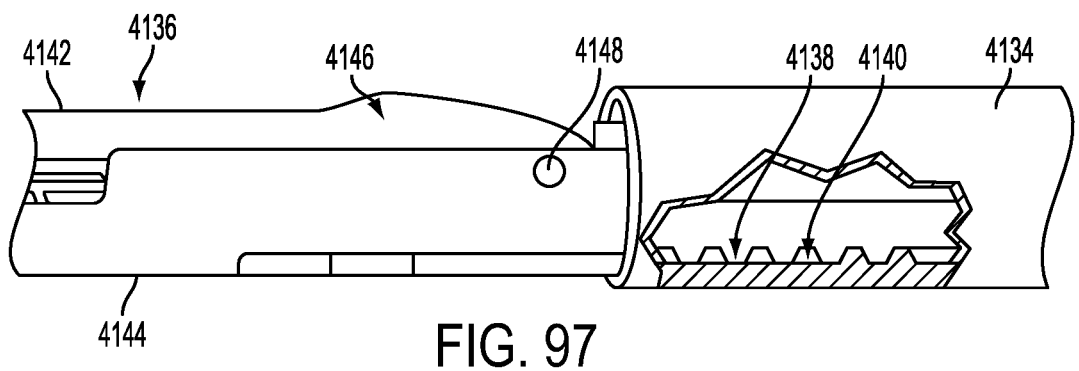
FIG. 97 is a side, partially transparent view of the device of FIG. 96.
Figure 98:
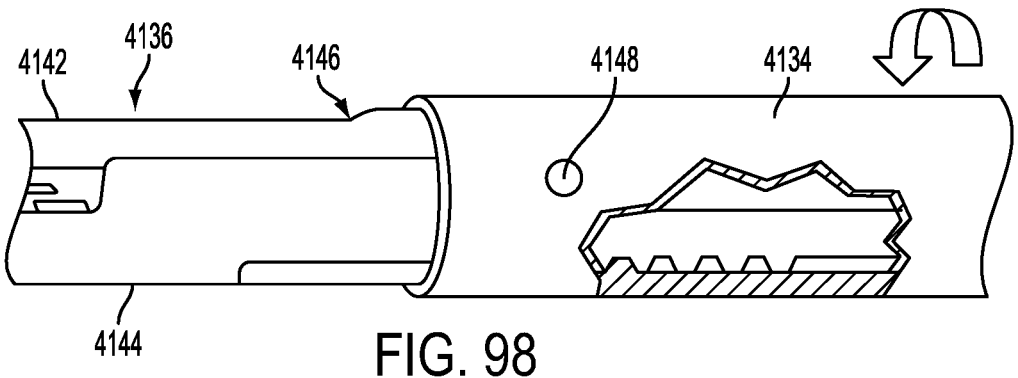
FIG. 98 is a side, partially transparent view of the device of FIG. 96, the end effector being in a closed position.
Figure 99:
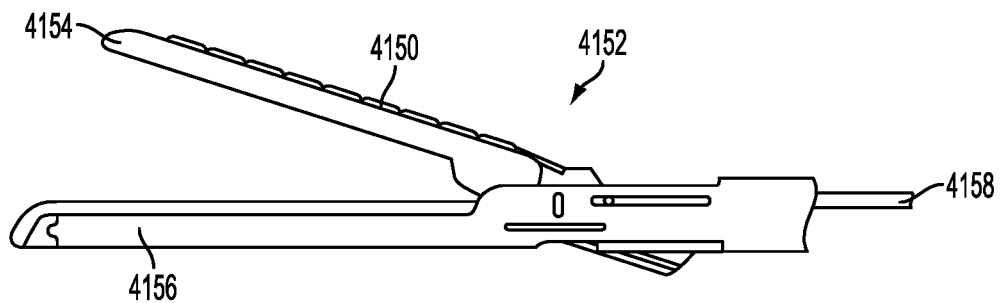
FIG. 99 is a side view of one embodiment of a surgical device including an end effector and a closure mechanism in the form of a truss, the end effector being in an open position and the truss being in a collapsed position.

In some embodiments, a surgical device can include a closure mechanism in the form of a closure tube. FIG. 96, FIG. 97, and FIG. 98 illustrate one embodiment of a surgical device that includes a closure mechanism 4134 in the form of a closure tube. In general, the closure tube 4134 can be configured to rotate to provide increased moment arm to the device's end effector 4136.

The closure tube 4134 can have a variety of sizes, shapes, and configurations, and can be configured to move longitudinally in a variety of ways. As in the illustrated embodiment, the closure tube 4134 can include an internal thread 4138 matable with a corresponding thread 4140 on a stationary one of the end effector's upper and bottom jaws 4142, 4144, e.g., the bottom jaw 4144. The closure tube 4134 can be configured to rotate about a longitudinal axis thereof so as to threadably move the end effector 4136 proximally or distally, depending on a direction of the closure tube's rotation. The internal threads 4138, 4140 can have a consistent size, e.g., have consistent leads therealong, which can allow the end effector 4136 to move longitudinally at a constant rate. Alternatively, as in the illustrated embodiment, the internal threads 4138, 4140 can have a variable size, e.g., have varying leads therealong, which can allow the end effector 4136 to move longitudinally at a variable rate. In this way, the end effector 4136 can be closed at a first rate, e.g., by having larger leads or coarser proximal threads 4138, 4140, and then close at a second, slower rate, e.g., by having smaller leads or finer distal threads 4138, 4140, so as to provide a higher force when the closure tube 4134 is rotating at the second, slower rate so as to provide a greater mechanical advantage.

In response to the closure tube's rotation, the end effector 4136 can be proximally advanced into the closure tube 4136 when closing the end effector 4136, and the end effector 4136 can be distally advanced out of the closure tube 4136 when opening the end effector 4136. A pivot point 4148 about which the end effector 4136 opens and closes, e.g., about which the upper jaw 4142 moves relative to the bottom jaw 4144, can be configured to move in and out of the closure tube 4134. In general, the more proximally located the pivot point 4148, the more force that can be applied to the end effector 4136 to effect its closure and clamping.

The closure tube 4134 can be configured to rotate any number of degrees to fully move the end effector 4136 between the open and closed positions. In an exemplary embodiment, the closure tube 4134 can rotate at least 360°, e.g., one full 360° rotation, three full 360° rotations, five full 360° rotations, six full 360° rotations, etc.

The closure tube 4136 can be configured to be moved longitudinally in a variety of ways. For example, the device can include an actuator (not shown), e.g., a rotatable knob, a movable lever, a rack/pinion mechanism, etc., manipulatable at a handle (not shown) of the device that can be configured to be manipulated to effect movement of the closure tube 4136. For another example, the closure tube 4136 can be configured to rotate in response to an actuator, e.g., a firing trigger, etc., configured to be manipulated to fire fasteners from the device. For yet another example, the rotation of the closure tube 4136 can be configured to be motor-powered. For another example, the closure tube 4136 can be configured to be manually rotated by hand.

The end effector 4136 can include a protruding lobe 4146 extending radially outward therefrom. The protruding lobe 4146 can be configured to increase a force exerted by the closure tube 4134 on the end effector 4136 when the closure tube 4134 engages the protruding lobe 4146, e.g., when the protruding lobe 4146 is at least partially disposed within the tube 4134. FIG. 96 and FIG. 97 show the protruding lobe 4146 outside the closure tube 4134, and FIG. 98 shows the protruding lobe 4146 partially disposed within the closure tube 4134.

In some embodiments, a surgical device can include a closure mechanism in the form of a truss. FIG. 99, FIG. 100, FIG. 101, FIG. 102, and FIG. 103 illustrate one embodiment of a surgical device that includes a closure mechanism 4150 in the form of a truss. In general, the truss 4150 can be configured to improve closing of the device's end effector 4152 and clamping of tissue by the end effector 4152. The smaller an end effector 4152, e.g., the smaller the end effector's diameter, the less bending stiffness the end effector 4152 has, and the more likely the end effector 4152 is to bend and reduce the closure and clamping effectiveness of the end effector 4152. The truss 4150 can be configured to provide increased being stiffness and, thus, make the end effector 4152 less likely to bend, even if the end effector 4152 is small.

The truss 4150 can have a variety of sizes, shapes, and configurations. The truss 4150 can be configured to increase a size of the end effector 4152, e.g., a size of one of the upper and bottom jaws 4154, 4156 thereof, which can increase structural strength the end effector 4152, e.g., by increasing a rigidity of the end effector 4152. This increased structural strength of the end effector 4152 can allow the end effector 4152 to more forcefully close and clamp when the truss 4150 is deployed, e.g., is expanded. In an exemplary embodiment, the truss 4150 can be configured to move between a collapsed position and an expanded position. In the collapsed position, shown in FIG. 99 and FIG. 102 (with the end effector 4152 in solid lines), the end effector 4152 can have a first size and a first strength. As in this illustrated embodiment, the truss 4150 in the collapsed position can be configured to be disposed within one of the jaws 4154, 4156, e.g., the upper jaw 4154. In the expanded position, shown in FIG. 100, FIG. 101, FIG. 102 (with the end effector 4152 in dotted lines), and FIG. 103, the end effector 4152 can have a second size that is greater than the first size and a second strength that is greater than the first strength. As in this illustrated embodiment, the truss 4150 in the expanded position can be configured to extend outward from the one of the jaws 4154, 4156 in which the truss 4150 is disposed when in the collapsed position. The truss 4150 being movable between the collapsed and expanded configurations can allow the device to be advanced into a patient's body with a first, smaller size, e.g., with the truss 4150 in the collapsed position, which can facilitate use of the device in a minimally invasive surgical procedure.

Figure 100:
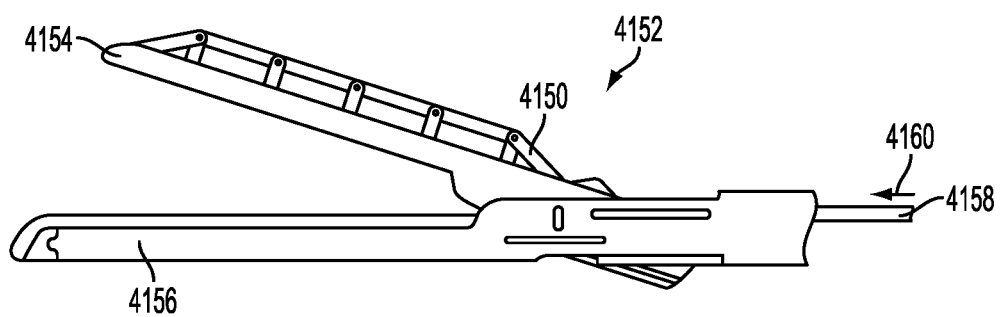
FIG. 100 is a side view of the device of FIG. 99, the truss being in an expanded position.
Figure 101:
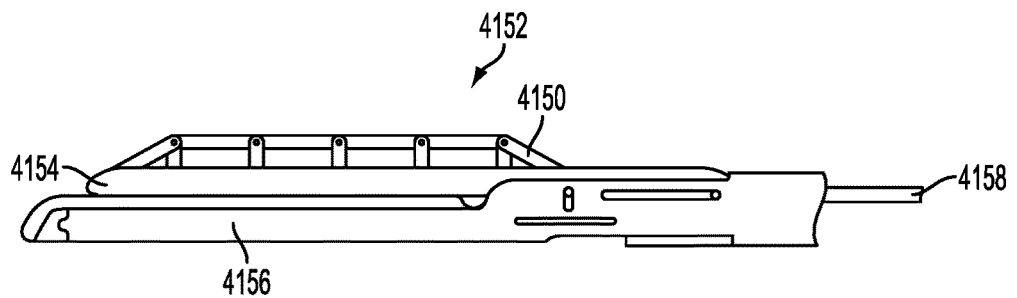
FIG. 101 is a side view of the device of FIG. 100, the end effector being in a closed position.
Figure 102:
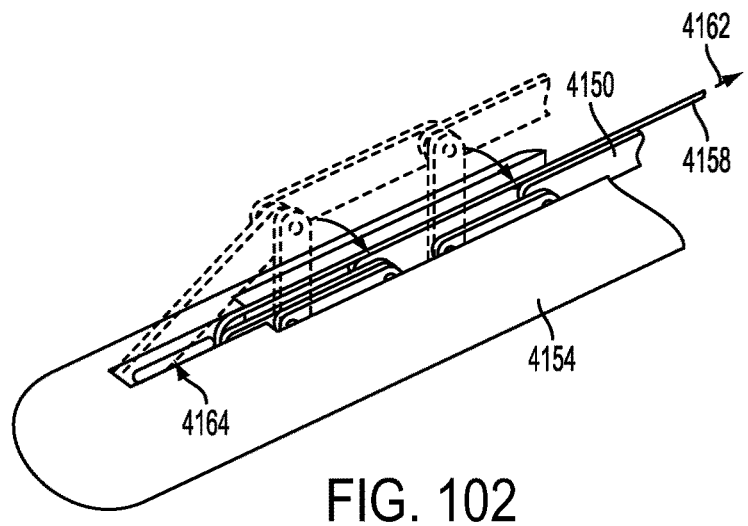
FIG. 102 is a perspective view of a portion of the device of FIG. 99.
Figure 103:
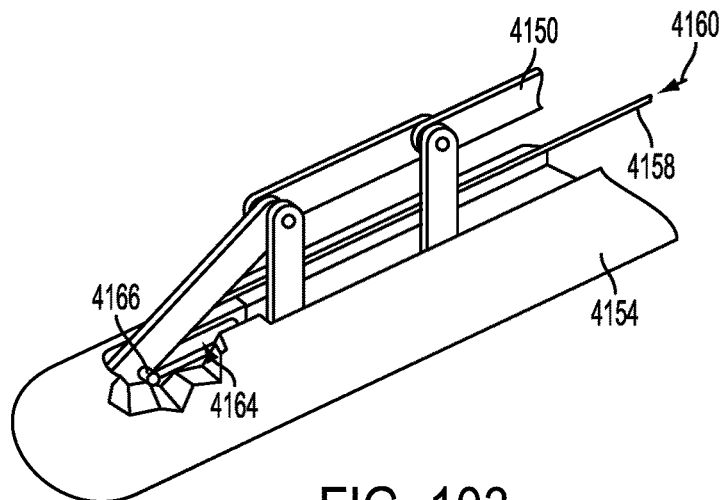
FIG. 103 is a perspective view of a portion of the device of FIG. 100.
Figure 104:
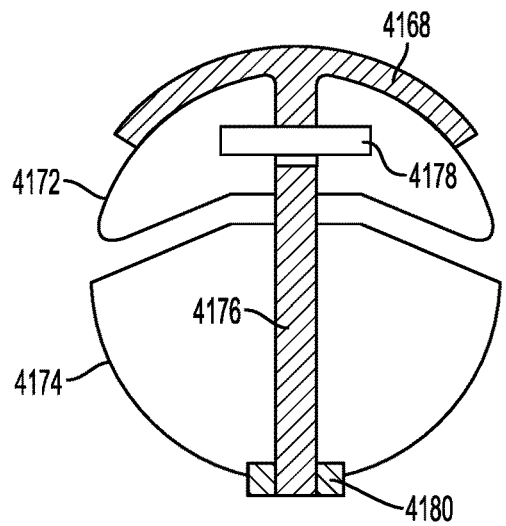
FIG. 104 is a cross-sectional front end view of one embodiment of a surgical device including an end effector and a closure mechanism in the form of an external compression member.
Figure 105:
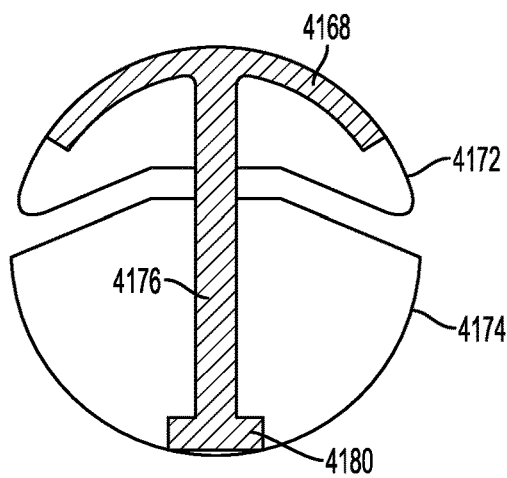
FIG. 105 is cross-sectional back end view of the device of FIG. 104.
Figure 106:
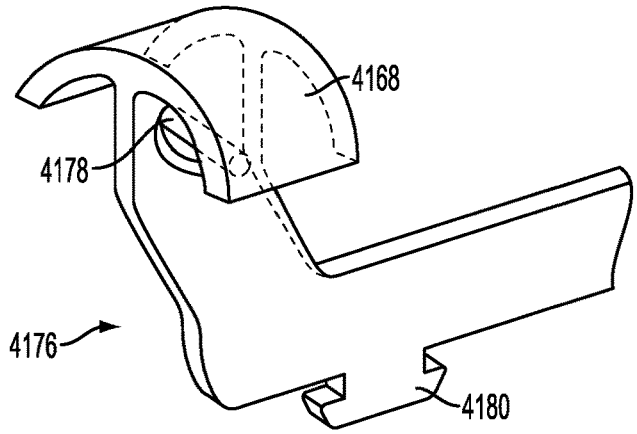
FIG. 106 is a perspective view of the external compression member of FIG. 104.

The truss 4150 can be configured to move between the expanded and collapsed positions in a variety of ways. The device can include an actuator 4158, e.g., a rod, a cable, etc., configured to be manipulated at a handle (not shown) of the device to selectively collapse and expand the truss 4150. In this illustrated embodiment, the actuator 4158 includes a cable. In response to movement of the actuator 4158 in a distal direction 4160, as shown in FIG. 100 and FIG. 103, the truss 4150 can be configured to move from the collapsed position to the expanded position. In response to movement of the actuator 4158 in a proximal direction 4162, as shown in FIG. 102, the truss 4150 can be configured to move from the expanded position to the collapsed position. In other embodiments, proximal movement of an actuator can cause a truss to move from a collapsed position to an expanded position, and distal movement of the actuator can cause the truss to move from the expanded position to the collapsed position.

As in this illustrated embodiment, the truss 4150 can include a plurality of movable links connected together. The truss 4150 includes eight movable links in this illustrated embodiment, but a truss can include another number of movable links.

The end effector 4152 can include a slot 4164 formed therein, as shown in FIG. 102 and FIG. 103, in which the truss 4150 can be configured to slide to facilitate movement between the collapsed and expanded positions. The truss 4150 can include a pin 4166 configured to slide within the slot 4164, as shown in FIG. 103. As in this illustrated embodiment, a distal-most one of the movable links can include the pin 4166. The slot 4164 and the pin 4166 can cooperate to facilitate a smooth, controlled transition of the truss 4150 between the collapsed and expanded positions.

In some embodiments, a surgical device can include a closure mechanism in the form of an external compression member. FIG. 104, FIG. 105, FIG. 106, FIG. 107, and FIG. 108 illustrate one embodiment of a surgical device that includes a closure mechanism 4168 in the form of an external compression member. In general, the external compression member 4168 can be configured to improve closing of the device's end effector 4170 and clamping of tissue by the end effector 4170. The end effector 4170 can include an upper jaw 4172 and a bottom jaw 4174. The external compression member 4168 can be configured to translate along the end effector 4170 externally thereto to apply a closing force thereto, thereby improving the moment arm. The external compression member 4168, being external to the end effector 4170, can be configured as an exoskeleton. Being located to the end effector 4170 can allow the external compression member 4168 to help prevent twisting and/or shifting of the end effector 4170 during firing of fasteners from the end effector 4170. By being located external to the end effector 4170, the external compression member 4168 can be positioned radially outward from a longitudinal axis of the end effector 4170, which can allow the external compression member 4168 to provide support and closing force to the end effector 4170, e.g., to the one of the jaws 4172 along whose external surface the external compression member 4168 translates.

The device includes a single external compression member 4168 in this illustrated embodiment, but in some embodiments, a device can include a plurality of external compression members. For example, a first compression member can be configured to translate along a first end effector jaw, and a second compression member can be configured to translate along a second end effector jaw.

The external compression member 4168 can have a variety of sizes, shapes, and configurations. In an exemplary embodiment, the external compression member 4168 can be formed on an I-beam 4176 configured to translate along the end effector 4170, as discussed herein. The I-beam 4176 can thus be configured translate along the end effector 4170 with a portion thereof, e.g., the external compression member 4168, translating outside the end effector 4170. The external compression member 4168 can thus be configured to be actuated in conjunction with actuation of the I-beam 4176, which can make the external compression member 4168 easy for a user to actuate. The external compression member 4168 can be formed on an upper portion of the I-beam 4176, as in this illustrated embodiment, such that the external compression member 4168 can form a "roof" of the I-beam 4176.

The I-beam 4716 can include other features, as will be appreciated by a person skilled in the art, such as a guide pin 4178 configured to translate along the upper jaw 4172, e.g., in a channel formed therein, to facilitate closing of the end effector 4170, and such as a foot 4180 configured to translate along the bottom jaw 4174, e.g., in a longitudinal slot formed therein, to facilitate smooth, controlled translation of the I-beam 4176 through the end effector 4170.

Figure 107:
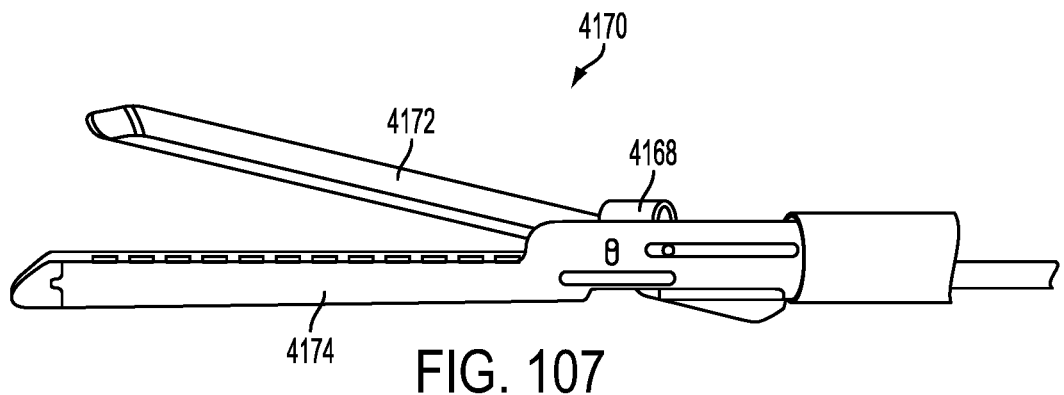
FIG. 107 is a side view of the end effector and the external compression member of FIG. 104, the end effector being in an open position.
Figure 108:
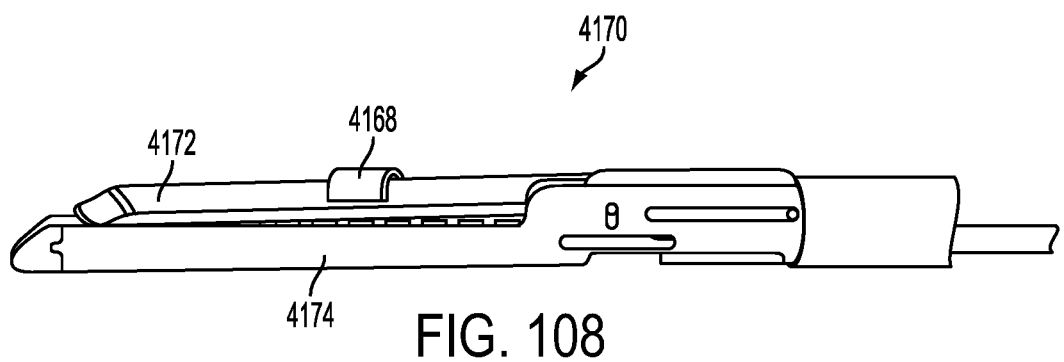
FIG. 108 is a side view of the end effector and the external compression member of FIG. 104, the end effector being in a closed position.

When the end effector 4170 is in an open position, as shown in FIG. 107, the external compression member 4168 can be located adjacent a proximal end of the end effector 4170. As shown in FIG. 108, as the end effector 4170 moves from the open position to a closed position, the external compression member 4168 can translate distally along the end effector 4168 so as to provide a compressive force thereto during firing of fasteners disposed within the end effector 4170, as discussed herein.

Figure 109:
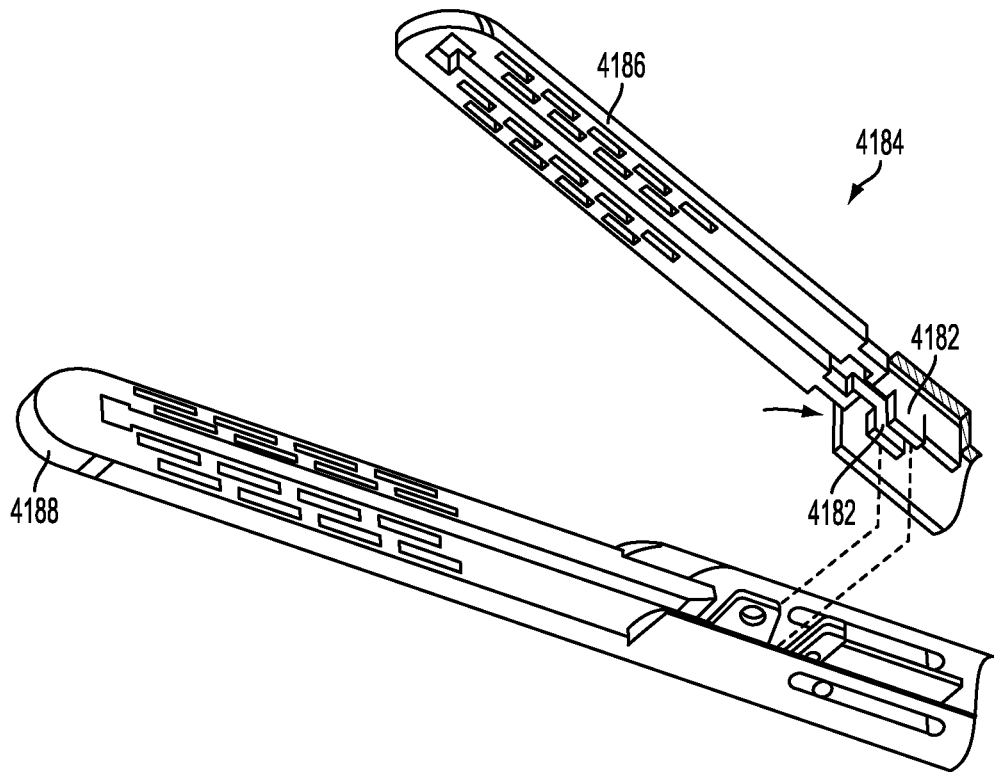
FIG. 109 is an exploded perspective view of one embodiment of a surgical device including an end effector and a closure mechanism in the form of an internal end effector protrusion.
Figure 110:
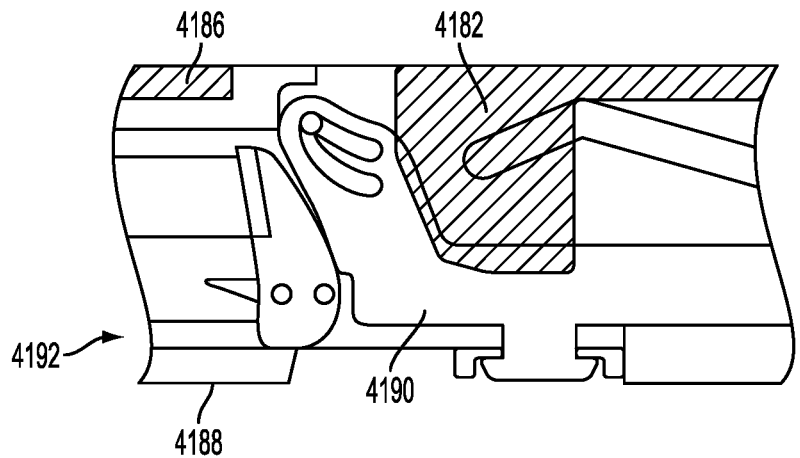
FIG. 110 is a side, cross-sectional view of the end effector and the closure mechanism of FIG. 109.

In some embodiments, a surgical device can include a closure mechanism in the form of an internal end effector protrusion. FIG. 109 and FIG. 110 illustrate one embodiment of a surgical device that includes a closure mechanism 4182 in the form of an internal end effector protrusion. In general, the internal end effector protrusion 4182 can be configured to improve closing of the device's end effector 4184 and clamping of tissue by the end effector 4184. The end effector 4184 can include an upper jaw 4186 and a bottom jaw 4188. The internal end effector protrusion 4182 can be configured to increase stiffness of the end effector 4184 to improve the moment arm.

The internal end effector protrusion 4182 can have a variety of sizes, shapes, and configurations. As in this illustrated embodiment, the internal end effector protrusion 4182 can include one or more support members located adjacent a proximal end of the end effector 4184. By being located near the end effector's proximal end, the closure mechanism 4182 can be configured to provide increased strength to the effector's proximal end, which can increase a moment of inertia of the end effector's proximal end, thereby increasing the moment arm. The closure mechanism 4182 can be formed on the upper jaw 4186, as in this illustrated embodiment, and extend in a direction toward the bottom jaw 4188.

The device in this illustrated embodiment includes two support members 4182, but a device can include another number of lateral support members. The two support members 4182 can be positioned on either side of an I-beam 4190, as shown in FIG. 110, that can be configured to translate through the end effector 4184 and advance a sled 4192 therethrough, as discussed herein. The support members 4182 can thus be configured to help guide and support the I-beam 4190 and/or help prevent buckling of the I-beam 4190 in embodiments in which the I-beam 4190 is flexible.

In some embodiments, a surgical device such as the above-mentioned surgical device 1100 can include at least one adjunct material to help improve surgical procedures performed using the surgical device. In general, an end effector of a surgical device can be configured to deliver one or more synthetic materials and/or biologic materials, collectively referred to herein as "adjunct materials," to a surgical site during a surgical procedure to help improve the surgical procedure. The one or more adjunct materials can be disposed between and/or on one or both of first and second jaws of the device, incorporated into a cartridge disposed in the end effector and having a plurality of fasteners therein, or otherwise placed in proximity to fasteners configured to be deployed from the end effector. When the fasteners are deployed at a treatment site, the adjunct material(s) can remain at the treatment site with the fasteners. In at least some instances, the adjunct material(s) can be configured to help seal holes formed by the fasteners as they are implanted into tissue, and/or the adjunct material(s) can be configured to provide tissue reinforcement at the treatment site. In at least some instances, the adjunct material(s) can be configured to wick or absorb beneficial fluids, e.g., sealants, blood, glues, that further promote healing, and in at least some instances, the adjunct material(s) can be configured to degrade to form a gel, e.g., a sealant, that further promotes healing. In at least some instances, the adjunct material(s) can help reduce inflammation, promote cell growth, and otherwise improve healing.

The adjunct materials have any number of configurations and properties. Embodiments of adjunct materials and coupling adjunct materials to end effectors are further described in U.S. application Ser. No. 14/300,954 entitled "Adjunct Materials And Methods Of Using Same In Surgical Methods For Tissue Sealing" filed Jun. 10, 2014, which is hereby incorporated by reference in its entirety.

In the embodiments described below, staples are used as examples of fasteners, but as will be appreciated by a person skilled in the art, other types of fasteners can be similarly configured and used. In exemplary embodiments of surgical devices including one or more adjunct materials, the fasteners can include "D" shaped staples such as the above-mentioned staples 1116, and the fasteners can be frangibly attached to a carrier.

In some embodiments, a surgical device can include at least one adjunct material disposed on a tissue-engaging surface of a cartridge. The cartridge can have a plurality of fasteners, e.g., "D" shaped fasteners, disposed therein and frangibly attached to a carrier also disposed in the cartridge. The cartridge can be configured to be removably coupled to an end effector.

Figure 111:
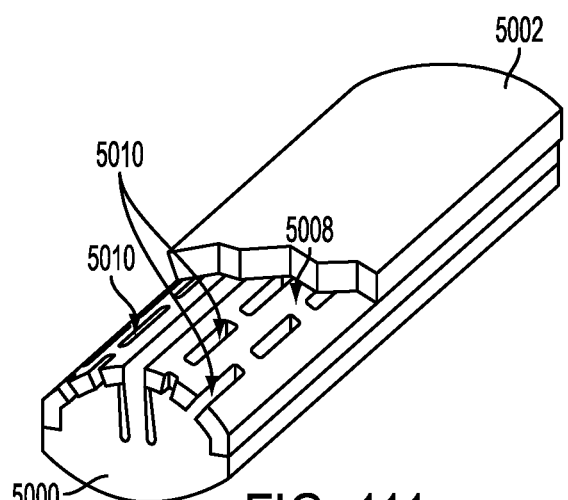
FIG. 111 is a perspective partially cross-sectional view of one embodiment of a cartridge having an adjunct material disposed thereon and having a plurality of fasteners disposed therein.
Figure 112:
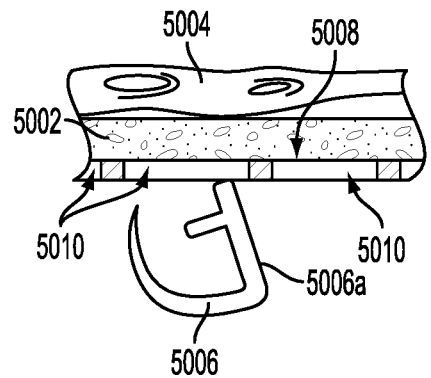
FIG. 112 is a side cross-sectional view of a portion of the cartridge of FIG. 111 with the adjunct material positioned adjacent a tissue.
Figure 113:
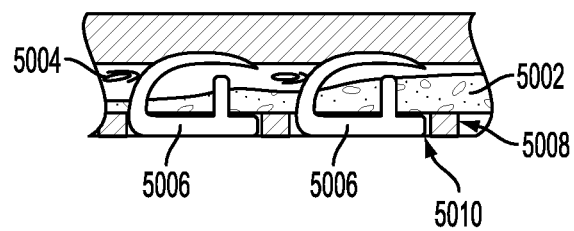
FIG. 113 is a side cross-sectional view of the cartridge of FIG. 112 with a plurality of fasteners ejected therefrom through the adjunct material and into the tissue.

FIG. 111, FIG. 112, and FIG. 113 illustrate one embodiment of a cartridge 5000 having at least one adjunct material 5002 coupled thereto. The at least one adjunct material 5002 in this illustrated embodiment includes a single adjunct material, but as mentioned herein, any number of adjunct materials can be used. Additionally, although the at least one adjunct material in this illustrated embodiment includes a foam, other types of adjunct materials can be used. In an exemplary embodiment, the foam can be bioabsorbable.

As in this illustrated embodiment, the at least one adjunct material 5002 can be coupled to the cartridge 5000 by being disposed on a tissue-engaging surface 5008 thereof. The tissue-engaging surface 5008 can have a plurality of openings 5010 formed therein through which fasteners 5006 disposed in the cartridge 5000 can be ejected. The at least one adjunct material 5002 can completely cover all of the openings 5010 such that the fasteners 5006 must each pass into the at least one adjunct material 5002 when ejected through the openings 5010 and into a tissue 5004, as shown in FIG. 112 and FIG. 113. The at least one adjunct material 5002 can cover the entire tissue-engaging surface 5008, as in this illustrated embodiment, so as to extend across an entire length and width thereof. The at least one adjunct material 5002 can thus be assured of covering all of the openings 5010 so that all fasteners 5006 can be ejected into the at least one adjunct material 5002 and then into tissue. In other embodiments, the at least one adjunct material 5002 can be disposed over one or more discrete portions of the tissue-engaging surface 5008 so as to not cover the entire length and width thereof, thereby requiring use of less adjunct material.

Figure 114:
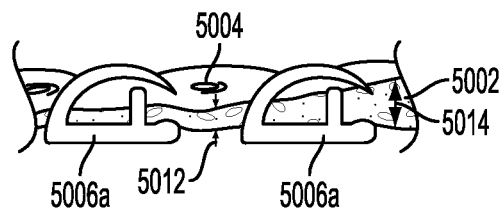
FIG. 114 is a side cross-sectional view of the fasteners, tissue, and adjunct material of FIG. 113.

FIG. 114 shows the fasteners 5006 deployed in the tissue 5004 with the at least one adjunct material 5002 sandwiched between substantially straight first legs 5006a of the fasteners 5006 and a lower surface of the tissue 5004. The at least one adjunct material 5002 can be configured, as also shown in FIG. 114, to compensate for a varying thickness of the tissue 5004, e.g., for a first tissue thickness 5012 that is less than a second tissue thickness 5014. The at least one adjunct material 5002 can be compressible, thereby facilitating such tissue thickness compensation.

Figure 116:
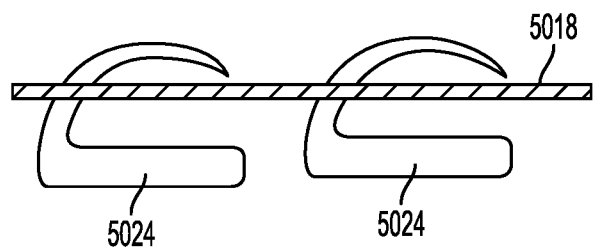
FIG. 116 is a side partially transparent view of two of the fasteners of FIG. 115 advanced through the adjunct material.
Figure 117:
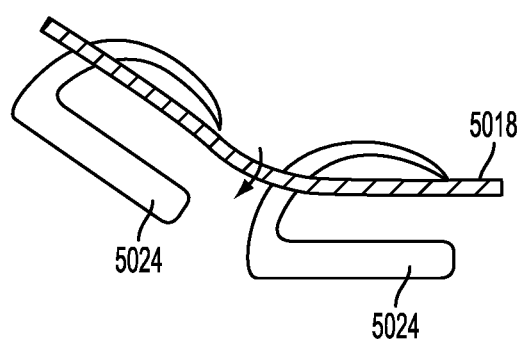
FIG. 117 is a side partially transparent view of the fasteners and the adjunct material of FIG. 116, the adjunct material flexing without breaking.

FIG. 114 illustrates another embodiment of a cartridge 5016 having at least one adjunct material 5018 coupled thereto. The at least one adjunct material 5018 in this illustrated embodiment includes a single adjunct material, but as mentioned herein, any number of adjunct materials can be used. The at least one adjunct material 5018 in this illustrated embodiments includes a plurality of independent adjunct materials that can each be configured to span across at least two openings 5020 formed in a tissue-engaging surface 5022 of the cartridge 5016. Each of the adjunct materials 5018 can thus be configured to have at least two fasteners 5024, shown in FIG. 115 and FIG. 116, pass therethrough from within the cartridge 5016 when ejected through the at least two openings 5020 underlying the adjunct material 5018. By having at least two fasteners 5024 pass therethrough and secured thereto when the fasteners 5024 are secured in tissue, the adjunct material 5018 can help prevent any one of the fasteners 5024 from rotating and/or otherwise shifting in the tissue, as shown in FIG. 117, since the one of the fasteners 5024 is interconnected with at least one other fastener 5024 via the adjunct material 5018. By having a single adjunct material 5018 have a subset of a total number of fasteners 5024 secured in tissue, the adjunct material 5018 can be configured to provide the adjunct material's benefits while allowing the fasteners 5024 to shift as needed for, e.g., tissue thickness accommodations, tissue movement during healing, etc.

As in this illustrated embodiment, each of the adjunct materials 5018 can be configured to cover at least two longitudinally aligned ones of the openings 5020. Accordingly, at least two longitudinally aligned fasteners 5024 can be ejected through each of the independent adjunct materials 5018. Longitudinal alignment of interconnected fasteners 5024 can further help prevent any one of the fasteners 5024 from rotating and/or otherwise shifting in the tissue in which the fasteners 5024 are deployed, since the "D" shaped fasteners 5024 would tend to rotate along the longitudinal axis of the adjunct material 5018.

Figure 115:
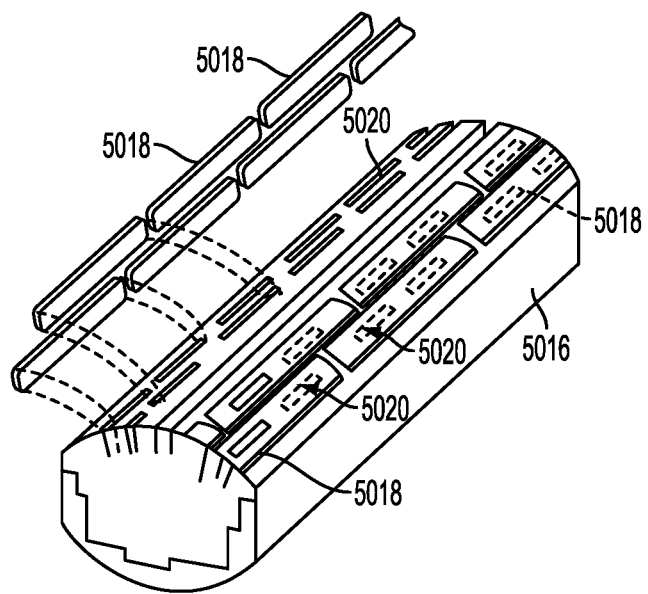
FIG. 115 is a perspective partially exploded view of another embodiment of a cartridge having an adjunct material disposed thereon and having a plurality of fasteners disposed therein.
Figure 118:
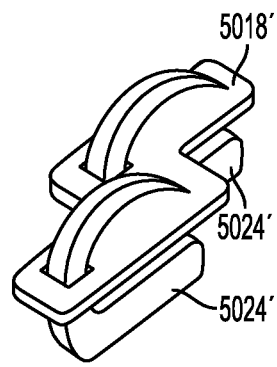
FIG. 118 is a perspective view of another embodiment of an adjunct material having two fasteners disposed therethrough.
Figure 119:
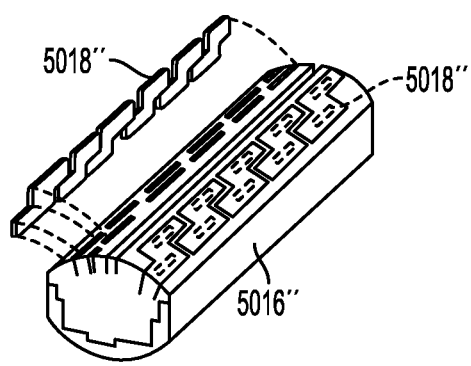

FIG. 118 illustrates an alternate embodiment of an adjunct material 5018' that can be configured and used similar to the adjunct material 5018 of FIG. 115. Instead of being configured to cover at least two longitudinally aligned openings formed in a cartridge's tissue-engaging surface and have at least two longitudinally aligned fasteners deployed therethrough, the adjunct material 5018' in this illustrated embodiment can be configured to cover at least two laterally offset and longitudinally offset openings (not shown) formed in a cartridge's tissue-engaging surface (not shown) and have at least two laterally offset and longitudinally offset fasteners 5024' deployed therethrough.

Figure 120:
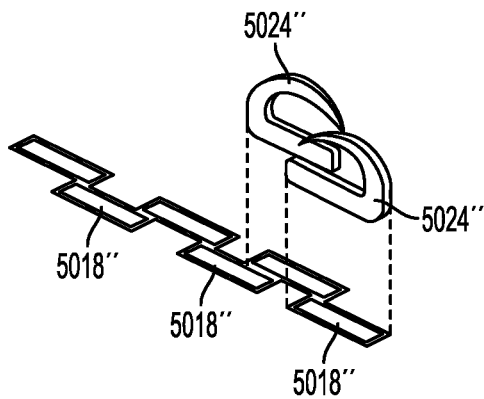
Figure 121:
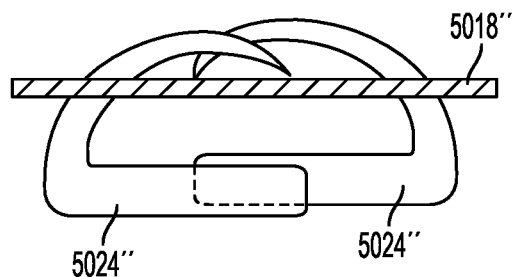
Figure 122:
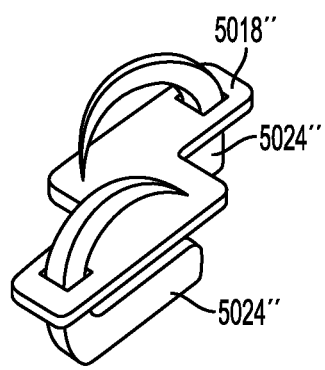

FIG. 119, FIG. 120, FIG. 121, and FIG. 122 illustrate an alternate embodiment of an adjunct material 5018" that can be configured and used similar to the adjunct material 5018 of FIG. 118. Instead of being configured to receive at least two fasteners facing in a same direction when deployed, such as the fasteners 5024' of FIG. 118, the adjunct material 5018" can be configured to receive at least two fasteners 5024" facing in opposite directions when deployed from a cartridge 5016". Each pair of two fasteners 5024" when deployed can effectively form a "B" shape, as shown in FIG. 120, FIG. 121, and FIG. 122, which can resist loads more effectively than the fasteners 5024" when not deployed in the "B" shape.

Figure 123:
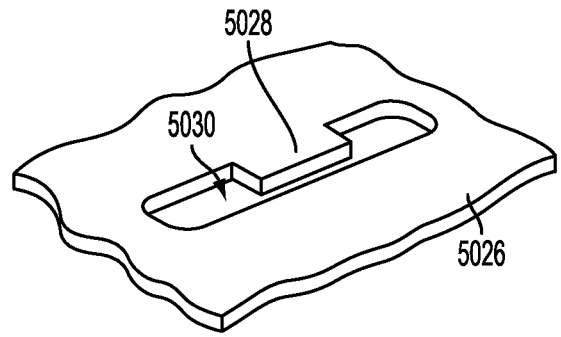
Figure 124:
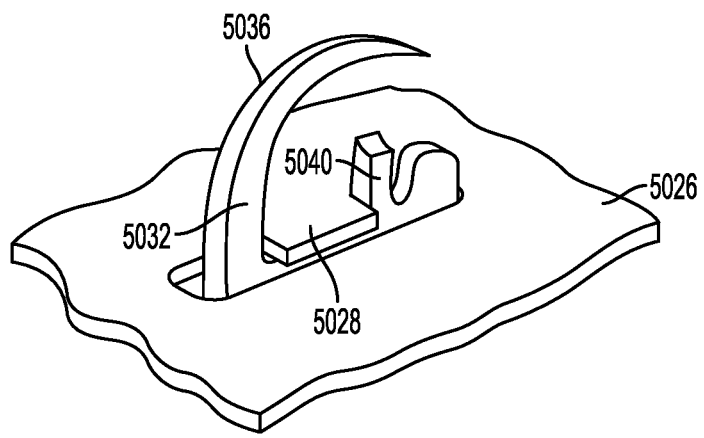
Figure 125:
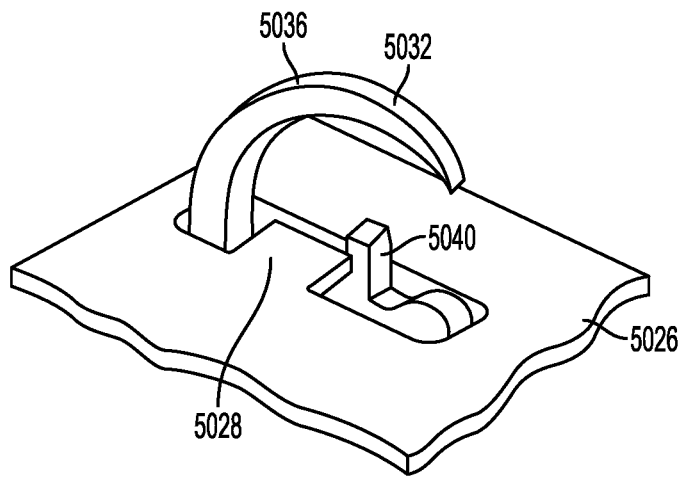

In some embodiments, an adjunct material can include an anti-rotation feature configured to help prevent rotation of a fastener deployed through the adjunct material when the fastener is secured in tissue and engaging the adjunct material. FIG. 123, FIG. 124, and FIG. 125 illustrate one embodiment of an adjunct material 5026 including an anti-rotation feature 5028. In this illustrated embodiment, the adjunct material 5026 includes a film, but as mentioned above, other types of adjunct materials can be used. The film can have a thickness in a range of e.g., about 0.003 mm to 0.009 mm or about 0.006 mm to 0.009 mm.

The anti-rotation feature 5028 can have a variety of sizes, shapes, and configurations. The adjunct material 5026 can include a plurality of openings 5030 formed therein that can each be aligned with a corresponding one of a plurality of openings (not shown) formed in a cartridge's tissue-engaging surface (not shown) through which fasteners 5032, also shown in FIG. 126, can be deployed. Each one of the openings can have one of the anti-rotation features 5028 extending laterally therein. The anti-rotation feature 5028 in this illustrated embodiment includes a tab having a rectangular shape, but the anti-rotation feature 5028 can have other shapes, e.g., semi-circular, square, etc. The anti-rotation feature 5028 can have a size and shape corresponding to a side and shape of a corresponding anti-rotation feature 5034 of the fastener 5032.

Figure 126:
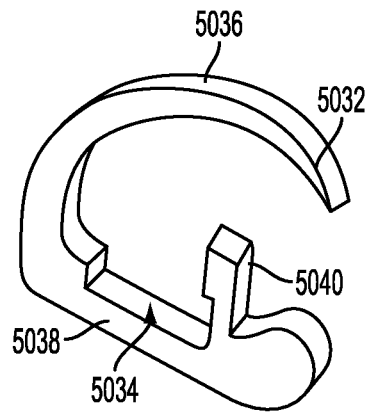

The fastener's anti-rotation feature 5034 can also have a variety of sizes, shapes, and configurations. In an exemplary embodiment, the fastener's anti-rotation feature 5034 can be formed in an inner-facing surface of a substantially straight first leg 5038 of the fastener 5032, which also includes a curved second leg 5036. The fastener 5032 can include an anti-rotation member 5040, e.g., a barb, etc., configured to help prevent the fastener's rotation in tissue when the fastener 5032 is deployed therein. The anti-rotation member 5040 can define a sidewall of the anti-rotation feature 5034, as shown in FIG. 126. The adjunct material's anti-rotation feature 5028 can be configured to be seated in the fastener's anti-rotation feature 5034 when the fastener 5032 rotates through the cartridge's opening and the adjunct material's opening 5030 so as to be positioned within tissue, as shown in FIG. 124 and FIG. 125. The fastener's anti-rotation member 5040 and the adjunct material's anti-rotation feature 5028 seated in the fastener's anti-rotation feature 5034 can each help prevent the fastener 5032 from rotating within tissue in which the fastener 5032 is deployed.

In some embodiments, a surgical device such as the above-mentioned surgical device 1100 can be configured to facilitate removable coupling of a cartridge to an end effector of a surgical device. In general, one of the cartridge and the surgical device can include at least one mating element, and the other of the cartridge and the surgical device can include at least one engagement feature configured to removably engage the at least one mating element. The engagement of the at least one mating element and the at least one engagement feature can help ensure that the cartridge is fully mated to the surgical device such that the surgical device can properly fire fasteners disposed within the cartridge. Some embodiments of surgical devices can be configured to prevent fastener firing unless the cartridge is fully seated therein. The engagement of the at least one mating element and the at least one engagement feature can be configured to provide a positive indication that the cartridge is fully seated in the end effector. The positive indication can be visually and/or audibly detectable by a user seating the cartridge in the surgical device's end effector, thereby allowing the user to verify proper seating of the cartridge. The visual detection of the at least one mating element and the at least one engagement feature's engagement can be from an outside of the device such that no further assembly or disassembly of the device is needed to perform the visual detection and/or such that no special tools, e.g., a magnifier, are needed for the visual detection.

Some end effectors have particularly small diameters, such as those appropriate for use in a minimally invasive surgical procedure, such that cartridges removably disposable therein are correspondingly small. It can be difficult to handle these small cartridges and to ensure that they are fully seated within these small end effectors. The surgical device and the cartridge including the at least one mating element and the at least one engagement feature can facilitate removable disposal of the cartridge within the end effector, even when the cartridge and the end effector have particularly small diameters.

A surgical device can be configured to facilitate removable coupling of a cartridge to a surgical device's end effector in a variety of ways. In the embodiments described below, staples are used as examples of fasteners, but as will be appreciated by a person skilled in the art, other types of fasteners can be similarly configured and used.

In some embodiments, a mating element can be in the form of a latch. FIG. 127, FIG. 128, FIG. 129, and FIG. 130 illustrate one embodiment of a mating element 6014 that includes a latch. In general, the mating element 6014 can be configured to removably couple to an engagement feature 6016, thereby facilitating removable seating of a cartridge 6008 within an end effector 6004 of a surgical device 6000. The end effector 6004 can be coupled to a distal end of the device's elongate shaft 6002, and can include an upper jaw 6020 and a bottom jaw 6008. As discussed herein, one of the jaws 6020, 6018 can include a channel (not shown) formed therein that can be configured to removably seat the cartridge 6008 therein. In this illustrated embodiment, the bottom jaw 6018 includes the channel configured to releasably and replaceably seat the cartridge 6008.

As in this illustrated embodiment, the surgical device 6000 can include the mating element 6014, and the cartridge 6008 can include the engagement feature 6016. The mating element 6014 can be formed on a distal portion of the device 6000 adjacent the end effector 6004, and the engagement feature 6016 can be formed on a proximal portion of the cartridge 6008, as in this illustrated embodiment. In other embodiments, as mentioned above, on the cartridge 6008 can include the mating element 6014, e.g., in a proximal portion thereof, and the surgical device 6000 can include the engagement feature 6016, e.g., in a distal portion thereof adjacent the end effector 6004. There is only one mating element 6014 in this illustrated embodiment and one engagement feature 6016, but one or more mating elements 6014, e.g., two latches, and one or more corresponding engagement features 6016 can be used.

The latch 6014 and the engagement feature 6016 can each have a variety of sizes, shapes, and configurations. As in this illustrate embodiment, the latch 6014 can include an arm having a first end fixedly attached to the device 6000, e.g., to the shaft 6002. The latch 6014 can also include a second, opposite end freely movable relative to the device 6000, e.g., to the shaft 6002 and the end effector 6004, when the latch 6014 is not fully mated with the engagement feature. The second end can include a protrusion formed thereon and extending radially inward. The latch 6014 can be configured to dynamically move in response to insertion of the cartridge 6008 into the bottom jaw 6018, thereby allowing the latch 6014 to automatically engage the engagement feature 6016 when the cartridge 6008 is properly seated within the bottom jaw 6018, such as by the latch 6014 snapping into the engagement feature 6016. In some embodiments, this snapping can make an audibly detectable noise, thereby indicating proper seating of the cartridge 6008 within the bottom jaw 6018. The latch 6014 can be configured to so dynamically move by including a deflectable spring-arm, as in this illustrated embodiment.

As in this illustrated embodiment, the engagement feature 6016 can include a notch, also referred to herein as a "cut-out," configured to receive the mating element 6014, e.g., the protrusion thereof, therein. The engagement feature 6016 can have a size and shape corresponding to a size and shape of the mating element 6014, e.g., the protrusion thereof, so as to facilitate a tight, secure fit of the mating element 6014 within the engagement feature 6016.

Figure 127:
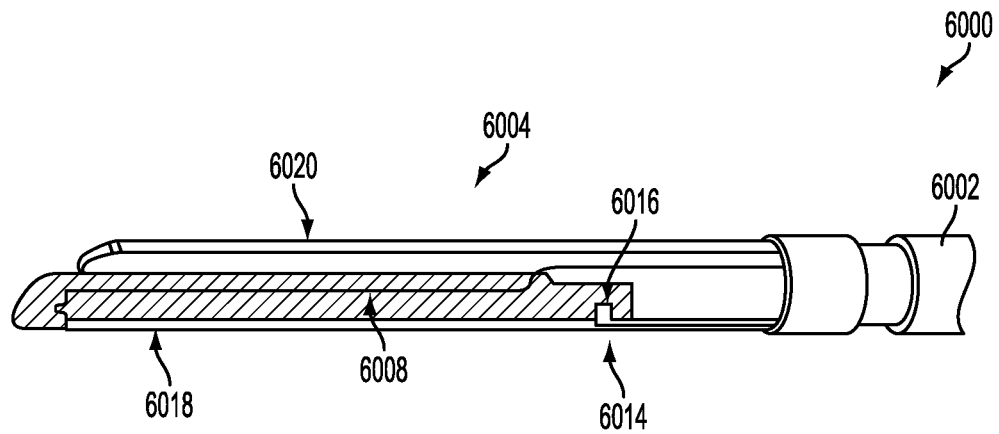
Figure 129:
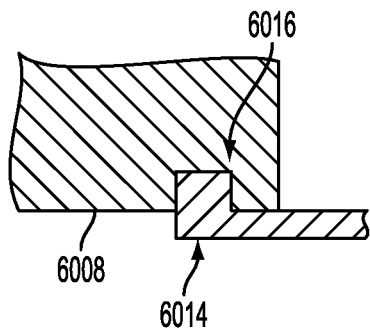
Figure 130:
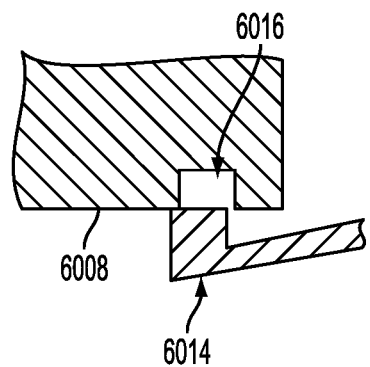

In general, the latch 6014 can be configured to extend into the engagement feature 6016 so as to be completely mated thereto. FIG. 127 and FIG. 129 show the mating element 6014 mated with the engagement feature 6016, the cartridge 6008 thus being fully seated within the bottom jaw 6018. The mating element 6014 being completely mated with the engagement feature 6016 can be visually detectable by looking at the device 6000, thereby indicating to a user that the device 6000 can be used to fire fasteners (not shown) from the cartridge 6008. The latch 6014 can be configured to protrude radially outward beyond an outer diameter of the shaft 6002 when the latch 6014 is not engaged with, e.g., is misaligned from, the engagement feature 6016. FIG. 128 and FIG. 130 show the mating element 6014 unengaged with the engagement feature 6016, thereby indicating that the cartridge 6008 is not fully seated within the bottom jaw 6018. The mating element 6014 being incompletely mated with the engagement feature 6016 can be visually detectable by looking at the device 6000, thereby allowing a user to readjust the cartridge 6008 so as to properly seat the cartridge 6008 in the end effector 6004. FIG. 128 also shows that the latch 6014 can extend a distance 6006 radially outward from the shaft's 6002 outer surface 6010 when the mating element 6014 and the engagement feature 6016 are not engaged together.

The mating element 6014 can be configured to prevent the end effector 6004 from being inserted into a patient, e.g., into a body cavity thereof, when the mating element 6014 is not fully mated to the engagement feature 6016. Thus, if a user does not realize that the cartridge 6008 is not properly seated in the bottom jaw 6018 of the end effector 6004 and tries to insert in the end effector 6004 into the patient, the mating element 6014 can indicate to the user that the cartridge 6008 is not properly seated in the bottom jaw 6018 and should be readjusted thereto before inserting the end effector 6004 into the patient for the device 6000 to properly function within the patient, e.g., for the device 6000 to properly fire fasteners therein.

As shown in one embodiment in FIG. 131, the mating element 6014 can be configured to prevent the end effector 6004 from being inserted into a patient's tissue 6012 to access a body cavity (not shown) underneath the tissue by abutting an access device 6022 disposed within the tissue 6012 through which the end effector 6004 is attempting to be advanced. The access device 6022 includes a trocar in this illustrated embodiment, but other types of access devices can be similarly used, as will be appreciated by a person skilled in the art. The access device 6022 can include a port 6024 extending therethrough through which the end effector 6004 can be inserted. The port 6024 can have a diameter. The end effector 6004 can have a diameter corresponding to the port's diameter in the closed position such that with the mating element 6014 extending the distance 6006 radially outward, the end effector's 6004 diameter can be effectively increased. This increased diameter can prevent the end effector 6004 from being advanced through the access device 6022. For example, the port's diameter can be configured to accommodate a device having a 5 mm diameter, and the end effector 6004 can have a 5 mm diameter when the cartridge 6008 is fully seated in the bottom jaw 6018. When the cartridge 6008 is not fully seated in the bottom jaw 6018, as shown in FIG. 131, the end effector's diameter can be effectively increased over 5 mm such that the end effector 6004 cannot be fully advanced through the port 6024.

FIG. 132, FIG. 133, and FIG. 134 illustrate another embodiment of a mating element that includes a latch configured to removably couple to an engagement feature. In this illustrated embodiment, the mating element includes first and second latches 6026a, 6026b, and the engagement feature includes first and second cut-outs 6028a, 6028b configured to receive the first and second latches 6026a, 6026b, respectively. The first and second latches 6026a, 6026b and the first and second cut-outs 6028a, 6028b can generally be configured and used similar to the mating element 6014 and the engagement feature 6016, respectively, of FIG. 127. In this illustrated embodiment, a bottom jaw 6030 of an end effector (not shown) includes the first and second cut-outs 6028a, 6028b and includes a channel 6032 configured to releasably and replaceably seat a cartridge 6034 that includes the first and second latches 6026a, 6026b. However, as mentioned above, in other embodiments, the end effector or other part of a device that includes the end effector can include the mating element, and the cartridge 6034 can include the engagement feature.

The first and second latches 6026a, 6026b can be positioned on opposite lateral sides of the cartridge 6034, and the first and second cut-outs 6028a, 6028b can be correspondingly positioned on opposite lateral sides of the bottom jaw 6030, e.g., on opposite lateral sides of the channel 6032. The mating element and the engagement feature being located on lateral sides of the cartridge 6034 and bottom jaw 6030 that seats the cartridge 6034 can help ensure that the cartridge 6034 is not skewed laterally within the channel 6032.

When the cartridge 6034 is inserted into the channel 6032 in a proximal direction 6036, as shown in FIG. 133, the first and second latches 6026a, 6026b can be configured to dynamically move in response to the insertion, e.g., flex radially inward, as shown in FIG. 134. Inserting the cartridge 6034 in the proximal direction 6036 allows the cartridge 6034 to be easily seated within the cartridge 6034 in one motion. When the first and second latches 6026a, 6026b align with the first and second cut-outs 6028a, 6028b, respectively, the first and second latches 6026a, 6026b can be configured to snap into the first and second cut-outs 6028a, 6-28b so as to secure the cartridge 6034 within the bottom jaw 6030. FIG. 133 shows the cartridge 6034 fully seated within the channel 6032 of the bottom jaw 6030 with the first and second latches 6026a, 6026b snapped into the first and second cut-outs 6028a, 6028b.

In some embodiments, a surgical device can include at least on biasing element configured to bias a cartridge out of an end effector to which the cartridge can be removably coupled. The at least one biasing element can facilitate removal of the cartridge from the end effector and/or can be configured to indicate when the cartridge is not fully seated within the end effector. As in this illustrated embodiment, the bottom jaw 6030 that seats the cartridge 6034 can include a biasing element 6038a, 6038b. There are two biasing elements 6038a, 6038b in this illustrated embodiment, but a surgical device can include another number of biasing elements. The at least one biasing element 6038a, 6038b can have a variety of sizes, shapes, and configurations. As in this embodiment, the biasing elements 6038a, 6038b can include a coil spring. In other embodiments, the at least one biasing element 6038a, 6038b can include, e.g., a volute spring, an elastic member similar to a rubber band, a leaf spring, etc. Each of the biasing element 6038*a*, 6038*b* can be biased in a distal direction 6038, as shown in FIG. 134.

When the cartridge 6034 is inserted into and seated within the bottom jaw 6030, the cartridge 6034 can compress the biasing elements 6038*a*, 6038*b*, as shown in FIG. 133. If the cartridge 6034 is not fully seated in the bottom jaw 6030, the bias of the at least one biasing element 6038*a*, 6038*b* can cause the cartridge 6034 to protrude out of the bottom jaw 6030, thereby indicating that the cartridge 6034 is not fully seated therein. When the cartridge 6034 is removed from the bottom jaw 6030, e.g., by pressing the first and second mating elements 6026*a*, 6026*b* radially inward, the biasing elements 6038*a*, 6038*b* can urge the cartridge 6034 in the distal direction 6040. This urging can cause the cartridge 6034 to extend a distance 6042 distally beyond where the cartridge 6034 is fully seated within the bottom jaw 6030, which can facilitate grasping of the cartridge 6034 and removal thereof from the bottom jaw 6030. A secondary tool thus need not be used to remove the cartridge 6034 from the bottom jaw 6030.

FIG. 135 illustrates an alternate embodiment of a biasing element 6044*a*, 6044*b* that can be configured and used similar to the biasing elements 6038*a*, 6038*b* of FIG. 133. The at least one biasing element 6044*a*, 6044*b* in this illustrated embodiment also includes a coil spring. In the embodiment of FIG. 133, the biasing element 6038*a*, 6038*b* extend from an inner surface of the bottom jaw 6030 in the distal direction 6040. In this illustrated embodiment, the biasing element 6044*a*, 6044*b* each extend from an inner surface of a bottom jaw 6050 that seats a cartridge 6052 in an upward direction 6046 that is substantially perpendicular to a distal direction 6048. The cartridge 6052 can be configured to be seated in the bottom jaw 6050 by being advanced in a downward direction 6054 into a channel 6056 thereof. The biasing elements 6044*a*, 6044*b* can be biased in the upward direction 6046 such that when the cartridge 6052 is removed from the bottom jaw 6050, the biasing elements 6044*a*, 6044*b* can urge the cartridge 6052 in the upward direction 6046, thereby facilitating grasping and removal of the cartridge 6052 from the bottom jaw 6050.

Instead of a cartridge being removably coupled to an end effector fixedly attached to an elongate shaft of a surgical device, the end effector can be removably coupled to the elongate shaft, as will be appreciated by a person skilled in the art. In other words, the end effector can be modular. The end effector can include a cartridge fixed therein, although in some embodiments, the end effector can be configured to have a cartridge releasably and replaceably seated therein. Such a surgical device can include one of at least one mating element and at least one engagement feature, and such a modular end effector can include the other of the at least one mating element and the at least one engagement feature. The at least one mating element and the at least one engagement feature can generally be configured and used similar to those discussed above.

FIG. 136 illustrates one embodiment of a surgical device that includes an elongate shaft 6058 and a modular end effector 6060 configured to removably couple to a distal end of the shaft 6058. The end effector 6060 in this illustrated embodiment includes a cartridge 6062 fixedly seated therein. The end effector 6060 can include at least one mating element 6072 configured to removably couple to at least one engagement feature 6074 of the shaft 6058. As in this illustrated embodiment, the at least one mating feature 6072 can include one or more protrusions, and the at least one engagement feature 6074 can include one or more notches that are each configured to seat one of the protrusions therein. Similar to that discussed above, if the at least one mating feature 6072 and the at least one engagement feature 6074 are only partially engaged, the end effector 6060 can be prevented from being inserted into a patient. The end effector 6060 includes two protrusions and the shaft 6058 includes two notches in this illustrated embodiment, but there can be a different number of protrusions and corresponding notches. In another embodiments, the end effector 6060 can include at least one engagement feature, and the shaft 6058 can include at least one mating element.

The shaft 6058 in this illustrated embodiment has a proximal portion 6064 of a first drive rod movably positioned therein and a proximal portion 6070 of a second drive rod movably positioned therein. The first drive rod can be configured to be actuated at a handle (not shown) of the device to effect opening and closing of the end effector 6060, e.g., opening and closing of the end effector's first and second jaws 6066, 6068. The second drive rod can be configured to be actuated at the handle to effect firing of fasteners (not shown) from the cartridge 6062. The end effector 6060 in this illustrated embodiment has a distal portion 6076 of the first drive rod movably positioned therein and has a distal portion 6078 of the second drive rod movably positioned therein, When the at least one mating element 6072 is removably coupled to the at least one engagement feature 6074 so as to removably couple the end effector 6060 and the shaft 6058, the proximal and distal portions 6064, 6072 of the first drive rod can be in operative contact, and the proximal and distal portions 6070, 6078 of the second drive rod can be in operative contact. A distal end of the first drive rod's proximal portion 6064 can include at least one mating element 6080 configured to removably mate with a corresponding at least one engagement feature 6082 at a proximal end of the first drive rod's distal portion 6076. Similarly, a distal end of the second drive rod's proximal portion 6070 can include at least one mating element 6084 configured to removably mate with a corresponding at least one engagement feature 6086 at a proximal end of the second drive rod's distal portion 6078. Although the proximal portions 6064, 6070 include engagement features in this illustrated embodiment, in other embodiments, the proximal portions 6064, 6070 can include engagement features configured to engage with corresponding mating elements of the distal portions 6072, 6078.

The end effector 6060 can be biased, e.g., spring biased, to an open position. The second drive rod can be configured such that after the fasteners have been fired from the cartridge 6062, e.g., by distally advancing the second drive rod through the cartridge 6062 with the end effector 6060 in a closed position, the second drive rod can be retracted so as to cause the end effector 6060 to move from the closed position to the open position. Retracting the end effector 6060 through an access device through which the end effector 6060 was inserted into a patient's body can be configured to cause the end effector 6060 to move from the open position to the closed position so as to allow the end effector 6060 to be removed from the patient's body, but the biasing of the end effector 6060 can cause the end effector 6060 to be in the open position once removed from the access device. The open position can indicate that the cartridge 6062 should be removed and replaced before again attempting to fire fasteners from the end effector 6060, thereby providing safety.

In some embodiments, a surgical device such as the above-mentioned surgical device 1100 can be configured to prevent at least one of closure of the end effector and firing of fasteners from the end effector when a cartridge is not fully seated in the end effector. The cartridge can be configured to be removably coupled to the end effector, as discussed herein. In some instances, the cartridge can be improperly loaded into the end effector such that the cartridge is not fully seated therein. In some instances, the end effector can be advanced into a body of a patient without a cartridge seated in the end effector at all. Preventing closure of an end effector and/or firing of fasteners from the end effector when a cartridge is not fully seated in the end effector can indicate to a user of the device that either the end effector does not have a cartridge seated therein at all or that the cartridge engaged with the end effector is not fully seated therein. The user can thus be aware that the device needs adjustment, either by seating a cartridge therein or readjusting the cartridge already attempted to be seated therein. Preventing closure of an end effector and/or firing of fasteners from the end effector when a cartridge is not fully seated in the end effector can help prevent the device and/or a cartridge partially seated in the end effector from being damaged by an attempt to close the end effector and/or an attempt to fire fasteners.

In an exemplary embodiment, a surgical device including an end effector configured to removably seat a cartridge can include a lockout element configured to prevent at least one of closure of the end effector and firing of fasteners from the end effector when a cartridge is not fully seated in the end effector. The lockout element can be configured to move between first and second positions. The lockout element being in the first position can indicate that no cartridge is seated in the end effector or that a cartridge is improperly seated in the end effector. The lockout element being in the second position can indicate that a cartridge is fully seated in the end effector. The lockout element can be configured to dynamically move between the first and second positions. Fully seating a cartridge in the end effector can cause the locking element to dynamically move from the first position to the second position. Partial or full removal of a fully seated cartridge from the end effector can cause the locking element to move from the second position to the first position. The locking element can thus be configured to provide an automatic safety feature by being configured to automatically prevent firing and/or prevent closing of the end effector if a cartridge is not fully seated in the end effector.

A surgical device can be configured to prevent at least one of closure of the end effector and firing of fasteners from the end effector in a variety of ways. In the embodiments described below, staples are used as examples of fasteners, but as will be appreciated by a person skilled in the art, other types of fasteners can be similarly configured and used.

In some embodiments, a lockout element can be in the form of a cam plate, also referred to herein as a "shuttle." FIG. 137 and FIG. 138 illustrate one embodiment of a surgical device that can include an elongate shaft 7000 and an end effector 7008 coupled to a distal end of the elongate shaft 7000. The end effector 7008 can include a first jaw 7002 pivotally coupled to a second jaw 7004 via a pivot pin 7010. The first and second jaws 7002, 7004 in this illustrated embodiment are identical to the above-mentioned first and second jaws 1110a, 1110b, which can be configured to open/close similar to that discussed herein for the first and second jaws 7002, 7004, but the device that includes the first and second jaws 7002, 7004 of this illustrated embodiment also includes a locking element configured to prevent at least one of closure of the end effector 7008 and firing of fasteners (not shown) from the end effector 7008 when a cartridge 7012 is not fully seated in the end effector 7008. FIG. 137 shows the cartridge 7012 partially seated in the bottom jaw 7002 such that the end effector 7008 cannot close and fasteners cannot be fired from the cartridge 7012. FIG. 138 shows the cartridge 7012 fully seated in the bottom jaw 7002 such that the end effector 7008 can close, as indicated by an arrow 7024 in a direction of closure and by the anvil 7004 in phantom in FIG. 138, and fasteners can be fired from the cartridge 7012.

As shown in FIG. 137 and FIG. 139, the anvil 7004 can include a first slot 7018 formed in a proximal portion thereof. The slot 7018 can be configured to receive a guide pin 7028 at a distal end of a drive rod 7030 configured to translate along the shaft 7000 to effect opening and closing of the end effector 7004. The guide pin 7028 can be configured to slide distally within the guide slot 7018 to close the end effector 7008 by causing the anvil 7004 to move toward the bottom jaw 7002, and can be configured to slide proximally within the guide slot 7018 to open the end effector 7008 by causing the anvil 7004 to move away from the bottom jaw 7002. As shown in FIG. 137 and FIG. 138, the bottom jaw 7002 can include a second slot 7020 formed therein. The slot 7020 can be configured to slidably receive the guide pin 7028 therein that also slides within the first closure slot 7018. The first and second slots 7018, 7020 via movement of the guide pin 7028 therein can cooperate to facilitate opening and closing of the end effector 7004. Although only one of each of the first and second slots 7018, 7020 are shown in FIG. 137 and FIG. 138, the anvil 7004 can have first slots 7018 formed in opposed lateral sides thereof, and the bottom jaw 7002 can have second slots 7020 formed in opposed lateral sides thereof.

The bottom jaw 7002 can include a third slot 7022 formed therein that can be configured to slidably receive the pivot pin 7010 therein. Although only one of third slots 7022 is shown in FIG. 137 and FIG. 138, the bottom jaw 7002 can have third slots 7022 formed in opposed lateral sides thereof.

The pivot pin 7010 can have a variety of sizes, shapes, and configurations. The pin 7010 can be a single pin laterally spanning the end effector 7008, or the pin 7010 can include two pins extending laterally. In an exemplary embodiment, the pin 7010 can be attached to the anvil 7004 in a fixed position relative thereto, and can be movably coupled to the bottom jaw 7002. The bottom jaw 7002 can have a slot 7014 formed therein in which the pin 7010 can be slidably movable. As shown in FIG. 139, the anvil 7004 can have a pin receiving hole 7016 formed therein configured to fixedly receive the pin 7010 therein. Alternatively, the pin 7010 can be integrally formed with the anvil 7004.

As shown in FIG. 140, the pivot pin 7010 can be configured to be slidably received within a cam plate 7026. The cartridge jaw 7002 can thus have two cam plates 7026 disposed therein, one at each of the laterally opposed second slots 7020 formed in the cartridge jaw 7002. The cam plate 7026 can include a center opening 7030 formed therethrough. The center opening 7030 can be defined by a bottom wall 7030b, an upper wall 7030u, a distal wall 7030d, and a proximal wall 7030p. The center opening 7030 can include a proximal extension 7032 in an upper portion thereof. The proximal end of the center opening 7030 can be at a higher position, e.g., more toward the anvil 7004, than the aperture's distal end. The cam plate 7026 can be disposed within the bottom jaw 7002 along an inner surface thereof adjacent the second slot 7020.

The cam plate 7026 can include a proximal tail 7034 in a bottom portion thereof. The proximal tail 7034 can be coupled to a bias element 7036, e.g., a coil spring wound around the tail 7034 as in this illustrated embodiment. The bias element 7036 can be configured to bias the cam plate 7026 in a distal direction, e.g., away from the proximal extension such that the pin 7010 can be configured to be biased to be in the proximal extension 7032.

The proximal extension 7032 can be configured to seat the pin 7010 therein when the end effector 7004 does not have the cartridge 7012 fully seated therein, as shown in FIG. 137 and FIG. 140. The bias element 7036 can facilitate this seating. As the cartridge 7012 is more proximally positioned within the bottom jaw 7002, the cartridge 7012 can be configured to move the cam plate 7026 proximally so as to shift a position of the pin 7010 within the aperture 7030. A length of the proximal extension 7032 in a proximal/distal direction can define how much the cam plate 7026 must move proximally before the pin 7010 can exit the proximal extension 7032 so as to move in a downward direction toward the bottom surface 7030b of the aperture 7030, as shown in FIG. 138 in which the pin 7010 has moved downward to the bottom surface 7030b. The pin 7010 not exiting the proximal extension 7032 can indicate that the cartridge 7012 has not been fully seated in the bottom jaw 7002, as shown in FIG. 137 and FIG. 141, as the cartridge 7012 has not caused the pin 7010 to exit the proximal extension 7032. The pin 7010 being in the proximal extension 7032 can effectively cause the pivot point about which the jaws 7002, 7004 pivot to a higher position, which can prevent closure of the jaws 7002, 7004.

FIG. 141 also shows that when the cartridge 7012 has not been fully seated in the bottom jaw 7002, and the end effector 7008 has hence not been fully closed, the lockout element can be configured to prevent the end effector 7008 from being inserted into a patient's tissue (not shown) to access a body cavity (not shown) underneath the tissue by abutting an access device 7006 disposed within the tissue through which the end effector 7008 is attempting to be advanced. The access device 7006 includes a trocar in this illustrated embodiment, but other types of access devices can be similarly used, as will be appreciated by a person skilled in the art. The access device 7006 can include a port 7038 extending therethrough through which the end effector 7006 can be inserted. The port 7038 can have a diameter. The end effector 7006 can have a diameter in the closed position corresponding to the port's diameter such that with the lockout element locking out closing/firing when the cartridge 7012 has been improperly loaded or not loaded at all, the end effector's 7006 diameter can be effectively increased. This increased diameter can prevent the end effector 7006 from being advanced through the access device 7006.

FIG. 142 and FIG. 143 illustrate an alternate embodiment of a cam plate 7040 that can be configured and used similar to the cam plate 7026 of FIG. 140. The cam plate 7040 in this illustrated embodiment can include an upper proximal extension 7042 and a lower proximal extension 7044. The cam plate 7040 can include a bias element (not shown) at a proximal tail 7058 thereof. When a cartridge 7046 has been fully seated in a cartridge jaw 7048 pivotally coupled at a pivot pin 7052 to an anvil 7050, as shown in FIG. 142 and FIG. 144, the pivot pin 7052 can be configured to be seated in the upper proximal extension 7042, thereby an I-beam 7052 to be properly aligned with the anvil 7050 so as to allow a guide pin 7054 of the I-beam 7052 to translate along the anvil 7050 in a channel 7056 formed therein to facilitate end effector closing and clamping. When the cartridge 7046 has not been fully seated in the cartridge jaw 7048, as shown in FIG. 143 and FIG. 145, the I-beam 7052, e.g., the guide pin 7054 thereof, can be misaligned from the anvil 7050, e.g., the channel 7056 thereof, thereby preventing the I-beam 7052 from translating through the anvil 7050 such that fasteners cannot be fired from the cartridge 7046.

In some embodiments, a lockout element can be in the form of a deflectable member. FIG. 146, FIG. 147, and FIG. 148 illustrate one embodiment of a surgical device that can include a lockout element in the form of a deflectable member 7058. The deflectable member 7058 can have a variety of sizes, shapes, and configurations. As in this illustrated embodiment, the deflectable member 7058 can include a spring member. The spring member 7058 can include two deflectable arms 7058a, 7058b extending in a distal direction. The spring member 7058 can be attached to the I-beam 7060, such as by being attached to a bottom side thereof with the arms 7058a, 7058b extending distally therefrom.

The deflectable member 7058 can be configured to automatically move from a first position, in which the deflectable member 7058 is not engaged with a cartridge 7062, to a second position, in which the deflectable member 7058 is engaged with the cartridge 7062, in response to the cartridge 7062 being fully seated in a bottom jaw 7064 movably coupled to an upper jaw 7066. The deflectable member 7058 can also be configured to automatically move from the second position to the first position in response to the cartridge 7062 being removed from the bottom jaw 7064. By being configured to automatically engage with and disengage from the cartridge 7062, the deflectable member 7058 can be a passive element that does not require positive user action in order for the lockout member 7058 to effectively provide lockout when the cartridge 7062 is improperly seated in the bottom jaw 7064 or is not seated therein at all. When the deflectable member 7058 is in the first position, as shown in FIG. 147, the I-beam 7060 can be prevented from translating through the anvil 7050, e.g., by crashing against the anvil 7050 instead of translating therealong. When the deflectable member 7058 is in the second position, as shown in FIG. 148, the I-beam 7060 can be allowed to translate through the anvil 7050. The first position can be a default position of the deflectable member 7058 such that the I-beam 7060 can be prevented from translating through the anvil 7050 unless the cartridge 7062 is fully seated in the bottom jaw 7064.

The deflectable member 7058 in the second position can be configured to engage the cartridge 7062 in a variety of ways. In an exemplary embodiment, the deflectable member 7058 can be configured to engage a sled 7068 of the cartridge 7062 to which a cutting element 7074 can be movably coupled, as discussed herein. As in this illustrated embodiment, the deflectable member 7058 can be configured to engage the sled 7068 by the arms 7058a, 7058b by abutting a proximal surface 7070 of the sled 7068. As discussed herein, the sled 7068 can have an initial position at a proximal end of the cartridge 7062, as shown in FIG. 146, FIG. 147, and FIG. 148. When the cartridge 7062 has not been fully seated in the bottom jaw 7064, as shown in FIG. 147, the deflectable member 7058 can be in the first position and not be engaged with the sled 7068, e.g., not be in contact with the sled's proximal surface 7070. In the first position, the deflectable member 7058 can be in a lower position in a direction away from the anvil 7066. In this lower position, the deflectable member 7058 can be positioned distal to a foot 7072 of the I-beam 7060 and can be positioned in a translation path thereof through which the foot 7072 can be configured to translate to effect firing of fasteners (not shown) from the cartridge 7062. When the cartridge 7062 is fully seated in the bottom jaw 7064, as shown in FIG. 148, the deflectable member 7058 can be in the second position and be engaged with the sled 7068, e.g., be in contact with the sled's proximal surface 7070. In the second position, the deflectable member 7058 can be in a higher position in a direction toward the anvil 7066. In this higher position, the deflectable member 7058 can be positioned distal to a foot 7072 of the I-beam 7060 but be positioned out of the translation path thereof through which the foot 7072 can be configured to translate to effect firing of the fasteners from the cartridge 7062. The deflectable member 7058 in the second position can thus allow firing, while the deflectable member 7058 in the first position can prevent firing.

The deflectable member 7058 being in either the first position or the second position can facilitate determination as to whether fasteners have been fired from the cartridge 7062 since the deflectable member's lockout relies on the sled 7068 being in its initial proximal position. For example, if a cartridge from which fasteners have already been fired is loaded into the bottom jaw 7064, the cartridge's sled is already in its distal, fired position. The deflectable member 7058 thus cannot engage the sled and firing cannot occur until the cartridge is removed from the bottom jaw 7064 and replaced with another, non-spent cartridge.

In some embodiments, a surgical device such as the above-mentioned surgical device 1100 can be configured to have an adjustable gap of space between a cartridge jaw and an anvil of the device's end effector when the end effector is in a closed position. In general, the end effector, e.g., the cartridge jaw, can be configured to removably couple to a cartridge, as discussed herein. The cartridge can be configured to define the gap of space between the cartridge jaw and the anvil when the end effector is in a closed position. In other words, the gap of space can be a function of the cartridge. The gap of space can be a minimum distance between facing tissue-engaging surfaces of the cartridge jaw and the anvil. The end effector can thus be configured to selectively accommodate tissues of different thicknesses since the end effector's tissue gap can be different based upon the specific cartridge loaded therein. In an exemplary embodiment, the cartridge can include an anvil coupling member configured to define the gap of space so as to provide a minimum distance between the facing tissue-engaging surfaces of the cartridge jaw and the anvil when the end effector is in the closed position. The anvil coupling member can form a partial portion of an I-beam configured to translate longitudinally along the end effector, as discussed herein. The anvil coupling member forming a partial portion of the I-beam can allow the I-beam to be appropriately sized for the tissue gap defined by the anvil coupling member such that the I-beam can properly translate along the cartridge, e.g., via a foot of the I-beam," and along the anvil, e.g., via a guide pin of the I-beam. The anvil coupling member forming a partial portion of the I-beam can result in the I-beam being different in the surgical device as a function of the cartridge seated in the end effector. The I-beam can thus be configured to be adjustable so as to correspond to the adjustable gap of space between the end effector's jaws.

A surgical device can be configured to have an adjustable gap of space between a cartridge jaw and an anvil of the device's end effector when the end effector is in a closed position in a variety of ways. In the embodiments described below, staples are used as examples of fasteners, but as will be appreciated by a person skilled in the art, other types of fasteners can be similarly configured and used.

In some embodiments, an anvil coupling member can be in the form of a partial portion of an I-beam. As discussed herein, an I-beam can be configured to translate longitudinally along an end effector to fire fasteners from a cartridge seated in the end effector. The I-beam can be configured to contact the end effector's bottom jaw with a first portion thereof, e.g., with a foot thereof, and the end effector's anvil with a second portion, e.g., with a guide pin thereof. The anvil coupling member can include the second portion of the I-beam configured to contact the anvil such that the cartridge being loaded into the bottom jaw of the end effector can define a gap of space between the cartridge's tissue-engaging surface and the anvil's tissue-engaging surface.

FIG. 149, FIG. 150, and FIG. 151 illustrate one embodiment of a cartridge 8004 that includes an anvil coupling member 8006 coupled thereto. The anvil coupling member 8006 can be configured to move relative to a housing 8008 of the cartridge 8004 that had fasteners (not shown) disposed therein, as discussed further below. In general, the cartridge 8004 can be configured to be removably coupled to an end effector 8010 coupled to a distal end of an elongate shaft 8012, such as by being releasably and replaceably seated in a channel 8017 formed in a bottom jaw 8000 of the end effector 8010. The cartridge 8004 can also be configured to be releasably and replaceably seated in a slot 8018 formed in an anvil 8002 of the end effector 8010, such as by coupling the anvil coupling member 8006 thereto. The anvil coupling member 8006 can be configured to slidably move within the slot 8018 as part of an I-beam 8014, shown in FIG. 152.

The anvil coupling member 8006 can have a variety of sizes, shapes, and configurations. As in this illustrated embodiment, the anvil coupling member 8006 can include a protrusion extending upwardly from the cartridge 8004 so as to extend above a tissue-engaging surface 8000*a* of the cartridge 8004. This protrusion can includes a guide pin 8016 extending laterally from the protrusion and being configured to slidably move with the anvil's slot 8018.

As in this illustrated embodiment, the anvil coupling member 8006 can include a proximal portion of the I-beam 8014. The anvil coupling member 8006 can include a first coupling element 8024 configured to removably couple to a second coupling element 8026 of a remainder of the I-beam 8014, e.g., a distal portion of the I-beam 8014. The distal portion of the I-beam 8014 in this illustrated embodiment includes a foot 8020 of the I-beam 8014, but in other embodiments, the anvil coupling member 8006 can include the foot 8020. As in this illustrated embodiment, the first coupling element 8024 includes at least one depression formed in a proximal side of the anvil coupling member 8006, and the second coupling element 8026 can include at least one protrusion formed in a distal side of the remainder of the I-beam 8014. In other embodiments, the first coupling element can include at least one protrusion, and the second coupling element can include at least one depression. When the cartridge 8004 is fully seated in the cartridge jaw 8000, as shown in FIG. 152, the first and second coupling elements can be coupled together so as to allow the I-beam 8014 include the anvil coupling member 8006 and the remainder of the I-beam 8014 to move as a single unit through the end effector 8004.

The anvil coupling member 8006 can be configured to define a distance 8022 between the tissue-engaging surface 8004*a* of the cartridge 8004 and a tissue-engaging surface 8002*a* of the anvil 8002. As shown in FIG. 152, a height of the anvil coupling member 8006, can define a distance that the anvil coupling member 8006 extends above the cartridge's tissue engaging surface 8004a and can define how far away the anvil 8002 can be from the bottom jaw 8000 when the end effector 8010 is in the closed position based on a location of the guide pin 8016 on the anvil coupling member 8006. The anvil coupling member 8006 can thus be configured to help ensure that the guide pin 8016 can slide within the slot 8018 when the end effector 8010 is in the closed position, thereby allowing for firing of the fasteners.

As shown in FIG. 149 and FIG. 150, the cartridge 8004 can be configured to be advanced into the channel 8017 of the bottom jaw 8000 simultaneously with the guide pin 8016 being advanced in a proximal direction into the slot 8018 of the anvil 8002. The guide pin 8016 can thus be properly seated within the slot 8018 when the cartridge 8004 is fully seated in the bottom jaw 8000.

FIG. 153 illustrates an alternate embodiment of an anvil coupling member 8026 that can be configured and used similar to the anvil coupling member 8006 of FIG. 149. The anvil coupling member 8026 in this illustrated embodiment includes a foot 8028 of an I-beam 8030 of which the anvil coupling member 8026 can form a proximal portion thereof.

As in this illustrated embodiment, the I-beam 8030 can be configured to be automatically released from an anvil 8032 such that the I-beam 8030 need not be retracted after advancing through the anvil 8032 and a cartridge jaw 8036 coupled thereto so as to fire fasteners 8038 into tissue 8040 clamped in a tissue gap 8042 between the anvil 8032 and the cartridge jaw 8036. The I-beam 8030 is configured to advance in a distal direction 8044 to fire the fasteners 8038 in this illustrated embodiment. The anvil 8032 can include an opening 8038 adjacent a distal end thereof configured to release the anvil coupling member 8026, e.g., a guide pin 8034 thereof, therefrom. The anvil coupling member 8026, and hence the I-beam 8030, can be configured to be automatically released 8042 from the anvil 8032 by the guide pin 8034 passing out of the opening 8038, which can be in communication with a slot in the anvil 8032 through which the guide pin 8034 can translate. The release of the anvil coupling member 8026, and hence the I-beam 8030, from the anvil 8032 can allow the anvil 8032 to open.

In some embodiments, a shim of a cartridge configured to be removably coupled to a bottom jaw of an end effector of a surgical device can be configured to define a gap of space between the bottom jaw and an anvil coupled thereto. In general, a size of the shim can define the gap of space. The larger the shim, the smaller the gap of space.

FIG. 154 and FIG. 155 illustrate one embodiment of a cartridge 8046 that includes a shim 8048. The cartridge 8046 can be configured to removably coupled to a cartridge jaw 8050 by being seated in a channel 8052 formed therein. The shim 8048 can have a variety of sizes, shapes, and configurations. As in this illustrated embodiment, the shim 8048 can include an upwardly extending protrusion that can be formed on a bottom inner surface of the cartridge 8046. The shim 8048 can extend along a longitudinal length of the cartridge 8046

The cartridge jaw 8050 can include a receiving slot 8054 formed therein that can be configured to slidably receive the shim 8048 therein. The cartridge 8046 can be configured to be seated within the channel 8052 by sliding the cartridge 8046 in a proximal direction 8058 with the shim 8048 sliding proximally within the slot 8054. The shim 8048 can thereby define a height 8062 of a gap of space 8064, shown in FIG. 155, between the cartridge jaw 8050 and an anvil 8060 coupled thereto. The shim 8048 extending along the cartridge's longitudinal length can help the shim 8048 define the height 8062 consistently along the end effector's longitudinal length.

A height 8064 of the shim 8048 can define the tissue gap's height 8062. By way of comparison, FIG. 156 shows a cartridge 8066 without a shim seated in a cartridge jaw 8068 coupled to an anvil 8070. A height 8072 of a tissue gap 8074 can thus be greater than the tissue gap's height 8062 defined by the shim 8048 of FIG. 155.

FIG. 157 illustrates another embodiment of a cartridge 8076 that includes a shim 8078. The shim 8078 can be generally configured and used similar to the shim 8048 of FIG. 154. The shim 8078 in this illustrated embodiment has a height 8080 that is greater than the height 8064 of the shim 8048 of FIG. 155. Thus, a height 8082 of a tissue gap 8084 can be less than the tissue gap's height 8062 defined by the shim 8048 of FIG. 155.

In some embodiments, a cutting element of a sled can be configured to define a gap of space between a bottom jaw and an anvil coupled thereto. As discussed herein, the sled can be part of a cartridge configured to be removably coupled to an end effector of a surgical device. The cartridge can thus be configured to define the gap of space.

FIG. 158 illustrates one embodiment of a cutting element 8088 configured to define a gap of space (not shown) between jaws of an end effector (not shown). The cutting element 8088 can be part of a sled (not shown) of a cartridge (not shown) configured to be removably coupled to an end effector (not shown), as discussed herein. The cutting element 8088 can include an I-beam mating feature 8090 formed on a proximal side thereof, opposite to a blade 8104 formed on a distal side thereof. The I-beam mating feature can include a ramped surface 8090 that can slope upward in a distal direction 8094 toward a pin stop depression 8092 that can extend in the distal direction 8094. The I-beam mating feature 8090 can be configured to removably couple to an I-beam 8096. The I-beam 8096 can include a guide pin 8098 configured to be movable relative to a remainder of the I-beam 8096. As in the illustrated embodiment, the I-beam 8096 can include an I-beam pin slot 8100 in which the pin 8098 can be configured to slide. The pin slot 8100 can extend in an upward/downward or vertical direction 8102 that can be substantially perpendicular to the distal direction 8094. The pin 8098 can thus be configured to slide in the slot 8100 in the upward/downward direction 8102.

The pin 8098 can be configured to engage the cutting element 8088 when the cartridge including the cutting element 8088 is removably coupled to the end effector that is attached to an elongate shaft (not shown) along which the I-beam 8096 extends. The pin 8098 can be configured to engage a lower portion of the ramped surface 8090 of the cutting element 8088 and slide upward therealong until the pin 8098 reaches the depression 8092, which can cause the pin's sliding to stop. The depression 8092 can seat the pin 8098 therein. An upward/downward location of the pin 8098 can thus be defined by the cutting element 8088. The guide pin 8098 seated in the depression 8092 can be configured to slide along an anvil of the end effector. In this way, a tissue gap between the anvil and a cartridge jaw of the end effector can be defined by the cutting element 8088.

FIG. 158 illustrates another embodiment of a cutting element 8088' that can be configured and used similar to the cutting element 8088. FIG. 158 also illustrates another embodiment of a cutting element 8088" that can be configured and used similar to the cutting element 8088. The ramped surfaces 8090, 8090', 8090" of the cutting elements 8088, 8088', 8088", respectively, can all start at a same location in a downward direction, thereby facilitating engagement of the pin 8098 with the ramped surface of the cutting element loaded into the surgical device's end effector. The cutting element 8088' has a longer ramped surface 8090' than the cutting element 8088 such that a depression 8092' of the cutting element 8088' is located at a higher location than the depression 8092 of the cutting element 8088. The pin 8098 seated in the depression 8092', as shown in FIG. 159, can thus be up higher than the pin 8098 when seated in the lower depression 8092. The tissue gap can thus be greater when using the cutting element 8088' versus the cutting element 8088. The cutting element 8088" has a longer ramped surface 8090" than the cutting element 8088 and the other cutting element 8088' such that a depression 8092" of the cutting element 8088" is located at a higher location than the depression 8092 of the cutting element 8088 and the depression 8092' of the cutting element 8088'. The pin 8098 seated in the depression 8092" can thus be up higher than the pin 8098 when seated in either of the lower depressions 8092, 8092'. The tissue gap can thus be greater when using the cutting element 8088" versus the cutting element 8088 and versus the cutting element 8088'.

FIG. 160 and FIG. 161 illustrates another embodiment of a cutting element 8106 that can be configured and used similar to the cutting elements 8088, 8088', 8088" and removably couple to the I-beam 8096. FIG. 160 shows the I-beam 8096 disengaged from the cutting element 8106. FIG. 161 shows the pin 8098 of the I-beam 8096 seated in a depression 8108 of the cutting element's mating feature 8110.

In some embodiments of a surgical device in which a cutting element of a sled can be configured to define a gap of space between a bottom jaw and an anvil coupled thereto, the surgical device can include a push rod configured to facilitate engagement of the I-beam's pin with the cutting element. The push rod can help ensure that the pin is seated within a depression of the cutting element's mating feature, thereby helping to ensure that the anvil is at an intended position relative to the bottom jaw when the bottom jaw and the anvil are closed. The push rod can help hold the pin within the depression, which can help prevent the pin from shifting position relative to the cutting element. The tissue gap can thus be less likely to change once the pin is seated in the depression.

FIG. 162, FIG. 163, and FIG. 164 illustrate one embodiment of a push rod 8112 configured to removably couple to the guide pin 8098 to facilitate engagement of the pin 8098 with the cutting element 8088'. Although the push rod 8112 is shown with the I-beam 8096 and the cutting element 8088' of FIG. 159, the push rod 8112 can be similar used with other I-beams and other cutting elements. The push rod 8112 can have a variety of sizes, shapes, and configurations. As in this illustrated embodiment, the push rod 8112 can include an elongate bar having a forked distal end 8114. The fork's tines can define spaces therebetween, each of which can be configured to removably seat the pin 8098 therein. The forked distal end 8114 in this illustrated embodiment includes four tines defining three spaces therebetween, but a push rod can include another plural number of tines to define at least one space.

In use, after the cartridge including the cutting element 8088' has been seated in the end effector so as to mate the pin 8098 with the cutting element's mating feature, as shown in FIG. 162 and FIG. 163, the push rod 8112 can be advanced in a distal direction 8116 until the forked distal end 8114 engages the pin 8098 so as to seat the pin 8098 in one of the spaces. FIG. 164 shows the pin 8098 seated in the depression 8092' and seated in a middle one of the push rod's spaces. Continued movement of the push rod 8112 in the distal direction 8116 can cause the I-beam 8096 and the sled including the cutting element 8088' to advance distally, thereby firing fasteners from the cartridge.

In some embodiments, a surface of a cartridge can be configured to define a gap of space between a bottom jaw and an anvil coupled thereto. As discussed herein, the cartridge can be configured to be removably coupled to an end effector that includes the bottom jaw and the anvil. The cartridge can thus be configured to define the gap of space.

FIG. 165 illustrates one embodiment of a cartridge 8118 configured to define a gap of space (not shown) between jaws of an end effector (not shown). In general, the cartridge 8118 can cooperate with an I-beam 8122 removably engageable with the cartridge 8118 to define the gap of space. The cartridge 8118 can include a proximal sloped surface 8120 that slopes upward in a distal direction. The sloped surface 8120 can be configured to engage a guide pin 8124 of the I-beam 8122 to facilitate positioning of the guide pin 8124 relative to the cartridge 8118 and, hence, to an anvil 8119, shown in FIG. 168. The guide pin 8124 of the I-beam 8122 can be configured to be movable relative to a remainder of the I-beam 8122.

As in the illustrated embodiment, the I-beam 8122 can include an I-beam pin slot 8126 in which the pin 8124 can be configured to move. The I-beam 8122 can include a bias element 8132 configured to bias the pin 8124 toward a bottom surface of the slot 8126, as shown in FIG. 165 and in FIG. 166. The bias element 8132 includes a coil spring in this illustrated embodiment, but the bias element 8132 can have other configurations. The pin slot 8126 can extend in an upward/downward or vertical direction 8128 that can be substantially perpendicular to a proximal/distal direction 8130 in which the I-beam 8122 can be configured to translate through the cartridge 8118. The pin slot 8126 can include a plurality of notches formed therein on a proximal side thereof, as also shown in FIG. 167. The pin slot 8126 includes three notches in this illustrated embodiment, but a pin slot can include another number of notches. Each of the notches can be configured to seat the pin 8124 therein, the one of the notches depending on the sloped surface 8120 of the cartridge 8118. The pin 8124 can thus be configured to move in the slot 8126 in the upward/downward direction 8128 and in the proximal/distal direction 8130.

The pin 8098 can be configured to engage the sloped surface 8020 when the cartridge 8118 is removably coupled to the end effector that is attached to an elongate shaft (not shown) along which the I-beam 8122 extends. The pin 8124 can be configured to engage and slide upward and distally along the sloped surface 8020 until the pin 8124 reaches a top end of the sloped surface 8020, e.g., until the sloped surface 8020 ends. The force of the sloped surface 8020 on the pin 8124 can exceed a force provided by the bias element 8132, thereby allowing the pin 8124 to slide along the sloped surface 8020 and move upward within the slot 8126. When the pin 8124 reaches the top end of the sloped surface 8020, e.g., when the cartridge 8118 has been fully seated in the end effector, the pin 8124 can automatically move proximally so as to be seated in one of the notches. With the pin 8124 seated in the one of the notches, the I-beam 8122 can be advanced distally so as to fire fasteners (not shown) from the cartridge 8118 with the tissue gap defined by the pin's vertical location within the slot 8126.

FIG. 165 illustrates another embodiment of a cartridge 8118' that can be configured and used similar to the cartridge 8118. FIG. 165 also illustrates another embodiment of a cartridge 8118" that can be configured and used similar to the cartridge 8118. In this illustrated embodiment, the cartridge 8118 has a first size, e.g., a first longitudinal length and a first height, the cartridge 8118' has a second size, e.g., a second longitudinal length greater than the first longitudinal length and a second height greater than the first height, and the cartridge 8118" has a third size, e.g., a third longitudinal length greater than the second longitudinal length and a third height greater than the second height. The sloped surfaces 8120, 8120', 8120" of the cartridges 8118, 8118', 8118", respectively, can all start at a same location in a downward direction, thereby facilitating engagement of the pin 8124 with the sloped surface of the cartridge loaded into the surgical device's end effector. The cartridge 8118' has a longer and steeper ramped surface 8120' than the cartridge 8118 such that the pin 8124 can move into one of the notches at a higher location than with the cartridge 8118. The pin 8124 seated in a middle one of the notches 8125 in response to the cartridge 8118', as shown in FIG. 168, can thus be up higher than the pin 8124 when using the cartridge 8118. The tissue gap can thus be greater when using the cartridge 8118' versus the cartridge 8118. The cartridge 8118" has a longer and steeper sloped surface 8120" than the cartridge 8118 and the other cartridge 8118' such that the pin 8124 can move into one of the notches at a higher location than with the cartridge 8118 and than with the cartridge 8118'. The pin 8124 seated in the notch in response to the cartridge 8118" can thus be up higher than the pin 8124 when using either of the cartridge 8118, 8118'. The tissue gap can thus be greater when using the cartridge 8118" versus the cartridge 8118 and versus the cartridge 8118'.

In some embodiments, a surgical device such as the above-mentioned surgical device 1100 can be configured to self-retract in the event of misfiring conditions, i.e., partial firing, jamming, etc. In general, the surgical device's end effector 1106 can be configured to engage tissues of various types and thicknesses. For example, in an endoscopic operation, the end effector 1106 portion of the device may be inserted into a patient to access a surgical site. A surgeon may refer to an endoscopic or other diagnostic imaging device to position tissue between the first and second jaws 1110a, 1110b of the end effector 1106. The surgeon may repeatedly grasp and position the tissue until the tissue is properly positioned between the jaws of the end effector 1106, and the tissue can then be clamped and locked in the end effector 1106. If the clamping is proper, and the tissue type and thickness is appropriate for the end effector, the surgeon may proceed with firing the surgical stapling and cutting element 1134. Specifically, the surgeon grasps the movable trigger 1122 and the handle 1102, depressing the movable trigger 1122 a predetermined number of times. The number of firing strokes necessary may be ergonomically determined based on a maximum hand size, maximum amount of force to be imparted on the instrument during each firing stroke, and the longitudinal distance and force needed to be transferred through a drive shaft to the end effector 1106 during firing.

The drive shaft is coupled to a drive beam (also referred to herein as a "drive rod" or an "I-beam") disposed within the end effector 1106 and configured to assist in driving fasteners (e.g., staples) into a tissue, as well as pushing a cutting element through the tissue. However, the drive beam may, in some instance, jam or only partially fire. This can be caused by a number of factors, including the cutting element 1134 becoming jammed on an improperly clamped tissue and/or a condition when the clamped tissue thickness is so great as to prevent the fasteners from being completely deployed and/or to prevent the cutting element from fully passing through tissue. A jammed or stuck drive beam can lead to confusion and unnecessary downtime during an operation and may require the surgeon to remove the end effector 1106 from the surgical site to resolve the problem, which can be a complex procedure to perform. Surgical devices configured to easily and quickly correct a misfiring condition without removing the end effector 1106 from the surgical site can help reduce surgery downtime and improve a surgeon's efficiency.

A surgical device can include a retraction mechanism configured to retract the drive beam from a jammed position in a variety of ways. As discussed below, various mechanisms are provided to easily correct a misfiring condition with minimal interruption to the surgical procedure.

FIG. 169 illustrates one embodiment of a surgical fastening device 9000 having a retraction mechanism configured to manually and positively retract a jammed or misfired drive beam (and associated components). Fastening device 9000, similar to fastening device 1100 shown and described above, includes a proximal handle portion 1102 and an elongate shaft 1104 extending therefrom. Although FIG. 169 is truncated, it includes an end effector (not shown) at a distal end of shaft 1104, as shown and described above with respect to device 1100. The handle includes a stationary handle 1124 and a movable trigger 1122, which as described above can be manipulated to effect the closing of the jaws of the end effector and the firing of staples from one of the jaws through action imparted to a drive shaft within the handle and a drive beam within the shaft as described above. Fastening device 9000 also includes, on a portion of handle housing 1102, an indicator 9024 configured to indicate a relative position of the drive beam, as will be described in more detail below.

Surgical fastening device 9000 also includes mechanisms to effect a manual retraction of the drive shaft and drive beam in the event of jamming or misfiring, as will be described in more detail below. One manual retraction element includes a knob or lever 9026 that is configured to slide linearly within a slot 9027 formed in the handle housing. While FIG. 169 illustrates only one side of the handle, it is understood that knob or lever 9026 can be on a single side of the handle or that each side of the handle can include a knob or lever to effect manual retraction. Another manual retraction element includes a movable lever 9030, shown for purposes of example only on a top portion of the handle housing. As will be described below, manual actuation of lever 9030 between a normal position 9030a and an actuated position 9030b, shown in phantom, will effect manual and positive retraction of the drive shaft and drive beam.

FIG. 169 and FIG. 170 illustrate one embodiment in which the surgical device 9000 can include a retraction mechanism 9001 and retraction tool that is integrated into the surgical device 9000. As described above, a drive shaft 9002 extends through the elongate shaft 1104, and is operably coupled to a drive beam and movable trigger 1122 to effect jaw closure and staple firing. Drive features 9003 are formed on one side (e.g., a bottom side) of the drive shaft 9002 and are configured to interact with features on or coupled to the movable trigger 1122 to effect distal movement of the drive shaft for purposes of closing the jaws and firing staples. Another surface of the drive shaft 9002 (e.g., a top surface) includes one or more retraction features configured to assist in the retraction of a drive beam (not shown) coupled to the drive shaft 9002. As illustrated in FIG. 169, retraction features can be in the form of a toothed rack 9005, which can be formed on one side of the drive shaft 9002 facing an opening 9004 on the outer casing (partially shown) of the surgical device 9000. The toothed rack 9005 is configured to interact with a retraction mechanism to move the drive shaft 9002 in a proximal direction, thereby retracting the drive beam. In an exemplary embodiment illustrated in FIG. 169 and FIG. 170, the retraction mechanism can be integrated with the fastening device. For example, the retraction mechanism can be in the form of an integrated lever 9030 that is coupled to a pawl 9012. As illustrated, the pawl 9012 includes at least one tooth 9014 configured to engage individual racks of a toothed rack 9005 formed on a drive shaft 9002. FIG. 170 illustrates the lever 9030 in a normal position 9030a in which it assumes a low profile to maintain a more sleek design of the tool, enabling more convenient storage, packaging, and handling of the device. The lever 9030 can be moved in a distal direction, as shown in FIG. 169, to an actuated position 9030b, shown in phantom in FIG. 169. As a result of movement of the lever 9030 to the actuated position, the pawl 9012 engages the toothed rack 9005 and moves the drive shaft proximally, thereby retracting the drive beam.

FIG. 171 illustrates another embodiment of a retraction mechanism 9009 with a removable retraction tool. It is understood that the retraction mechanism components of FIG. 171 can be incorporated into a surgical fastening device 9000 of the type shown in FIG. 169. Like the retraction mechanism described with reference to FIGS. 169 and 170, the retraction mechanism 9009 utilizes a toothed rack 9005' formed on one side (e.g., a top surface) of drive shaft 9002. The retraction mechanism 9009 further includes a gear 9006 having at least one tooth configured to engage individual teeth of the toothed rack 9005'. By applying a rotational force to the gear 9006, the gear 9006 engages the toothed rack 9005' and can advance the drive shaft 9002 either distally or proximally in a linearized fashion. For purposes of retracting the drive beam, the gear can rotate in a counter clockwise direction to move the drive shaft 9002 proximally, thereby retracting the drive beam. It is understood that the pawl and toothed rack can be designed to enable complete retraction of the drive beam with a single actuating movement of the lever 9030, or with multiple actuating movements of the lever.

The gear 9006 can be actuated in a number of ways using a variety of retraction tools. For example, an integrated lever of the type described above with respect to FIG. 169 and FIG. 170 can be used. In another embodiment, however, illustrated in FIG. 171, a removable wrench 9008 serve as a retraction tool. Removable wrench 9008 can extend through the opening 9004 formed in the handle housing and can be coupled to the gear 9006 by, for example, mounting onto a bolt 9010 on the gear 9006. Once connected to the gear, rotation of the removable wrench 9008 in a counter clockwise direction, effects a counter clockwise rotation of the gear as a result of the teeth on the gear 9006 engaging the toothed rack 9005' to move the drive shaft 9002 linearly in a proximal direction. Such movement of the drive shaft causes proximal movement of the drive beam, thereby retracting the drive beam. It is understood that the gear and toothed rack can be designed to enable complete retraction of the drive beam with a single actuating movement of the wrench 9008, or with multiple actuating movements of the wrench.

The embodiment illustrated in FIG. 171 advantageously provides a manual retraction method without having to integrate a retraction tool (e.g., wrench 9008) into the device 9000. The device 9000 can achieve a smaller size and be lighter in weight and easier to handle using a removable retraction tool such as wrench 9008.

A person skilled in the art will appreciate that the embodiments of FIG. 169, FIG. 170, and FIG. 171 provide mechanisms that conveniently enable the positive and manual retraction of a drive beam in the event of a jamming or misfiring condition. As described above, actuation of the retraction mechanism applies a counter rotating torque that retracts the drive shaft and drive beam. Both the lever and the wrench described above enable a user to apply a large moment arm to effect retraction. It will be further understood that retracting the drive shaft 9002 merely pushes a movable trigger 1122 back to a parked, pre-firing position where the surgical device 9000 is immediately ready for another round of firing, therefore causing no interruption to the stapling operation.

In some embodiments the surgical device 9000 may include mechanism for providing the surgeon with an indication of how far a drive shaft has been advanced and retracted. The surgeon can determine the relative positions of the drive shaft and/or the drive beam and thereby determine how many strokes of the movable trigger 1122 are required to complete a firing. As shown in FIG. 169 and FIG. 172, an indicator 9024 in the form of a knob or dial with an indicator needle 9028 is utilized to provide to the surgeon information about the relative position of the drive shaft 9002. As illustrated, the needle 9028 is configured to rotate in response to firing stroke action. As illustrated in FIG. 172, the indicator knob 9024 can be marked in increments of 0-4 indicating drive shaft 9002 and/or movable trigger 1122 positions to the surgeon. Increment 0 is indicative of pre-firing positions for the drive shaft 9002 and the movable trigger 1122 while increment 4 is indicative of complete firing. As the movable trigger 1122 is compressed for each firing stroke to close the jaws and/or fire or deploy the fasteners, the needle 9028 can rotate through increments 0-4 indicating to the surgeon the positions of the shaft 9002 and/or the trigger 1122, as well as the number of strokes remaining to complete a full firing. In the illustrated example, a full firing travel of a drive shaft 9002 requires four firing strokes and thus the needle 9028 rotates one increment shown on indicator 9024 for each stroke.

At any time during a procedure, where retraction might be necessary, the surgeon can ascertain the relative position of the drive shaft and elect to utilize a bailout or retraction mechanisms, such as lever 9030 or wrench 9008, to retract the drive shaft 9002.

In some embodiments, a surgical device such as the above-mentioned surgical fastening device 9000 can be configured to prevent a partially formed fastener from remaining in the tissue without being fully formed. Fasteners can have a tendency to form only partially when deployed into a tissue due to factors such as the tissue type, tissue thickness, shape of the fastener (e.g., a curved shape thereof), and a strength of a bias urging a fastener into a certain position or configuration. A partially formed fastener can detach from the tissue and potentially cause harm to a patient. As such, a surgical device with features configured to retrieve partially formed fasteners can help improve the surgical outcome and the overall wellbeing of the patient.

In the embodiments described below, staples are used as examples of fasteners, but as will be appreciated by a person skilled in the art, other types of fasteners can be similarly configured.

In some embodiments, a surgical device can include one or more features configured to retrieve partially formed staples thereby preventing the staples from remaining in the tissue. In general, staples can be deployed or driven into a tissue when pushed by a sled coupled to a drive beam, where the drive beam can be configured to receive driving force from a drive shaft. FIG. 173 illustrates two embodiments of a sled 9034, 9036 that includes one or more mating features 9038, 9040 configured to retrieve partially formed staples. The staples $9032_1$, $9032_2$ in this illustrated embodiment are generally configured like the previously described staple 1116 and each have a D-shape with a pointed tip, a first leg $9042_1$, $9042_2$ that is substantially straight and a second leg that is curved. The pointed tip can be a terminal end of the second leg, as in this illustrated embodiment. In one embodiment, the staple $9032_1$ can include one or more mating features $9044_1$ configured to engage the mating feature 9038 on the sled 9034. As illustrated, the mating feature 9038 can be in the form of a barb or tooth formed on an upper surface of the sled 9034 that is configured to be in contact with the staple $9032_1$. In one embodiment the barb is oriented in a direction that coincides with the direction in which the staple $9032_1$ is deployed into tissue. The mating feature $9044_1$ can be formed on an out facing surface of the first leg $9042_1$ in the form of a cavity configured to receive the mating feature 9038. In this illustrated embodiment, the staple $9032_1$ will rotate clockwise into the tissue when being driven by the sled 9034 and drive beam 9046. When the staple $9032_1$ fully formed into the tissue, the staple $9032_1$ will have reached a height such that the mating feature $9044_1$ is disengaged from the mating feature 9038. Otherwise, when the staple $9032_1$ is only partially formed and does not rotate fully into the tissue in a clockwise fashion, the mating features $9044_1$ and 9038 will remain engaged and the staple $9032_1$ will be retrieved when the sled 9034 is retracted by the drive beam 9046.

In another embodiment illustrated in FIG. 173, a mating feature can be in the form of a toothed rack 9040 with one or more teeth oriented in a direction that coincides with the direction in which the staple $9032_2$ is deployed into tissue. Furthermore, a mating feature $9044_2$ can be formed on an out facing surface of the first leg $9042_2$ of the staple $9032_2$ in the form of another toothed rack configured to receive the mating feature 9040. The two mating features $9044_2$, 9040 can be generally configured and used similar to the two mating features 9038, $9042_1$ illustrated above. The staple $9032_2$ illustrated in this embodiment will similarly be retrieved by the sled 9036 unless fully formed into the tissue.

The fastening device 9000 can also include safety features designed to ensure that a cutting element, such as knife blade, is not positioned in such a manner as to accidently or inadvertently cut tissue. In some instances, when a partial fastener line is deployed the cutting element 1134 can be left in the "upright position," (see FIG. 176, for example) which may lead to accidental cutting of a user of the device 9000 or premature cutting of tissue engaged by the end effector 1104. In an exemplary embodiment, a cutting element can include features configured to return the cutting element to the "stowed position," where the blade can be generally obscured and in an inoperative position.

FIG. 174, FIG. 175, FIG. 176, and FIG. 177 illustrate one embodiment of a cutting element 9046 with one or more features configured to rotate the cutting element 9046 between the upright and stowed or inoperative position. As illustrated in FIG. 174, the cutting element 9046 includes a first cam element 9048 oriented generally perpendicular to a blade 9052 and a second cam element 9050 oriented generally parallel to the blade 9052, where both the first 9048 and second 9050 cam elements are formed on a proximal end of the cutting element 9046. The cutting element 9046 further includes a pivot element 9054 such that the blade 9052 is configured to rotate around the pivot element 9054. FIG. 175 illustrates an exemplary embodiment in which the cutting element 9046 is coupled to a sled 9056 at the pivot element 9054, e.g., by a pin. Furthermore, a drive beam 9058 configured to advance distally can provide bias to the cutting element 9054 by engaging the first 9048 and the second cam element 9050 with an engagement feature 9060. As shown in FIG. 175, FIG. 176, and FIG. 177, the engagement feature 9060 can be a protrusion extending from underneath the drive beam 9058 configured to push or pull the cam elements 9048, 9050. For example, when the drive beam 9058 is advanced distally (FIG. 176), the engagement feature 9060 can push upon the second cam element 9050, causing the cutting element 9046 to rotate clockwise from a stowed, pre-firing position (FIG. 175) and transition into the upright position, where the blade 9052 becomes operative as it faces in the distal direction. Conversely, when the drive beam is being pulled proximally, such as in the event of retraction, the engagement feature 9060 can pull on the first cam element 9048, causing the cutting element 9046 to rotate counterclockwise and transition into the stowed position, where the blade 9052 become generally obscured, e.g., oriented generally downwardly as shown in FIG. 177.

The surgical fastening device 9000 can also include other features, such as audible indicators of the position or condition of the device with respect to closing or firing. In one embodiment, an indicator feature can be in the form of an audible indicator mechanism. As illustrated in FIG. 178 and FIG. 179, a needle 9062, or a similar device, is configured to generate audible indicator sounds upon interacting with a desired region of a drive shaft 9002. In an exemplary embodiment, the drive shaft 9002 can include a surface disruption formed on one surface thereof toothed rack 9066 that can interact with a device, such as a needle 9062, to provide a signal, e.g., an audible signal, which can be sensed by a surgeon. The surface disruption can be of any type that will interact with the needle 9062 (e.g., by causing it to bend, deflect, brush against) in one embodiment the surface disruption is a toothed rack 9066 formed on an upper surface of the drive shaft 9002, such as at a proximal end thereof. The toothed rack 9066 includes at least one tooth configured to interact with the needle 9062, which can be positioned above and adjacent to the surface disruption on the drive shaft such that the needle will contact the surface disruption and generate a signal (e.g., an audible signal) when the needle and the surface disruption interact. In operation, when the surgical fastening device is driving fasteners into a tissue, the drive shaft 9002 will advance linearly in a distal direction, e.g., by about 30 mm. As the drive shaft 9002 advances, the toothed rack 9066 will eventually come into contact with the needle 9062, where the needle 9062 is deflected and can generate audible sounds (e.g., clicking sounds) to inform the surgeon the general position of the drive shaft 9002. For example, the toothed rack 9066 can be formed on the drive shaft 9064 towards a proximal end, and when the needle 9062 is deflected and then released by the toothed racks 9066, the needle 9062 can generate an audible clip, twang, or ping indicating to the surgeon that the drive shaft 9002 and therefore the sleds within the staple cartridge are near their respective ends. This configuration can advantageously provide useful feedback to a device user without interfering with the normal operations of the device.

In some embodiments, a surgical device such as the above-mentioned surgical device 1100 can be configured to facilitate articulation of a surgical device's end effector relative to the surgical device's elongate shaft. In other words, the device can be configured to facilitate angularly offsetting the end effector relative to the shaft, e.g., angularly orienting a longitudinal axis of the end effector relative to a longitudinal axis of the shaft. Articulating the end effector relative to the shaft can help the end effector access target material at a surgical site. In general, a surgical device including an elongate shaft with an end effector at a distal end thereof can include at least one support feature configured to strengthen an articulation joint, also referred to herein as a "flex neck," where the device can bend to articulate the end effector relative to the shaft. The at least one support feature can be configured to provide support at the articulation joint, thereby helping to provide greater flexibility to the articulation joint, allowing the device to articulate to a higher degree than it could achieve without the at least one support feature, and/or helping to prevent collapse and/or buckling of the joint so as to reduce effectiveness of a rod extending therethrough. For example, a firing rod (e.g., an I-beam) configured to effect fastener firing and/or a closure rod configured to effect end effector opening/closing can extend through the articulation joint. When the joint bends, the rod(s) extending through the joint also bend, which can cause the rod(s) to collapse and/or buckle, particularly if the end effector is engaging relatively thick tissue, thereby reducing the effectiveness of the rod(s). The rods can even become entirely unusable if the articulation is to a high enough degree and/or the end effector is engaging thick enough tissue so as to require a higher closing force and/or firing force. The at least one support feature can be configured to help prevent such rod ineffectiveness.

A surgical device with an elongate shaft having a relatively small diameter and with an end effector having a relatively small diameter, such as surgical devices appropriate for use in minimally invasive surgery, can be particularly difficult to articulate because of the forces the device can experience during articulation. In some instances, an articulation joint where the device can bend to articulate the end effector can break or otherwise fail due to these forces, thereby interrupting and prolonging a surgical procedure and at least temporarily rendering the device unusable. The at least one support feature can be configured to help prevent such breakage and failure. A surgical device with an elongate shaft having a relatively small diameter and with an end effector having a relatively small diameter can be difficult to articulate to a desired degree, e.g., up to about 90° or up to about 80°. The at least one support feature can be configured to provide additional strength to the device's articulation joint, thereby facilitating articulation of the end effector to a relatively high degree, e.g., up to about 90° or up to about 80°.

In some embodiments, the at least one support feature can include a support beam having a plurality of notches formed therein. FIG. 180 illustrates one embodiment of an articulation joint 10000 that includes at least one support feature in the form of a support beam 10006 having a plurality of notches 10012 formed therein. The support beam 10006 can be disposed within a flexible casing 10002a, which can form at least a distal portion of the device's elongate shaft. The flexible casing 10002a can facilitate smooth advancement of the articulation joint 10000 into a patient's body and/or can help protect the notches 10012 disposed therein. A firing rod 10008a and a closure rod 10010a can extend through the support beam 10006, and hence also the casing 10002a. The rods 10008a, 10010a be located adjacent to each other laterally, which can reduce overall rod buckling, as the articulation join 10000 can be configured to articulate laterally, as shown in FIG. 180. As in this illustrated embodiment, the firing rod 10008a and closure rod 10010a can each be slidably disposed in discrete cavities extending through the support beam 10006.

A spacer beam 10004 can be located between the two rods 10008, 10010a within the support beam 10006, which can help insulate the firing rod 10008a from clamping forces generated by the closure rod 10010a and help insulate the closure rod 10010a from firing forces generated by the firing rod 10008a, thereby helping to improve precise control of the rods 10008a, 10010a. The spacer beam 10004 can be formed from one or more materials e.g., a polymer, a slick plastic, glass fillings, etc., that can allow the spacer 10004 beam to bend, as will be appreciated by a person skilled in the art, and facilitate insulation against rod forces.

The support beam 10006 can have a rectangular cross-sectional shape, as in this illustrated embodiment. The rectangular shape can help provide support to the rods 10008a, 10010a around an entire perimeter thereof, which can help prevent lateral or horizontal buckling as well as vertical buckling. The support beam 10006 can be formed from a relatively stiff material that has a relatively limited amount of flexibility, which can help provide stability to the rods 10008a, 10010a disposed therein, e.g., stability during longitudinal translation of the rods 10008a, 10010a within their respective cavities. The plurality of notches 100012 formed in the support beam 10006 can facilitate bending of the support beam 10006 while still allowing the support beam 1006 to provide the relatively stiff support to the rods 10008a, 10010a.

The notches 10012 can have a variety of sizes, shapes, and configurations. The notches 10012 can be configured to facilitate articulation (e.g., bending of the device at the articulation joint 10000). The notches 10012 can be configured to reduce an overall force needed to articulate the articulation joint 10000 since the notches 10012 can help compensate for the relatively stiff material of the support beam 10006 that would generally be more difficult to bend without the notches 10012 formed therein. As in this illustrated embodiment, the notches 10012 can include vertical cuts, e.g., cuts substantially perpendicular to a longitudinal axis of the articulation joint 10000. The notches 10012 can be formed in opposed lateral sides of the support beam 10006, thereby corresponding to the lateral articulation of the articulation join 10000. The support beam 10006 can include any number of notches 10012 formed therein.

FIG. 181 illustrates another embodiment of an articulation joint 10013 that includes at least one support feature in the form of a support beam having a plurality of notches 10014 formed therein. The support beam and the notches 10014 can generally be configured and used similar to the beam 10006 and the notches 10012 of FIG. 180. In this illustrated embodiment, instead of the support beam being a singular member as in the embodiment of FIG. 180, the support beam can include first and second support plates 10016a, 10016b that together can define the support beam through which a firing rod 10008b, a closure rod 10010b, and a spacer rod 10018 can longitudinal extend. A flexible casing 10002b can be disposed around the support beam, similar to the flexible casing 10002a of FIG. 180.

The first and second support plates 10016a, 10016b can have a variety of sizes, shapes, and configurations. As in this illustrated embodiment, the first and second support plates 10016a, 10016c can each have "L" shaped cross-sectional shapes. The "L" shaped first and second support plates 10016a, 10016b can be arranged relative to one another to provide support to opposed lateral sides of the rods 10008a, 10010b and to opposed top and bottom sides of the rods 10008a, 10010b, as in this illustrated embodiment. In some embodiments, the first and second support plates 10016a, 10016b can each be formed from a relatively stiff material. In some embodiments, the first and second support plates 10016a, 10016b can each be formed from a rigid material that generally cannot bend, e.g., a metal such as titanium, etc. The rigid plates can be attached to each other using a flexing connection element such as a spring, which can facilitate the bending of the articulation joint 100013. In some embodiments, the first and second support plates 10016a, 10016b can be fixed together at one end and coupled to the device's end effector (not shown). In other embodiments, the first and second support plates 10016a, 10016b can be entirely floating within the casing 10002b, and as such, even when the rods 10008b, 10010b are highly articulated, the support plates 10016a, 10016c can be configured to not pinch either of the rods 10008b, 10010b.

The notches 10012 can have a variety of sizes, shapes, and configurations. As in this illustrated embodiment, the notches 10012 can each include corner cuts be formed in corners of the first and second support plates 10016a, 10016b, e.g., where the "L" bends.

FIG. 182 and FIG. 183 illustrate another embodiment of an articulation joint 10026 that includes at least one support feature in the form of a support beam 10019. The support beam 10019 can generally be configured and used similar to the beam 10006 of FIG. 180. The beam 10019 can have a plurality of discrete channels formed therein, each of the channels being configured to movably seat therein one of a first articulation rod 10024a configured to articulate the beam 10019 in a first lateral direction (e.g., to the right), a second articulation rod 10024b configured to articulate the beam 10019 in a second, opposite lateral direction (e.g., to the left), a firing rod 10020, and a closure rod 10022. Each of the rods 10020, 10022 and the bands 10024a, 10024b being disposed in its own independent channel within which it can longitudinally move can help insulate the element 10020, 10022, 10024a, 10024b within any one of the channels from forces created by the elements in the other three channels. As in this illustrated embodiment, the firing and closure rods 10020, 10022 can be arranged vertically, e.g., in a direction substantially perpendicular to the beam's lateral articulation, which can help insulate one of the rods 10020, 10022 from forces from the other one of the rods 10020, 10022 and from forces of the articulation bands 10024a, 10024b. The beam 10019 can be enclosed by a flexible casing 10027, which is only partially shown in FIG. 182 for clarity of illustration of the articulation joint 10026. As shown in this illustrated embodiment, the firing rod 10020 can include a plurality of flexible laminate bands, and the closure rod 10022 can include a plurality of flexible laminate bands.

FIG. 184 illustrates another embodiment of an articulation joint that includes at least one support feature in the form of a support beam 10029. The support beam 10029 can generally be configured and used similar to the beam 10006 of FIG. 180 and can be enclosed by a flexible casing 10034. Similar to the beam 10019 of FIG. 182, the beam 10029 of FIG. 184 can include a plurality of discrete channels 10033a, 1033b, 1033c, 1033d formed therein, each of the channels 10033a, 1033b, 1033c, 1033d being configured to movably seat therein one of a first articulation rod 10035a configured to articulate the beam 10029 in a first lateral direction (e.g., to the right), a second articulation rod 10035b configured to articulate the beam 10029 in a second, opposite lateral direction (e.g., to the left), a firing rod 10038, and a closure rod 10037.

In some embodiments, a channel formed in a support beam can include one or more friction features configured to reduce frictional contact of a rod extending through and being movable within the channel. When the rod moves within the channel, e.g., slides longitudinally therein, the rod can contact one or more of opposed lateral inner walls and opposed top and bottom inner walls of the channel. This contact can increase friction and impede the movement of the rod, thereby making the rod's movement more difficult. The one or more friction features can be formed on one or more of the channel's opposed lateral inner walls and opposed top and bottom inner wall, thereby reducing the rod's friction with the wall(s) that include the friction feature(s). The one or more friction features can be configured to help prevent buckling by helping to support the rod which the one or more friction features can contact when the beam articulates and/or when the rod longitudinally slides within the channel.

FIG. 184 illustrates one embodiment of a friction feature 10028 that can be formed in a support beam channel 10033a, which is also illustrated in FIG. 185. Only one of the channels 10033a, 1033b, 1033c, 1033d of the beam 10029 includes a friction feature, but any one or more of the channels 10033a, 1033b, 1033c, 1033d can include a friction feature. Additionally, although the at least one friction feature 10028 is formed on opposed lateral inner walls 10036 of the firing rod's channel 10033a, the at least one friction feature 10028 can be formed on any one or more of the channel's inner walls. The at least one friction feature 10028 can have a variety of sizes, shapes, and configurations. As in this illustrated embodiment, the at least one friction feature 10028 can include at least one protrusion extending radially inward so as to extend into the channel 10033a.

FIG. 186, FIG. 187, and FIG. 188 illustrate another embodiment of an articulation joint 10040 that includes at least one support feature in the form of a support beam 10042. The support beam 10042 can generally be configured and used similar to the beam 10006 of FIG. 180. The beam 10029 can have a plurality of discrete channels $10032_1$, $10032_2$, $10032_3$, and $10032_4$ formed therein, each of the channels $10032_1$, $10032_2$, $10032_3$, and $10032_4$ being configured to movably seat therein one of a first articulation rod 10044 configured to articulate the beam 10029 in a first lateral direction (e.g., to the right, as shown in FIG. 187 and FIG. 188), a second articulation rod 10406 configured to articulate the beam 10012 in a second, opposite lateral direction (e.g., to the left), a firing rod 10048, and a closure rod 10500. The firing rod 10048 and the closure rod 10050 in this illustrated embodiment each include a plurality of flexible laminate bands, as shown in FIG. 188. The rods 1044, 1046, 1048, 1050 are omitted from FIG. 186 and FIG. 187 for clarity of illustration.

The beam 10029 can be a single element, as in this illustrated embodiment. The channels $10032_1$, $10032_2$, $10032_3$, and $10032_4$ can be formed in the beam 10029 in a variety of ways, such as by laser cutting the channels $10032_1$, $10032_2$, $10032_3$, and $10032_4$ therein. Dimensions of the channels $10032_1$, $10032_2$, $10032_3$, and $10032_4$ can be tailored to resist vertical bending while not inhibiting lateral or horizontal bending.

The beam 10029 of this illustrated embodiment can be formed from a more flexible material than the beam 10019 of FIG. 182, which also has a plurality of discrete channels formed therein, because the beam 10029 of this illustrated embodiment can have a cylindrical shape matching a cylindrical shape of the device's elongate shaft. In contrast, a beam such as the beam 10019 of FIG. 182 having a shape that does not match a cylindrical shape of the device's elongate shaft can contain less space within the shaft such that it can be more stiff. Being formed on a more flexible material, the beam 10029 can be configured to flex in more directions than a beam formed from a stiffer material.

The beam 10029 can be enclosed by a flexible casing 10030. The casing 10030 is omitted from FIG. 188 for clarity of illustration.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
    an end effector including first and second jaws configured to engage tissue between the first and second jaws with the end effector in a closed position;
    a staple cartridge configured to be removably seated in the end effector; and
    an I-beam configured to, with the staple cartridge removably seated in the end effector, engage the first and second jaws and translate along the end effector relative to the first and second jaws, wherein a size of the I-beam is defined by the staple cartridge removably seated in the end effector;
    wherein the staple cartridge and the I-beam are configured such that upon removal of the staple cartridge from the end effector, a portion of the I-beam is removed from the end effector, and a remainder of the I-beam remains in the end effector.

2. The device of claim 1, wherein the staple cartridge and the I-beam are configured such that upon seating of the staple cartridge into the end effector, the I-beam is defined.

3. The device of claim 2, further comprising a shaft slidably coupled to the end effector;
    wherein a portion of the shaft defines part of the I-beam and a portion of the staple cartridge defines a remainder of the I-beam; and
    the portion of the shaft and the portion of the staple cartridge are configured to mate together as a result of the removable seating of the staple cartridge into the end effector, thereby defining the I-beam.

4. The device of claim 1, further comprising a shaft slidably coupled to the end effector;
    wherein the shaft includes a first portion of the I-beam and the staple cartridge includes a second portion of the I-beam such that the I-beam is configured to be defined by the staple cartridge being removably seated in the end effector.

5. The device of claim 4, wherein, with the staple cartridge removably seated in the end effector, the first portion of the I-beam is seated in the first jaw and the staple cartridge is removably seated in the first jaw with the second portion of the I-beam being seated in the second jaw.

6. The device of claim 4, wherein the second portion of the I-beam includes a cutting element configured to cut the tissue engaged between the first and second jaws.

7. The device of claim 4, wherein the shaft is slidably seated in an elongate shaft, and the end effector is coupled to a distal end of the elongate shaft.

8. The device of claim 1, wherein, with the staple cartridge removably seated in the end effector, the staple cartridge defines a minimum distance between facing tissue-engaging surfaces of the first and second jaws with the end effector in the closed position.

9. The device of claim 1, further comprising a second staple cartridge configured to be removably seated in the end effector after the staple cartridge has been removed from the end effector; and
    with the second staple cartridge removably seated in the end effector, the I-beam is adjusted and is engaged with the first and second jaws and translate along the end effector relative to the first and second jaws, wherein a size of the adjusted I-beam is defined by the second staple cartridge removably seated in the end effector;
    wherein a size of the adjusted I-beam is different from the size of the I-beam.

10. The device of claim 9, further comprising a shaft slidably coupled to the end effector;
    wherein a portion of the shaft defines part of the I-beam;
    the portion of the shaft and a portion of the staple cartridge are configured to mate together as a result of the removable seating of the staple cartridge into the end effector, thereby defining the I-beam; and
    the portion of the shaft and a portion of the second staple cartridge are configured to mate together as a result of the removable seating of the second staple cartridge into the end effector, thereby defining the adjusted I-beam.

11. The device of claim 1, wherein the translation of the I-beam along the end effector is configured to cause staples to be ejected from the staple cartridge into the tissue engaged between the first and second jaws.

12. The device of claim 11, wherein the translation of the I-beam along the end effector is configured to cause the tissue engaged between the first and second jaws to be cut.

13. A surgical method, comprising:
    removably seating the staple cartridge of the surgical device of claim 9 into the end effector of the surgical device of claim 1; and
    after removably seating the staple cartridge into the end effector, engaging the tissue between the first and second jaws of the end effector and thereafter causing the I-beam to translate along the end effector.

14. A surgical device, comprising:

an end effector including first and second jaws configured to engage tissue therebetween;

a first staple cartridge configured to be removably seated in the end effector, wherein the removable seating of the first staple cartridge into the end effector is configured to define a first I-beam engaging each of the first and second jaws and configured to translate along the end effector relative to the first and second jaws; and a second staple cartridge configured to be removably seated in the end effector after the first staple cartridge has been removed from the end effector, wherein upon seating of the second staple cartridge into the end effector, an adjusted I-beam engaging each of the first and second jaws is defined and is also configured to translate along the end effector relative to the first and second jaws.

15. The device of claim 14, further comprising a shaft slidably coupled to the end effector;

wherein a portion of the shaft and a portion of the first staple cartridge are configured to mate together as a result of the removable seating of the first staple cartridge into the end effector, thereby defining the first I-beam; and the portion of the shaft and a portion of the second staple cartridge are configured to mate together as a result of the removable seating of the second staple cartridge into the end effector, thereby defining the adjusted I-beam.

16. The device of claim 15, wherein, with the first staple cartridge removably seated in the end effector, a size of a gap of space between tissue-engaging surfaces of the first and second jaws is defined by the portion of the first staple cartridge; and with the second staple cartridge removably seated in the end effector, a size of the gap of space between the tissue-engaging surfaces of the first and second jaws is defined by the portion of the second staple cartridge and is different from the size of the gap of space defined by the portion of the first staple cartridge.

17. The device of claim 14, wherein, with the first staple cartridge removably seated in the end effector, tissue-engaging surfaces of the first and second jaws are configured to have a first minimum distance therebetween; and with the second staple cartridge removably seated in the end effector, the tissue-engaging surfaces of the first and second jaws are configured to have a second, different minimum distance therebetween.

18. The device of claim 14, wherein, with the first staple cartridge removably seated in the end effector, the first I-beam is configured to translate along the end effector relative to the first and second jaws and thereby cause staples to be ejected into the tissue engaged between the first and second jaws; and with the second staple cartridge removably seated in the end effector, the adjusted I-beam is configured to translate along the end effector relative to the first and second jaws and thereby cause staples to be ejected into the tissue engaged between the first and second jaws.

19. A surgical method, comprising:

removably seating the first staple cartridge of the surgical device of claim 14 into the end effector of the surgical device of claim 14;

after removably seating the first staple cartridge into the end effector, engaging the tissue between the first and second jaws of the end effector and thereafter causing the first I-beam to translate along the end effector; and after causing the translation of the first I-beam, removing the first staple cartridge from the end effector, thereby removing a portion of the first I-beam from the end effector with another portion of the first I-beam remaining in the end effector.

\* \* \* \* \*